United States Patent
Burnier et al.

(10) Patent No.: US 8,367,701 B2
(45) Date of Patent: *Feb. 5, 2013

(54) CRYSTALLINE PHARMACEUTICAL AND METHODS OF PREPARATION AND USE THEREOF

(75) Inventors: John Burnier, Pacifica, CA (US); Thomas Gadek, Oakland, CA (US); Frederic Naud, Binningen (CH)

(73) Assignee: SARcode Bioscience Inc., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/289,172

(22) Filed: Nov. 4, 2011

(65) Prior Publication Data

US 2012/0107404 A1 May 3, 2012

Related U.S. Application Data

(63) Continuation of application No. 12/386,361, filed on Apr. 15, 2009, now Pat. No. 8,080,562.

(60) Provisional application No. 61/045,142, filed on Apr. 15, 2008.

(51) Int. Cl.
*A61K 31/47* (2006.01)
*C07D 217/00* (2006.01)

(52) U.S. Cl. ........................... 514/307; 546/146
(58) Field of Classification Search .......... 514/307; 546/146

See application file for complete search history.

(56) References Cited

U.S. PATENT DOCUMENTS

| | | | |
|---|---|---|---|
| 3,773,919 A | 11/1973 | Boswell et al. | |
| 4,668,506 A | 5/1987 | Bawa | |
| 4,713,244 A | 12/1987 | Bawa | |
| 4,767,628 A | 8/1988 | Hutchinson | |
| 4,908,202 A | 3/1990 | Schulz | |
| 4,931,279 A | 6/1990 | Bawa et al. | |
| 4,992,445 A | 2/1991 | Lawter et al. | |
| 5,001,139 A | 3/1991 | Lawter et al. | |
| 5,023,252 A | 6/1991 | Hseih | |
| 5,134,122 A | 7/1992 | Orsolini | |
| 5,149,780 A | 9/1992 | Plow et al. | |
| 5,192,741 A | 3/1993 | Orsolini et al. | |
| 5,236,704 A | 8/1993 | Fujioka et al. | |
| 5,288,854 A | 2/1994 | Diamond et al. | |
| 5,298,492 A | 3/1994 | Neustadt et al. | |
| 5,340,800 A | 8/1994 | Liu et al. | |
| 5,397,791 A | 3/1995 | Hartman et al. | |
| 5,424,289 A | 6/1995 | Yang et al. | |
| 5,424,399 A | 6/1995 | Arnaout | |
| 5,445,832 A | 8/1995 | Orsolini et al. | |
| 5,470,953 A | 11/1995 | Gallatin et al. | |
| 5,585,359 A | 12/1996 | Breslin et al. | |
| 5,597,567 A | 1/1997 | Whitcup et al. | |
| 5,612,052 A | 3/1997 | Shalaby | |
| 5,622,700 A | 4/1997 | Jardieu et al. | |
| 5,672,659 A | 9/1997 | Shalaby et al. | |
| 5,747,035 A | 5/1998 | Presta et al. | |
| 5,840,332 A | 11/1998 | Lerner et al. | |
| 5,849,327 A | 12/1998 | Berliner et al. | |
| 5,877,224 A | 3/1999 | Brocchini et al. | |
| 5,893,985 A | 4/1999 | Luo et al. | |
| 5,922,356 A | 7/1999 | Koseki et al. | |
| 5,968,895 A | 10/1999 | Gefter et al. | |
| 5,973,188 A | 10/1999 | Alig et al. | |
| 5,980,945 A | 11/1999 | Ruiz | |
| 6,180,608 B1 | 1/2001 | Gefter et al. | |
| 6,204,280 B1 | 3/2001 | Gante et al. | |
| 6,294,522 B1 | 9/2001 | Zablocki et al. | |
| 6,331,640 B1 | 12/2001 | Fotouhi et al. | |
| 6,340,679 B1 | 1/2002 | Peyman et al. | |
| 6,358,976 B1 | 3/2002 | Wityak et al. | |
| 6,515,124 B2 | 2/2003 | Fotouhi et al. | |
| 6,524,581 B1 | 2/2003 | Adamis | |
| 6,605,597 B1 | 8/2003 | Zablocki et al. | |
| 6,620,422 B1 | 9/2003 | Maquin et al. | |
| 6,642,225 B2 | 11/2003 | Albert et al. | |
| 6,653,478 B2 | 11/2003 | Urbanski et al. | |

(Continued)

FOREIGN PATENT DOCUMENTS

| | | |
|---|---|---|
| EP | 0314863 A2 | 5/1989 |
| EP | 0314863 A3 | 4/1990 |

(Continued)

OTHER PUBLICATIONS

Boschelli, et al. 3-Alkoxybenzo[b]thiophene-2-carboxamides as inhibitors of neutrophil-endothelial cell adhesion. J Med Chem. 1994; 37(6): 717-8.

(Continued)

*Primary Examiner* — Raymond Henley, III
(74) *Attorney, Agent, or Firm* — Wilson Sonsini Goodrich & Rosati

(57) ABSTRACT

Novel crystalline polymorphic forms, Forms A, B, C, D, and E of a compound of Formula I, which has been found to be a potent inhibitor of LFA-1, are disclosed. Methods of preparation and uses thereof in the treatment of LFA-1 mediated diseases are also disclosed in this invention.

Formula I

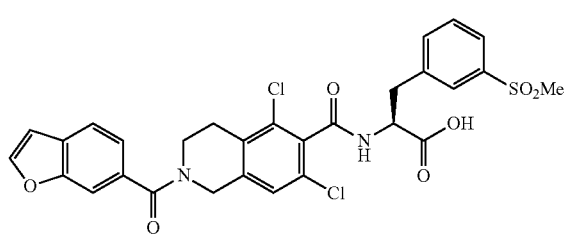

41 Claims, 48 Drawing Sheets

U.S. PATENT DOCUMENTS

| | | |
|---|---|---|
| 6,667,060 B1 | 12/2003 | Vandecruys et al. |
| 6,667,318 B2 | 12/2003 | Burdick et al. |
| 6,670,321 B1 | 12/2003 | Adamis |
| 6,773,916 B1 | 8/2004 | Thiel et al. |
| 6,803,384 B2 | 10/2004 | Fotouhi et al. |
| 6,872,382 B1 | 3/2005 | Gamache et al. |
| 6,872,735 B2 | 3/2005 | Burdick et al. |
| 7,097,851 B1 | 8/2006 | Takada |
| 7,211,586 B2 | 5/2007 | Fenton et al. |
| 7,217,728 B2 | 5/2007 | Fotouhi et al. |
| 7,314,938 B2 | 1/2008 | Shen et al. |
| 7,785,578 B2 | 8/2010 | Miller et al. |
| 7,989,626 B2 | 8/2011 | Shen et al. |
| 8,080,562 B2 * | 12/2011 | Burnier et al. ............... 514/307 |
| 8,084,047 B2 | 12/2011 | Shen et al. |
| 2001/0031260 A1 | 10/2001 | Lee et al. |
| 2002/0019446 A1 | 2/2002 | Brocchini et al. |
| 2002/0115692 A1 | 8/2002 | Archibald et al. |
| 2002/0119994 A1 | 8/2002 | Burdick et al. |
| 2002/0132807 A1 | 9/2002 | Wang et al. |
| 2002/0176841 A1 | 11/2002 | Barker et al. |
| 2002/0177591 A1 | 11/2002 | O'Donnell et al. |
| 2003/0044406 A1 | 3/2003 | Dingivan |
| 2003/0064105 A1 | 4/2003 | Kim et al. |
| 2003/0068320 A1 | 4/2003 | Dingivan |
| 2003/0068384 A1 | 4/2003 | Brocchini et al. |
| 2003/0138488 A1 | 7/2003 | Kohn et al. |
| 2003/0166630 A1 | 9/2003 | Auvin et al. |
| 2003/0171296 A1 | 9/2003 | Gefter et al. |
| 2003/0216307 A1 | 11/2003 | Kohn et al. |
| 2004/0006236 A1 | 1/2004 | Fotouhi et al. |
| 2004/0028648 A1 | 2/2004 | Adamis |
| 2004/0058968 A1 | 3/2004 | Burdick et al. |
| 2004/0120960 A1 | 6/2004 | Jardieu et al. |
| 2005/0080119 A1 | 4/2005 | Fotouhi et al. |
| 2005/0148588 A1 | 7/2005 | Burdick et al. |
| 2005/0267098 A1 | 12/2005 | Shen et al. |
| 2006/0281739 A1 | 12/2006 | Gadek et al. |
| 2007/0025990 A1 | 2/2007 | Dingivan |
| 2007/0155671 A1 | 7/2007 | Fotouhi et al. |
| 2008/0019977 A1 | 1/2008 | Adamis |
| 2008/0176896 A1 | 7/2008 | Shen et al. |
| 2008/0182839 A1 | 7/2008 | Shen et al. |
| 2009/0155176 A1 | 6/2009 | Burnier et al. |
| 2009/0298869 A1 | 12/2009 | Burnier et al. |
| 2010/0092541 A1 | 4/2010 | Burnier et al. |
| 2010/0092542 A1 | 4/2010 | Burnier et al. |
| 2011/0092707 A1 | 4/2011 | Burnier et al. |
| 2011/0124669 A1 | 5/2011 | Shen et al. |
| 2011/0165228 A1 | 7/2011 | Burnier et al. |
| 2011/0165229 A1 | 7/2011 | Burnier et al. |

FOREIGN PATENT DOCUMENTS

| | | |
|---|---|---|
| EP | 0362526 A2 | 4/1990 |
| EP | 0362531 A1 | 4/1990 |
| EP | 0362526 A3 | 7/1990 |
| EP | 0326151 B1 | 6/1993 |
| EP | 0656789 B1 | 12/1997 |
| EP | 0467389 B1 | 10/1999 |
| EP | 1392306 B1 | 1/2008 |
| JP | 4193895 | 7/1992 |
| WO | WO 90/03400 A1 | 4/1990 |
| WO | WO 90/10652 A1 | 9/1990 |
| WO | WO 90/13316 A1 | 11/1990 |
| WO | WO 91/19511 A1 | 12/1991 |
| WO | WO 92/03473 A1 | 3/1992 |
| WO | WO 93/16702 A1 | 9/1993 |
| WO | WO 93/24150 A1 | 12/1993 |
| WO | WO 94/03481 A1 | 2/1994 |
| WO | WO 94/11400 A1 | 5/1994 |
| WO | WO 94/15587 A2 | 7/1994 |
| WO | WO 94/15587 A3 | 9/1994 |
| WO | WO 95/04531 A1 | 2/1995 |
| WO | WO 95/28170 A1 | 10/1995 |
| WO | WO 96/09836 A1 | 4/1996 |
| WO | WO 97/04744 A1 | 2/1997 |
| WO | WO 97/26015 A1 | 7/1997 |
| WO | WO 97/40085 A2 | 10/1997 |
| WO | WO 97/40085 A3 | 1/1998 |
| WO | WO 98/13029 A1 | 4/1998 |
| WO | WO 98/25642 A2 | 6/1998 |
| WO | WO 98/25642 A3 | 7/1998 |
| WO | WO 98/46599 A1 | 10/1998 |
| WO | WO 99/49856 A2 | 10/1999 |
| WO | WO 99/49856 A3 | 11/1999 |
| WO | WO 00/21920 A1 | 4/2000 |
| WO | WO 00/38714 A1 | 7/2000 |
| WO | WO 00/44731 A1 | 8/2000 |
| WO | WO 01/01964 A2 | 1/2001 |
| WO | WO 01/12233 A2 | 2/2001 |
| WO | WO 01/27102 A1 | 4/2001 |
| WO | WO 01/01964 A3 | 6/2001 |
| WO | WO 01/49249 A2 | 7/2001 |
| WO | WO 01/49311 A1 | 7/2001 |
| WO | WO 01/58853 A1 | 8/2001 |
| WO | WO 01/12233 A3 | 11/2001 |
| WO | WO 01/87840 A1 | 11/2001 |
| WO | WO 01/49249 A3 | 1/2002 |
| WO | WO 02/30398 A2 | 4/2002 |
| WO | WO 02/38129 A2 | 5/2002 |
| WO | WO 02/50080 A1 | 6/2002 |
| WO | WO 02/058672 A2 | 8/2002 |
| WO | WO 02/059114 A1 | 8/2002 |
| WO | WO 02/074247 A2 | 9/2002 |
| WO | WO 02/058672 A3 | 12/2002 |
| WO | WO 02/074247 A3 | 12/2002 |
| WO | WO 02/098426 A1 | 12/2002 |
| WO | WO 02/38129 A3 | 2/2003 |
| WO | WO 02/30398 A3 | 3/2003 |
| WO | WO 03/053401 A2 | 7/2003 |
| WO | WO 03/075887 A1 | 9/2003 |
| WO | WO 03/053401 A3 | 1/2004 |
| WO | WO 2004/026406 A1 | 4/2004 |
| WO | WO 2005/014532 A1 | 2/2005 |
| WO | WO 2005/014533 A2 | 2/2005 |
| WO | WO 2005/014533 A3 | 4/2005 |
| WO | WO 2005/042710 A1 | 5/2005 |
| WO | WO 2005/044817 A1 | 5/2005 |
| WO | WO 2005/123706 A1 | 12/2005 |
| WO | WO 2006/125119 A1 | 11/2006 |
| WO | WO 2009/139817 A2 | 11/2009 |
| WO | WO 2009/139817 A3 | 1/2010 |

OTHER PUBLICATIONS

Boschelli, et al Inhibition of E-Selectin-, ICAM-1-, and VCAM-1-mediated cell adhesion by benzo[b]thiophene-, benzufuran-, indole-, and naphthalene-2-carboxamides: Identification of PD 144795 as an antiinflammatory agent. J Med Chem. 1995; 38: 4597-614.

Burdick, et al. N-Benzoyl amino acids as ICAM/LFA-1 inhibitors. Part 2: Structure-activity relationship of the benzoyl moiety. Bioorganic & Medicinal Chemistry Letters. 2004; 14(9): 2055-9.

Burdick, et al. N-Benzoyl amino acids as LFA-1/ICAM inhibitors 1: amino acid structure-activity relationship. Bioorganic & Medicinal Chemistry Letters. 2004; 13(6): 1015-8.

Chang, et al. Effects of pharmacologic agents on the reversed passive Arthus reaction in the rat. Eur J Pharmacol. 1981; 69(2): 155-64.

Chavanpatil, et al. Novel sustained release, swellable and bioadhesive gastroretentive drug delivery system for ofloxacin. Int J Pharm. 2006; 316(1-2): 86-92.

Coleman, et al. Chemoselective Cleavage of Benzyl Ethers, Esters, and Carbamates in the Presence of Other Easily Reducible Groups. Synthesis. 1999;1399-1400.

Cosimi, et al. In vivo effects of monoclonal antibody to ICAM-1 (CD54) in nonhuman primates with renal allografts. J Immunol. 1990; 144(12): 4604-12.

Crocker, et al. The role of fluorine substitution in the structure-activity relationships (SAR) of classical cannabinoids. Bioorg med chem lett. 2007; 17(6):1504-1507.

Davies et al. Physiological Parameters in Laboratory Animals and Humans. *Pharmaceutical Research*. 1993;10:1093-1095.

Diamond, et al. The dynamic regulation of integrin adhesiveness. Current Biology. 1994; 4(6): 506-32.

Earle et al. A Simplified Clinical Procedure for Measurement of Glomerular Filtration Rate and Renal Plasma Flow. *Proc. Soc. Exp. Biol. Med.* 1946;62:262-269.

European Office Action dated Nov. 9, 2010 for Application No. 6770607.7.

European search report dated May 20, 2009 for Application No. 06770607.7.

Fischer, et al. Prevention of graft failure by an anti-HLFA-1 monoclonal antibody in HLA-mismatched bone-marrow transplantation. The Lancet. 1986; 2: 1058-60.

Fox. Systemic diseases associated with dry eye. Int Ophthalmol Clin, 1994 Winter, 34(1):71-87.

Gadek, et al. Generation of an LFA-1 antagonist by the transfer of the ICAM-1 immunoregulatory epitope to a small molecule. Science. 2002; 295: 1086-9.

Gao, et al. ICAM-1 expression predisposes ocular tissues to immune-based inflammation in dry eye patients and Sjögrens syndrome-like MRL/lpr mice. Exp Eye Res. Apr. 2004;78(4):823-35.

Gorski, A. The role of cell adhesion molecules in immunopathology. Immunology Today. 1994; 15: 251-5.

Hecht, et al. Effects of methyl and fluorine substitution on the metabolic activation and tumorigenicity of polycyclic aromatic hydrocarbons. ACS Symposium series. 1985; 283(5):85-105. Abstract only.

Hildreth, et al. Monoclonal antibodies against porcine LFA-1: Species cross-reactivity and functional effects of β-subunit-specific antibodies. Molecular Immunology. 1989; 26(9): 883-95.

Hoffman, et al. Pharmacokinetic and pharmacodynamic aspects of gastroretentive dosage forms. Int J Pharm. 2004; 277(1-2): 141-53.

Huang, et al. A binding interface of the I domain of lymphocyte function-associated antigen-1 (LFA-1) required for specific interaction with intercellular adhesion molecule 1 (ICAM-1). J Biological Chemistry. 1995; 270(32): 19008-16.

International search report and written opinion dated Dec. 22, 2010 for PCT Application No. US10/53571.

International search report and written opinion dated Sep. 24, 2009 for PCT Application No. US2009/02391.

International search report dated Sep. 19, 2006 for PCT Application No. PCT/US2006/19327.

Kavanaugh, et al. Treatment of refractory rheumatoid arthritis with a monoclonal antibody to intercellular adhesion molecule 1. Arthritis Rheum. 1994; 37(7): 992-1004.

Keating, et al. Competition between intercellular adhesion molecule-1 and a small-molecule antagonist for a common binding site on the alpha1 subunit of lymphocyte function-associated antigen-1. Protein Sci. 2006; 15(2):290-303.

Keating, et al. Putting the pieces together : Contribution of fluorescence polarization assays to small molecule lead optimization. Proc. SPIE. 2000; vol. 3913, p. 128-137. (Online Publication Date: Jul. 2, 2003).

Kishimoto, et al. Integrins, ICAMs, and selectins: Role and regulation of adhesion molecules in neutrophil recruitment to inflammatory sites. Adv Pharmacol. 1994; 25: 117-69.

Klausner, et al. Novel gastroretentive dosage forms: evaluation of gastroretentivity and its effect on levodopa absorption in humans. Pharm Res. 2003; 20(9): 1466-73.

Kunert, et al. Analysis of Topical Cyclosporine Treatment of Patients with Dry Eye Syndrome. Arch Ophthalmol, vol. 118, Nov. 2000, 1489-1496.

Le Mauff, et al. Effect of anti-LFA1 (CD11a) monoclonal antibodies in acute rejection of human kidney transplantation. Transplantation. 1991; 52(2): 291-5.

Legarreta Eye Center, Dry Eye, Jan. 2002, printed from http://www.legarretaeyecenter.com/dry-eye.html with Google date entry, 3 pages.

Ley, et al. Getting to the site of inflammation: the leukocyte adhesion cascade updated. Nat Rev Immunol. Sep. 2007;7(9):678-689.

Liu, G. Inhibitors of LFA-1/ICAM-1 interaction: from monoclonal antibodies to small molecules. Drugs of the Future. 2001; 26: 767-78.

Liu, G. Small molecule antagonists of the LFA-1/ICAM-1 interaction as potential therapeutic agents. Expert Opin Ther Patents. 2001; 11: 1383-93.

Lu, et al. The binding sites for competitive antagonistic, allosteric antagonistic, and agonistic antibodies to the I domain of the integrin LFA-1. J Immunol. 2004; 173: 3972-8.

Murphy, et al. The Pharmacologic Assessment of a Novel Lymphocyte Function-Associated Antigen-1 Antagonist (SAR 1118) for the Treatment of Keratoconjunctivitis Sicca in Dogs. Invest Ophthalmol Vis Sci. May 16, 2011;52(6):3174-80.

Musza, et al. Potent new cell adhesion inhibitory compounds from the root of Trichilia rubra. Tetrahedron. 1994; 50(39): 11369-78.

Office action dated Jun. 7, 2011 for U.S. Appl. No. 11/436,906.
Office Action dated Jun. 8, 2011 for U.S. Appl. No. 12/508,367.
Office Action dated Sep. 28, 2010 for U.S. Appl. No. 12/508,311.
Office Action dated Sep. 28, 2010 for U.S. Appl. No. 12/508,367.
Office Action dated Dec. 21, 2010 for U.S. Appl. No. 11/436,906.

Park, et al. Effects of fluorine substitution on drug metabolism: pharmacological and toxicological implications. Drug Metab Rev. 1994;26(3):605-43.

Park, et al. Metabolism of fluorine-containing drugs. Annu Rev Pharmacol Toxicol. 2001;41:443-70.

Plobeck, et al. New diarylmethylpiperazines as potent and selective nonpeptidic δ opioid receptor agonists with increased in vitro metabolic stability. J Med Chem. 2000; 43: 3878-94.

Rothlein, et al. 1. Leukocyte adhesion in inflammation: From discovery to the clinic. Adhesion Molecules. Wegner, C.D., Ed.; 1994: 1-8.

Salas, et al. Rolling adhesion through an extended conformation of integrin αLβ2 and relation to α I and β I-like domain interaction. Immunity. 2004; 20(4): 393-406.

Sanfilippo, et al. Novel thiazole based heterocycles as inhibitors of LFA-1/ICAM-1 mediated cell adhesion. J Med Chem. 1995; 38: 1057-9.

Sapirstein et al. Volumes of Distribution and Clearances of Intravenously Injected Creatinine in the Dog. *American Journal of Physiology.* 1955;181:330-336.

Shimaoka, et al. Reversibly locking a protein fold in an active conformation with a disulfide bond: Integrin alpha L I domains with high affinity and antagonist activity in vivo. PNAS. 2001; 98(11): 6009-14.

Shimaoka, et al. Small molecule integrin antagonists that bind to the β2 subunit I-like domain and activate signals in one direction and block them in the other. Immunity. 2003; 19(3): 391-402.

Shimaoka, et al. Structures of the αL I domain and its complex with ICAM-1 reveal a shape-shifting pathway for integrin regulation. Cell. 2003; 112(1): 99-111.

Shimaoka, et al. Therapeutic antagonists and the conformational regulation of the β2 integrins. Curr Topics Med Chem. 2004; 4: 1485-95.

Shulman, et al. Lymphocyte crawling and transendothelial migration require chemokine triggering of high-affinity LFA-1 integrin. Immunity. Mar. 20, 2009;30(3):384-396.

Springer, T. Adhesion receptors of the immune system. Nature. 1990; 346: 425-34.

Stern, et al. Conjunctival T-cell subpopulations in Sjögren's and non-Sjögren's patients with dry eye. Invest Ophthalmol Vis Sci. Aug. 2002;43(8):2609-14.

Streubel, et al. Gastroretentive drug delivery systems. Expert Opin Drug Deliv. 2006; 3(2): 217-33.

The Eye Digest, Eye Exam for Dry Eyes, Mar. 2003, printed from http://www.agingeye.net/dryeyes/dryeeyeseyeexam.php and google date entry, 4 pages.

Ward, S. Millipede-like lymphocyte crawling: feeling the way with filopodia. Immunity. Mar. 20, 2009;30(3):315-317.

Welzenbach, et al. Small molecule inhibitors induce conformational changes in the I domain and the I-like domain of lymphocyte function-associated antigen-1. J Biological Chemistry. 2002; 277(12): 10590-8.

Wermuth. The practice of medicinal chemistry-molecular variations based on isosteric replacements. Academic Press Limited. 1996; 226-228.

European office action dated Nov. 24, 2011 for Application No. 06770607.7.

Frishberg, et al. Cyclosporine A regulates T cell-epithelial cell adhesion by altering LFA-1 and ICAM-1 expression. Kidney Int. Jul. 1996;50(1):45-53.

Kunert, et al. Goblet cell numbers and epithelial proliferation in the conjunctiva of patients with dry eye syndrome treated with cyclosporine. Arch Ophthalmol. Mar. 2002;120(3):330-7.
Office action dated Sep. 15, 2011 for U.S. Appl. No. 13/011,760.
Office action dated Oct. 5, 2011 for U.S. Appl. No. 13/011,775.
Patani, et al. Bioisosterism: A rational approach in drug design. Chem. Rev. 1996; 96:3147-3176.
Goodman, et al. Amino acid active esters. III. Base-catalyzed racemization of peptide active ester. Journal of Organic Chemistry, 1962; 27:3409-3416.
Kaiser, et al. Hydrolysis-induced racemization of amino acids. Limnol. Oceanogr. Methods. 2005; 3:318-325.
U.S. Appl. No. 13/398,542, filed Feb. 16, 2012, Gadek et al.
European office action dated Mar. 28, 2012 for Application No. 11181066.9.
Solomans. Fundamentals of Organic Chemistry. 5th ed. 1982; 630.
Zhong, et al. Discovery and Development of Potent LFA-1/ICAM-1 Antagonist SAR 1118 as an Ophthalmic Solution for Treating Dry Eye. ACS Med. Chem. Lett. DOI: 10.1021/ml2002482. Publication Date (Web): Jan. 31, 2012.
Office action dated Jun. 25, 2012 for U.S. Appl. No. 12/909,241.
Office action dated Sep. 8, 2011 for U.S. Appl. No. 12/386,361.

* cited by examiner

FIG. 23 Form D

Form E

Tear $C_{min}$ Levels of the compound of Formula I (1% formulation)

Mean (SD) plasma compound of Formula I concentration in male and female Dogs (n=6-10) following a single intravenous dose of 3, 10, or 30 mg/kg of test article on Day 1.

CRYSTALLINE PHARMACEUTICAL AND METHODS OF PREPARATION AND USE THEREOF

REFERENCE

This application is a continuation of U.S. application Ser. No. 12/386,361 filed on Apr. 15, 2009, now U.S. Pat. No. 8,080,562, which claims the benefit of U.S. Provisional Application No. 61/045,142, filed Apr. 15, 2008, which applications are incorporated herein by reference.

CROSS-REFERENCE

Cross reference is made to co-pending applications U.S. application Ser. No. 12/288,330, filed on Oct. 17, 2008; U.S. Ser. No. 12/386,359, filed on Apr. 15, 2009; U.S. Ser. No. 12/386,363, filed on Apr. 15, 2009; and U.S. Ser. No. 12/386,347, filed on Apr. 15, 2009, which are hereby incorporated by reference in their entirety.

BACKGROUND OF THE INVENTION

The compound of Formula I:

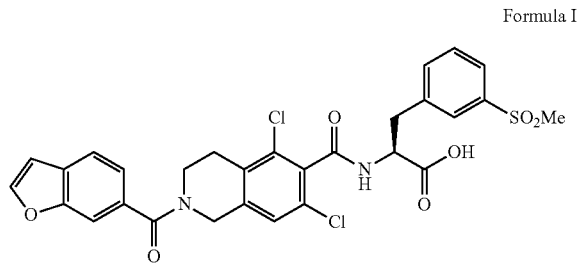 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

Formula I has been found to be an effective inhibitor of Lymphocyte Function-Associated Antigen-1 (LFA-1) interactions with the family of Intercellular Adhesion Molecules (ICAM), and has desirable pharmacokinetic properties, including rapid systemic clearance. Improved forms, including crystalline forms, and their uses in treatment of disorders mediated by the interaction of LFA-1 and ICAM are described herein. Novel polymorphs of the compound of Formula I which may afford improved purity, stability, bioavailability and other like characteristics for use in pharmaceutical formulations and methods of use thereof are useful in treating disease.

SUMMARY OF THE INVENTION

In a first aspect the invention provides a composition comprising a compound of Formula I:

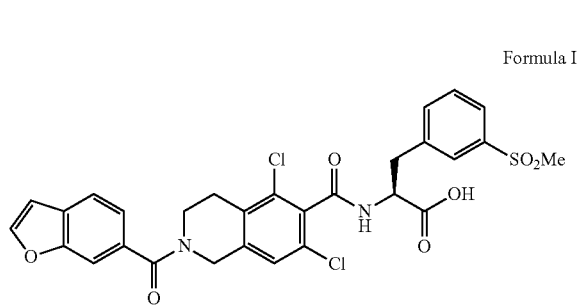 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

Formula I which comprises a purity of greater than about 90%, and its pharmaceutically acceptable salts. In some embodiments, the purity is greater than about 98%. In other embodiments, the compound comprises at least about 95% of an S-enantiomer. In yet other embodiments, the compound is not the calcium salt of the free acid. Alternatively, the compound is a sodium salt.

In some embodiments of the composition of a compound of Formula I, the compound is a crystalline form (Form A) comprising an X-ray powder diffraction pattern having characteristic peaks at a reflection angle 2θ of about 18.2, 21.4, and 22.7 degrees. In some embodiments, the crystalline form (Form A) undergoes a predominant endotherm at about 145° C. In other embodiments, the form (Form A) form is produced by isolating the form from a suspension of the compound in an organic solvent which is acetonitrile, methyl ethyl ketone, or water.

In other embodiments of the composition of a compound of Formula I, the compound is a crystalline form (Form B) comprising an X-ray powder diffraction pattern having characteristic peaks at a reflection angle 2θ of about 12.1, 17.1, and 18.5 degrees.

In another embodiment of the composition of a compound of Formula I, the compound is a crystalline form (Form C) form comprising an X-ray powder diffraction pattern having characteristic peaks at a reflection angle 2θ of about 4.8, 17.8, and 21.5 degrees.

In a further embodiment of the composition of a compound of Formula I, the compound is a crystalline form (Form D) comprising an X-ray powder diffraction pattern having characteristic peaks at a reflection angle 2θ of about 17.6, 21.7, and 24.8 degrees.

In another embodiment of the composition of a compound of Formula I, the compound is a crystalline form (Form E) form comprising an X-ray powder diffraction pattern having characteristic peaks at a reflection angle 2θ of about 5.12, 8.26, and 17.8 degrees.

In yet another embodiment of the composition of a compound of Formula I, the compound is an amorphous form.

The invention provides other compositions of a compound of Formula I, wherein the compound comprises less than 0.5% of any one byproduct of chemical synthesis of the compound. In other embodiments, the compound comprises less than a total of 1.5% of all byproducts of the chemical synthesis. In yet other embodiments, the compound comprises less than a total of 1.5% of all byproducts of the chemical synthesis.

In a second aspect, the invention provides a method of producing the form (Form A) comprising an X-ray powder diffraction pattern having characteristic peaks at a reflection angle 2θ of about 18.2, 21.4, and 22.7 degrees; comprising the steps of: suspending the compound of Formula I in a solvent; filtering the suspension to isolate a crystalline product; and washing the crystalline product with water thereby obtaining the form (Form A). In some embodiments, the solvent is acetonitrile or methyl ethyl ketone.

In a third aspect, the invention, provides a pharmaceutical composition comprising a pharmaceutically acceptable carrier and the compound of Formula I, which comprises a purity of greater than about 90%, and its pharmaceutically acceptable salts. In some embodiments, the compound has been converted to a salt. In other embodiments of the pharmaceutical composition, the compound comprises the amorphous form or any of crystalline Forms A, B, C, D, or E, or a combination thereof, of the compound of Formula I, which comprises a purity of greater than about 90%. In yet other embodiments, the pharmaceutical composition further comprises one or more pharmaceutically acceptable excipients. Alternatively, the pharmaceutical composition comprising a pharmaceutically acceptable carrier and the compound of Formula I, which comprises a purity of greater than about 90%, and its pharmaceutically acceptable salts, may further comprise at least one additional therapeutic agent. In some embodiments, the additional therapeutic agent is an antioxidant, antiinflammatory agent, antimicrobial agent, antiangiogenic agent, anti-apoptotic agent, vascular endothelial growth factor inhibitor, antiviral agent, calcineurin inhibitor, corticosteroid, antihistamine, mast cell stabilizing agent, or immunomodulator.

In other embodiments, the pharmaceutical composition comprising a pharmaceutically acceptable carrier and the compound of Formula I, which comprises a purity of greater than about 90%, and its pharmaceutically acceptable salts, is a gel comprising about 1% W/V of the compound of Formula I; up to about 15% W/V Dimethyl Isosorbide; up to about 25% W/V Transcutol; up to about 12% W/V Hexylene glycol, up to about 0.15% W/V Methylparaben; up to about 0.05% W/V Propylparaben; up to about 1% W/V Hydroxyethyl Cellulose; and water.

In various embodiments, the pharmaceutical composition comprising a pharmaceutically acceptable carrier and the compound of Formula I, which comprises a purity of greater than about 90%, is an ointment comprising about 1% W/V of the compound of Formula I, up to about 10% W/V Dimethyl Isosorbide; up to about 0.02% W/V Butylated Hydroxytoluene; up to about 2% W/V Span 80; up to about 10% W/V White Wax; and White Petrolatum.

In other embodiments, the pharmaceutical composition comprising a pharmaceutically acceptable carrier and the compound of Formula I, which comprises a purity of greater than about 90%, is a water based lotion comprising about 1% W/V of the compound of Formula I, up to about 15% W/V Dimethyl Isosorbide; up to about 25% W/V Transcutol; up to about 12% W/V Hexylene glycol; up to about 5% W/V Propylene Glycol; and pH 6.0 25% Trolamine, wherein the lotion is buffered to a pH of about pH4.0 to about pH7.5.

In some embodiments, the pharmaceutical composition comprising a pharmaceutically acceptable carrier and the compound of Formula I, which comprises a purity of greater than about 90%, is an aqueous solution buffered to a pH of about 6.0 to about 8.0 with Sodium Phosphate, Monobasic, comprising about 1% W/V of the compound of Formula I, up to about 0.1% W/V EDTA, and, optionally, up to about 0.4% w/w Methylparaben and up to about 0.02% w/w Propylparaben.

In some embodiments, the pharmaceutical composition comprising a pharmaceutically acceptable carrier and the compound of Formula I, which comprises a purity of greater than about 90%, is a biocompatible solid. In some embodiments the biocompatible solid is biodegradable. In other embodiments, composition is suitable for administration via instillation, via aerosol, via inhalation, orally, topically, transdermally, via insert, or via injection. In yet other embodiments, the pharmaceutical composition is formulated to deliver a therapeutically effective amount of the compound of Formula I locally. In some embodiments, the pharmaceutical composition is formulated to deliver less than a therapeutically effective amount of the compound of Formula I systemically.

In a fourth aspect, the invention provides a pharmaceutical composition comprising a compound of Formula I:

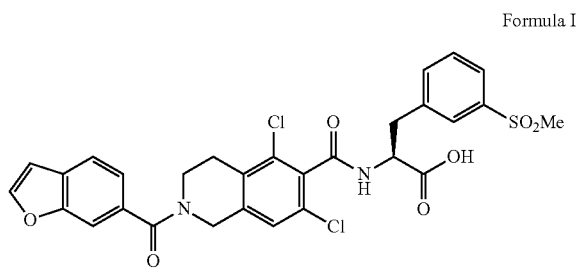 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

Formula I and a pharmaceutically acceptable biocompatible matrix wherein the compound comprises a solid form within the biocompatible matrix. In some embodiments, the solid form is the amorphous form or any of crystalline Forms A, B, C, D, or E, or a combination thereof, of the compound of Formula I. In other embodiments, the biocompatible matrix is a gel or a solid. In yet other embodiments, the biocompatible matrix is a polyacrylate, methacyrlate, polyolefin, polyamide, fluoropolymer, cellulose derivative, polyvinyl alcohol, polyvinylpyrrolidone, coated zeolite, or PLGA microsphere or nanosphere. In some embodiments, the biocompatible matrix is biodegradable. The invention also provides embodiments wherein a release of the compound from the biocompatible matrix comprises a slow release profile or a sustained release profile.

In a fifth aspect, a method is provided for treating disease in a subject, comprising the steps of administering an effective amount of the pharmaceutical composition comprising a pharmaceutically acceptable carrier and the compound of Formula I, which comprises a purity of greater than about 90%, to the subject in need thereof.

In a sixth aspect, a method of treating disease in a subject, comprising administering an effective amount of the pharmaceutical composition comprising a compound of Formula I which comprises a purity greater than about 90%, and a pharmaceutically acceptable biocompatible matrix wherein the compound comprises a solid form within the biocompatible matrix to the subject in need thereof.

In some embodiments, the disease is an inflammatory eye disorder which is intraocular, periocular and ocular surface inflammation, Keratoconjunctivitis, keratoconjunctivitis sicca (KCS, aka Dry Eye), KCS in patients with Sjogren's syndrome, allergic conjunctivitis, uveitis, inflammation of the eye, the cornea and periocular tissue from contact lens wear, inflammation of the eye following surgery including LASIK, intraocular inflammation including inflammation of the retina and the anterior and posterior segments of the eye, uveitis, retinitis, edema and retinopathies including diabetic macular edema and diabetic retinopathy, corneal inflammation including rejection of corneal transplants Graves' disease (Basedow disease), or Graves ophthalmopathy. In other embodiments, the disease is an allergic disease which is allergic conjunctivitis, allergic rhinitis, allergic asthma, or allergic contact dermatitis. In yet other embodiments, the disease is psoriasis, irritant contact dermatitis, eczematous dermatitises, seborrhoeic dermatitis, cutaneous manifestations of immunologically-mediated disorders, alopecia, alopecia greata, or scar formation.

In a seventh aspect of the invention, a compound and its pharmaceutically acceptable salts having the following formula is provided:

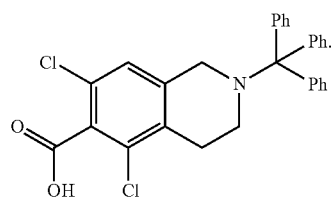 [SMILES: O=C(O)c1c(Cl)cc2c(c1Cl)CCN(C(c1ccccc1)(c1ccccc1)c1ccccc1)C2]

In an eighth aspect of the invention, a compound and its pharmaceutically acceptable salts having the following formula is provided:

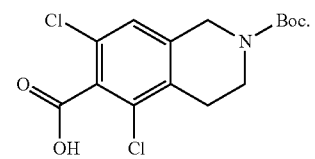

21

In a ninth aspect of the invention, a compound and its pharmaceutically acceptable salts having the following formula is provided:

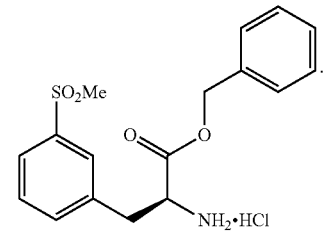

In a tenth aspect of the invention, a compound and its pharmaceutically acceptable salts having the one of the following formulae is provided:

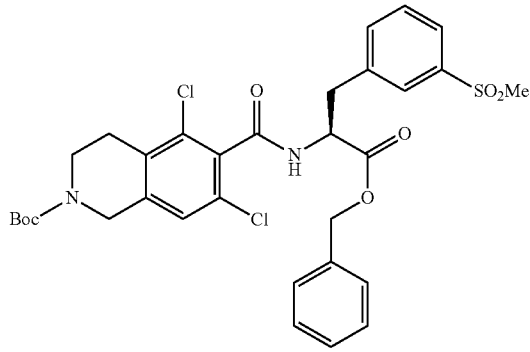

or

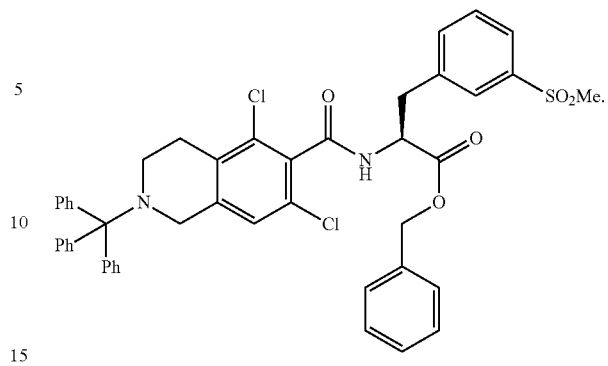

In an eleventh aspect of the invention, a reaction mixture is provided comprising the compound having one of the following formulae:

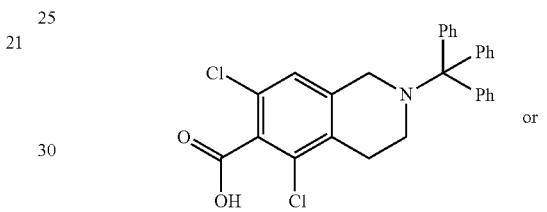

or

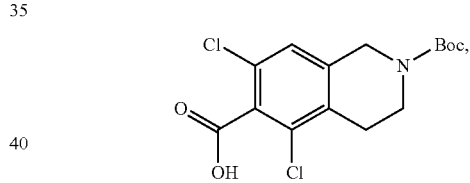

21 a solvent, and a coupling reagent. In some embodiments, the reaction mixture further comprises a base. In other embodiments, the reaction mixture further comprises a compound or its pharmaceutically acceptable salt, having the formula:

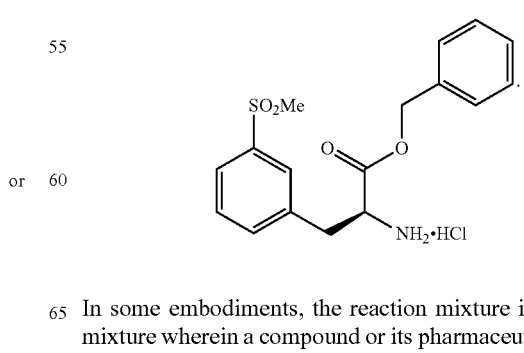

In some embodiments, the reaction mixture is the reaction mixture wherein a compound or its pharmaceutically acceptable salts having one of the following formulae:

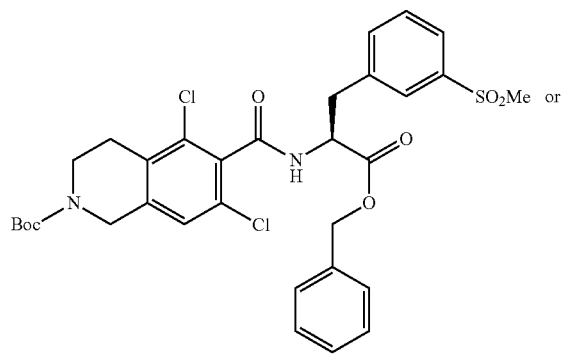

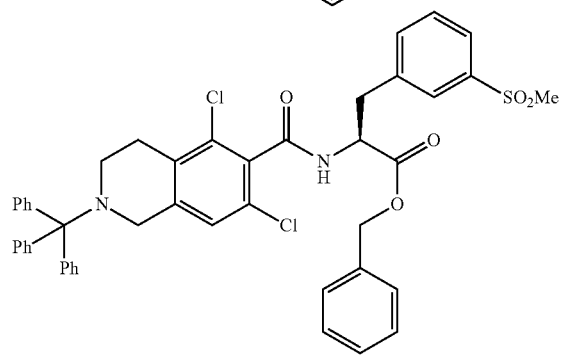

is produced. In some embodiments, the solvent is DMF. In other embodiments, the coupling reagent is 2-(7-Aza-1H-benzotriazole-1-yl)-1,1,3,3-tetramethyluronium hexafluorophosphate (HATU). In yet other embodiments, the base is triethylamine.

In a twelfth aspect of the invention, a compound and its pharmaceutically acceptable salts having the following formula is provided:

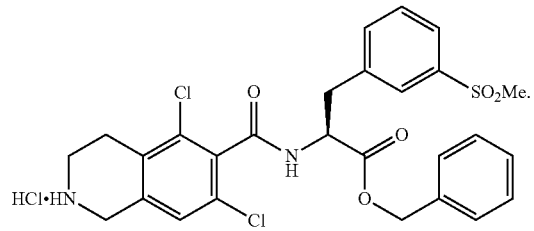

In a thirteenth aspect of the invention, a reaction mixture is provided comprising a compound or its salt having one of the following formulae:

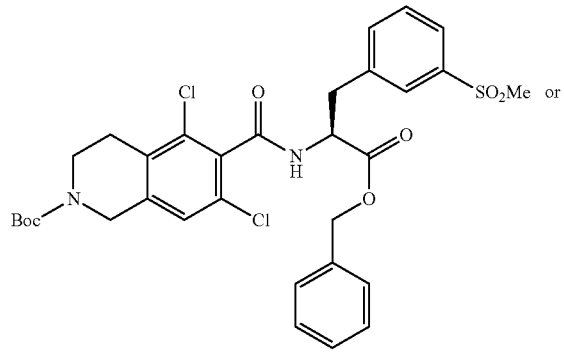

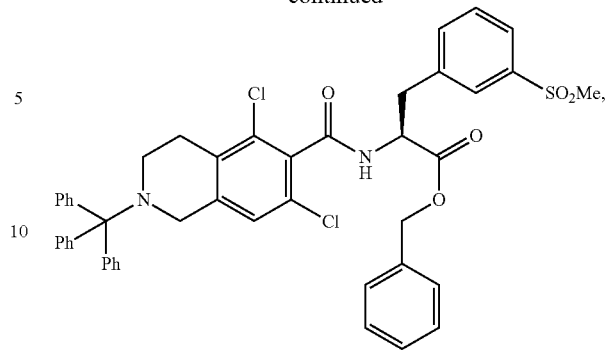

a solvent, and an acid. In some embodiments, the reaction mixture is the reaction mixture wherein a compound of the following formula:

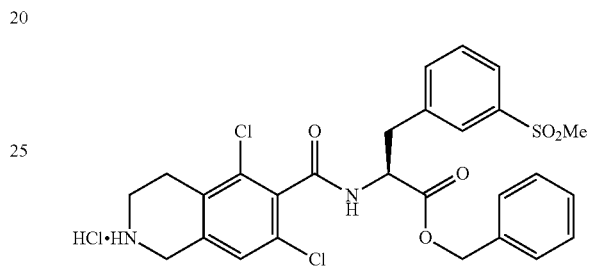

is produced. In some embodiments, the solvent is dioxane. In other embodiments, the acid is HCl.

In a fourteenth aspect of the invention, a compound and its pharmaceutically acceptable salts having the following formula is provided:

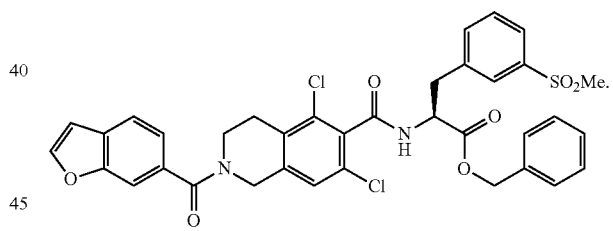

In a fifteenth aspect of the invention, a reaction mixture is provided comprising a compound of the following formula:

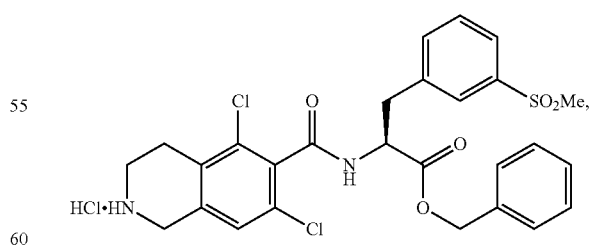

a solvent, and a base. In some embodiments, the reaction mixture further comprises benzofuranoyl chloride. In some embodiments, the solvent is methylene chloride. In yet other embodiments, the base is diisopropylethylamine. In other embodiments, the reaction mixture is the mixture wherein a compound of Formula A is produced.

In a sixteenth aspect of the invention, a method of synthesizing a compound of Formula I is provided:

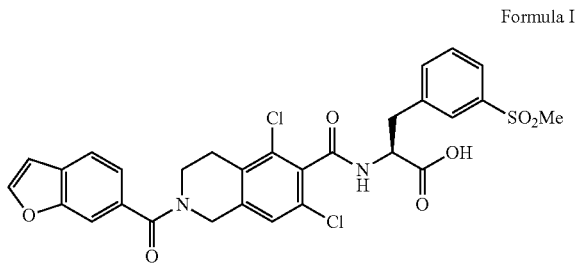 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

Formula I comprising the steps: a) hydrogenolyzing an ester of Formula A:

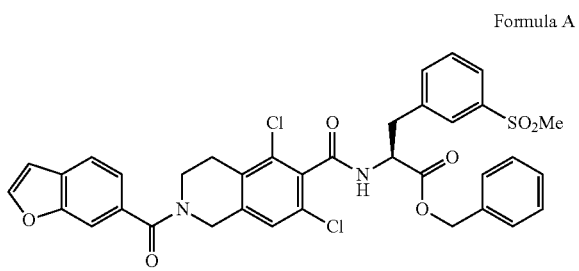 [SMILES: CS(=O)(=O)c1cccc(C[C@H](NC(=O)c2c(Cl)cc3c(c2Cl)CCN(C(=O)c2ccc4ccoc4c2)C3)C(=O)OCc2ccccc2)c1]

Formula A with a palladium catalyst and a source of protons; and b) isolating a compound of Formula I. In some embodiments, the palladium catalyst is 10% palladium on carbon. In other embodiments, the proton source is formic acid.

Incorporation By Reference

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
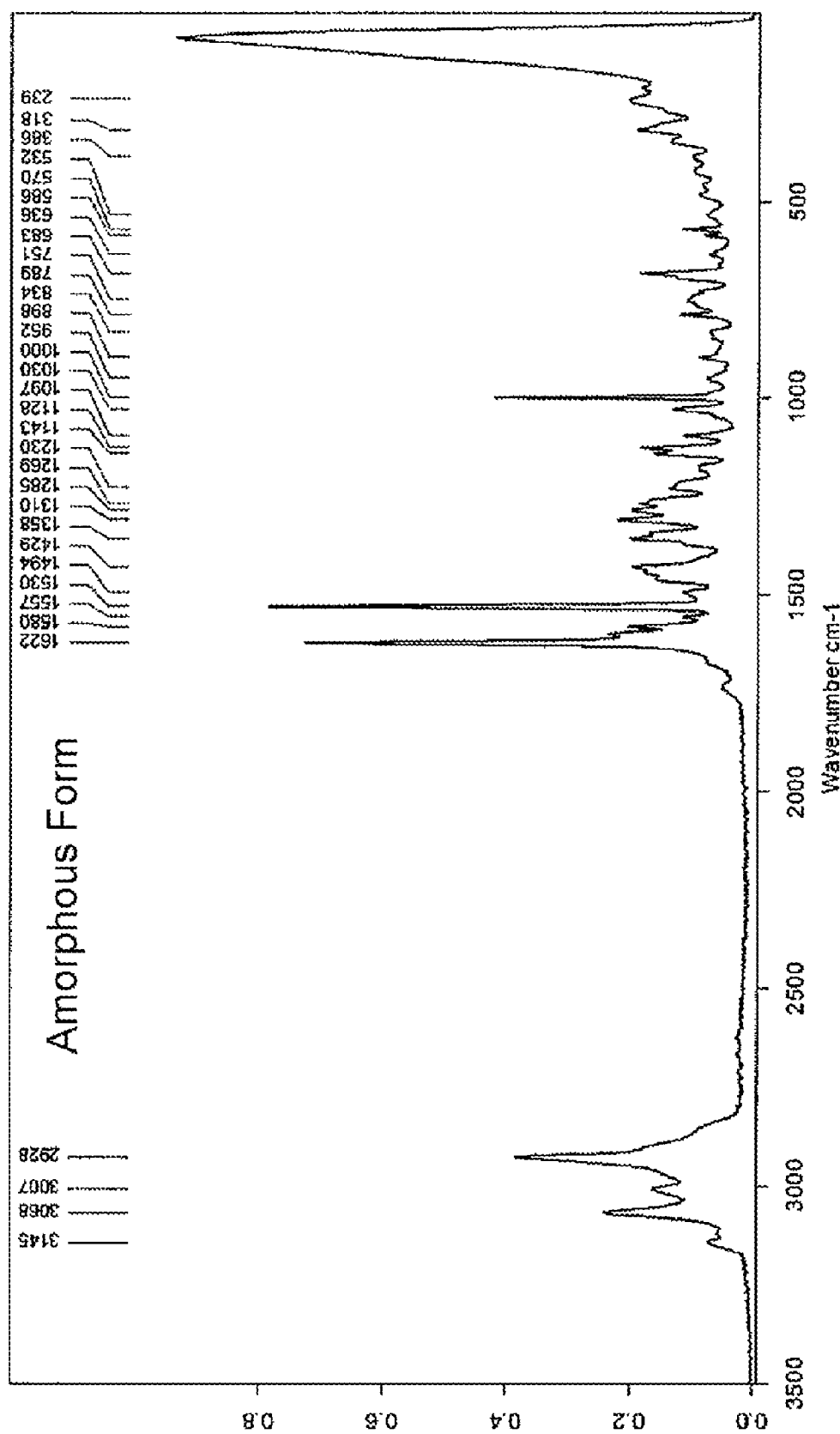
FIG. 1 is a graphical representation of the FT-Raman spectrum of the amorphous form of the compound of Formula I.

While selected embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

As used herein, "agent" or "biologically active agent" refers to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist of LFA-1, for example, is associated with an undesired inflammatory or immune response as manifested in inflammatory or autoimmune disease, respectively.

A "directly competitive inhibitor" or "directly competitive antagonist" refers to a ligand, which includes biomolecules, peptides, and synthetic small organic molecules, which binds directly to the active site of the biological target molecule, and directly prevents a substrate from binding to it. For example, a directly competitive inhibitor of the interaction of LFA-1 and ICAM-1, binds to LFA-1 at the site where ICAM-1 binds, and thus directly prevents ICAM-1 from binding.

"Allosteric inhibitor" as used herein refers to a ligand which includes biomolecules, peptides, and synthetic small organic molecules, that binds to a biological target molecule at a site other than the binding site of the interaction which is being inhibited. The interaction changes the shape of the biological target molecule so as to disrupt the usual complex between the biological target molecule and its substrate. This results in inhibition of the normal activity of such complex formation. For example, an allosteric inhibitor of the interaction of LFA-1 and ICAM-1, binds to LFA-1 at a site other than that where ICAM-1 binds, but it disrupts the binding site of ICAM-1 such that the interaction of LFA-1 and ICAM-1 is reduced.

The term "selective inhibition" or "selectively inhibit" as applied to a biologically active agent refers to the agent's ability to selectively reduce the target signaling activity as compared to off-target signaling activity, via direct or interact interaction with the target.

"Th1" and "Th2" as used herein refer to helper T cells which are found in two distinct cell types, Th1 and Th2, distinguished by the cytokines they produce and respond to and the immune responses they are involved in. Th1 cells produce pro-inflammatory cytokines like IFN-g, TNF-b and IL-2, while Th2 cells produce the cytokines IL-4, IL-5, IL-6 and IL-13.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. The compositions may be administered to a subject to prevent progression of physiological symptoms or to prevent progression of the underlying disorder A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the term "pharmaceutically acceptable salt" refers to those salts which are suitable for pharmaceutical use, preferably for use in the tissues of humans and lower animals without undue irritation, allergic response and the like. Pharmaceutically acceptable salts of amines, carboxylic acids, and other types of compounds, are well known in the art. For example, S. M. Berge, et al., describe pharmaceutically acceptable salts in detail in J Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzoate, bisulfate, borate, butyrate, camphorate, camphorsulfonate, citrate, cyclopentanepropionate, digluconate, dodecylsulfate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, nicotinate, nitrate, oleate, oxalate, palmitate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed by direct reaction with the drug carboxylic acid or by using counterions such as halide, hydroxide, carboxylate, sulfate, phosphate, nitrate, sulfonate and aryl sulfonate.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, i.e. an ester, but is converted in vivo to an active compound, for example, by hydrolysis to the free carboxylic acid. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

"Localized treatment" as used herein refers to treatment of an immune or inflammatory disorder wherein the drug is delivered locally and is not delivered via systemic delivery. This may include many different local areas or a few different local areas within, for example, the gastrointestinal tract to which drug is delivered to the gastrointestinal mucosa from within the lumen of the GI tract. Another example is treatment of skin, wherein the drug may be applied to many different locations or a few different locations on the skin, and wherein drug is delivered to tissues within and adjacent to the skin by absorption through the skin. Alternatively, drug may be delivered via suppository to anal mucosa and absorbed through the epithelial surfaces to tissue within and adjacent to the mucosa of the lower GI tract.

"Local delivery" as used herein refers to drug compound being carried to the site of therapeutic use. It includes, for example, applying a formulation directly to area of skin that is being treated, spraying a formulation to an area of skin being treated, spraying or inhaling a formulation intranasally to administer drug to the nasal passages, or instilling eye drops to an eye to treat the eye. In the present invention, "local delivery" also encompasses orally or nasally administering a formulation which is carried to the gastrointestinal tract, wherein the drug is brought in contact with the gastrointestinal mucosa, where the drug is absorbed into the surrounding tissue and exerts a therapeutic effect, without being directly delivered to that site from the blood circulatory system.

"Local tissue concentration" as used herein, refers to the concentration of LFA-1 antagonist within the tissue area to which the LFA-1 antagonist has been delivered and absorbed.

"Subject" refers to an animal, such as a mammal, for example a human. The methods described herein can be useful in both human therapeutics and veterinary applications. In some embodiments, the patient is a mammal, and in some embodiments, the patient is human.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

Unless otherwise stated, structures depicted herein are also meant to include compounds which differ only in the presence of one or more isotopically enriched atoms. For example, compounds having structures wherein a hydrogen is replaced by a deuterium or tritium, or a carbon is replaced by $^{13}C$- or $^{14}C$-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present invention, whether radioactive or not, are encompassed within the scope of the present invention.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

Abbreviations used herein have their conventional meaning within the chemical and biological arts.

Human blood contains white blood cells (leukocytes) which are further classified as neutrophils, lymphocytes (with B- and T-subtypes), monocytes, eosinophils, and basophils. Several of these classes of leukocytes, neutrophils, eosinophils, basophils and lymphocytes, are involved in inflammatory disorders. LFA-1, also known as CD11a/CD18 or the integrin αLβ2, is one of a group of leukointegrins which are expressed on most leukocytes, and is considered to be the lymphoid integrin which interacts with a number of ICAMs as ligands. The expression of LFA-1 in humans is almost exclusively limited to cells of the immune system, particularly the extracellular surface of leukocytes, including lymphocytes. As such, LFA-1 regulates the adhesion, migration, proliferation, and inflammatory response of lymphocytes, particularly T-lymphocytes (T-cells), in normal immune function as well as in a number of inflammatory and autoimmune disease settings. Disrupting LFA-1/ICAM interactions, and thus the immune/inflammatory response, provides for reduction of inflammation.

For example, ICAM-1 (CD54) is a member of the ICAM family of adhesion receptors (ICAM-1, ICAM-2, ICAM-3, ICAM-4) in the immunoglobulin protein super family, and is expressed on activated leukocytes, dermal fibroblasts, and endothelial cells. It is normally expressed on the endothelial cells lining the vasculature, and is upregulated upon exposure to cytokines or other inflammatory signals such as IL-1, LPS and TNF during immune/inflammatory initiation.

Functional studies of the binding of LFA-1 and ICAM-1 have shown that this interaction is crucial in processes which contribute to disease mechanism including: leukocyte and lymphocyte adhesion to vascular endothelial cells; their extravasation from the vasculature at a site of inflammation; homotypic interactions between lymphocytes, as well as interactions between T-cells and dendritic cells in inflamed tissue; the formation of the immunologic synapse and in the transmission of costimulatory signals in concert with MHC/T-cell Receptor crucial for lymphocyte proliferation and cytokine release. Consequently, antagonists of LFA-1/ICAM binding may provide blockade of the adhesive, migratory, proliferative, and inflammatory signaling components of lymphocyte mediated inflammation. As such, they may provide more comprehensive inhibition of T-cell mediated diseases than is currently offered by steroid or calcineurin antagonist (i.e., cyclosporine) immunomodulators. Without being bound by mechanistic theory, antagonists of LFA-1 may show anti-inflammatory and immunosuppressive effects on lymphocytes in vitro and in T-cell mediated diseases in vivo, particularly when administered systemically to treat inflammatory diseases throughout the body, or when administered locally to treat local manifestations of inflammatory diseases.

The compound of Formula I:

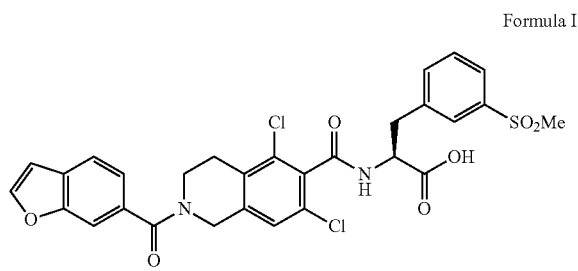 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

Formula I has been found to be an effective inhibitor of LFA-1 interactions with ICAM-1. It is a member of a class of directly competitive inhibitors of LFA-1, binding to ICAM's binding site on LFA-1 directly, and thus excludes ICAM binding. Directly competitive inhibitors of LFA-1 may offer the potential for more effective modulation of the inflammatory and/or immunologic response than allosteric inhibitors provide, precisely because these inhibitors occlude the binding site more effectively.

Additionally, the compound of Formula I has a rapid systemic clearance rate. LFA-1 interaction with ICAMs exert various systemic effects throughout the body. Treatment of a disorder using an LFA-1 antagonist may result in unwanted effects due to LFA-1 antagonist activity in unwanted locations, for example, other than at the site of administration. The present invention utilizes the compound of Formula I which is cleared quickly from systemic circulation. The compound of Formula I may have minimal systemic LFA-1 antagonist activity. In some embodiments, the compound of Formula I may have undetectable systemic LFA-1 antagonist activity. Therefore, the compound of Formula I may be particularly well suited for treatment of a disorder mediated by the interaction between LFA-1 and ICAM-1, where localized treatment is desirable and/or where such localized treatment is administered for many months or years.

The systemic clearance rate can be calculated by various means known in the art. For example, the clearance rate for a drug may be calculated from an analysis of the drug concentration time profile for the drug concentration time profile for the rate of disappearance of a drug from the plasma following administration of the formulation, for example after a single intravenous injection. One of skill in the art could use a variety of methods to calculate and determine systemic clearance rates. For example, the rate of disappearance may be measured by analysis of the absorption, distribution, metabolism and excretion of a radiolabelled form of a drug or other means of measuring the level of drug in plasma, such as gas chromatography (Sapirstein et al., 1955, Am. Jour. Physiol., Vol. 181, pp. 330; U.S. Pat. No. 4,908,202), liquid chromatography-mass spectrometry methods (LCMS) or HPLC methods. As another example, the clearance rate may be calculated by introducing the formulation to the subject by continuous intravenous infusion until an equilibrium is reached at which the plasma level of the substance (as determined by analysis of plasma samples) is steady, at which point the infusion rate is equal to the rate of clearance from plasma (Earle et al., 1946, Proc. Soc. Exp. Biol. Med., Vol. 62, pp. 262 ff.)

Rapid systemic clearance may be through clearance or metabolism in the liver, kidney or other organs. Where clearance occurs in a particular organ, the clearance rate is related to the blood flow to that particular organ. By knowing the mechanism in which a compound is cleared for a particular species, the clearance rate for other animals may be calculated by allometric scaling. The compound of the present invention is known to be cleared through the liver in rats. Based on the rate of clearance calculated in rat, the clearance of the compound may be scaled for various animals based on the known blood flow in rats compared to other animals (see Davies and Morris, "Physiological Parameters in Laboratory Animals and Humans" *Pharmaceutical Research* (1993) 10:1093-5). For example, 100% of rat hepatic blood flow would be approximately 55 mL/min/kg while 100% of human hepatic blood flow would be approximately 20 mL/min/kg. The compound of Formula I has a clearance rate in rats of greater than 100 mL/min/kg.

In order to develop clinically useful therapeutics, drug candidates need to be chemically pure enough to administer to a subject and of an acceptable physical form in order to be formulated in pharmaceutically acceptable dosage forms. One advantageous route to obtain higher purity, reproducibility of physical form, and stability is to identify one or more useful crystalline forms. The capacity to exist in different crystalline forms is known as polymorphism and is known to occur in many organic molecules. These different crystalline forms are known as "polymorphic modifications" or "polymorphs." While polymorphic modifications have the same chemical composition, they differ in packing, geometric arrangement, and other descriptive properties of the crystalline solid state. As such, these modifications may have different solid-state physical properties to affect, for example, the solubility, dissolution rate, bioavailability, chemical and physical stability, flowability, fractability, and compressibility of the compound as well as the safety and efficacy of drug products based on the compound. In the process of preparing a polymorph, further purification, in terms of gross physical purity or optical purity, may be accomplished as well.

A number of different forms, including crystalline forms, of the compound of Formula I have been discovered. While crystallization is often performed on organic compounds, it is not predictable in advance as to which conditions will provide suitable conditions to lead to formation of a particular crystalline form. Further, it is not predictable as to which particular crystalline form will provide the necessary mixture of physical properties, nonlimiting examples of which are described above, to yield a desirable drug dosage form, once formulated.

Experimental Instrumentation and Conditions

Fourier Transform-Raman Spectroscopy (FT-Raman) was performed with a Bruker RFS100 instrument, using Nd:YAG 1064 nm excitation, 300 mW laser power, Ge detector, using 64 scans over the range of 25-3500 $cm^{-1}$, and with 2 $cm^{-1}$ resolution.

Power X-ray Diffraction (PXDR) was performed with a Bruker D8 Advance X-ray diffractometer with CuKα-radiation. The standard measuring conditions were: tube power 35 kV/45 mA; step size 0.017° (2θ); step time 105±5 sec; scanning range 2°-50° (2θ); divergence slit equal to variable V12; the samples were rotated; a Vantec1 detector was used; the opening angle 3°; channel number 360±10; the y-axis shows the value intensity/number of active detector channels/sec; silicon single crystal sample holders; and the sample dimensions depth/diameter was 0.1 mm/~12 mm.

Thermogravimetric-Fourier transform Infrared Spectroscopy (TG-FTIR) was performed with a Netzsch Thermo-Microbalance TG 209 coupled with a Bruker FT-IR Spectrometer Vector 22, using an aluminum crucible (open or with a microhole), under a nitrogen atmosphere, and at a heating rate of 10° C./min over the range of 25° C. to 350° C.

Differential Scanning calorimetry (DSC) was performed with a Perkin Elmer Differential Scanning calorimeter 7, using closed gold crucibles, a heating rate of 10° C. $min^{-1}$ or 20° C. $min^{-1}$ over a range from −50° C. to 250° C.

Dynamic Vapor Sorption (DVS) analysis was performed with a Surface Measurement Systems DVS-1 water vapor sorption analyzer. The experiments were run by placing the sample on a quartz holder on top of a microbalance, and allowing the sample to equilibrate at 50% relative humidity (r.h.) before starting the pre-defined humidity program. The program proceeded in the following steps: 1 hour at 50% r.h.; 50% to 0% r.h. at a rate of 5% r.h. change per hour; 5 hours at 0% r.h; 0% r.h to 96% r.h. at 5% r.h change per hour; 5 hours at 95% r.h.; 95% r.h. to 50% r.h. at a rate of 5% r.h. change per hour, and followed by one hour at 50% r.h.

Amorphous Form

Figure 2:
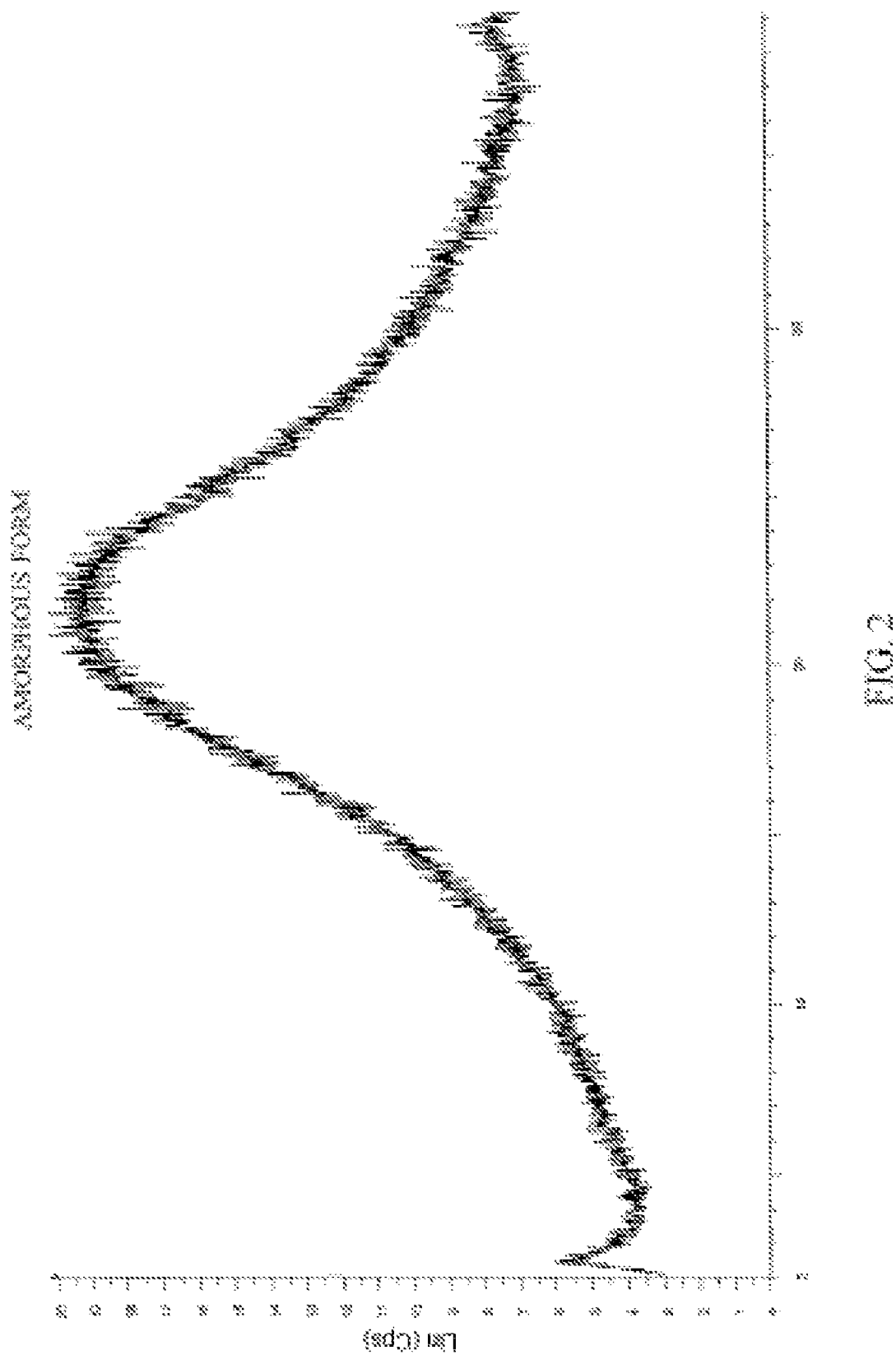
FIG. 2 is a graphical representation of the PXDR pattern of the amorphous form of the compound of Formula I.
Figure 3:
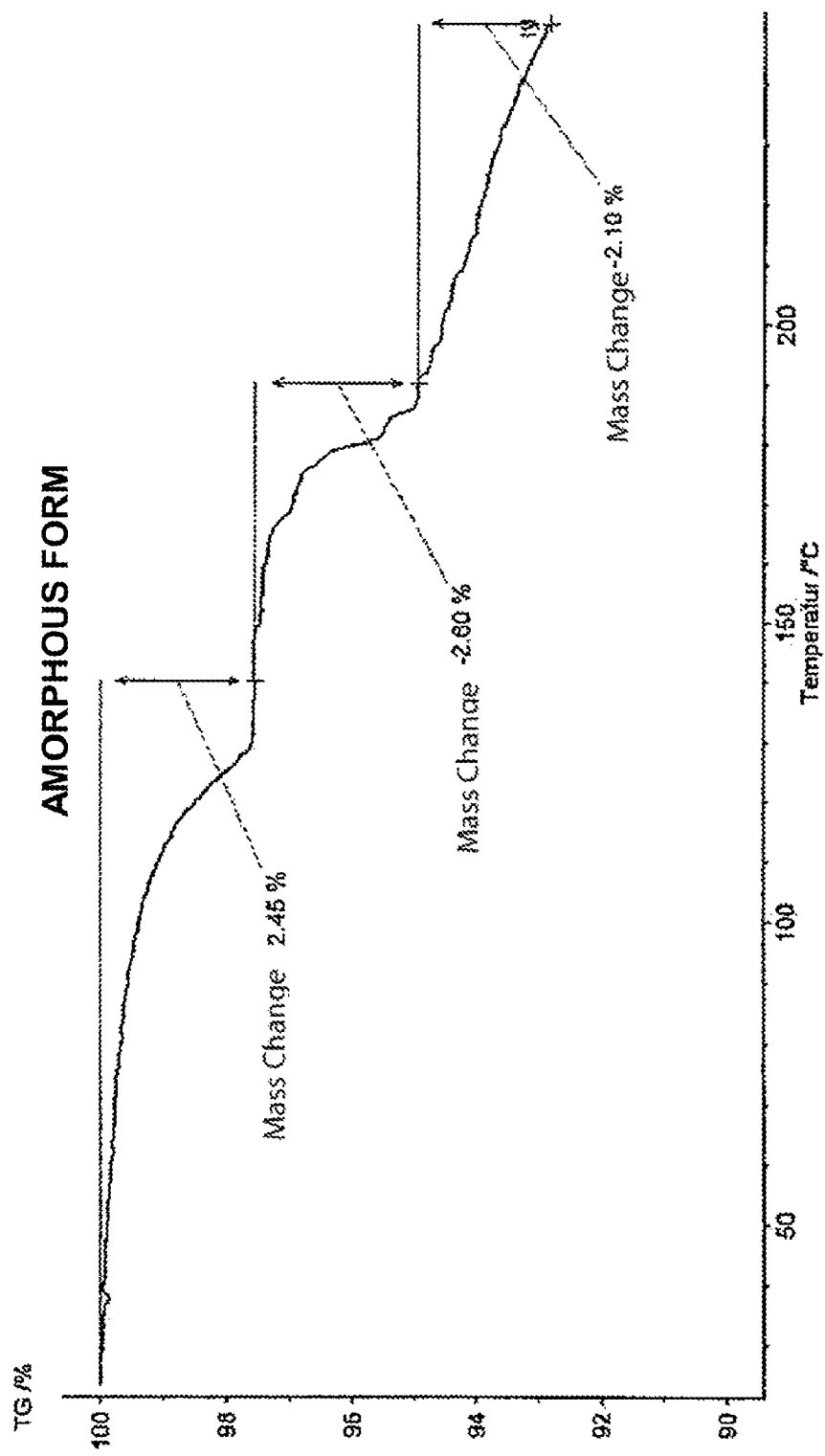
FIG. 3 is a graphical representation of the TG-FTIR chromatogram of the amorphous form of the compound of Formula I.

The reaction product, resulting from synthesis of the compound of Formula I, using the synthetic methods described in U.S. Pat. No. 7,314,938, was isolated by concentration from an ethyl acetate extract. It may be further purified to remove calcium impurities or convert the calcium salt to the free acid. The free acid thus obtained has a FT-Raman chromatogram with broad peaks (FIG. 1), and an X-ray powder diffraction chromatogram with no peaks (FIG. 2), thus revealing that the reaction product is an amorphous form. The amorphous form has a thermogravimetric/Fourier transform infrared chromatogram which demonstrates that the amorphous form loses about 5.1% of its mass as temperature is raised to just below 190° C., which is attributed to loss of ethyl acetate. As the temperature is raised above 190° C., the amorphous form begins to decompose, as shown in FIG. 3. The purity of the amorphous solid as determined by high pressure liquid chromatography is 96.6% of the total area under the curve as observed at 220 nm, and 97.1% of the total area under the curve at 254.4 nm (Table 1).

Crystallization in selected solvents and under selected conditions resulted in the discovery of several crystalline forms with distinct physical behavior.

Crystalline Form A

The amorphous form (free acid, 129 mg) was suspended in 0.2 ml acetonitrile which had been previously dried over molecular sieves and let stand for 3 days. Another addition of 0.5 ml dry acetonitrile was made and the suspension was exposed to ultrasonic radiation. The suspension was then stirred for one day, filtered and rinsed with 1.5 ml dry acetonitrile to produce crystalline Form A. The crystalline Form A was also produced by slurrying amorphous form in methyl ethyl ketone (MEK). As a third alternative, slurrying the amorphous form in water will also provide crystalline Form A.

The crystalline Form A was characterized by several analytical techniques. High pressure liquid chromatography was performed on an Agilent HP1100 instrument, with analysis by Agilent Chemstation software, using a YMC ODS AQ, 3 μm, 350×4.6 mm ID column, and 0.1% o-phosphoric acid in water as Eluent A and 0.1% o-phosphoric acid in acetonitrile as Eluent B. The chromatography was performed with a flow rate of 1 ml/min, with a gradient program consisting of 35% B at T=0, to 75% B at 25 min, to 90% B at 30 min, return to 35% B at 30.1 min, and continue to 35 min at 35% B. Alternatively, a Zorbax SB C18 50×4.6 mm ID column was used, Eluent C was 0.1% TFA in water and Eluent D was 0.1% TFA in acetonitrile, with a ratio of C:D equal to 2:8, with a flow rate of 1 ml/min. The column temperature was controlled at 40° C. Detection was performed at either 220 nm or 254 nm.

Form A has a high pressure liquid chromatogram comprising a total area under the curve of 98.0% for Form A, as observed at 220 nm, and a total area under the curve of 98.5% for Form A when observed at 254 nm (Table 1 μl). The method of producing crystalline Form A removes more impurities that were introduced to the compound of Formula I throughout the synthetic route, which may be due to one or more of by-products of the synthesis, impurities introduced with reagents used in the synthesis, trapped organic solvents used in prior reaction steps, such as methylene chloride, and contaminants due to degradation of an intermediate product of the synthetic sequence. Removal of methylene chloride is particularly important in preparation of formulations for ocular application. Additionally, the level of methylene chloride must be lower than that permitted by the FDA guidelines. Impurities which must be removed from the product of the synthetic process include residual palladium catalyst and residual organic solvents including MEK, ethyl acetate, THF, and toluene. Other impurities which are intermediates and/or starting materials of the synthesis include compounds 12, 18, and 19 (shown in Scheme 5), which may be designated byproducts of the synthesis.

TABLE 1A

HPLC Purity of Amorphous Form and Crystalline Form A.

| Form of the compound of Formula I | Area % (220 nm) | Area % (254 nm) |
|---|---|---|
| Amorphous Form | 96.6 | 97.1 |
| Crystalline Form A | 98.0 | 98.5 |

Form A was also analyzed by chiral high pressure liquid chromatography to determine the chiral purity of the S enantiomer. The mobile phase was 350 ml acetonitrile mixed with 650 ml of water which had previously been adjusted to pH 3.0 with formic acid. The chromatography was isocratic, using a Chiralcel OJ-RH column, 150×4.6 mm, temperature controlled to 40° C., and detection was performed at 260 nm.

TABLE 1B

Stereochemical Purity of Crystalline Form A.

| Form of the compound of Formula I | Stereochemical Purity |
|---|---|
| Crystalline Form A | 98.5% S enantiomer |

Crystalline Form A was analyzed by $^1$H—Nuclear Magnetic Resonance spectroscopy. The resultant spectrum showed a number of the peaks which were narrowed in comparison to that of the amorphous form, and removal of trapped ethyl acetate was accomplished.

Figure 4:
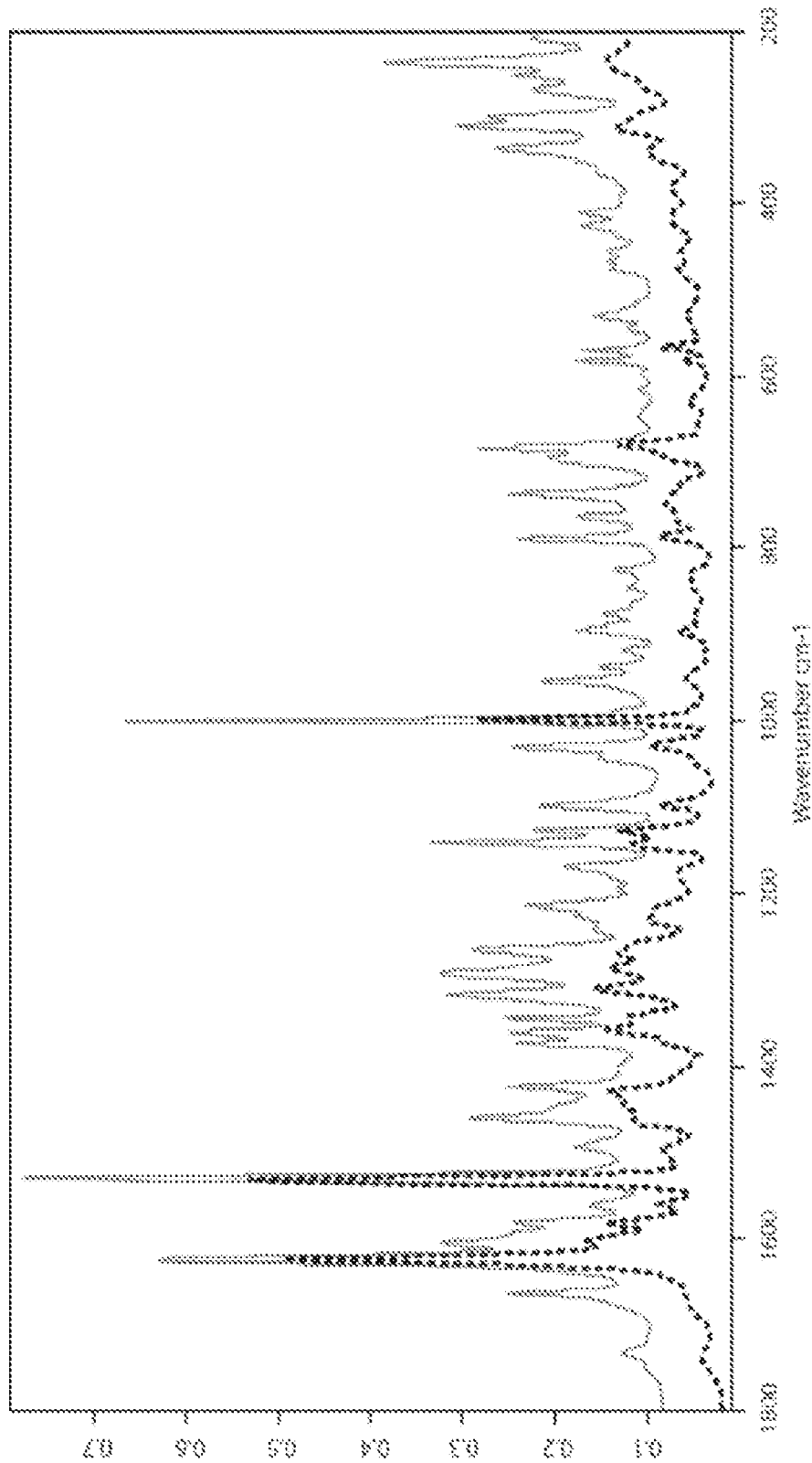
FIG. 4 is a graphical representation of the FT-Raman spectrum of the amorphous form of the compound of Formula I overlaid for comparison with the FT-Raman spectrum of crystalline Form A.
Figure 5:
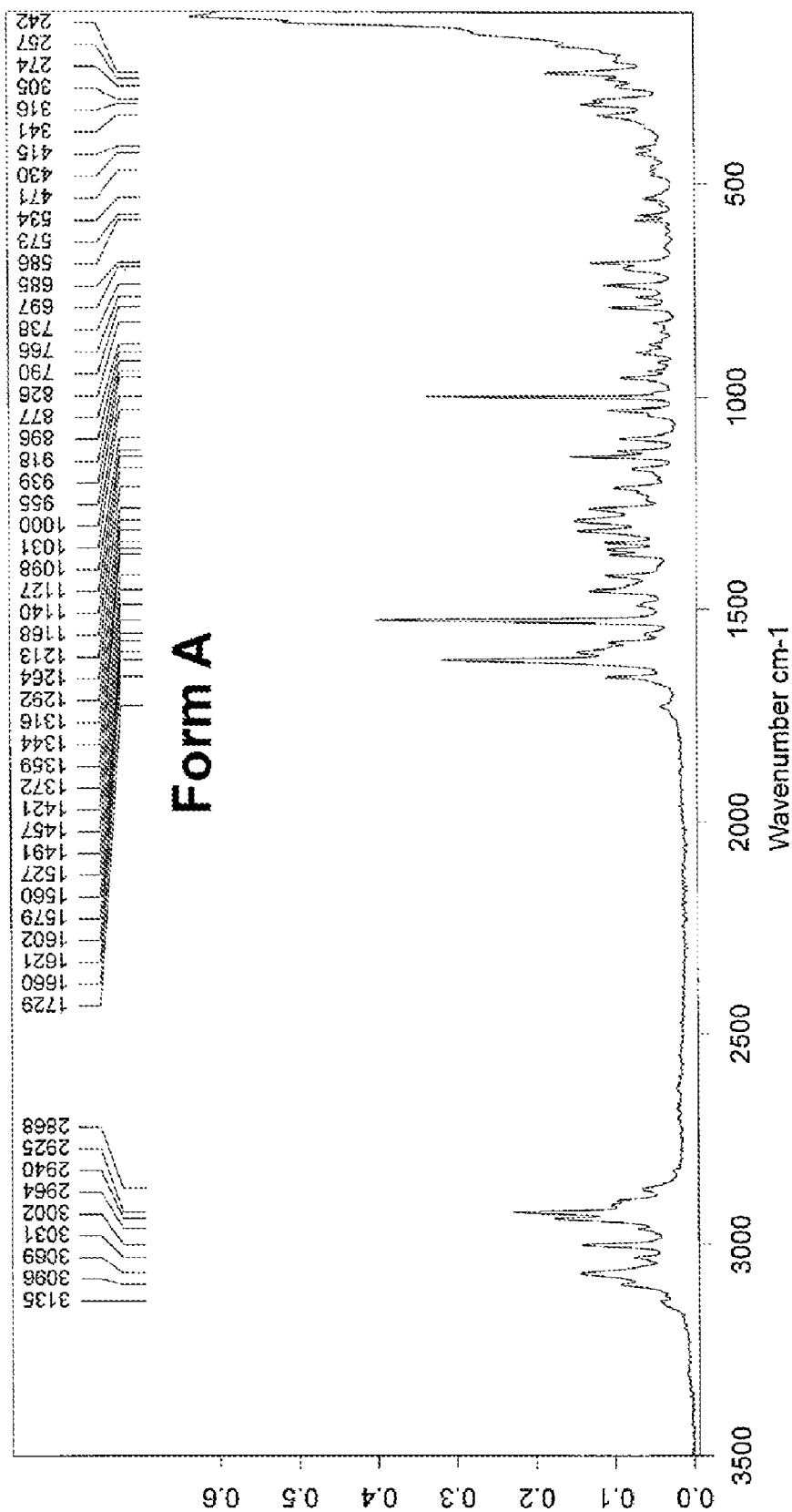
FIG. 5 is a graphical representation of the FT-Raman spectrum of crystalline Form A.
Figure 6:
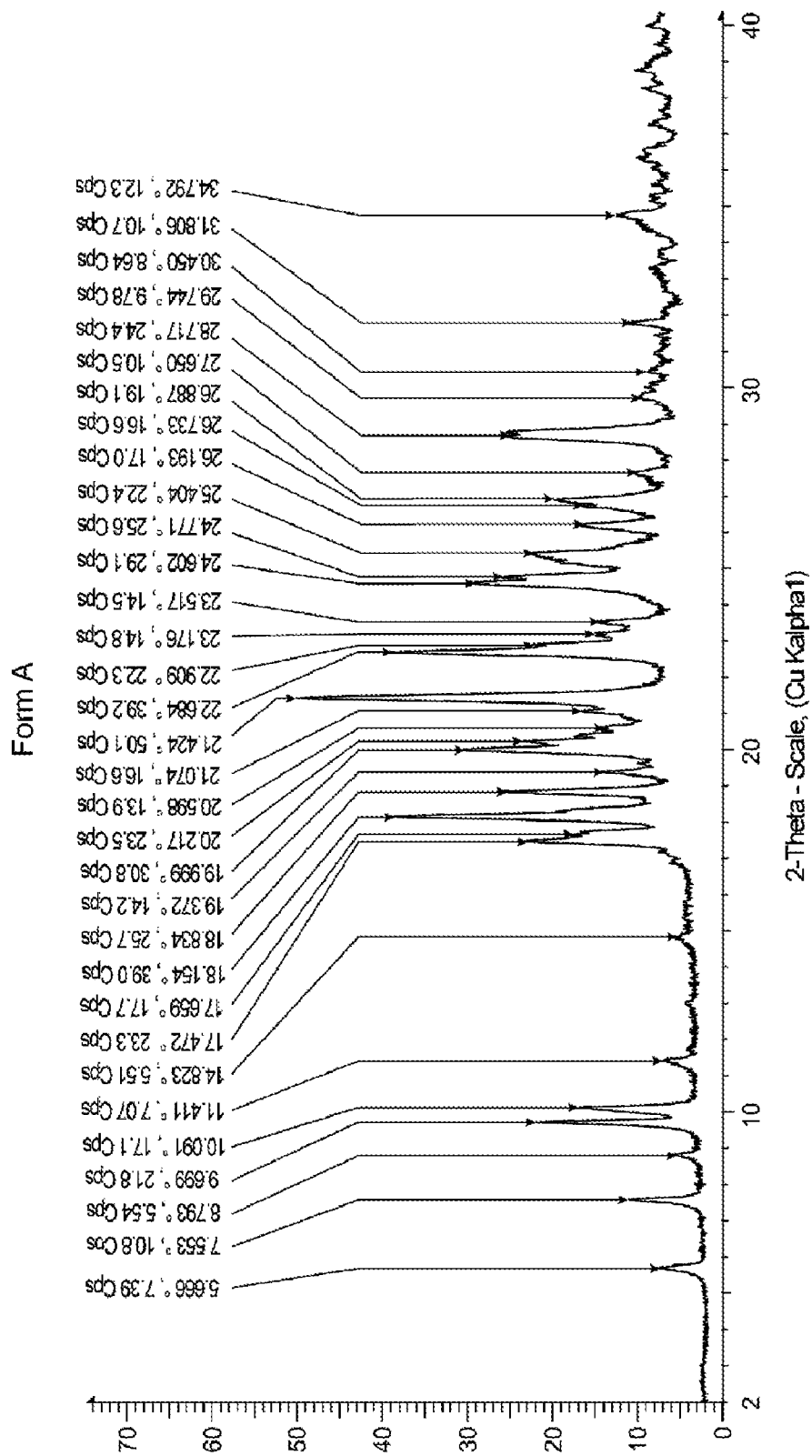
FIG. 6 is a graphical representation of the PXDR pattern of crystalline Form A.

Crystalline Form A, when analyzed by Raman spectroscopy, has a chromatogram which has narrowed peaks relative to the above amorphous form, as is shown in the overlaid spectra of both forms in FIG. 4. Several peaks were shifted relative to the amorphous form. The Raman chromatogram of crystalline Form A is shown in FIG. 5. Crystalline Form A comprises a powder x-ray diffraction pattern as shown in FIG. 6. The peak assignments corresponding to the diffraction pattern for crystalline Form A and their relative intensities are listed in Table 2.

TABLE 2

Peak Assignments and Intensities of the PXDR Pattern for Crystalline Form A.

| Angle 2-Theta ° | d value Angstrom | Intensity Cps | Intensity % |
|---|---|---|---|
| 5.67 | 15.6 | 7 | 15 |
| 7.55 | 11.7 | 11 | 22 |
| 8.79 | 10.0 | 6 | 11 |
| 9.70 | 9.1 | 22 | 44 |
| 10.09 | 8.8 | 17 | 34 |
| 11.41 | 7.7 | 7 | 14 |
| 14.82 | 6.0 | 6 | 11 |
| 17.47 | 5.07 | 23 | 47 |
| 17.66 | 5.02 | 18 | 36 |
| 18.15 | 4.88 | 39 | 78 |
| 18.83 | 4.71 | 26 | 51 |
| 19.37 | 4.58 | 14 | 28 |
| 20.00 | 4.44 | 31 | 62 |
| 20.22 | 4.39 | 24 | 47 |
| 20.60 | 4.31 | 14 | 28 |
| 21.07 | 4.21 | 17 | 33 |
| 21.42 | 4.14 | 50 | 100 |
| 22.68 | 3.92 | 39 | 78 |
| 22.91 | 3.88 | 22 | 45 |
| 23.18 | 3.84 | 15 | 30 |
| 23.52 | 3.78 | 15 | 29 |
| 24.60 | 3.62 | 29 | 58 |
| 24.77 | 3.59 | 26 | 51 |
| 25.40 | 3.50 | 22 | 45 |
| 26.19 | 3.40 | 17 | 34 |
| 26.73 | 3.33 | 17 | 33 |
| 26.89 | 3.31 | 19 | 38 |
| 27.65 | 3.22 | 11 | 21 |
| 28.72 | 3.11 | 24 | 49 |
| 29.74 | 3.00 | 10 | 20 |
| 30.45 | 2.93 | 9 | 17 |
| 31.81 | 2.81 | 11 | 21 |
| 34.79 | 2.58 | 12 | 25 |

Figure 7:
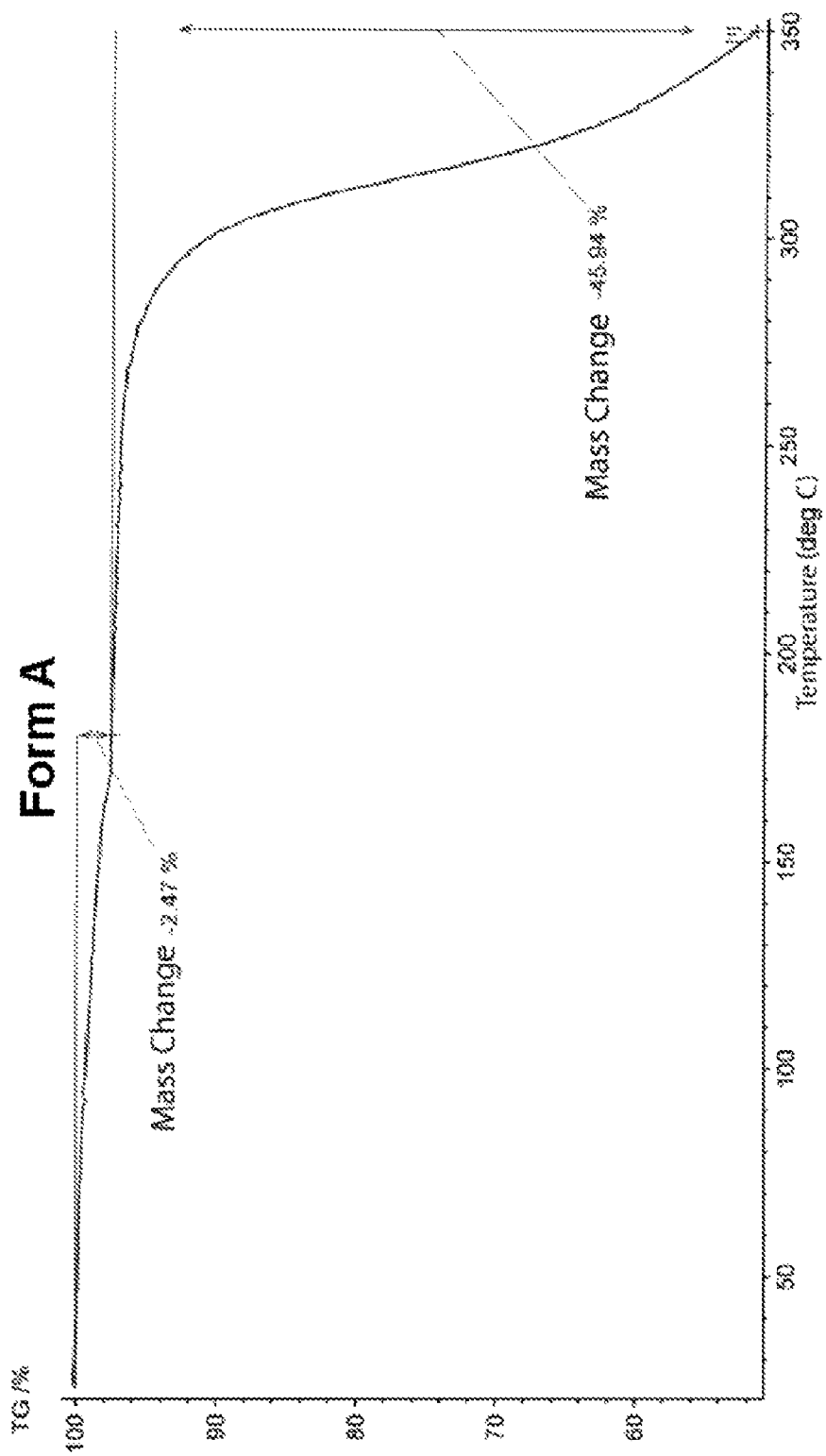
FIG. 7 is a graphical representation of the TG-FTIR chromatogram of crystalline Form A.

Thermogravimetric analysis graph of crystalline Form A is shown in FIG. 7. A mass loss of about 2.5% between room temperature and 180° C. is observed. From the coupled FTIR analysis carried out simultaneously, the loss is attributable to loss of water. Without being bound by theory, the results suggest that Form A is a hydrate, with a theoretical mass loss of 2.8%, and that the water of hydration may be derived from the amorphous form or may have been introduced adventitiously in the crystallization experiment.

Figure 8:
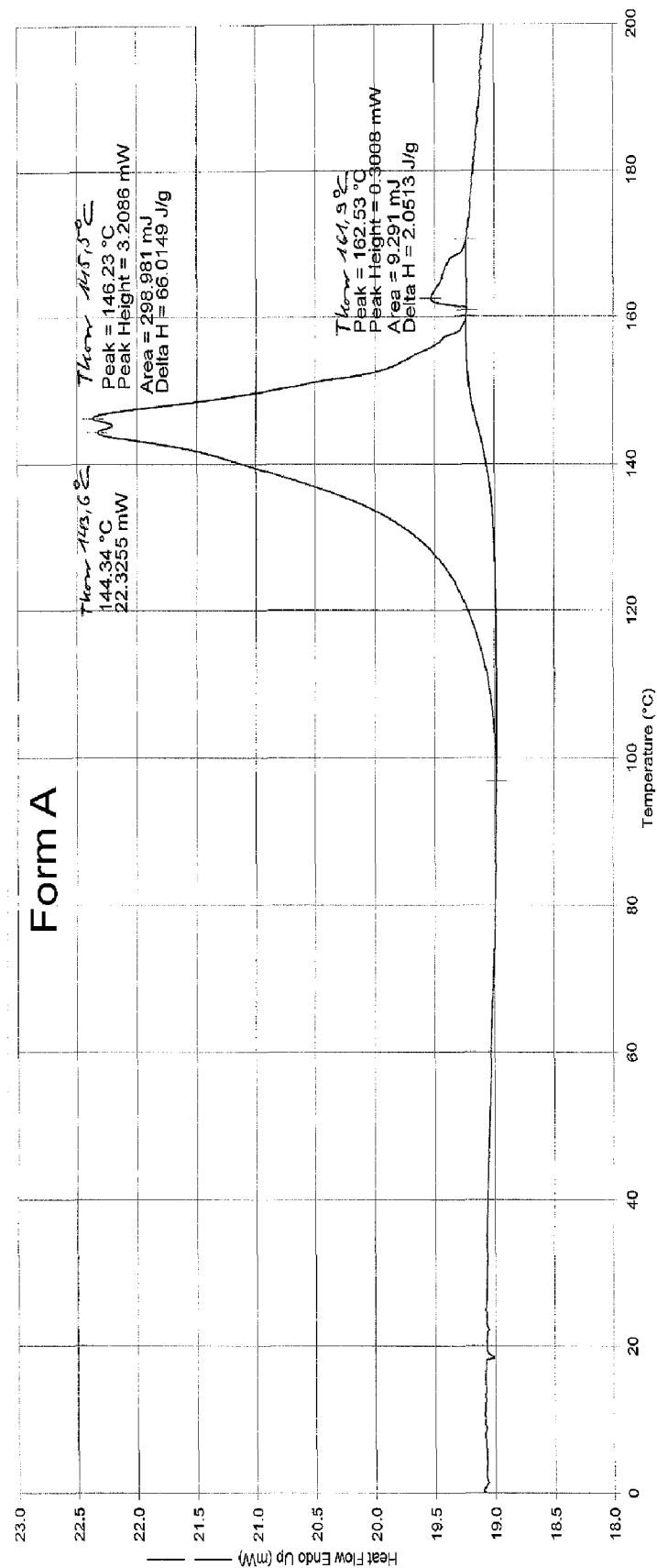
FIG. 8 is a graphical representation of the DSC chromatogram of crystalline Form A.
Figure 9:
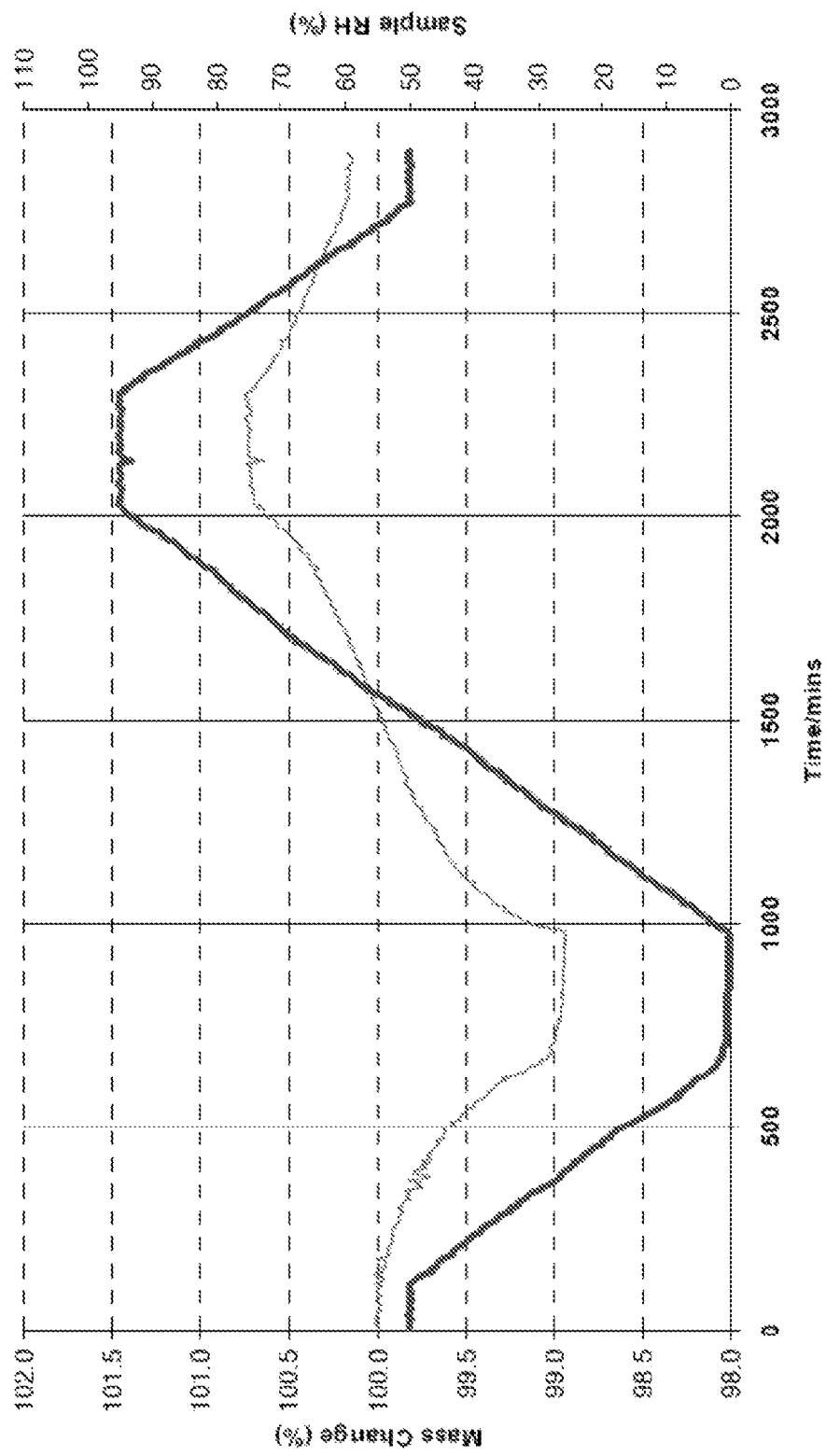
FIG. 9 is a graphical representation of the DVS chromatogram of crystalline Form A with time as the X axis.
Figure 10:
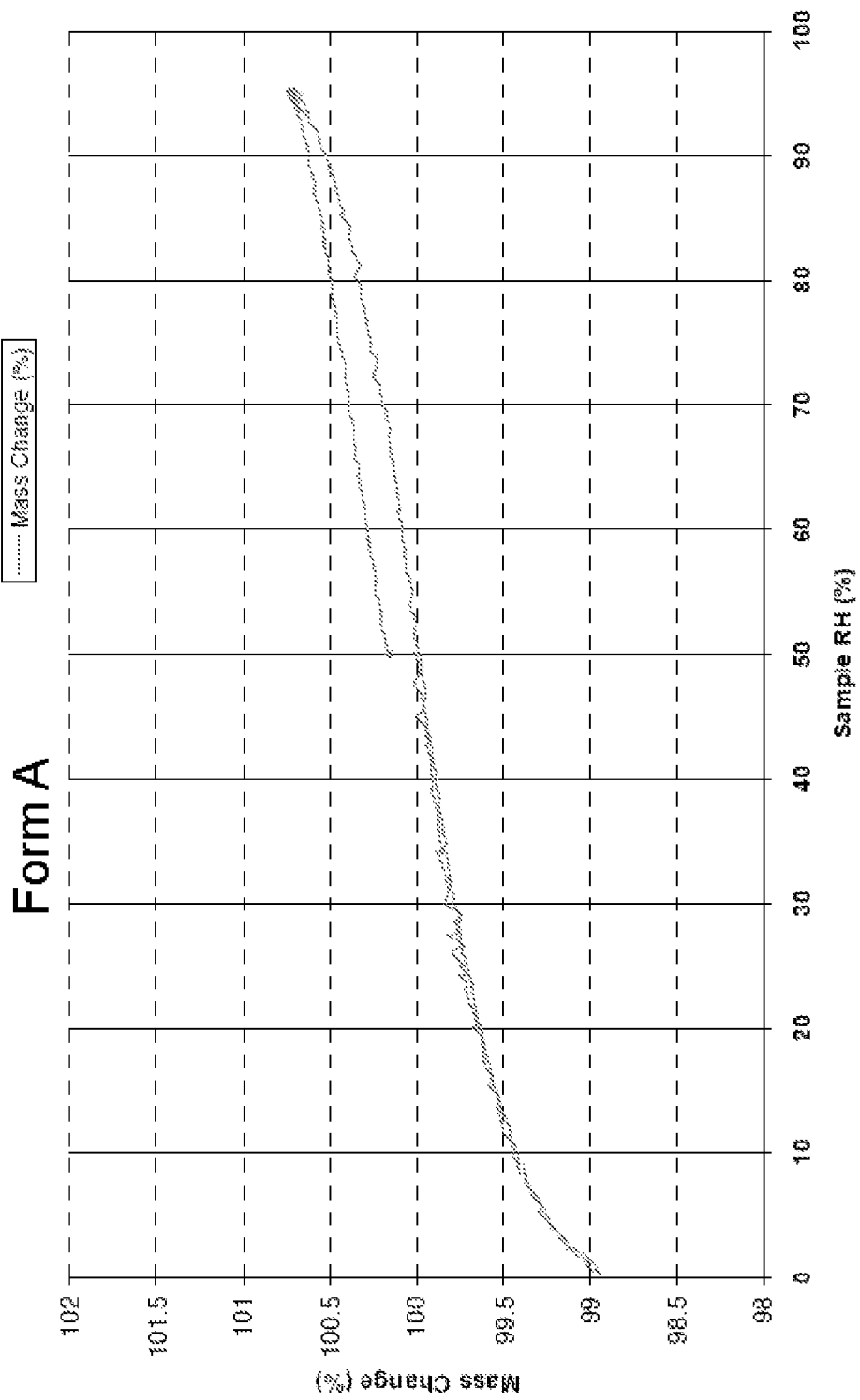
FIG. 10 is a graphical representation of the DVS chromatogram of crystalline Form A with relative humidity as the X axis.
Figure 11:
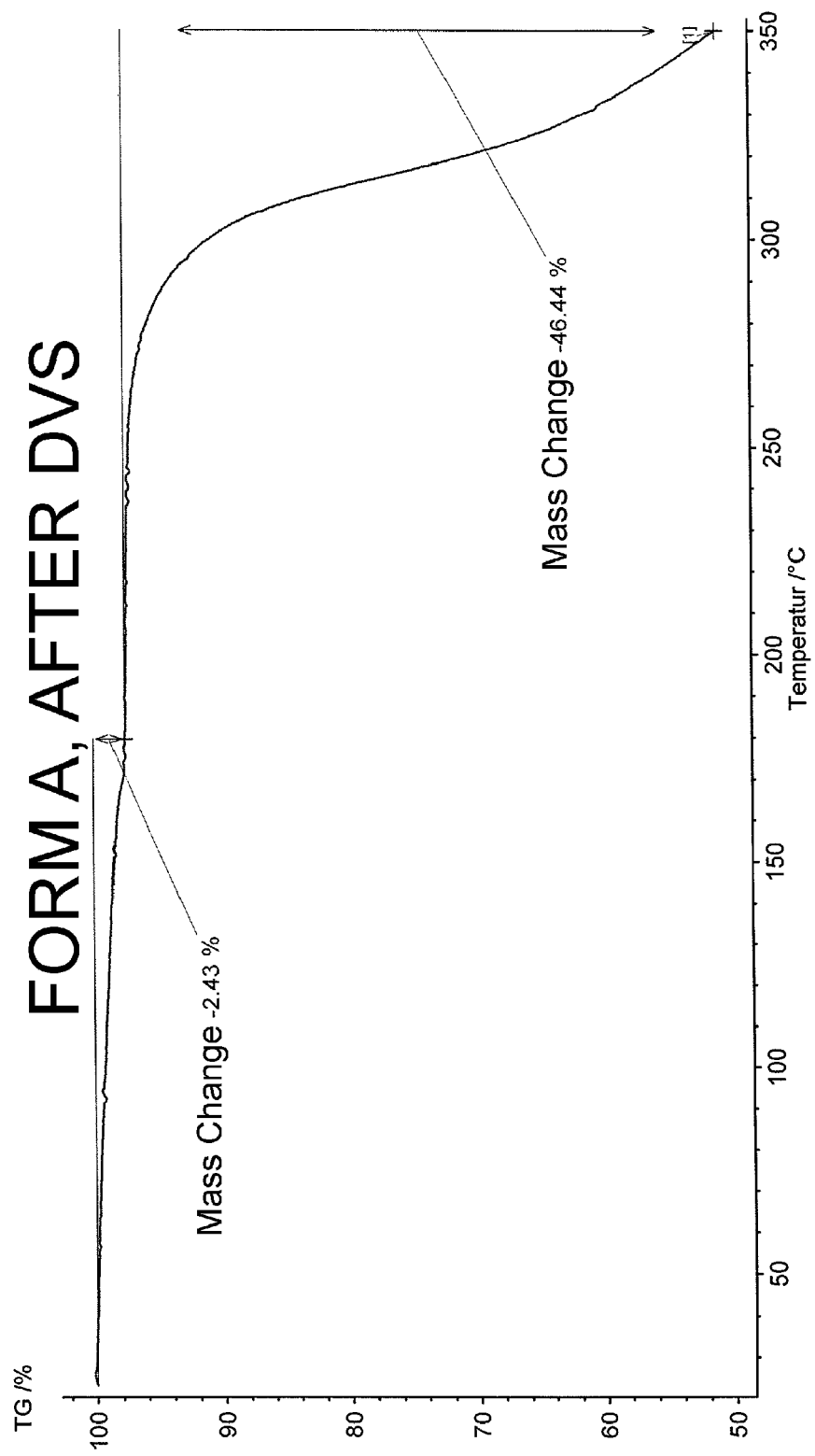
FIG. 11 is a graphical representation of a TG-FTIR chromatogram of crystalline Form A, using material previously subjected to DVS analysis.

The graph of differential scanning calorimetry of crystalline Form A, performed at a rate of change of 10° C./min, is shown in FIG. 8. A double peak is seen at about 145° C., and correlates with the loss of water observed in the TG-FTIR. Additionally, crystalline Form A was analyzed using DVS. FIG. 9 and FIG. 10 show its behavior over the standard experimental protocol. FIG. 9 shows the change in mass of crystalline Form A over the timecourse of the experiment, first decreasing in mass as the relative humidity is decreased, stabilizing at the lowest relative humidity of 0.4%, then increasing with increasing relative humidity, and stabilizing at 95% relative humidity. The amount of mass loss is consistent with the presence of a hemi hydrate (0.5 mole water per mole free acid) and the mass gain at 95% relative humidity is consistent with the presence of 1.1 mole water per mole free acid. The material at the start of the experiment has a water content of about 0.9 mole water per mole free acid. The behavior of crystalline Form A versus the relative humidity axis of this experiment is shown in FIG. 10. A second TG-FTIR analysis was performed on crystalline Form A material after it had been treated according to the DVS experimental conditions. This data is shown in FIG. 11 and demonstrates that the changes in mass seen over the course of the DVS analysis are reversible as the same curve is obtained.

Crystalline Form B

Figure 12:
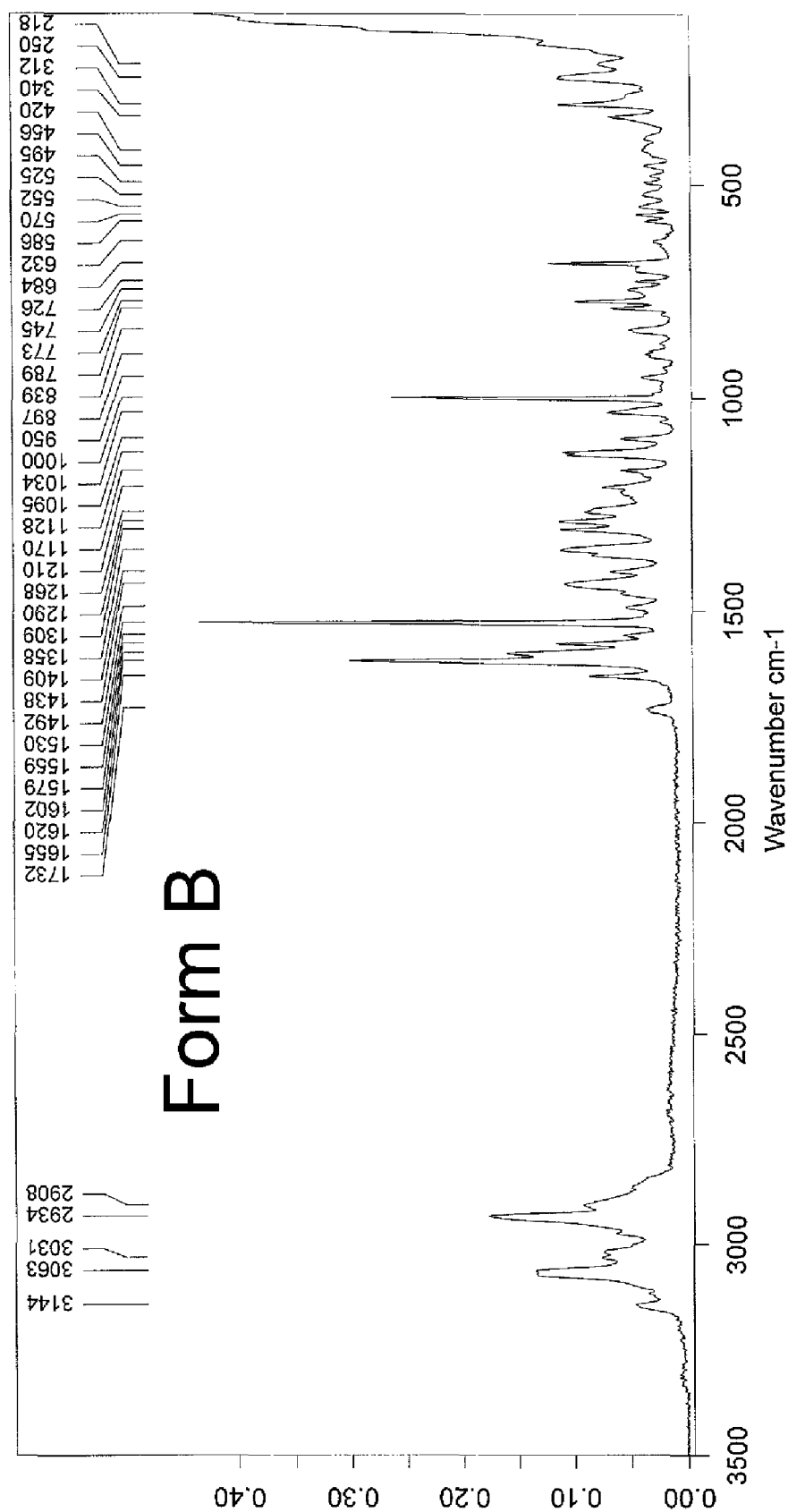
FIG. 12 is a graphical representation of the FT-Raman spectrum of crystalline Form B.
Figure 13:
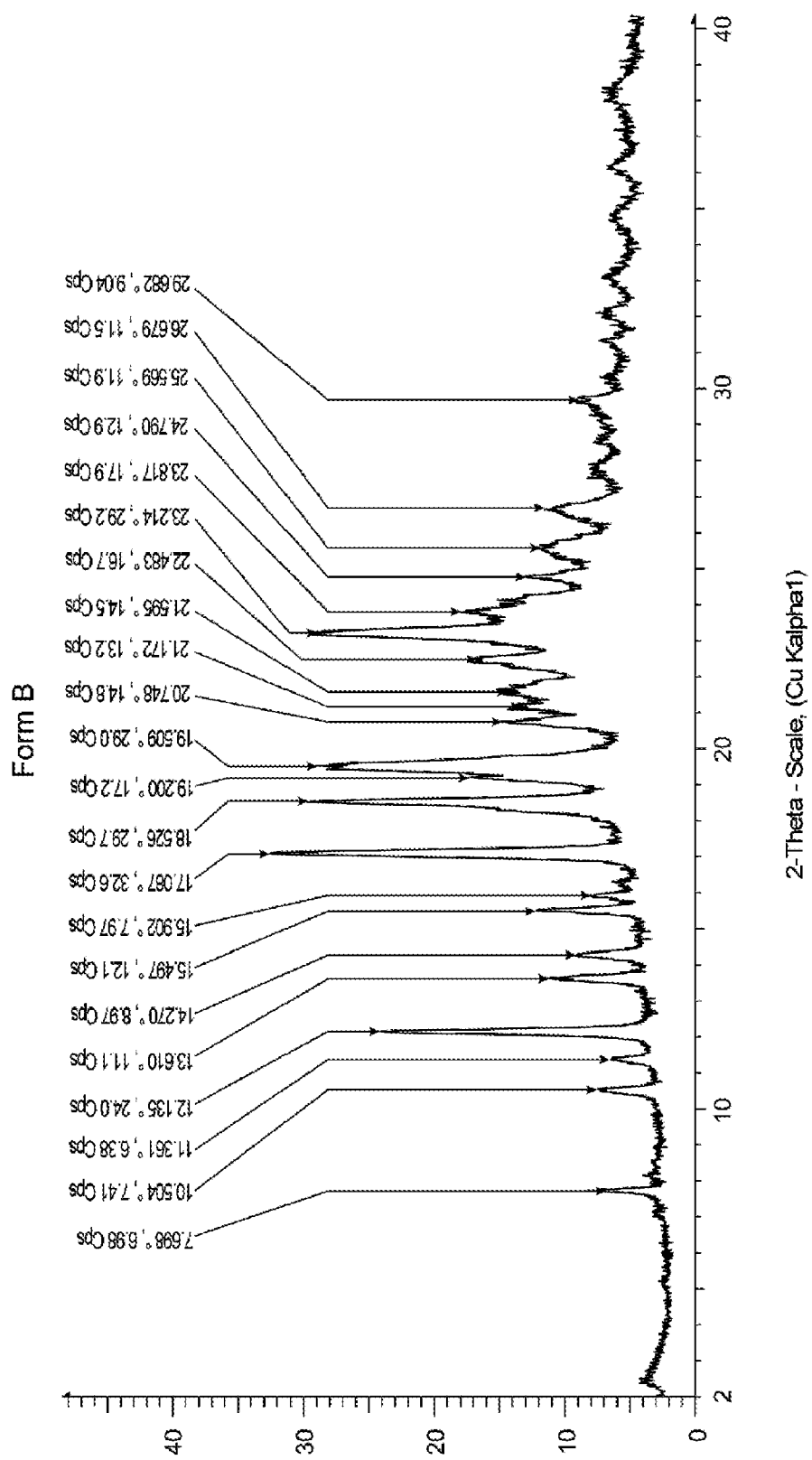
FIG. 13 is a graphical representation of the PXDR pattern of crystalline Form B.

Crystalline Form B was produced from crystalline Form A, by suspending 100 mg of crystalline Form A in ethyl acetate, which had been previously dried over molecular sieves, stirring for four days, and then filtering to isolate crystalline Form B. It was also formed to an extent by slurrying Form A in tert-butyl methyl ether. Crystalline Form B was analyzed by most of the same techniques as crystalline Form A. The FT-Raman spectrum of Crystalline Form B is shown in FIG. 12. The PXDR pattern of crystalline Form B is distinct from that of cystalline Form A, and is shown in FIG. 13. The peak assignments and their relative intensities are listed in Table 3.

TABLE 3

Peak Assignments and Intensities for the PXDR Pattern of Crystalline Form B.

| Angle 2-Theta ° | d value Angstrom | Intensity Cps | Intensity % |
|---|---|---|---|
| 7.70 | 11.5 | 7 | 21 |
| 10.50 | 8.4 | 7 | 23 |
| 11.36 | 7.8 | 6 | 20 |
| 12.14 | 7.3 | 24 | 74 |
| 13.61 | 6.5 | 11 | 34 |
| 14.27 | 6.2 | 9 | 28 |
| 15.50 | 5.71 | 12 | 37 |
| 15.90 | 5.57 | 8 | 25 |
| 17.09 | 5.19 | 33 | 100 |
| 18.53 | 4.79 | 30 | 91 |
| 19.20 | 4.62 | 17 | 53 |
| 19.51 | 4.55 | 29 | 89 |
| 20.75 | 4.28 | 15 | 45 |
| 21.17 | 4.19 | 13 | 41 |
| 21.60 | 4.11 | 15 | 44 |
| 22.48 | 3.95 | 17 | 51 |
| 23.21 | 3.83 | 29 | 90 |
| 23.82 | 3.73 | 18 | 55 |
| 24.79 | 3.59 | 13 | 40 |
| 25.57 | 3.48 | 12 | 37 |
| 26.68 | 3.34 | 12 | 35 |
| 29.68 | 3.01 | 9 | 28 |

Figure 14:
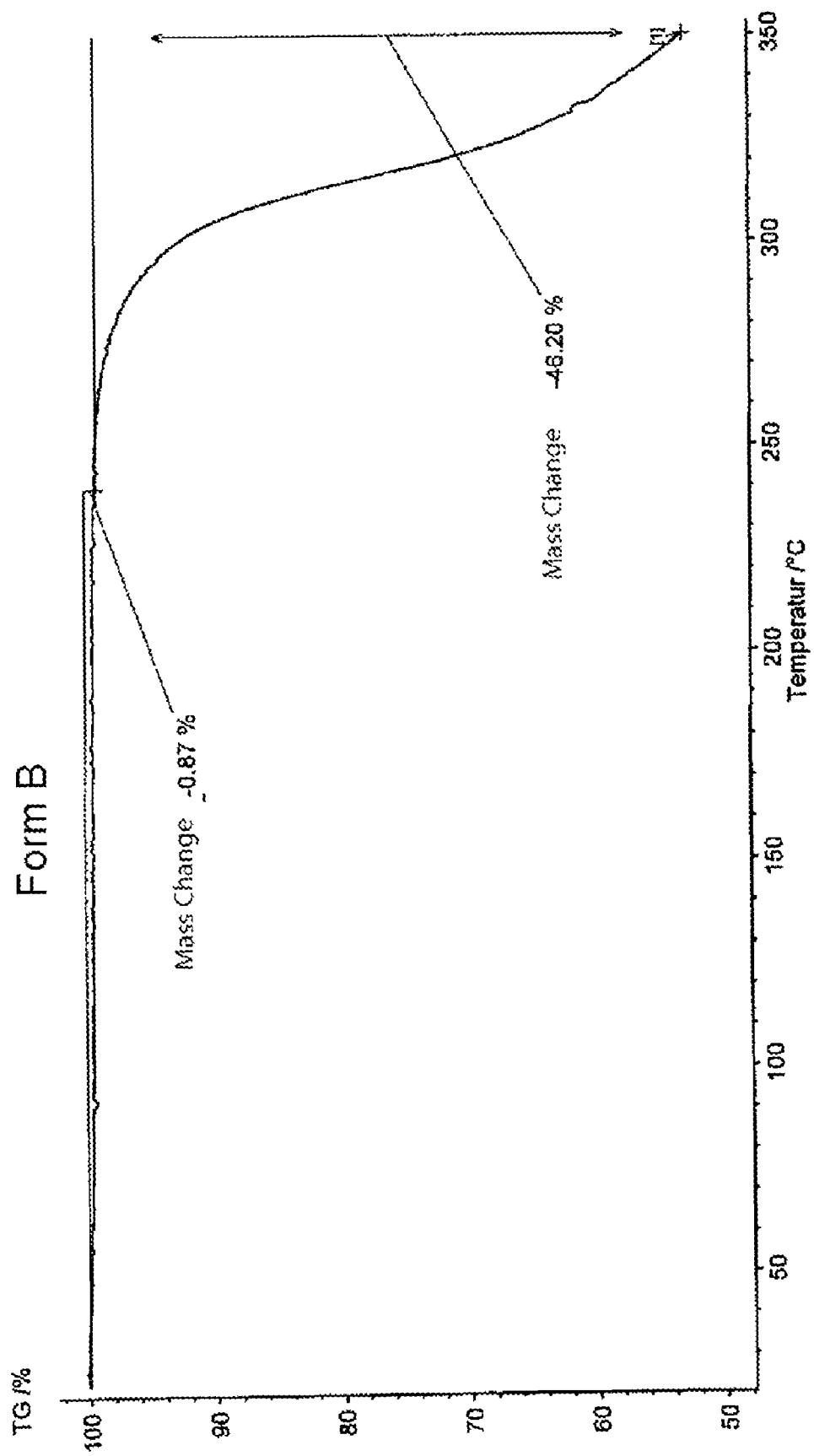
FIG. 14 is a graphical representation of the TG-FTIR chromatogram of crystalline Form B.
Figure 15:
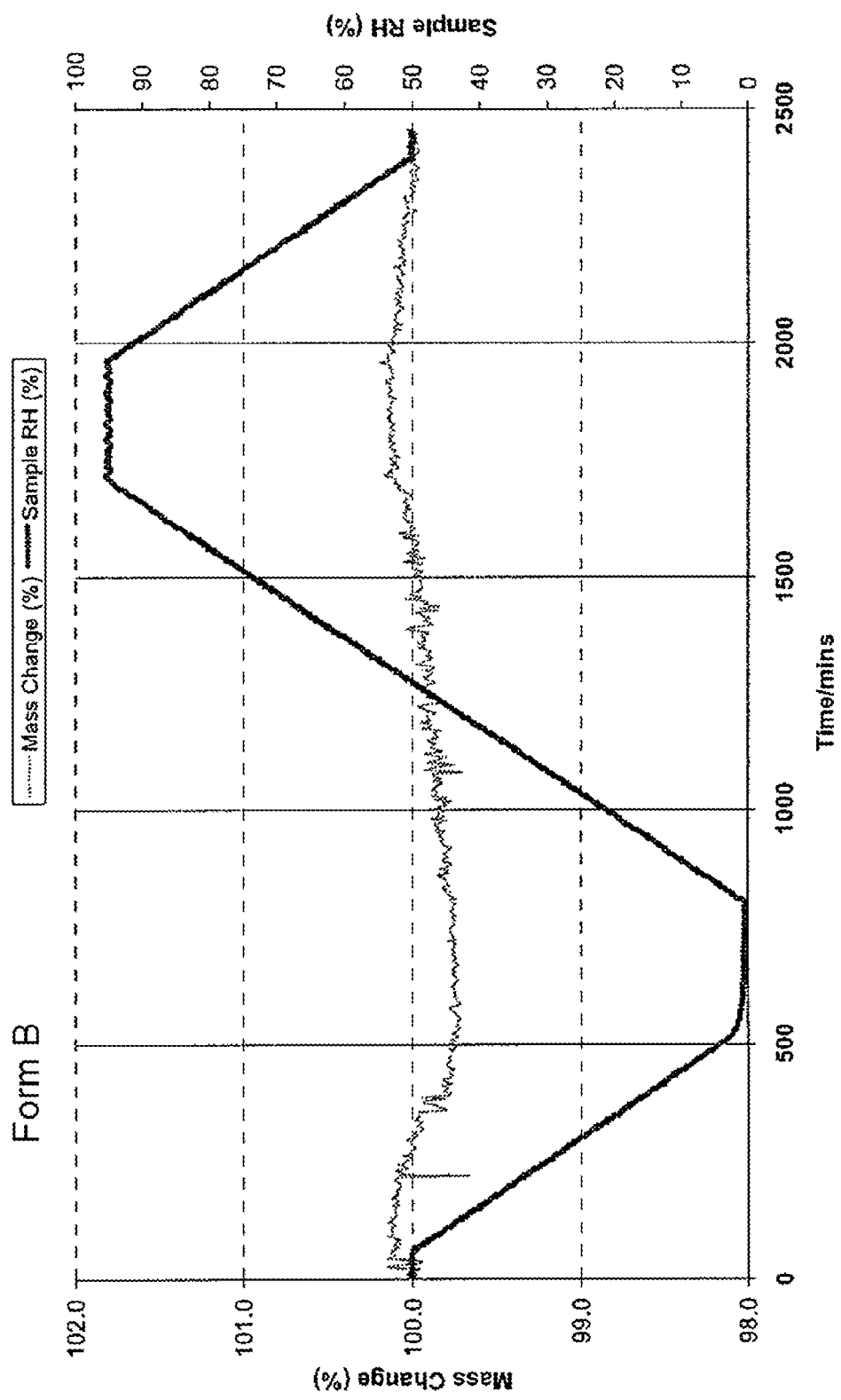
FIG. 15 is a graphical representation of the DVS chromatogram of crystalline Form B with time as the X axis.
Figure 16:
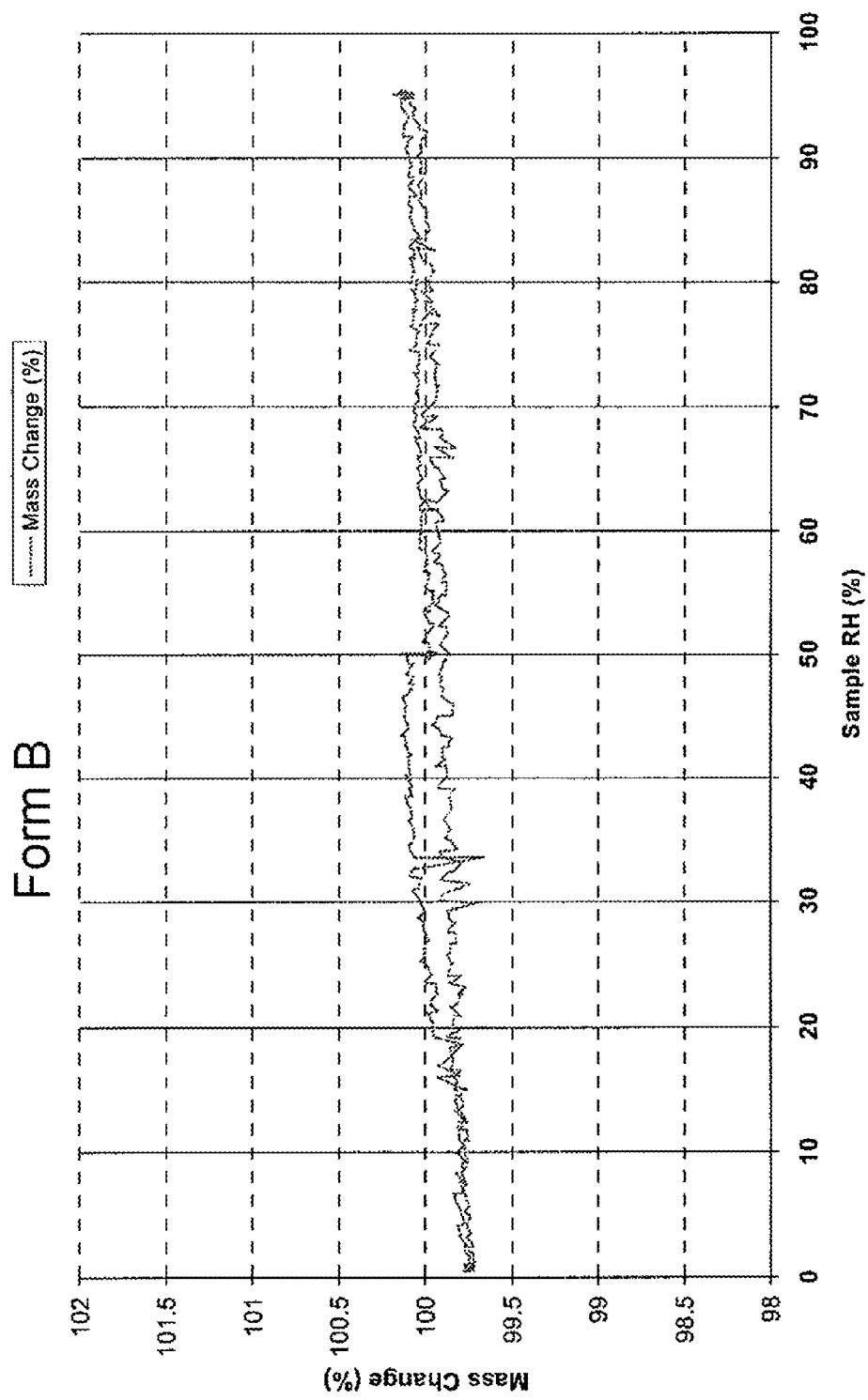
FIG. 16 is a graphical representation of the DVS chromatogram of crystalline Form B with relative humidity as the X axis.
Figure 17:
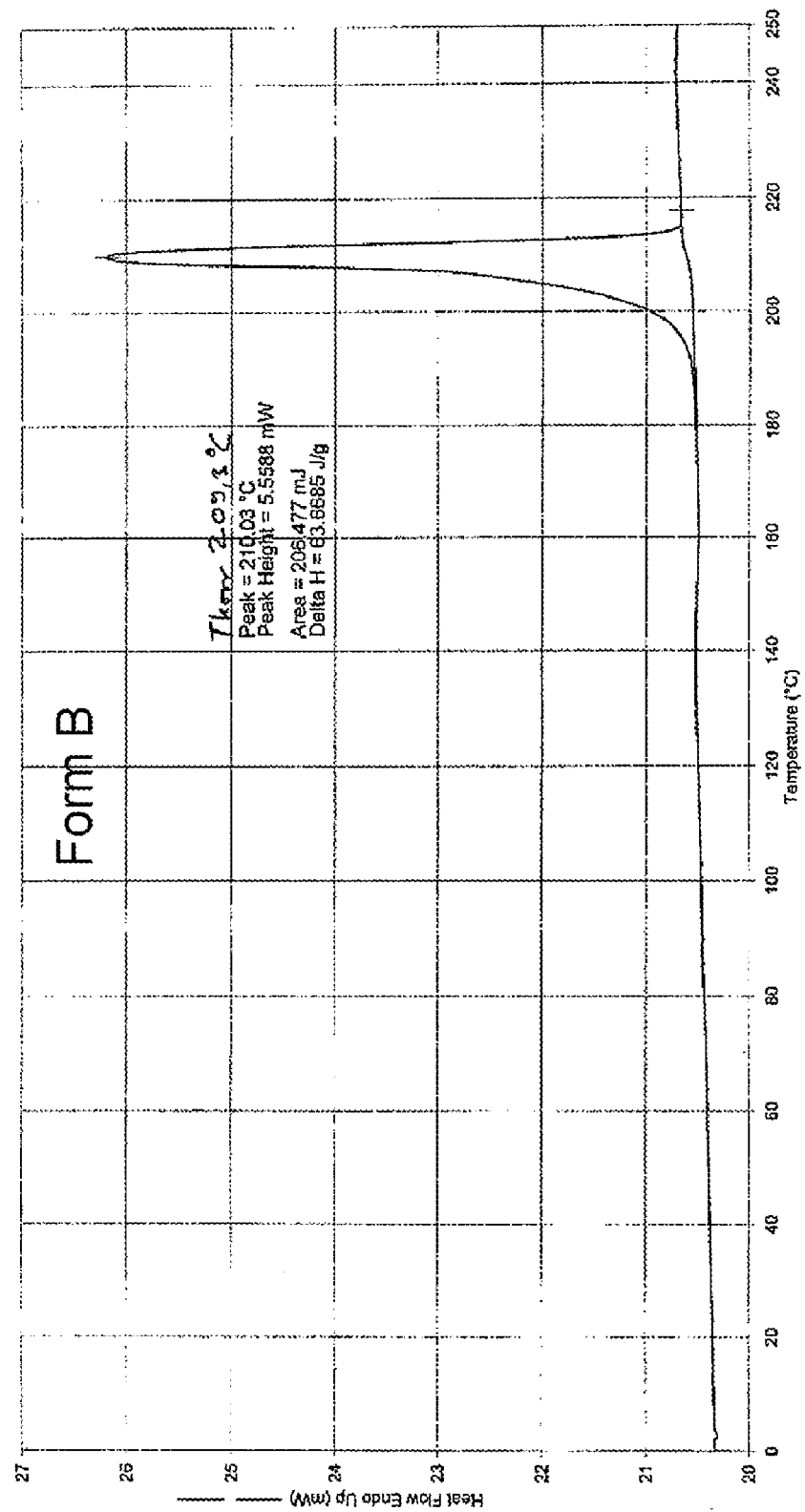
FIG. 17 is a graphical representation of the DSC chromatogram of crystalline Form B.

TG-FTIR data for Form B is displayed in FIG. 14. Residual ethyl acetate and water, in the amount of 0.87% of the total mass, was released from Form B as the temperature was increased to 240° C., and may be attributed to solvent adsorbed to the surface of Form B. DVS analysis of Form B is shown in FIG. 15 and FIG. 16, mass change versus time in FIG. 15 and mass change versus relative humidity in FIG. 16, respectively. The mass loss upon reduction of the relative humidity to 0.4% is 0.30% and 0.19% mass gain is seen upon equilibration at 95% relative humidity. The decomposition of Form B itself occurred at the same temperature as that observed for Form A. The graph of the DSC analysis of Form B is shown in FIG. 17, where the peak at 209° C. may be attributed to melting of Form B. Accordingly, this form does not appear to be hygroscopic and appears to be consistent with an anhydrate which does not convert to a hydrate over the time scale of the DVS experiment (50 hours, and 5 hours at 95% relative humidity).

Crystalline Form C

Figure 18:
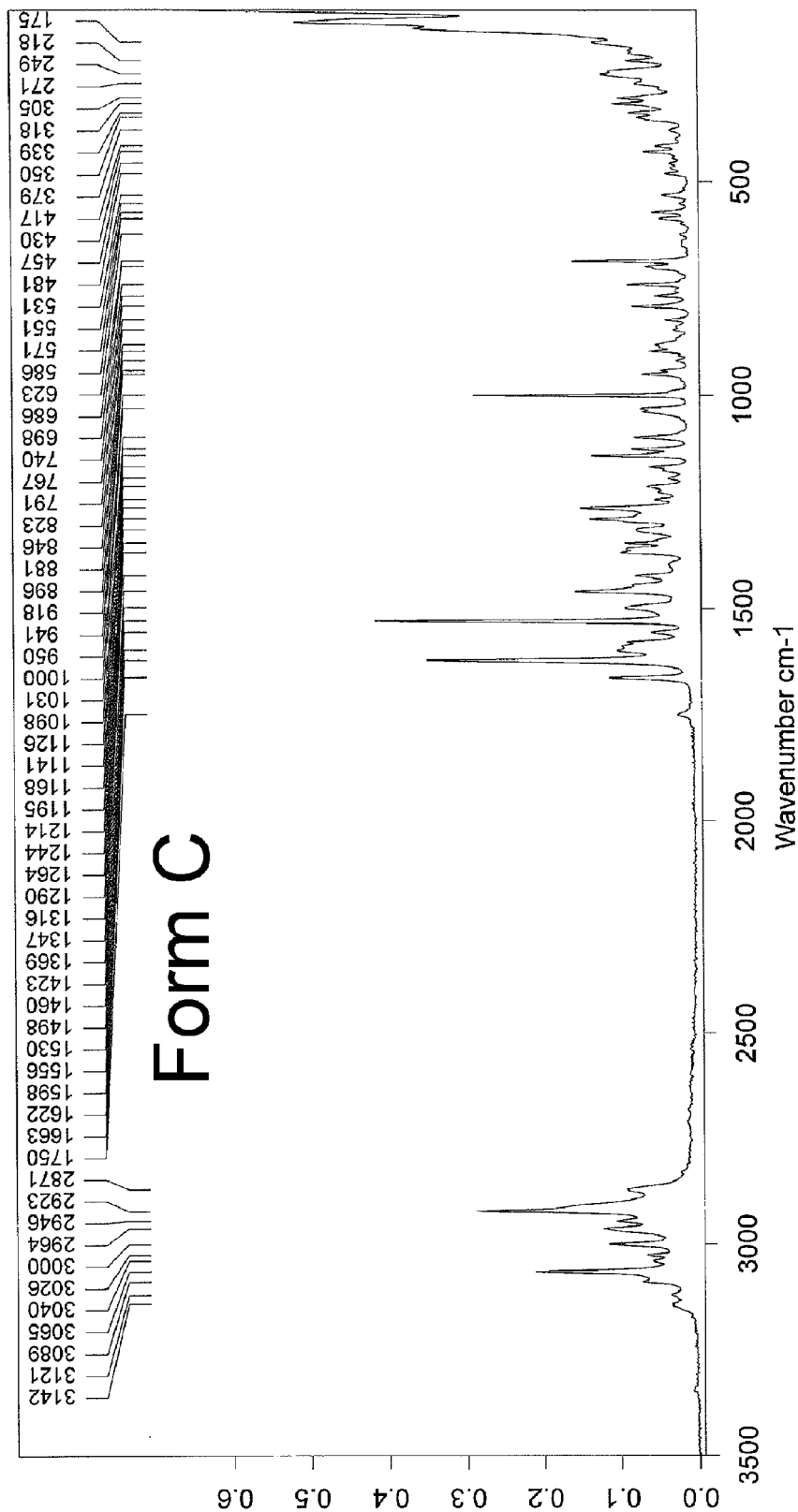
FIG. 18 is a graphical representation of the FT-Raman spectrum of crystalline Form C.
Figure 19:
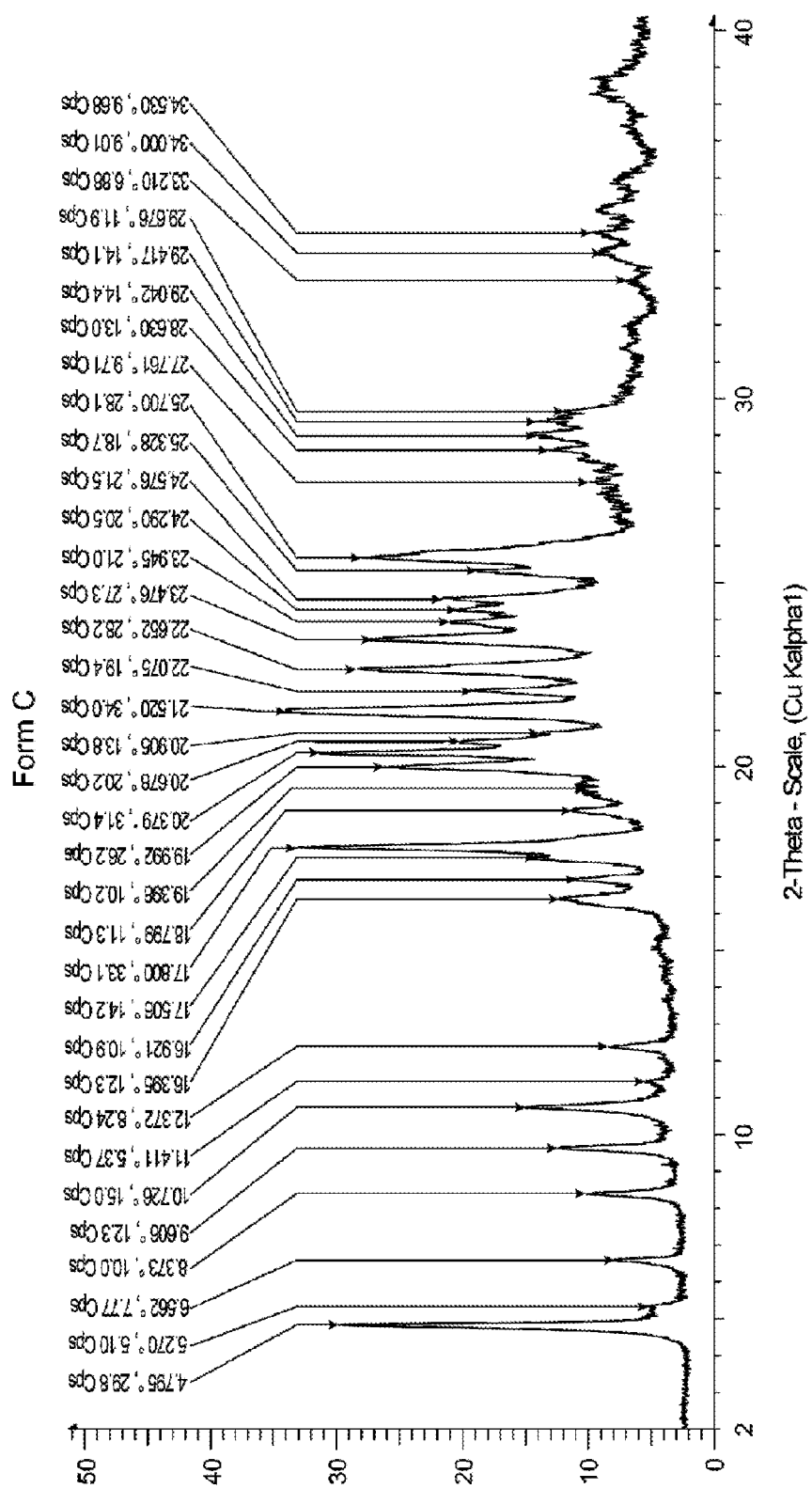
FIG. 19 is a graphical representation of the PXDR pattern of crystalline Form C.
Figure 20:
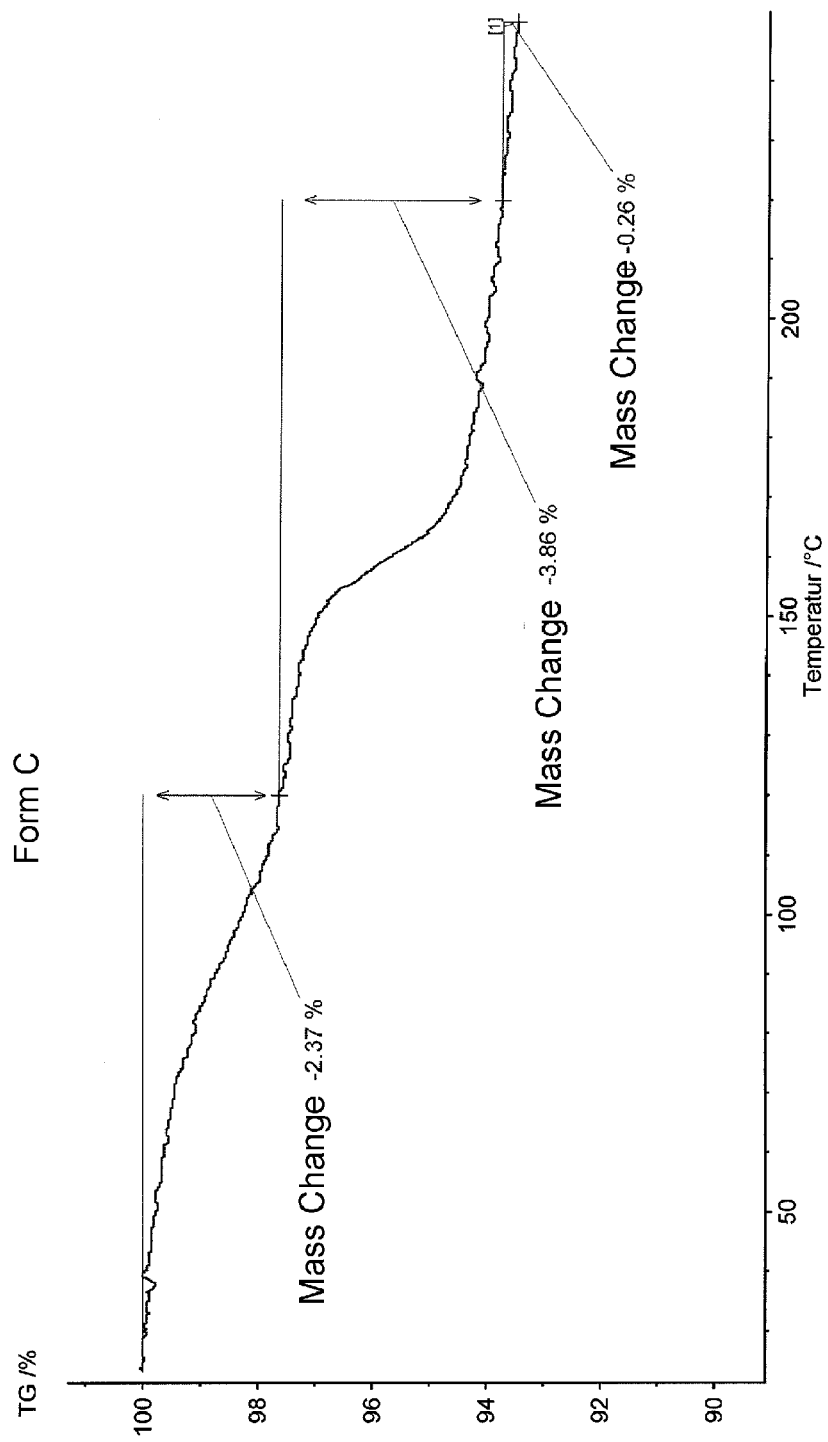
FIG. 20 is a graphical representation of the TG-FTIR chromatogram of crystalline Form C.

Crystalline Form C was produced by suspending 104 mg of crystalline Form A in ethanol, which had been dried over molecular sieves, and stirring the resultant slurry for four days. Crystalline Form C was isolated upon filtering. The FT-Raman chromatogram of crystalline Form C is shown in FIG. 18. The PXDR graph of Crystalline Form C (FIG. 19) shows that a distinct and new crystalline form has been isolated. The peak assignments and relative intensities for PXDR pattern for crystalline Form C are listed in Table 4. The graph of the TG-FTIR data for crystalline Form C is shown in FIG. 20. As the temperature is raised, the first mass loss is attributable to water and ethanol loss, up to about 120° C. The pronounced loss at about 155° C. of about 3.86% is attributable to loss of ethanol, and may be consistent with crystalline Form C existing as a hemi ethanol solvate, which converts to Form A upon drying in a humid atmosphere.

TABLE 4

Peak Assignments and Intensities for the PXDR Pattern of Form C.

| Angle 2-Theta ° | d value Angstrom | Intensity Cps | Intensity % % |
|---|---|---|---|
| 4.80 | 18.4 | 30 | 88 |
| 5.27 | 16.8 | 5 | 15 |
| 6.56 | 13.5 | 8 | 23 |
| 8.37 | 10.6 | 10 | 30 |
| 9.61 | 9.2 | 12 | 36 |
| 10.73 | 8.2 | 15 | 44 |
| 11.41 | 7.7 | 5 | 16 |
| 12.37 | 7.1 | 8 | 24 |
| 16.40 | 5.40 | 12 | 36 |
| 16.92 | 5.24 | 11 | 32 |
| 17.51 | 5.06 | 14 | 42 |
| 17.80 | 4.98 | 33 | 98 |
| 18.80 | 4.72 | 11 | 33 |
| 19.40 | 4.57 | 10 | 30 |
| 19.99 | 4.44 | 26 | 77 |
| 20.38 | 4.35 | 31 | 92 |
| 20.68 | 4.29 | 20 | 59 |
| 20.91 | 4.25 | 14 | 41 |
| 21.52 | 4.13 | 34 | 100 |
| 22.08 | 4.02 | 19 | 57 |
| 22.65 | 3.92 | 28 | 83 |
| 23.48 | 3.79 | 27 | 80 |
| 23.95 | 3.71 | 21 | 62 |
| 24.29 | 3.66 | 21 | 60 |
| 24.58 | 3.62 | 22 | 63 |
| 25.33 | 3.51 | 19 | 55 |
| 25.70 | 3.46 | 28 | 83 |
| 27.76 | 3.21 | 10 | 29 |
| 28.63 | 3.12 | 13 | 38 |
| 29.04 | 3.07 | 14 | 42 |
| 29.42 | 3.03 | 14 | 42 |
| 29.68 | 3.01 | 12 | 35 |
| 33.21 | 2.70 | 7 | 20 |

TABLE 4-continued

Peak Assignments and Intensities for the PXDR Pattern of Form C.

| Angle 2-Theta ° | d value Angstrom | Intensity Cps | Intensity % % |
|---|---|---|---|
| 34.00 | 2.64 | 9 | 27 |
| 34.53 | 2.60 | 10 | 29 |

Crystalline Form D

Figure 21:
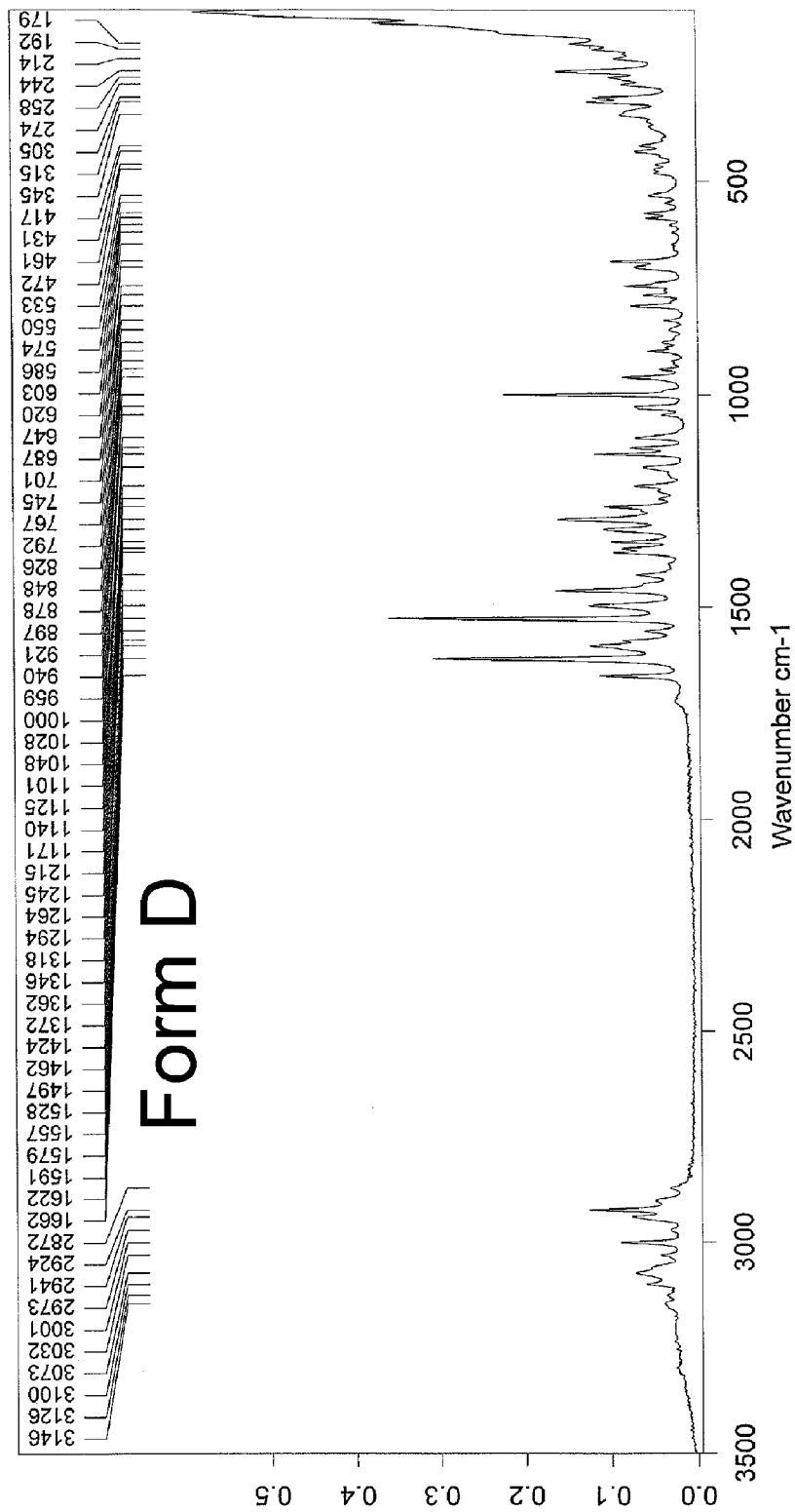
FIG. 21 is a graphical representation of the FT-Raman spectrum of crystalline Form D.
Figure 22:
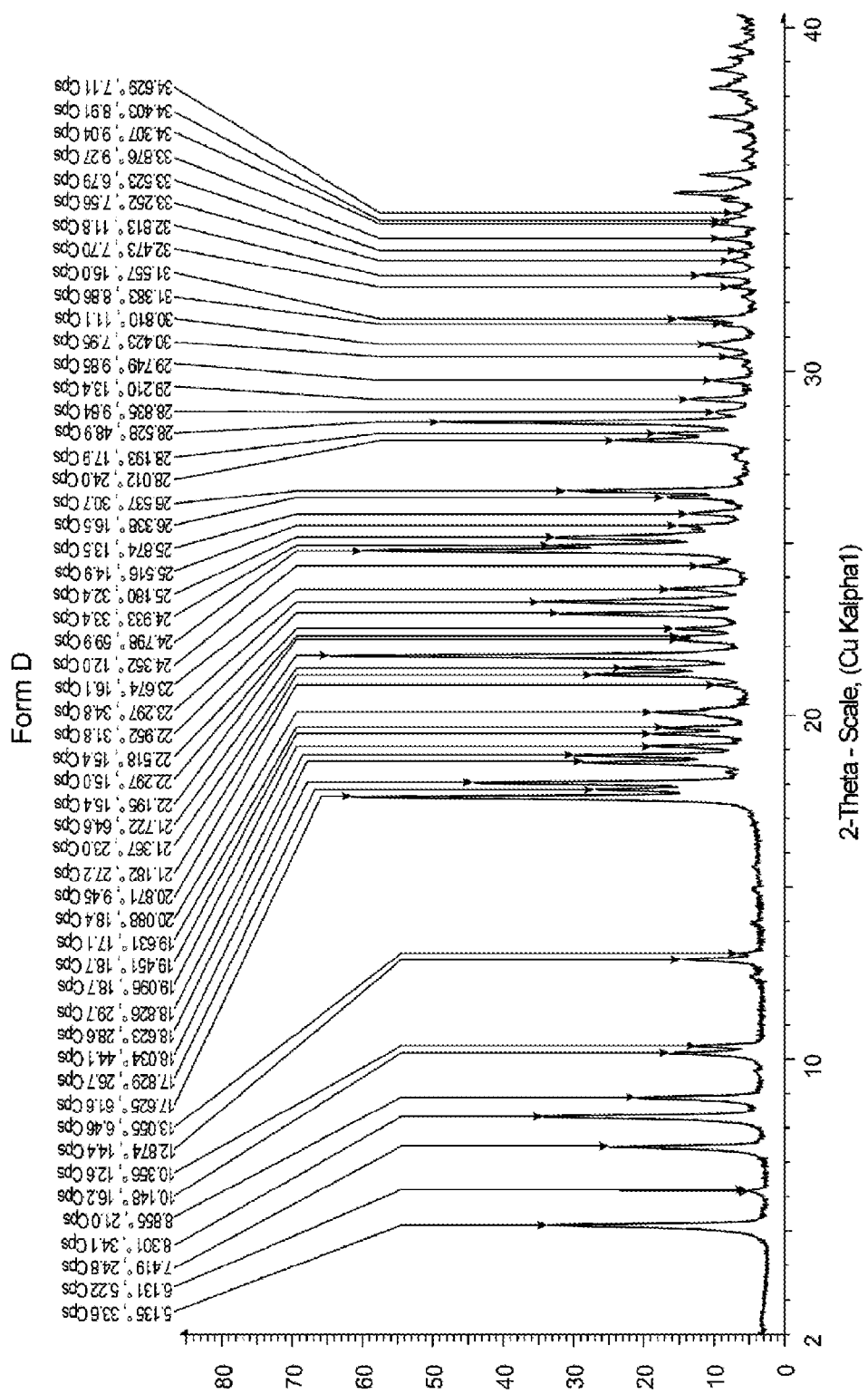
FIG. 22 is a graphical representation of the PXDR pattern of crystalline Form D.

Crystalline Form D was produced by suspending 97 mg of Form A in 1.0 ml of water, stirring for four days, and then filtering to isolate crystalline Form D. The FT-Raman chromatogram is shown in FIG. 21. The PXDR pattern of crystalline Form D is shown in FIG. 22, and represents another novel crystalline form. The peak assignments and intensities for the PXDR pattern are listed in Table 5.

TABLE 5

Peak Assignments and Intensities for the PXDR Pattern of Crystalline Form D.

| Angle 2-Theta ° | d value Angstrom | Intensity Cps | Intensity % % |
|---|---|---|---|
| 5.14 | 17.2 | 34 | 52 |
| 6.13 | 14.4 | 5 | 8 |
| 7.42 | 11.9 | 25 | 38 |
| 8.30 | 10.6 | 34 | 53 |
| 8.86 | 10.0 | 21 | 33 |
| 10.15 | 8.7 | 16 | 25 |
| 10.36 | 8.5 | 13 | 20 |
| 12.87 | 6.9 | 14 | 22 |
| 13.06 | 6.8 | 6 | 10 |
| 17.63 | 5.03 | 62 | 95 |
| 17.83 | 4.97 | 27 | 41 |
| 18.03 | 4.92 | 44 | 68 |
| 18.62 | 4.76 | 29 | 44 |
| 18.83 | 4.71 | 30 | 46 |
| 19.10 | 4.64 | 19 | 29 |
| 19.45 | 4.56 | 19 | 29 |
| 19.63 | 4.52 | 17 | 27 |
| 20.09 | 4.42 | 18 | 29 |
| 20.87 | 4.25 | 9 | 15 |
| 21.18 | 4.19 | 27 | 42 |
| 21.37 | 4.16 | 23 | 36 |
| 21.72 | 4.09 | 65 | 100 |
| 22.20 | 4.00 | 15 | 24 |
| 22.30 | 3.98 | 15 | 23 |
| 22.52 | 3.95 | 15 | 24 |
| 22.95 | 3.87 | 32 | 49 |
| 23.30 | 3.82 | 35 | 54 |
| 23.67 | 3.76 | 16 | 25 |
| 24.35 | 3.65 | 12 | 19 |
| 24.80 | 3.59 | 60 | 93 |
| 24.93 | 3.57 | 33 | 52 |
| 25.18 | 3.53 | 32 | 50 |
| 25.52 | 3.49 | 15 | 23 |
| 25.87 | 3.44 | 14 | 21 |
| 26.34 | 3.38 | 17 | 26 |
| 26.54 | 3.36 | 31 | 48 |
| 28.01 | 3.18 | 24 | 37 |
| 28.19 | 3.16 | 18 | 28 |
| 28.53 | 3.13 | 49 | 76 |
| 28.84 | 3.09 | 10 | 15 |
| 29.21 | 3.06 | 13 | 21 |
| 29.75 | 3.00 | 10 | 15 |
| 30.42 | 2.94 | 8 | 12 |
| 30.81 | 2.90 | 11 | 17 |
| 31.38 | 2.85 | 9 | 14 |
| 31.56 | 2.83 | 15 | 23 |
| 32.47 | 2.76 | 8 | 12 |
| 32.81 | 2.73 | 12 | 18 |
| 33.25 | 2.69 | 8 | 12 |
| 33.52 | 2.67 | 7 | 11 |
| 33.88 | 2.64 | 9 | 14 |

TABLE 5-continued

Peak Assignments and Intensities for the
PXDR Pattern of Crystalline Form D.

| Angle 2-Theta ° | d value Angstrom | Intensity Cps | Intensity % % |
|---|---|---|---|
| 34.31 | 2.61 | 9 | 14 |
| 34.40 | 2.61 | 9 | 14 |
| 34.63 | 2.59 | 7 | 11 |

Figure 23:
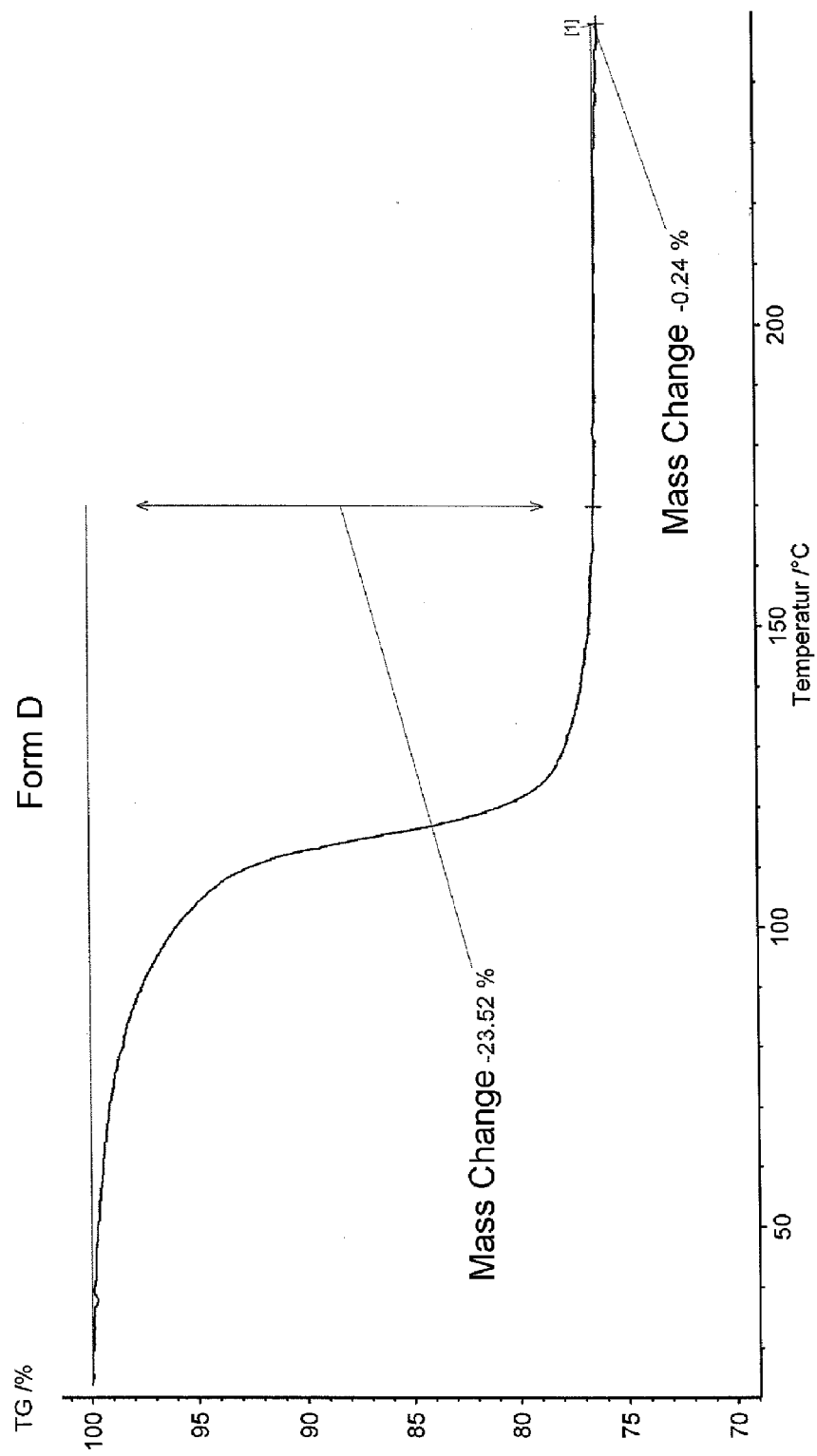
FIG. 23 is a graphical representation of the TG-FTIR chromatogram of crystalline Form D.

TG-FTIR data is shown in FIG. 23 and is consistent with conversion of crystalline Form D into crystalline Form A upon heating. A mass loss of about 23.5% was observed about 110° C., but does not appear to be consistent with a dehydration step converting a hydrate to an anhydrate, but appears to be consistent with the loss of water from the surface of the solid.

Crystalline Form E

Figure 24:
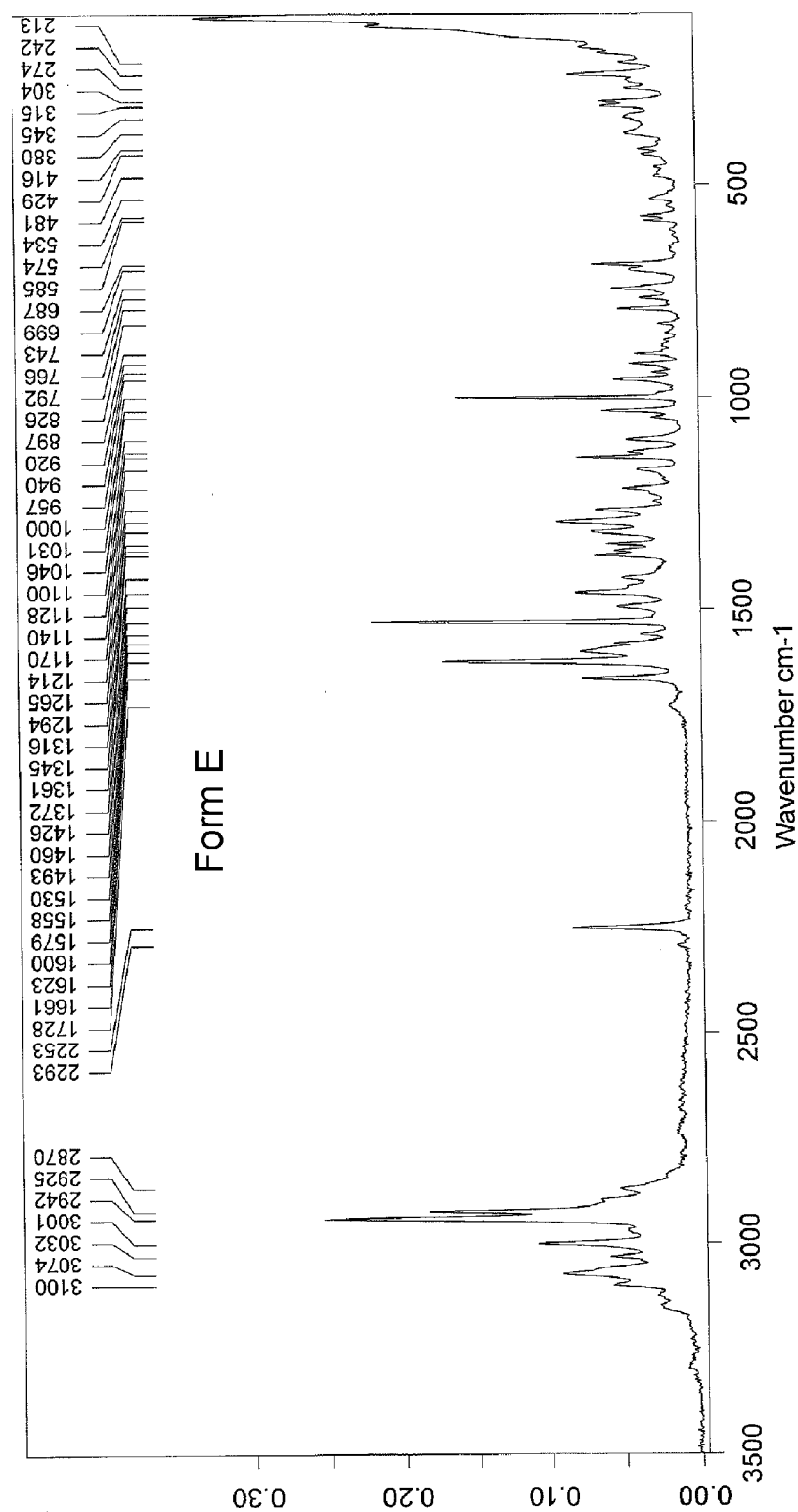
FIG. 24 is a graphical representation of the FT-Raman spectrum of crystalline Form E.
Figure 25:
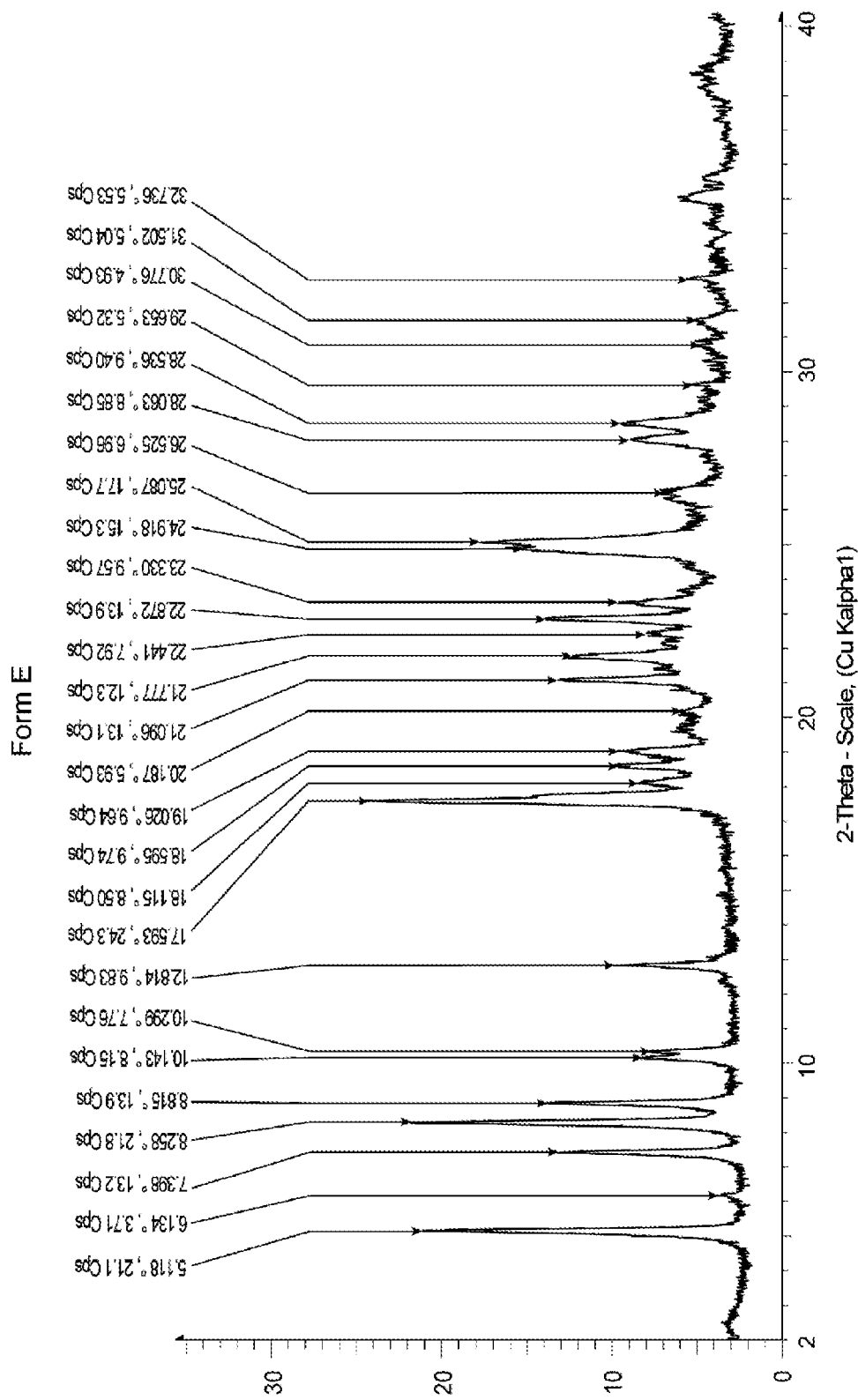
FIG. 25 is a graphical representation of the PXDR pattern of crystalline Form E.
Figure 26:
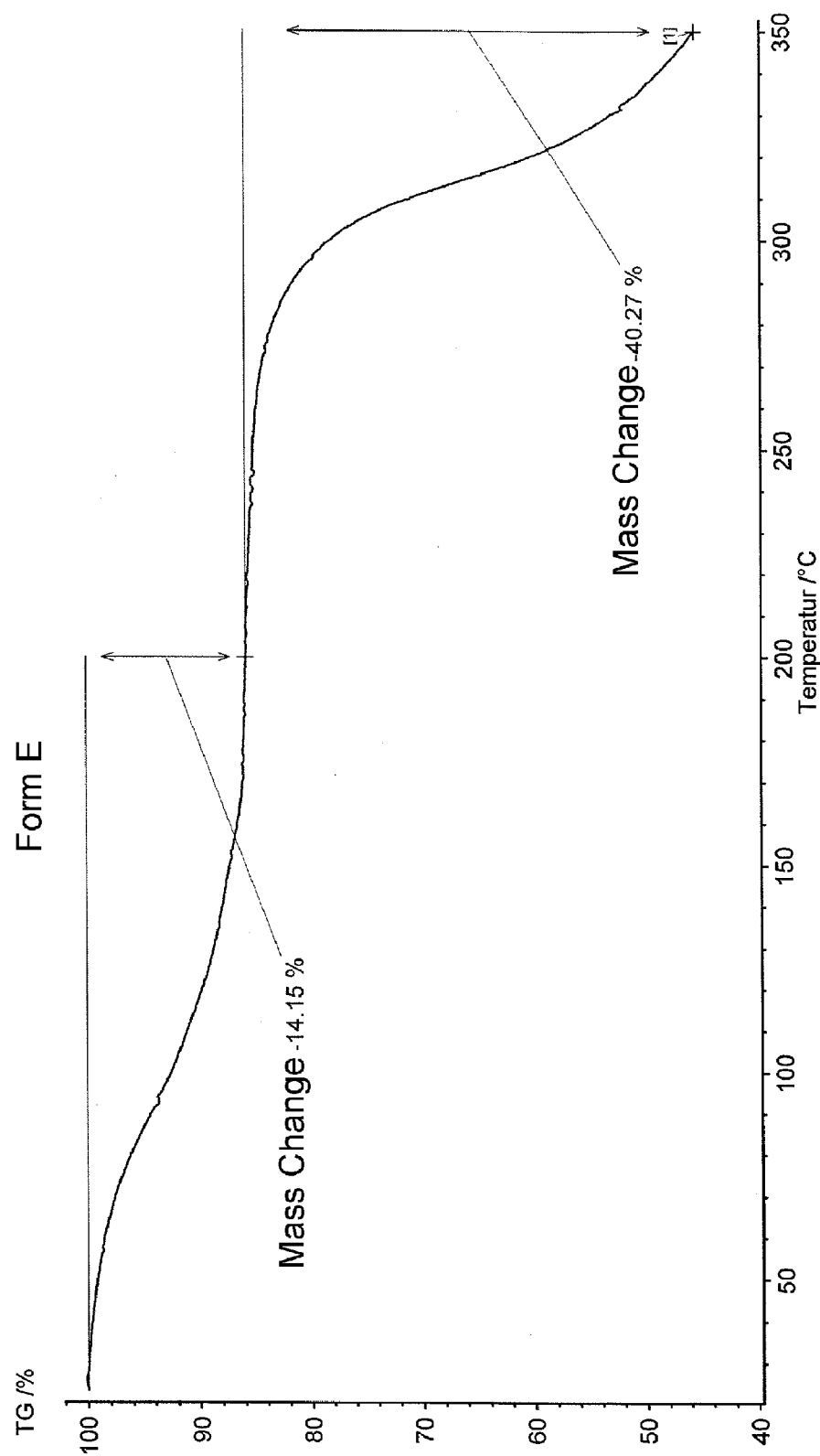
FIG. 26 is a graphical representation of the TG-FTIR chromatogram of crystalline Form E.

Crystalline Form E was produced similarly to that of crystalline Form A, using 103 mg of the Amorphous Form described above, suspending the amorphous Form in 0.7 ml acetonitrile, previously dried over molecular sieves, and seeded with crystalline Form A. After stirring, crystalline Form E was isolated by filtration, and investigated while still in wet stage. Crystalline Form E converts into crystalline Form A upon drying. The FT-Raman chromatogram of crystalline Form E is shown in FIG. 24, and its PXDR pattern is shown in FIG. 25. The assignment of peaks and their intensities for the PXDR of crystalline Form E is listed in Table 6. The data from the TG-FTIR analysis of Form E is shown in FIG. 26. The large loss of mass of 14.15% which stabilizes prior to reaching 190° C., is probably due to residual water and acetonitrile in the wet sample. A step attributable to dehydration of a solvate is not consistent with the data in FIG. 26.

TABLE 6

Peak Assignments and Intensities for the PXDR Pattern of Form E.

| Angle 2-Theta ° | d value Angstrom | Intensity Cps | Intensity % % |
|---|---|---|---|
| 5.12 | 17.3 | 21 | 87 |
| 6.13 | 14.4 | 4 | 15 |
| 7.40 | 11.9 | 13 | 54 |
| 8.26 | 10.7 | 22 | 90 |
| 8.82 | 10.0 | 14 | 57 |
| 10.14 | 8.7 | 8 | 34 |
| 10.30 | 8.6 | 8 | 32 |
| 12.81 | 6.9 | 10 | 40 |
| 17.59 | 5.04 | 24 | 100 |
| 18.12 | 4.89 | 9 | 35 |
| 18.60 | 4.77 | 10 | 40 |
| 19.03 | 4.66 | 10 | 40 |
| 20.19 | 4.40 | 6 | 24 |
| 21.10 | 4.21 | 13 | 54 |
| 21.78 | 4.08 | 12 | 51 |
| 22.44 | 3.96 | 8 | 33 |
| 22.87 | 3.89 | 14 | 57 |
| 23.33 | 3.81 | 10 | 39 |
| 24.92 | 3.57 | 15 | 63 |
| 25.09 | 3.55 | 18 | 73 |
| 26.53 | 3.36 | 7 | 29 |
| 28.06 | 3.18 | 9 | 36 |
| 28.54 | 3.13 | 9 | 39 |
| 29.65 | 3.01 | 5 | 22 |
| 30.78 | 2.90 | 5 | 20 |
| 31.50 | 2.84 | 5 | 21 |
| 32.74 | 2.73 | 6 | 23 |

The above methods can be used to manufacture crystalline Forms A, B, C, D, and E. While the manufacture of each of crystalline Forms A, B, C, D, and E has been exemplified employing a specific solvent system and crystallization conditions, it is envisioned that each form can be obtained employing a different solvent or combination of solvents and/or different crystallization conditions. Further, crystals of any of crystalline Forms A, B, C, D, or E may be added to solutions or slurries of the amorphous form to seed the crystallization of that specific form. Therefore the above description is not meant to limit the invention in any way.

Additionally, it is envisioned that any of the crystalline Forms A, B, C, D, and/or E may be treated to regenerate an amorphous form. In some embodiments of the invention, while the use of the higher level of purity of Forms A, B, C, D, and/or E may be desirable, it is also desirable to utilize an amorphous form in the formulation therein to deliver therapeutically effective amounts of the compound of Formula I. An amorphous form with equivalent purity to that of crystalline Form A, B, C, D, or E was produced by dissolving the crystalline form in aqueous sodium bicarbonate, acidifying, and extracting the compound of Formula I into ethyl acetate. Removal of the ethyl acetate yielded the amorphous form having the same purity as that of any of crystalline Forms A, B, C, D, or/and E.

A partial list of useful solvents includes, i.e., for example, water, aliphatic solvents such as pentane, petroleum ether, and hexane; aromatic solvents such as toluene and xylene, aliphatic ketones and esters such as methyl ethyl ketone, acetone ethyl acetate, and butyl acetate, alcohols, such as ethyl alcohol, propyl alcohol, and methyl alcohol, acetonitrile, ethers, such as ethyl ether, tert-butyl methyl ether (TBME), and tetrahydrofuran, alkenes and alkynes, alkenyl esters and alcohols, alkynyl esters and alcohols, and aromatic esters and alcohols.

In some of the embodiments of the invention, the purity of the amorphous form of the compound of Formula I as measured by high pressure liquid chromatography is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% total area under the curve as observed at about 220 nm. In some embodiments of the invention, the amorphous form of the compound of Formula I is about 100.0% pure as measured by high pressure liquid chromatography as area under the curve as observed at about 220 nm.

In some of the embodiments of the invention, the purity of the amorphous form of the compound of Formula I as measured by high pressure liquid chromatography is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% total area under the curve as observed at about 254 nm or about 260 nm. In some embodiments of the invention, the amorphous form of the compound of Formula I is about 100.0% pure as measured by high pressure liquid chromatography as area under the curve as observed at about 254 nm or about 260 nm.

In some of the embodiments of the invention, the purity of crystalline Form A of the compound of Formula I as measured by high pressure liquid chromatography is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% total area under the curve as observed at about 220 nm. In some embodiments of the invention, the crystalline Form A of the compound of Formula I is about 100.0% pure as measured by high pressure liquid chromatography as area under the curve as observed at about 220 nm.

In some of the embodiments of the invention, the purity of crystalline Form A of the compound of Formula I as measured by high pressure liquid chromatography is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% total area under the curve as observed at about 254 nm or about 260 nm. In some embodiments of the invention, the crystalline Form A of the compound of Formula I is about 99.9% pure as measured by high pressure liquid chromatography as area under the curve as observed at about 254 nm or about 260 nm.

In some of the embodiments of the invention, the purity of crystalline Form B of the compound of Formula I as measured by high pressure liquid chromatography is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% total area under the curve as observed at about 220 nm. In some embodiments of the invention, the crystalline Form B of the compound of Formula I is about 100.0% pure as measured by high pressure liquid chromatography as area under the curve as observed at about 220 nm.

In some of the embodiments of the invention, the purity of crystalline Form B of the compound of Formula I as measured by high pressure liquid chromatography is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% total area under the curve as observed at about 254 nm or about 260 nm. In some embodiments of the invention, the crystalline Form B of the compound of Formula I is about 100.0% pure as measured by high pressure liquid chromatography as area under the curve as observed at about 254 nm or about 260 nm.

In some of the embodiments of the invention, the purity of crystalline Form C of the compound of Formula I as measured by high pressure liquid chromatography is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% total area under the curve as observed at about 220 nm. In some embodiments of the invention, the crystalline Form C of the compound of Formula I is about 100.0% pure as measured by high pressure liquid chromatography as area under the curve as observed at about 220 nm.

In some of the embodiments of the invention, the purity of crystalline Form C of the compound of Formula I as measured by high pressure liquid chromatography is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% total area under the curve as observed at about 254 nm or about 260 nm. In some embodiments of the invention, the crystalline Form C of the compound of Formula I is about 100.0% pure as measured by high pressure liquid chromatography as area under the curve as observed at about 254 nm or about 260 nm.

In some of the embodiments of the invention, the purity of crystalline Form D of the compound of Formula I as measured by high pressure liquid chromatography is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% total area under the curve as observed at about 220 nm. In some embodiments of the invention, the crystalline Form D of the compound of Formula I is about 100.0% pure as measured by high pressure liquid chromatography as area under the curve as observed at about 220 nm.

In some of the embodiments of the invention, the purity of crystalline Form D of the compound of Formula I as measured by high pressure liquid chromatography is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% total area under the curve as observed at about 254 nm or about 260 nm. In some embodiments of the invention, the crystalline Form D of the compound of Formula I is about 100.0% pure as measured by high pressure liquid chromatography as area under the curve as observed at about 254 nm or about 260 nm.

In some of the embodiments of the invention, the purity of crystalline Form E of the compound of Formula I as measured by high pressure liquid chromatography is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% total area under the curve as observed at about 220 nm. In some embodiments of the invention, the crystalline Form E of the compound of Formula I is about 100.0% pure as measured by high pressure liquid chromatography as area under the curve as observed at about 220 nm.

In some of the embodiments of the invention, the purity of crystalline Form E of the compound of Formula I as measured by high pressure liquid chromatography is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% total area under the curve as observed at about 254 nm or about 260 nm. In some embodiments of the invention, the crystalline Form E of the compound of Formula I is about 100.0% pure as measured by high pressure liquid chromatography as area under the curve as observed at about 254 nm or about 260 nm.

In some of the embodiments of the methods of manufacture of the invention, the chiral purity of the amorphous form of the compound of Formula I as measured by chiral chromatography at 260 nm is greater than about 75%, about 75.5%, about 76%, about 76.5%, about 77%, about 77.5%, about 78%, about 78.5%, about 79%, about 79.5%, about 80%, about 80.5%, about 81%, about 81.5%, about 82%, about 82.5%, about 83%, about 83.5%, about 84%, about 84.5%, about 85%, about 85.5%, about 86%, about 86.5%, about 87%, about 87.5%, about 88%, about 88.5%, about 89%, about 89.5%, about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% of the S-enantiomer. In some embodiments, the chiral purity of the amorphous form of the compound of Formula I as measured by chiral chromatography at 260 nm is about 100%.

In some of the embodiments of the methods of manufacture of the invention, the chiral purity of crystalline Form A of the compound of Formula I as measured by chiral chromatography at 260 nm is greater than about 75%, about 75.5%, about 76%, about 76.5%, about 77%, about 77.5%, about 78%, about 78.5%, about 79%, about 79.5%, about 80%, about 80.5%, about 81%, about 81.5%, about 82%, about 82.5%, about 83%, about 83.5%, about 84%, about 84.5%, about 85%, about 85.5%, about 86%, about 86.5%, about 87%, about 87.5%, about 88%, about 88.5%, about 89%, about 89.5%, about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% of the S-enantiomer. In some embodiments, the chiral purity of the Form A of the compound of Formula I as measured by chiral chromatography at 260 nm is about 100%.

In some of the embodiments of the methods of manufacture of the invention, the chiral purity of crystalline Form B of the compound of Formula I as measured by chiral chromatography at 260 nm is greater than about 75%, about 75.5%, about 76%, about 76.5%, about 77%, about 77.5%, about 78%, about 78.5%, about 79%, about 79.5%, about 80%, about 80.5%, about 81%, about 81.5%, about 82%, about 82.5%, about 83%, about 83.5%, about 84%, about 84.5%, about 85%, about 85.5%, about 86%, about 86.5%, about 87%, about 87.5%, about 88%, about 88.5%, about 89%, about 89.5%, about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% of the S-enantiomer. In some embodiments, the chiral purity of the Form B of the compound of Formula I as measured by chiral chromatography at 260 nm is about 100%.

In some of the embodiments of the methods of manufacture of the invention, the chiral purity of crystalline Form C of the compound of Formula I as measured by chiral chromatography at 260 nm is greater than about 75%, about 75.5%, about 76%, about 76.5%, about 77%, about 77.5%, about 78%, about 78.5%, about 79%, about 79.5%, about 80%, about 80.5%, about 81%, about 81.5%, about 82%, about 82.5%, about 83%, about 83.5%, about 84%, about 84.5%, about 85%, about 85.5%, about 86%, about 86.5%, about 87%, about 87.5%, about 88%, about 88.5%, about 89%, about 89.5%, about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% of the S-enantiomer. In some embodiments, the chiral purity of the Form C of the compound of Formula I as measured by chiral chromatography at 260 nm is about 100%.

In some of the embodiments of the methods of manufacture of the invention, the chiral purity of crystalline Form D of the compound of Formula I as measured by chiral chromatography at 260 nm is greater than about 75%, about 75.5%, about 76%, about 76.5%, about 77%, about 77.5%, about 78%, about 78.5%, about 79%, about 79.5%, about 80%, about 80.5%, about 81%, about 81.5%, about 82%, about 82.5%, about 83%, about 83.5%, about 84%, about 84.5%, about 85%, about 85.5%, about 86%, about 86.5%, about 87%, about 87.5%, about 88%, about 88.5%, about 89%, about 89.5%, about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% of the S-enantiomer. In some embodiments, the chiral purity of the Form D of the compound of Formula I as measured by chiral chromatography at 260 nm is about 100%.

In some of the embodiments of the methods of manufacture of the invention, the chiral purity of crystalline Form E of the compound of Formula I as measured by chiral chromatography at 260 nm is greater than about 75%, about 75.5%, about 76%, about 76.5%, about 77%, about 77.5%, about 78%, about 78.5%, about 79%, about 79.5%, about 80%, about 80.5%, about 81%, about 81.5%, about 82%, about 82.5%, about 83%, about 83.5%, about 84%, about 84.5%, about 85%, about 85.5%, about 86%, about 86.5%, about 87%, about 87.5%, about 88%, about 88.5%, about 89%, about 89.5%, about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% of the S-enantiomer. In some embodiments, the chiral purity of the Form E of the compound of Formula I as measured by chiral chromatography at 260 nm is about 100%.

In some of the embodiments of the methods of manufacture of the invention, the amorphous form of the compound of Formula I has less than about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, or about 0.009% of any one impurity introduced, obtained or produced as a result of the chemical synthesis, as measured by chromatography at about 220 nm. In some embodiments, the impurity is a by-product of the synthesis.

In some of the embodiments of the methods of manufacture of the invention, crystalline Form A of the compound of Formula I has less than about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, or about 0.009% of any one impurity introduced, obtained or produced as a result of the chemical synthesis, as measured by chromatography at 220 nm. In some embodiments, the impurity is a by-product of the synthesis.

In some of the embodiments of the methods of manufacture of the invention, crystalline Form B of the compound of Formula I has less than about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, or about 0.009% of any one impurity introduced, obtained or produced as a result of the chemical synthesis, as measured by chromatography at about 220 nm. In some embodiments, the impurity is a by-product of the synthesis.

In some of the embodiments of the methods of manufacture of the invention, crystalline Form C of the compound of Formula I has less than about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, or about 0.009% of any one impurity introduced, obtained or produced as a result of the chemical synthesis, as measured by chromatography at 220 nm. In some embodiments, the impurity is a by-product of the synthesis.

In some of the embodiments of the methods of manufacture of the invention, crystalline Form D of the compound of Formula I has less than about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, or about 0.009% of any one impurity introduced, obtained or produced as a result of the chemical synthesis, as measured by chromatography at 220 nm. In some embodiments, the impurity is a by-product of the synthesis.

In some of the embodiments of the methods of manufacture of the invention, crystalline Form E of the compound of Formula I has less than about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, or about 0.009% of any one impurity introduced, obtained or produced as a result of the chemical synthesis, as measured by chromatography at 220 nm. In some embodiments, the impurity is a by-product of the synthesis.

In some of the embodiments of the method of manufacture of the invention, the amorphous form of the compound of Formula I comprises less than about 3.0%, about 2.8%, about 2.6%, about 2.4%, about 2.2%, about 2.1%, about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, or about 0.09% of total impurities introduced, obtained or produced as a results of the chemical synthesis, as measured by chromatography at 220 nm. In some embodiments the impurities comprise a by-product of the chemical synthesis.

In some of the embodiments of the method of manufacture of the invention, crystalline Form A of the compound of Formula I comprises less than about 3.0%, about 2.8%, about 2.6%, about 2.4%, about 2.2%, about 2.1%, about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, or about 0.09% of total impurities introduced, obtained or produced as a results of the chemical synthesis, as measured by chromatography at 220 nm. In some embodiments the impurities comprise a by-product of the chemical synthesis.

In some of the embodiments of the method of manufacture of the invention, crystalline Form B of the compound of Formula I comprises less than about 3.0%, about 2.8%, about 2.6%, about 2.4%, about 2.2%, about 2.1%, about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, or about 0.09% of total impurities introduced, obtained or produced as a results of the chemical synthesis, as measured by chromatography at 220 nm. In some embodiments the impurities comprise a by-product of the chemical synthesis.

In some of the embodiments of the method of manufacture of the invention, cystalline Form C of the compound of Formula I comprises less than about 3.0%, about 2.8%, about 2.6%, about 2.4%, about 2.2%, about 2.1%, about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, or about 0.09% of total impurities introduced, obtained or produced as a results of the chemical synthesis, as measured by chromatography at 220 nm. In some embodiments the impurities comprise a by-product of the chemical synthesis.

In some of the embodiments of the method of manufacture of the invention, crystalline Form D of the compound of Formula I comprises less than about 3.0%, about 2.8%, about 2.6%, about 2.4%, about 2.2%, about 2.1%, about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, or about 0.09% of total impurities introduced, obtained or produced as a results of the chemical synthesis, as measured by chromatography at 220 nm. In some embodiments the impurities comprise a by-product of the chemical synthesis.

In some of the embodiments of the method of manufacture of the invention, crystalline Form E of the compound of Formula I comprises less than about 3.0%, about 2.8%, about 2.6%, about 2.4%, about 2.2%, about 2.1%, about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, about 0.1%, or about 0.09% of total impurities introduced, obtained or produced as a results of the chemical synthesis, as measured by chromatography at 220 nm. In some embodiments the impurities comprise a by-product of the chemical synthesis.

Method of Manufacture of the Compound of Formula I.

The compound of Formula I was synthesized as in the following Schemes 1-6. Two alternative protection schemes in the route were utilized, differing in protecting group strategy for one intermediate. Both variants of this overall route yield superior yields, cost of goods and superior chiral purity compared to previously described methods. The final product of this synthesis yields crystalline Form A directly.

Scheme 1

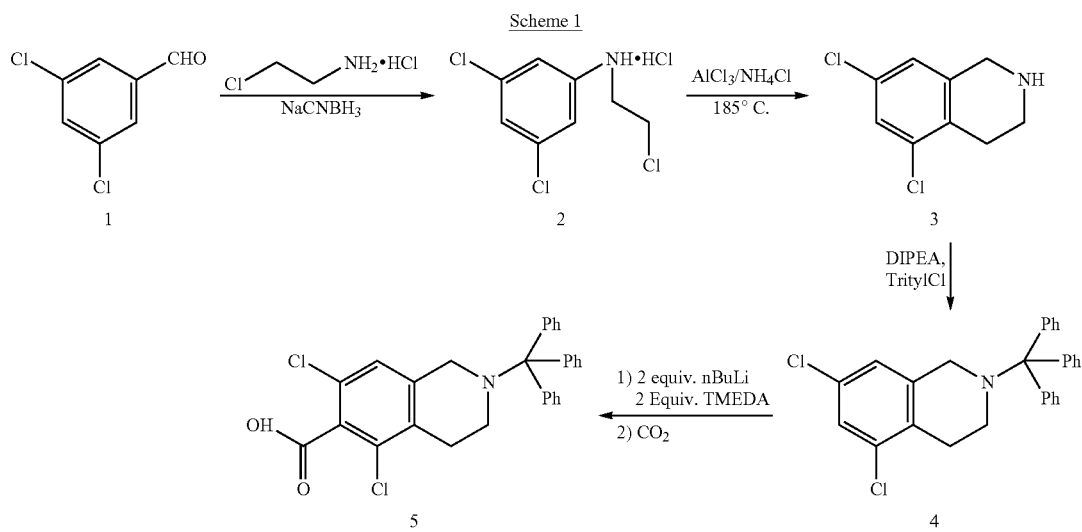

The first alternative protecting strategy produces compound 5, a trityl protected species as shown in Scheme 1. The synthesis begins by reductively aminating 3,5, dichlorobenzaldehyde, compound 1, with 1-chloro-2-aminoethane and sodium cyanoborohydride in 35% yield. Cyclization of compound 2 using aluminum chloride catalysis and ammoniun chloride at 185° C. provided compound 3 in 91% yield. Protection of the free amine of compound 3 as the trityl protected species afforded compound 4 in 89% yield. A carboxylic acid functionality was introduced by treatment of compound 4 with n-butyllithium and Tetramethylethylenediamine (TMEDA), with subsequent introduction of carbon dioxide, to produce compound 5 in 75% yield.

Scheme 2

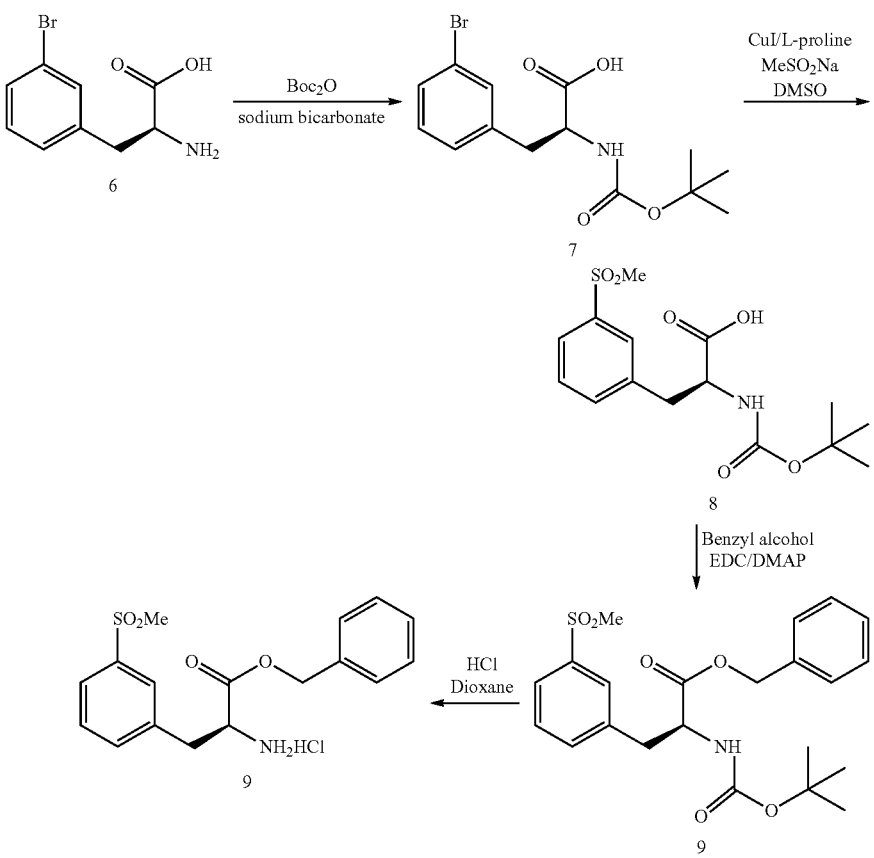

Bromophenylalanine was used as the starting material for the right hand portion of the final molecule as shown in Scheme 2. t-Butylcarbamate (Boc) protection of the amino group was accomplished, using sodium bicarbonate (3 equivalents), t-butyl dicarbonate (Boc₂O, 1.1 equivalent) in dioxane and water, to obtain compound 7 in 98% yield. A N-(3-dimethylaminopropyl)-N-ethylcarbodiimide (EDC, 1.0 equivalent). The amino group of compound 9 is deprotected by adding a 4N solution of HCl in dioxane to compound 9 at 0° C. in methylene chloride. The HCl salt of the free amino species, compound 10 was isolated in 94% yield.

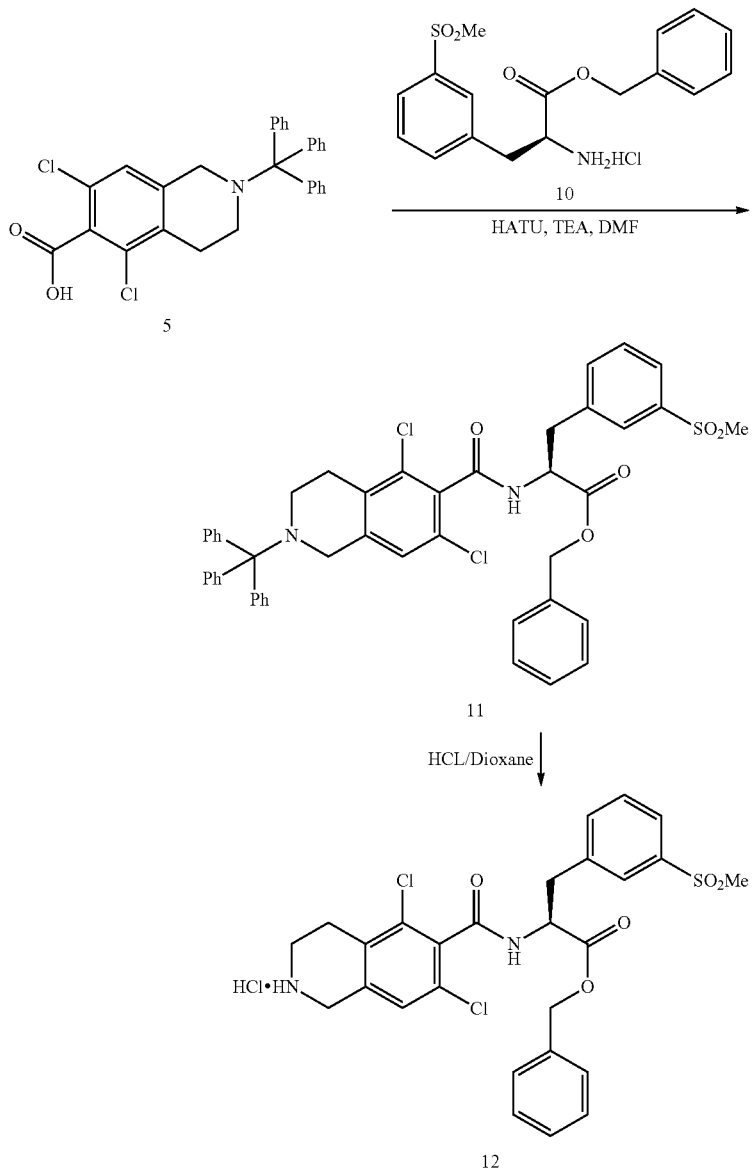

Scheme 3 methyl sulfone functionality was introduced by treating the bromo compound 7 with copper iodide (0.4 equivalents), cesium carbonate (0.5 equivalents), L-proline (0.8 equivalents), and the sodium salt of methanesulfinic acid (3.9 equivalents) in dimethylsulfoxide (DMSO) at 95-100° C. for a total of 9 hours, with two further additions of copper iodide (0.2 equivalents)) and L-proline (0.4 equivalents) during that period. Compound 8 was isolated in 96% yield. The carboxylic acid of compound 8 was converted to the benzyl ester, compound 9, in 99% yield, using benzyl alcohol (1.1 equivalent), dimethylaminopyridine (DMAP, 0.1 equivalent) and Compound 5 was treated with triethylamine (TEA, 5 equivalents) and 2-(7-Aza-1H-benzotriazole-1-yl)-1,1,3,3-tetramethyluronium hexafluorophosphate (HATU, 1.25 equivalents) for 10 minutes in dimethylformamide (DMF), and then compound 10 was added to the solution. After stifling at room temperature for 18 hours, the product, compound 11 was isolated in 70% yield. Removal of the trityl protecting group was accomplished by treating compound 1, with HCL in dioxane (4N, excess) at room temperature for 2 hours, diethyl ether added, and the solid product, compound 12, was isolated by filtration in 95% yield.

Scheme 4

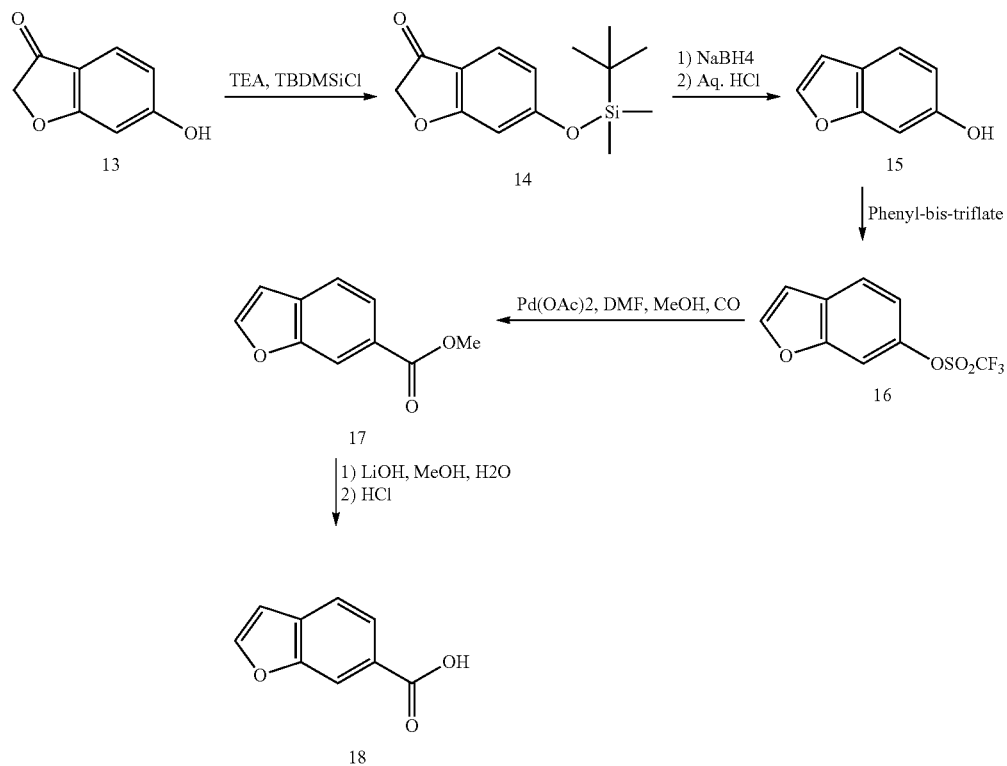

The benzofuranyl carbonyl moiety of the compound of Formula I was prepared by protecting the hydroxyl group of compound 13 by reacting with tert-butyldimethylsilyl chloride (1.0 equivalents) and TEA (1.1 equivalents) in acetone, to give compound 14 in 79% yield. A solution of compound 14 in methanol was then treated with sodium borohydride (1.0 equivalent) at room temperature overnight. The reaction was quenched with an addition of acetone, stirred at room temperature for a further 2.5 hours, aqueous HCl (4N) was added with the temperature controlled to below 28 C., tetrahydrofuran (THF) was added, and the solution stirred overnight under argon and in the absence of light. The product, compound 15, was isolated quantitatively by extraction into methylene chloride, concentrated at low heat, and used without further purification. The triflate ester, compound 16, was produced in 69% yield from compound 15 by reacting it with N-phenyl-bis(trifluoromethanesulfonimide) (1.0 equivalent) in methylene chloride for 72 hours. Compound 16 in a mixture of DMF, methanol, and triethylamine, was added to a prepared solution of palladium acetate, diphenyl, DMF and methanol in an autoclave. Carbon monoxide was charged into the autoclave to a pressure of 8 bar, and the reaction mixture was heated at 70° C. for 6 hours. After workup, compound 17 was isolated in 91% yield. Lithium hydroxide (4 equivalents) in methanol and water was used to hydrolyze the ester and permit the isolation of compound 18 in 97% yield.

Scheme 5

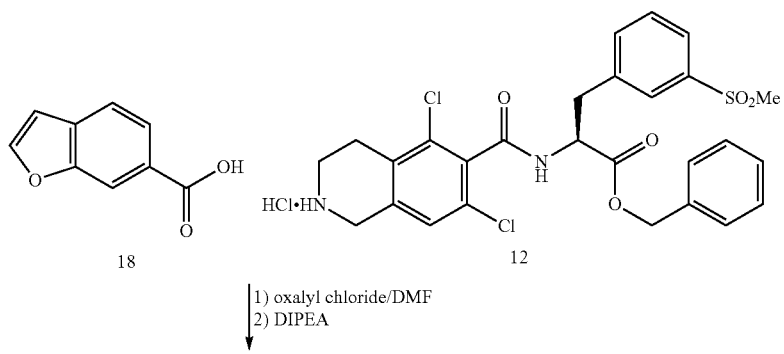

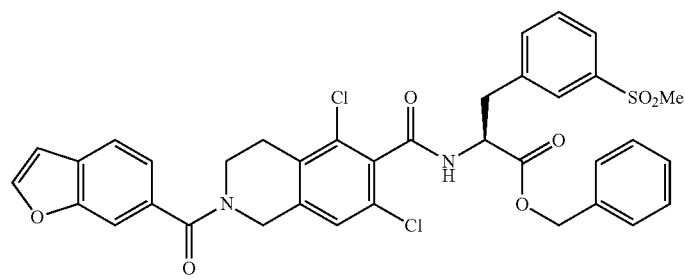

19

10% Pd/C, HCOOH/NEt₃
MeOH/THF 5:1

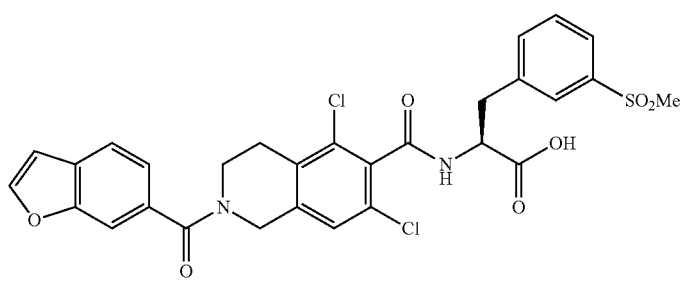

Formula I

MEK/H₂O

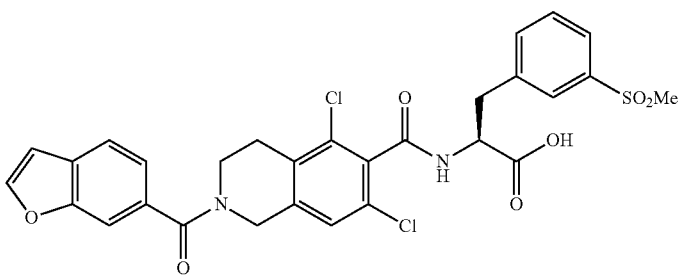

Form A of Formula I

The benzofuran carboxylic acid 18 was treated with oxalyl chloride (1.2 equivalents) and a catalytic amount of DMF, stirring for 5.5 hours until a clear solution was obtained. The solvent was removed under reduced pressure and the acid chloride of compound 18 was stored under argon until use, on the next day. The acid chloride, in methylene chloride was added slowly to a methylene chloride solution of the compound of Formula I and diisopropylethylamine (DIPEA) which was cooled to 0-5° C. The reaction was not permitted to rise above 5° C., and after completion of addition, was stirred at 5° C. for a further 0.5 hour. Upon aqueous workup and extraction with methylene chloride, the product, compound 19, was isolated in quantitative yield. The benzyl ester of compound 19 was removed by transfer hydrogenolysis using 10% palladium on carbon, using formic acid and triethylamine in a 5:1 mixture of methanol:THF, to produce the compound of Formula I in 95% yield. A final step of slurrying in methyl ethylketone (MEK) produced Form A of the compound of Formula I. The product was washed with water to remove residual MEK. Alternatively, the product of the hydrogenolysis step was slurried in acetonitrile yielded Form A of the compound of Formula I.

Taking the compound of Formula I directly as the crude reaction product after transfer hydrogenolysis, and reconcentrating down from a solution in methylene chloride, the amorphous form of the compound of Formula I was obtained in 97% purity.

The alternative protection strategy in this synthetic approach is illustrated in Scheme 6.

Scheme 6

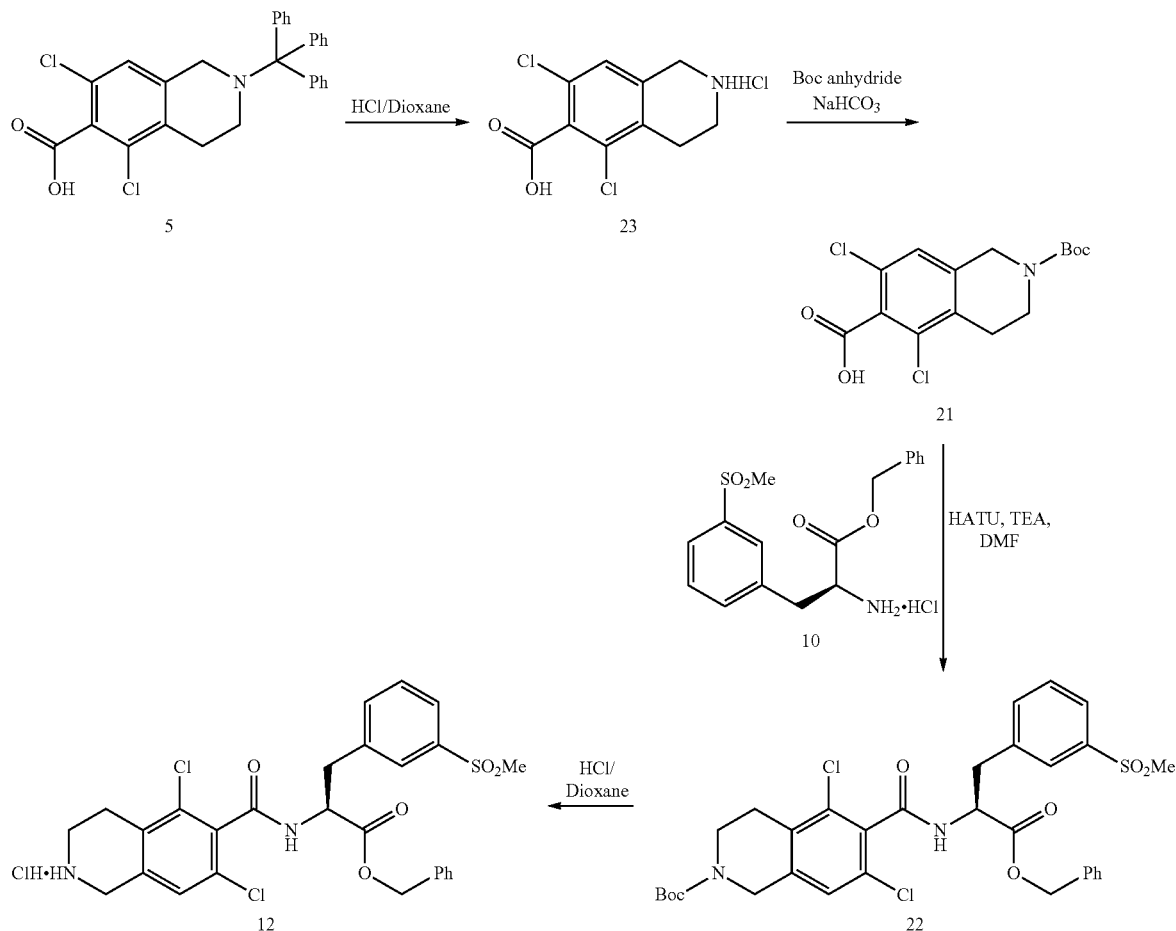

In this alternative approach, Boc-protection was used for the ring nitrogen in the intermediates 20, 21, and 22. Compound 5 was deprotected with HCl in dioxane to produce compound 20 in better than 97% yield. Boc-protection was introduced, using di-tert-butyl dicarbonate (1.1 equivalent), and compound 21 was obtained in better than 95% yield. Compound 10 was coupled with compound 21 to obtain compound 22, using HATU and triethylamine in DMF. The product, compound 22, was obtained in quantitative yield, and greater than 90% purity. Deprotection with HCl yields the compound of Formula I in 97.4% yield and the synthesis rejoins the process described in Scheme 5.

One of the advantages of the foregoing synthesis, is the use of a benzyl ester to protect the carboxylic acid originating in the bromophenylalanine starting material. The resultant transfer hydrogenolysis of compound 19 produces the compound of Formula I with a much higher optical purity (98.5% S enantiomer) than the optical purity obtained (79-94.5% S enantiomer) by hydrolysis of a corresponding methyl ester.

Methods of Use

Diseases and Disorders for which the Amorphous Form or any of the Crystalline Forms A, B, C, D, and E of the Compound of Formula I are Useful.

Not intending to limit the invention by a single mechanism of action, the methods of the present invention involve the inhibition of initiation and progression of inflammation related disease by inhibiting the interaction between LFA-1 and ICAM-1 by administering the amorphous form or any of the crystalline Forms A, B, C, D, or E, or a combination thereof, of the compound of Formula I. In some embodiments, such methods provide anti-inflammatory effects in-vitro and in-vivo, and are useful in the treatment of inflammation mediated diseases.

Formula I

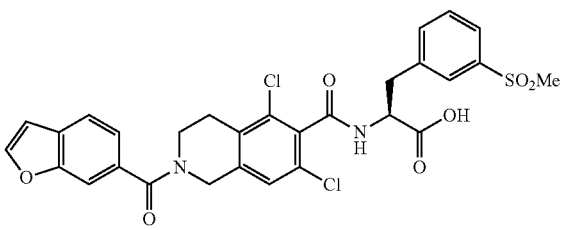

In particular, the amorphous form or any of the crystalline Forms A, B, C, D, or E, or a combination thereof, of the compound of Formula I can modulate inflammation mediated by leukocytes. The amorphous form or any of the crystalline Forms A, B, C, D, or E, or a combination thereof, of the compound of Formula I can be used as a therapeutic agent in any disorder in which antibodies to LFA-1 are shown to be effective. In one embodiment of the invention, a subject is administered the amorphous form or any of the crystalline Forms A, B, C, D, or E, or a combination thereof, of the compound of Formula I to modulate inflammation associated with ocular inflammation. Another embodiment of the methods, a subject with inflammation associated with dry eye syndrome is administered the amorphous form or any of the crystalline Forms A, B, C, D, or E, or a combination thereof, of the compound of Formula I.

One embodiment of the invention provides methods for treating a subject in need thereof for symptoms of dry eye due to allergies, diabetes, lacrimal gland deficiency, lupus, Parkinson's disease, Sjogren's disease, rheumatoid arthritis, or rosaceaby administering the amorphous form or any of the crystalline Forms A, B, C, D, or E, or a combination thereof, of the compound of Formula I. Another embodiment of the invention provides methods for treating a subject in need thereof for symptoms of dry eye disorder due to complications arising from LASIK therapy for vision correction, use of contact lenses, exposure to arid climates, exposure to air pollution, exposure to windy climates, or exposure due to cigarette smoke by administering the amorphous form or any of the crystalline Forms A, B, C, D, or E, or a combination thereof, of the compound of Formula I.

The invention also provides methods for treating a subject in need thereof for symptoms of dry eye disorder due to keratoconjunctivitis sicca, corneal injury, conjunctival fibrosis, age-related dry eye, Stevens-Johnson syndrome, or congenital alachrima, by administering the amorphous form or any of the crystalline Forms A, B, C, D, or E, or a combination thereof, of the compound of Formula I.

In yet other embodiments, methods are providing for treating a subject in need thereof for symptoms of dry eye disorder due to pharmacological side effects of other drugs being taken by the patient by administering the amorphous form or any of the crystalline Forms A, B, C, D, or E, or a combination thereof, of the compound of Formula I. Additionally, methods are provided for treating a subject in need thereof for symptoms of dry eye disorder due to infection by administering the amorphous form or any of the crystalline Forms A, B, C, D, or E, or a combination thereof, of the compound of Formula I in combination with an antibiotic or antimicrobial agent. A subject with symptoms of dry eye disorder due to eye stress, including that due to computer use, may be treated by administering the amorphous form or any of the crystalline Forms A, B, C, D, or E, or a combination thereof, of the compound of Formula I.

Other embodiments of the invention provide methods of treating a subject in need thereof for symptoms of dry eye disorder due to Riley-Day syndrome, glandular and tissue destruction, ocular cicatrical pemphogoid, blepharitis, autoimmune and other immunodeficient disorders, an inability to blink, by administering the amorphous form or any of the crystalline Forms A, B, C, D, or E, or a combination thereof, of the compound of Formula I.

In another aspect of the invention, methods are provided for treating a subject in need thereof for symptoms of psoriasis, of bullous skin diseases, dermatitis, inflammatory bowel disease (including but not limited to Crohn's disease and ulcerative colitis), hidradentitis supperativa, discoid lupus erythrematosus, erythema multiforme, Whipple's disease, or gluten-sensitive enteropathy, by administering the amorphous form or any of the crystalline Forms A, B, C, D, or E, or a combination thereof, of the compound of Formula I.

In other embodiments of the invention, methods are provided for treating a subject in need thereof for symptoms of adult respiratory distress syndrome, pulmonary fibrosis, meningitis, uveitis, eczema, encephalitis, or atopic dermatitis, by administering the amorphous form or any of the crystalline Forms A, B, C, D, or E, or a combination thereof, of the compound of Formula I.

In yet another aspect of the invention, methods are provided for treating a subject in need thereof for symptoms of allergic rhinitis, allergic conjunctivitis, rhinitis, food hypersensitivity, asthma, eczema, or skin hypersensitivity reactions by administering the amorphous form or any of the crystalline Forms A, B, C, D, or E, or a combination thereof, of the compound of Formula I. In other embodiments, methods are provided for treating a subject in need thereof for symptoms of atherosclerosis, rheumatoid arthritis, juvenile chronic arthritis, osteoarthritis, oral lichen planus, systemic lupus erythematosus (SLE) by administering the amorphous form or any of the crystalline Forms A, B, C, D, or E, or a combination thereof, of the compound of Formula I.

Methods of the present invention also include methods for treating a subject in need thereof for symptoms of diabetes mellitus, multiple sclerosis, idiopathic demyelinating polyneuropathy, Guillain-Barre syndrome, Reynaud's syndrome, or autoimmune thrombocytopenia, by administering the amorphous form or any of the crystalline Forms A, B, C, D, or E, or a combination thereof, of the compound of Formula I. In other embodiments of the invention, methods are provided for treating a subject in need thereof for symptoms of thyroiditis, immune mediated renal disease, experimental autoimmune encephalomyelitis, tuberculosis, or sarcoidosis by administering the amorphous form or any of the crystalline Forms A, B, C, D, or E, or a combination thereof, of the compound of Formula I. In some other embodiments of the invention, methods are provided for treating a subject in need thereof for symptoms of polymyositis, granulomatosis, vasculitis, pernicious anemia, by administering the amorphous form or any of the crystalline Forms A, B, C, D, or E, or a combination thereof, of the compound of Formula I.

In another aspect of the invention, methods are provided for treating a subject in need thereof for symptoms of chronic obstructive pulmonary disease (COPD), eosinophilic pneumonias, idiopathic pulmonary fibrosis, hypersensitivity pneumonitis, bronchitis by administering the amorphous form or any of the crystalline Forms A, B, C, D, or E, or a combination thereof, of the compound of Formula I.

Additionally, the invention provides methods for treating a subject in need thereof for symptoms of insulinitis, urticaria, glomerulonephritis, autoimmune chronic active hepatitis, sclerosing cholangitis, diabetic retinopathy, CNS inflammatory disorder, organ injury syndrome secondary to septicaemia or trauma, autoimmune hemolytic anemia, or myasthemia gravis by administering the amorphous form or any of the crystalline Forms A, B, C, D, or E, or a combination thereof, of the compound of Formula I. In other embodiments, methods are provided for treating a subject in need thereof for symptoms of antigen-antibody complex mediated diseases, symptoms of malignancies (e.g., B-cell malignancies such as chronic lymphocytic leukemia or hairy cell leukemia), nephrotic syndrome, chronic lymphocytic leukemia, or hairy cell leukemia by administering the amorphous form or any of the crystalline Forms A, B, C, D, or E, or a combination thereof, of the compound of Formula I.

In yet a further aspect of the invention, methods are provided for treating a subject in need thereof for symptoms of post surgical inflammation of the eye, graft versus host disease (including but not limited to corneal, kidney, or islet cell transplantation), host versus graft disease (including but not limited to corneal, kidney, or islet cell transplantation), or inflammatory response associated with transplantation, by administering the amorphous form or any of the crystalline Forms A, B, C, D, or E, or a combination thereof, of the compound of Formula I. An embodiment of the invention treats a subject with symptoms of HIV and rhinovirus infections by administering the amorphous form or any of the crystalline Forms A, B, C, D, or E, or a combination thereof, of the compound of Formula I.

The amorphous form or any of the crystalline Forms A, B, C, D, or E, or a combination thereof, of the compound of Formula I may be formulated in a manner such that a therapeutically effective amount of the compound of Formula I is delivered only locally, for example, i.e. to the dermis, and a less than therapeutically effective amount of the compound is distributed systemically. Other formulations of the amorphous form or any of the crystalline Forms A, B, C, D, or E, or a combination thereof of the compound of Formula I, may be chosen such that a therapeutically effective amount of the compound of Formula I is delivered systemically.

Pharmaceutical Compositions

In various embodiments of the methods of the invention, the amorphous form or any of the crystalline Forms A, B, C, D, or E, or a combination thereof of the compound of Formula I are administered in pharmaceutical compositions. The pharmaceutical compositions of the invention comprise pharmaceutically acceptable carriers and excipients as well as the amorphous form or any of the crystalline Forms A, B, C, D, or E, or a combination thereof of the compound of Formula I, in order to formulate the composition for appropriate administration to the subject.

In some of the embodiments of the invention, the crystalline form remains in crystalline form in the pharmaceutical composition. In other embodiments, the amorphous form and/or crystalline form is solubilized and is no longer crystalline. In the latter case, however, the superior purity or other physicochemical properties of the amorphous form and/or crystalline form contributes to, i.e., for example, ease of handling the form of the compound of Formula I to form the composition, superior storage capabilities of crystalline form prior to formulation, better therapeutic index, tolerability of the compound of Formula I to the subject, or decreased side effects of the compound of Formula I. The amorphous form or crystalline Forms A, B, C, D, or E may be milled to provide desirable properties for formulation.

Combination of Therapeutic Agents

Combinations of agents can be used to treat LFA-1 mediated disorders or to modulate the side-effects of one or more agents in the combination. Since the pathological events in these disorders may be marked by a combination of impaired autoregulation, apoptosis, ischemia, neovascularization, and inflammatory stimuli, it may be desirable to administer the amorphous form or any of the crystalline Forms A, B, C, D, or E, or a combination thereof of the compound of Formula I in combination with other therapeutic agents to additionally or synergistically intervene. In some embodiments, the second therapeutic agent is an antioxidant, antiinflammatory agent, antiviral agent, antihistamine, mast cell stabilizer, antimicrobial, antiangiogenic agent, and/or anti-apoptotic agent. In some embodiments of the invention, in addition to administering the amorphous form or any of crystalline Forms A, B, C, D, or E, or a combination thereof, of the compound of Formula I which directly competes for binding to LFA-1, an additional therapeutic agent may be administered which is an allosteric, but not a directly competitive, antagonist of LFA-1 as discussed above, potentially resulting in synergistic efficacy. An example of such allosteric antagonist is the class of hydantoin inhibitors of LFA-1.

Another class of therapeutic agents which may be useful to administer in combination, prior to, after, or concomitantly with the amorphous form or any of crystalline Forms A, B, C, D, or E, or a combination thereof, of the compound of Formula I is the group of drugs which inhibit Vascular Endothelial Growth Factor and thus may target another route of initiation of neovascularization. Any VEGF inhibitor may be of use in the compositions of the invention. 1) neutralizing monoclonal antibodies against VEGF or its receptor, 2) small molecule tyrosine kinase inhibitors of VEGF receptors, 3) soluble VEGF receptors which act as decoy receptors for VEGF, and 4) ribozymes which specifically target VEGF. Some examples of antibodies which are active against VEGF are, for example, e.g., Lucentis (ranibizumab), and Avastin (bevacizumab). An example of an oligonucleotide drug is, e.g., Macugen (pegaptanib sodium injection). Small molecule tyrosine kinase inhibitors include, for example, pazopanib, sorafenib, sutent, and the like.

Inflammation may be induced by the process of leukocyte adhesion and neovascularization. Therefore, other anti-inflammatory agents may be administered in combination, prior to, after, or concomitantly with the amorphous form or any of crystalline Forms A, B, C, D, or E, or a combination thereof, of the compound of Formula I. The anti-inflammatory agents can be chosen from corticosteroid related drugs including but not limited to dexamethasone, fluorometholone, medrysone, betamethasone, triamcinolone, triamcinolone acetonide, prednisone, prednisolone, hydrocortisone, rimexolone, and pharmaceutically acceptable salts thereof, prednicarbate, deflazacort, halomethasone, tixocortol, prednylidene, prednival, paramethasone, methylprednisolone, meprednisone, mazipredone, isoflupredone, halopredone acetate, halcinonide, formocortal, flurandrenolide, fluprednisolone, fluprednidine acetate, fluperolone acetate, fluocortolone, fluocortin butyl, fluocinonide, fluocinolone acetonide, flunisolide, flumethasone, fludrocortisone, fluclorinide, enoxolone, difluprednate, diflucortolone, diflorasone diacetate, desoximetasone (desoxymethasone), desonide, descinolone, cortivazol, corticosterone, cortisone, cloprednol, clocortolone, clobetasone, clobetasol, chloroprednisone, cafestol, budesonide, beclomethasone, amcinonide, allopregnane acetonide, alclometasone, 21-acetoxypregnenolone, tralonide, diflorasone acetate, deacylcortivazol, RU-26988, budesonide, deacylcortivazol, and the like. Similarly, the anti-inflammatory agents can be chosen from cyclosporine related drugs (e.g. calcineurin antagonist) including but not limited to members of the cyclosporine family, and other related calineurin antagonists, including sirolimus, tacrolimus, and pimecrolimus. Alternatively, the anti-inflammatory agents can be chosen from the group of NSAIDs including but not limited to acetaminophen, acemetacin, aceclofenac, alminoprofen, amfenac, bendazac, benoxaprofen, bromfenac, bucloxic acid, butibufen, carprofen, celecoxib, cinmetacin, clopirac, diclofenac, etodolac, etoricoxib, felbinac, fenclozic acid, fenbufen, fenoprofen, fentiazac, flunoxaprofen, flurbiprofen, ibufenac, ibuprofen, indomethacin, isofezolac, isoxicam, isoxepac, indoprofen, ketoprofen, lonazolac, loxoprofen, mefenamic acid, meclofenamic acid, meloxicam, metiazinic acid, mofezolac, miroprofen, naproxen, niflumic, oxaprozin, pirozolac, pirprofen, pranoprofen, protizinic acid, rofecoxib, salicylic acid and its derivatives (i.e. for example, asprin), sulindac, suprofen, suxibuzone, triaprofenic acid, tolmetin, valdecoxib, xenbucin, ximoprofen, zaltoprofen, zomepirac, aspirin, acemetcin, bumadizon, carprofenac, clidanac, diflunisal, enfenamic acid, fendosal, flufenamic acid, flunixin, gentisic acid, ketorolac, mesalamine, prodrugs thereof, and the like.

Another class of therapeutic agents which may be useful to administer in combination, prior to, after, or concomitantly with the amorphous form or any of crystalline Forms A, B, C, D, or E, or a combination thereof, of the compound of Formula I is antihistamines, including alkylamine, ethanolamine and phenothiazine classes, such as, for example, chlorpheniramine maleate, chlorphenamiramine tannate, diphenydramine hydrochloride, promethazine hydrochloride, acrivastine, azatadine maleate, azelastine hydrochloride, brompheniramine maleate, carbinoxamine maleate, cetirizine hydrochloride, clemastine fumarate, cyproheptadine hydrochloride, desloratadine, dexbrompheniramine maleate, dexchlorpheniramine maleate, dimenhydriunate, diphenydramine hydrochloride, emedastine difumarate, fexofenadine hydrochloride, hydroxyzine hydrochloride, ketotifen fumarate, loratadine, meclizine hydrochloride, olopatadine hydrochloride, phenindamine tartrate, quetiapine, tripelennamine citrate, tripelennamine hydrochloride, and triprolidine hydrochloride.

Another class of therapeutic agents which may be useful to administer in combination, prior to, after, or concomitantly with the amorphous form or any of crystalline Forms A, B, C, D, or E, or a combination thereof, of the compound of Formula I is mast cell stabilizers such as cromolyn sodium and nedocromil.

Oxidative stress may be induced in cells with impaired autoregulatory processes induced by LFA-1 mediated disorders. Therefore, anti-oxidants may be useful to administer in combination, prior to, after, or concomitantly with the amorphous form or any of crystalline Forms A, B, C, D, or E, or a combination thereof, of the compound of Formula I. Examples of suitable anti-oxidants useful in the methods of the invention include, but are not limited to, ascorbic acid, tocopherols, tocotrienols, carotinoids, glutathione, alpha-lipoic acid, ubiquinols, bioflavonoids, carnitine, and superoxide dismutase mimetics, such as, for example, 2,2,6,6-tetramethyl-1-piperidinyloxy (TEMPO), DOXYL, PROXYL nitroxide compounds; 4-hydroxy-2,2,6,6-tetramethyl-1-piperidinyloxy (Tempol), M-40401, M-40403, M-40407, M-40419, M-40484, M-40587, M-40588, and the like.

In some embodiments of the invention, methods are provided wherein anti-apoptotic therapeutic agents may be administered in combination, prior to, after, or concomitantly with the amorphous form or any of crystalline Forms A, B, C, D, or E, or a combination thereof, of the compound of Formula I. Examples of suitable anti-apoptotic agents are, for example, inhibitors of caspases, cathepsins, and TNF-α.

Another class of therapeutic agents which may be useful to administer in combination, prior to, after, or concomitantly with the amorphous form or any of crystalline Forms A, B, C, D, or E, or a combination thereof, of the compound of Formula I, are antimicrobial agents. Suitable antimicrobial compounds, include, but are not limited to, penicillins, such as, for example, amoxicillin, ampicillin, azlocillin, carbenicillin, cloxacillin, dicloxacillin, flucloxacillin, mezlocillin, nafcillin, penicillin, piperacillin, ticarcillin, and the like; beta-lactamase inhibitors; carbapenems, such as, for example, ertapenem, imipenem, meropenem, and the like; cephalosporins, such as, for example, cefaclor, cefamandole, cefoxitin, cefprozil, cefuroxime, cefixime, cefdinir, cefditoren, cefoperazone, cefotaxime, cefpodoxime, cefadroxil, ceftazidime, ceftibuten, ceftizoxime, ceffriaxone, cefazolin, cefixime, cephalexin, cefepime, and the like; quinolones, such as, for example, ciprofloxacin, enoxacin, gatifloxacin, levofloxacin, lomefloxacin, morifloxacin, norfloxacin, ofloxacin, trovafloxacin, and the like; macrolides, such as, for example, azithromycin, clarithromycin, dirithromycin, erythromycin, milbemycin, troleandomycin, and the like; monbactams, such as, for example, aztreonam, and the like; tetracyclins, such as, for example, demeclocyclin, doxycycline, minocycline, oxytetracyclin, tetracycline, and the like; aminoglycosides, such as, for example, amikacin, gentamicin, kanamycin, neomycin, netilmicin, paromomycin, streptomycin, tobramycin, and the like; carbacephem, such as, for example, loracarbef, and the like; streptogramins; sulfonamides, such as, for example, mefanide, prontosil, sulfacetamide, sulfamethizole, sulfanilamide, sulfasalazine, sulfisoxazole, trimethoprim, trimethoprim-sultamethoxazole, and the like; and the combination drugs such as for example, sulfamethoxazole and trimethoprim, and the like; and polypeptides, such as, for example, bacitracin, colistin, polymyxin B, and the like.

Examples of other therapeutic agents which may be useful to administer in combination, prior to, after, or concomitantly with the amorphous form or any of crystalline Forms A, B, C, D, or E, or a combination thereof, of the compound of Formula I, include, but are not limited to: (a) anti-diabetic agents such as insulin and insulin mimetics, sulfonylureas (e.g., glyburide, meglinatide), biguanides, e.g., metformin (Glucophage®), .alpha-glucosidase inhibitors (acarbose), insulin sensitizers, e.g., thiazolidinone compounds, rosiglitazone (Avandia®), troglitazone (Rezulin®) ciglitazone, pioglitazone (Actos®) and englitazone; (b) cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fabric acid derivatives (e.g., gemfibrozil, clofibrate, fenofibrate and benzafibrate), probucol, nitroglycerin, and inhibitors of cholesterol absorption (e.g., beta-sitosterol and acyl-CoA-cholesterol acyltransferase (ACAT) inhibitors such as melinamide), HMG-CoA synthase inhibitors, squalene epoxidase inhibitors and squalene synthetase inhibitors; and (c) antithrombotic agents, such as thrombolytic agents (e.g., streptokinase, alteplase, anistreplase and reteplase), heparin, hirudin and warfarin derivatives, beta-blockers (e.g., atenolol), beta-adrenergic agonists (e.g., isoproterenol), ACE inhibitors and vasodilators (e.g., sodium nitroprusside, nicardipine hydrochloride, nitroglycerin and enaloprilat).

Examples of other therapeutic agents which may be useful to administer in combination, prior to, after, or concomitantly with the amorphous form or any of crystalline Forms A, B, C, D, or E, or a combination thereof, of the compound of Formula I, are antiviral agents, which include, but are not limited to therapeutic agents such as entry inhibitors, reverse transcriptase inhibitors, nucleoside or nucleotide analogs, protease inhibitors, and inhibitors of viral release from host cells. Some illustrative therapeutic agents of this group, include, but are not limited to abacavir, acyclovir, adefovir, amantadine, amprenavir, arbidol, atazanavir, atripla, brivudine, cidofovir, combivir, darunavir, delavirdine, didanosine, docosanol, edoxudine, efavirenz, emtricitabine, enfuvirtide, entecavir, famciclovir, fomivirsen, foscarnet, fosfonet, ganciclovir, gardasil, ibacitabine, immunovir, idoxuridine, imiquimod, indinavir, inosine, interferon type III, interferon type II, interferon type I, interferon, lamivudine, lopinavir, loviride, maraviroc, moroxydine, nelfinavir, neviapine, nexavir, oseltamivir, penciclovir, peramivir, pleconaril, podophyllotoxin, raltegravir, ribavirin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

In some of the embodiments of the invention, the formulations administered to the skin comprise one or more antimicrobial or antibiotic agents.

Secretagogues may also be administered in combination, prior to, concomitantly with, or subsequent to administration of the LFA-1 antagonist. Increasing mucin or other fluid production in the eye may be beneficial. Examples include but are not limited to Diquafasol, Rebamipide, and Eicosanoid 15-(S)-HETE.

Additionally, lubricants may be administered in combination, prior to, concomitantly with, or subsequent to ocular administration of the LFA-1 antagonist. Examples include but are not limited to Refresh Dry Eye Therapy® and other lubricating eye drops.

Administration

Administration of a pharmaceutical composition comprising the amorphous form or any of crystalline Forms A, B, C, D, or E, or a combination thereof, of the compound of Formula I may be by any suitable means. In some embodiments, a pharmaceutical composition comprising the amorphous form or any of crystalline Forms A, B, C, D, or E, or a combination thereof, of the compound of Formula I, is administered by oral, transdermal, by injection, slow release intraocular implantation, aerosol administration.

In another aspect of the invention, a pharmaceutical composition comprising the amorphous form or any of crystalline Forms A, B, C, D, or E, or a combination thereof, of the compound of Formula I, is administered locally to achieve therapeutically effective concentration locally and does not distribute systemically at pharmacologically effective concentrations, which may be by oral, transdermal, depot, injection, ocular insert, instillation, inhalation, or pump administration. In other embodiments, a pharmaceutical composition comprising the amorphous form or any of crystalline Forms A, B, C, D, or E, or a combination thereof, of the compound of Formula I, is administered locally with a sustained release profile to achieve therapeutically effective concentration locally and does not distribute systemically at pharmacologically effective concentrations, which may be by oral, transdermal, depot, injection, ocular insert, instillation, inhalation, or pump administration. In yet other embodiments, a pharmaceutical composition comprising the amorphous form or any of crystalline Forms A, B, C, D, or E, or a combination thereof, of the compound of Formula I, is administered orally, transdermally, via periocular implant, or via suppository with a slow release profile. Alternatively, a pharmaceutical composition comprising the amorphous form or any of crystalline Forms A, B, C, D, or E, or a combination thereof, of the compound of Formula I, is administered topically.

In some embodiments, a pharmaceutical composition comprising the amorphous form or any of crystalline Forms A, B, C, D, or E, or a combination thereof, of the compound of Formula I, have a clearance rate of at least 5% of hepatic blood flow. In humans, this would mean a clearance rate of 1 mL/min/kg. In other embodiments, a pharmaceutical composition comprising the amorphous form or any of crystalline Forms A, B, C, D, or E, or a combination thereof, of the compound of Formula I, have a clearance rate of at least about 10%, 20%, 30%, 40%, 50%, 60%, 70%, 80%, 90% or about 100% of hepatic blood flow rate in humans (which would be a clearance rate in human liver of 20 mL/min/kg). In yet other embodiments, a pharmaceutical composition comprising the amorphous form or any of crystalline Forms A, B, C, D, or E, or a combination thereof, of the compound of Formula I, may have a clearance rate of at least about 110%, 120%, 130%, 140%, 150%, 175%, 200%, 220%, 240%, 260%, 280%, 300%, 320%, 340%, 360%, 380%, 400%, 420%, 440%, 460%, 480%, or 500% of hepatic blood flow rate in humans.

The clearance rates of a pharmaceutical composition comprising the amorphous form or any of crystalline Forms A, B, C, D, or E, or a combination thereof, of the compound of Formula I, may include clearance rates scaled to humans of approximately 1-500 mL/min/kg. In some embodiments a pharmaceutical composition comprising the amorphous form or any of crystalline Forms A, B, C, D, or E, or a combination thereof, of the compound of Formula I, may have a systemic clearance rate of approximately 1 mL/min/kg or greater. In other embodiments, a pharmaceutical composition comprising the amorphous form or any of crystalline Forms A, B, C, D, or E, or a combination thereof, of the compound of Formula I, may have a systemic clearance rate of approximately 2 mL/min/kg or greater. In other embodiments, a pharmaceutical composition comprising the amorphous form or any of crystalline Forms A, B, C, D, or E, or a combination thereof, of the compound of Formula I, may have a systemic clearance rate of approximately 3 mL/min/kg or greater. In other embodiments, a pharmaceutical composition comprising the amorphous form or any of crystalline Forms A, B, C, D, or E, or a combination thereof, of the compound of Formula I, may have a systemic clearance rate of approximately 5 mL/min/kg or greater. In other embodiments, the compositions of the invention may have a systemic clearance rate of approximately 7 mL/min/kg or greater. In some embodiments, a pharmaceutical composition comprising the amorphous form or any of crystalline Forms A, B, C, D, or E, or a combination thereof, of the compound of Formula I, may have a systemic clearance rate of approximately 10 mL/min/kg or greater. In other embodiments, a pharmaceutical composition comprising the amorphous form or any of crystalline Forms A, B, C, D, or E, or a combination thereof, of the compound of Formula I, may have a systemic clearance rate of approximately 15 mL/min/kg or greater. In other embodiments a pharmaceutical composition comprising the amorphous form or any of crystalline Forms A, B, C, D, or E, or a combination thereof, of the compound of Formula I, may have a systemic clearance rate of approximately 20 mL/min/kg or greater. In other embodiments, a pharmaceutical composition comprising the amorphous form or any of crystalline Forms A, B, C, D, or E, or a combination thereof, of the compound of Formula I, may have a systemic clearance rate of approximately 25 mL/min/kg or greater. In some embodiments, a pharmaceutical composition comprising the amorphous form or any of crystalline Forms A, B, C, D, or E, or a combination thereof, of the compound of Formula I, may have a systemic clearance rate of approximately 30 mL/min/kg or greater. In some embodiments, a pharmaceutical composition comprising the amorphous form or any of crystalline Forms A, B, C, D, or E, or a combination thereof, of the compound of Formula I, may have a systemic clearance rate of approximately 40 mL/min/kg or greater. In other embodiments, a pharmaceutical composition comprising the amorphous form or any of crystalline Forms A, B, C, D, or E, or a combination thereof, of the compound of Formula I, may have a systemic clearance rate of approximately 50 mL/min/kg or greater. In yet other embodiments, a pharmaceutical composition comprising the amorphous form or any of crystalline Forms A, B, C, D, or E, or a combination thereof, of the compound of Formula I, may have a systemic clearance rate of at least about 60, 65, 70, 75, 80, 85, 90, 95, or 100 mL/min/kg.

If additional therapeutic agents are administered as separate compositions, they may be administered by the same route or by different routes. If additional therapeutic agents are administered in a single pharmaceutical composition with the amorphous form or any of crystalline Forms A, B, C, D, or E, or a combination thereof, of the compound of Formula I, it may be administered by any suitable route, including but not limited to oral, transdermal, injection, or topically.

In some embodiments, a pharmaceutical composition comprising the amorphous form or any of crystalline Forms A, B, C, D, or E, or a combination thereof, of the compound of Formula I is administered in a single dose. A single dose of a pharmaceutical composition comprising the amorphous form or any of crystalline Forms A, B, C, D, or E, or a combination thereof, of the compound of Formula I may also be used when it is co-administered with another substance (e.g., an analgesic) for treatment of an acute condition.

In some embodiments, a pharmaceutical composition comprising the amorphous form or any of crystalline Forms A, B, C, D, or E, or a combination thereof, of the compound of Formula I is administered in multiple doses. Dosing may be about once, twice, three times, four times, five times, six times, seven times, eight times, nine times, ten times or more than ten times per day. Dosing may be about once a year, twice a year, every six months, every 4 months, every 3 months, every 60 days, once a month, once every two weeks, once a week, or once every other day. In another embodiment the administration of the pharmaceutical composition comprising the amorphous form or any of crystalline Forms A, B, C, D, or E, or a combination thereof, of the compound of Formula I, continues for less than about 7 days. In yet another embodiment the administration continues for more than about 6, 10, 14, 28 days, two months, six months, or one year. In some cases, dosing is maintained as long as necessary, e.g., dosing for chronic inflammation.

In another embodiment, a pharmaceutical composition comprising the amorphous form or any of crystalline Forms A, B, C, D, or E, or a combination thereof, of the compound of Formula I, is administered in combination with another therapeutic agent about once per day to about 10 times per day. In another embodiment the co-administration of the pharmaceutical composition comprising the amorphous form or any of crystalline Forms A, B, C, D, or E, or a combination thereof, of the compound of Formula I, with another therapeutic substance continues for less than about 7 days. In yet another embodiment the co-administration continues for more than about 6, 10, 14, 28 days, two months, six months, or one year. In some cases, co-administered dosing is maintained as long as necessary, e.g., dosing for chronic inflammation. In some embodiments, the co-administration is in the same composition.

In another embodiment, the co-administration is in separate pharmaceutical compositions. In some embodiments, the co-administration is concomitant. In some embodiments, the administration of the second therapeutic agent is before the administration of the pharmaceutical composition comprising the amorphous form or any of crystalline Forms A, B, C, D, or E, or a combination thereof, of the compound of Formula I. In some embodiments, the administration of the second therapeutic agent is after the administration of the pharmaceutical composition comprising the amorphous form or any of crystalline Forms A, B, C, D, or E, or a combination thereof, of the compound of Formula I. In one embodiment, the second therapeutic agent is an analgesic, antibiotic, or antihistamine.

In some embodiments, the amorphous form or any of crystalline Forms A, B, C, D, or E, or a combination thereof, of the compound of Formula I, is present in an amount sufficient to exert a therapeutic effect to reduce symptoms of an immune related disorder by an average of at least about 5, 10, 15, 20, 25, 30, 40, 50, 60, 70, 80, 90, more than 90%, or substantially eliminate symptoms of the immune related disorder. For many inflammatory diseases, there are well recognized clinical assessments of therapeutic effect (e.g. PASI score for psoriasis and EASI score for eczema).

In some embodiments, the amorphous form or any of crystalline Forms A, B, C, D, or E, or a combination thereof, of the compound of Formula I, is present in an amount sufficient to decrease neovascularization and erythema in a treated individual by an average of at least about 5, 10, 15, 20, 25, 30, 40, 50, 60, 70, 80, 90, more than 90%, or substantially eliminate neovascularization.

In some embodiments, the amorphous form or any of crystalline Forms A, B, C, D, or E, or a combination thereof, of the compound of Formula I, is present in an amount sufficient to decrease fibrovascular growth of an individual by an average of at least about 5, 10, 15, 20, 25, 30, 40, 50, 60, 70, 80, 90, more than 90%, or substantially eliminate fibrovascular growth.

Administration of the compositions of the invention may continue as long as necessary. In some embodiments, a composition of the invention is administered for more than 1, 2, 3, 4, 5, 6, 7, 14, or 28 days. In some embodiments, a composition of the invention is administered for less than 28, 14, 7, 6, 5, 4, 3, 2, or 1 day. In some embodiments, a composition of the invention is administered chronically on an ongoing basis, e.g., for the treatment of chronic pain.

In some embodiments, the composition of the invention delivers a therapeutically effective amount of the amorphous form or any of crystalline Forms A, B, C, D, or E, or a combination thereof, of the compound of Formula I locally and not systemically. In other embodiments, the composition of the invention delivers a therapeutically effective amount of the amorphous form or any of crystalline Forms A, B, C, D, or E, or a combination thereof, of the compound of Formula I systemically.

Dosing for the amorphous form or any of crystalline Forms A, B, C, D, or E, or a combination thereof, of the compound of Formula I, in the methods of the invention may be found by routine experimentation. The daily dose can range from about $1 \times 10^{-10}$ g to 5000 mg. Daily dose range may depend on the form of form of the compound of Formula I e.g., the esters or salts used, and/or route of administration, and/or solubility of the specific amorphous or crystalline form as described herein. For example, for systemic administration, typical daily dose ranges are, e.g. about 1-5000 mg, or about 1-3000 mg, or about 1-2000 mg, or about 1-1000 mg, or about 1-500 mg, or about 1-100 mg, or about 10-5000 mg, or about 10-3000 mg, or about 10-2000 mg, or about 10-1000 mg, or about 10-500 mg, or about 10-200 mg, or about 10-100 mg, or about 20-2000 mg or about 20-1500 mg or about 20-1000 mg or about 20-500 mg, or about 20-100 mg, or about 50-5000 mg, or about 50-4000 mg, or about 50-3000 mg, or about 50-2000 mg, or about 50-1000 mg, or about 50-500 mg, or about 50-100 mg, about 100-5000 mg, or about 100-4000 mg, or about 100-3000 mg, or about 100-2000 mg, or about 100-1000 mg, or about 100-500 mg. In some embodiments, the daily dose of the amorphous form or any of crystalline Forms A, B, C, D, or E, or a combination thereof, of the compound of Formula I is about 100, 200, 300, 400, 500, 600, 700, 800, 900, or 1000 mg. In some embodiments, the daily dose of the amorphous form or any of crystalline Forms A, B, C, D, or E, or a combination thereof, of the compound of Formula I is 0.1 mg. In some embodiments, the daily dose of the amorphous form or any of crystalline Forms A, B, C, D, or E, or a combination thereof, of the compound of Formula I is 1.0 mg. In some embodiments, the daily dose of the amorphous form or any of crystalline Forms A, B, C, D, or E, or a combination thereof, of the compound of Formula I is 10 mg. In some embodiments, the daily dose of the amorphous form or any of crystalline Forms A, B, C, D, or E, or a combination thereof, of the compound of Formula I is 100 mg. In some embodiments, the daily dose of the amorphous form or any of crystalline Forms A, B, C, D, or E, or a combination thereof, of the compound of Formula I is 500 mg. In some embodiments, the daily dose of the amorphous form or any of crystalline Forms A, B, C, D, or E, or a combination thereof, of the compound of Formula I is 1000 mg.

In some embodiments, the amorphous form or any of crystalline Forms A, B, C, D, or E, or a combination thereof, of the compound of Formula I is present in an amount sufficient to exert a therapeutic effect to reduce symptoms of a disorder mediated by LFA-1, by an average of at least about 5, 10, 15, 20, 25, 30, 40, 50, 60, 70, 80, 90, more than 90%, or substantially eliminate symptoms of the disorder mediated by LFA-1.

In some embodiments, an effective amount of the amorphous form or any of crystalline Forms A, B, C, D, or E, or a combination thereof, of the compound of Formula I is a daily dose of about $1 \times 10^{-11}$, $1 \times 10^{-10}$, $1 \times 10^{-9}$, $1 \times 10^{-8}$, $1 \times 10^{-7}$, $1 \times 10^{-6}$, $1 \times 10^{-5}$, $1 \times 10^{-4}$, $1 \times 10^{-3}$, $1 \times 10^{-2}$, $1 \times 10^{-1}$, $1 \times 10^{1}$, $1 \times 10^{2}$ grams.

For topical delivery to the ocular surface, the typical daily dose ranges are, e.g. about $1 \times 10^{-10}$ g to 5.0 g, or about $1 \times 10^{-10}$ g to 2.5 g, or about $1 \times 10^{-10}$ g to 1.00 g, or about $1 \times 10^{-10}$ g to 0.5 g, or about $1 \times 10^{-10}$ g to 0.25 g, or about $1 \times 10^{-10}$ g to 0.1 g, or about $1 \times 10^{-10}$ g to 0.05 g, or about $1 \times 10^{-10}$ g to 0.025 g, or about $1 \times 10^{-10}$ g to $1 \times 10^{-2}$ g, or about $1 \times 10^{-10}$ g to $5 \times 10^{-3}$ g, or about $1 \times 10^{-10}$ g to $2.5 \times 10^{-3}$ g, or about $1 \times 10^{-10}$ g to $1 \times 10^{-3}$ g, or about $1 \times 10^{-10}$ g to $5 \times 10^{-4}$ g, or $1 \times 10^{-10}$ g to $2.5 \times 10^{-4}$ g, or about $1 \times 10^{-10}$ g to $1 \times 10^{-4}$ g, or about $1 \times 10^{-10}$ g to $5 \times 10^{-5}$ g, or $1 \times 10^{-10}$ g to $2.5 \times 10^{-5}$ g, or about $1 \times 10^{-10}$ g to $1 \times 10^{-5}$ g, or about $1 \times 10^{-10}$ g to $5 \times 10^{-6}$ g, or about $1 \times 10^{-9}$ g to 1.00 g, or about $1 \times 10^{-9}$ g to 0.5 g, or about $1 \times 10^{-9}$ g to 0.25 g, or about $1 \times 10^{-9}$ g to 0.1 g, or about $1 \times 10^{-9}$ g to 0.05 g, or about $1 \times 10^{-9}$ g to 0.025 g, or about $1 \times 10^{-9}$ g to $1 \times 10^{-2}$ g, or about $1 \times 10^{-9}$ g to $5 \times 10^{-3}$ g, or about $1 \times 10^{-9}$ g to $2.5 \times 10^{-3}$ g, or about $1 \times 10^{-9}$ g to $1 \times 10^{-3}$ g, or about $1 \times 10^{-9}$ g to $5 \times 10^{-4}$ g, or about $1 \times 10^{-8}$ g to 5.0 g, or about $1 \times 10^{-8}$ g to 2.5 g, or about $1 \times 10^{-8}$ g to 1 g, or about $1 \times 10^{-8}$ g to 0.5 g, or about $1 \times 10^{-8}$ g to 0.25 g, or about $1 \times 10^{-8}$ g to 0.1 g, or about $1 \times 10^{-8}$ g to $5 \times 10^{-2}$ g, or about $1 \times 10^{-8}$ to $5 \times 10^{-2}$ g, or about $1 \times 10^{-8}$ g to $2.5 \times 10^{-2}$ g, or about $1 \times 10^{-8}$ g to $1 \times 10^{-2}$ g, or about $1 \times 10^{-8}$ g to $5 \times 10^{-3}$ g, or about $1 \times 10^{-8}$ to $2.5 \times 10^{-3}$ g, or about $1 \times 10^{-8}$ g to $1 \times 10^{-3}$ g, or about $1 \times 10^{-8}$ to $5 \times 10^{-4}$ g, or about $1 \times 10^{-7}$ g to 5.0 g, or about $1 \times 10^{-7}$ g to 2.5 g, or about $1 \times 10^{-7}$ g to 1 g, or about $1 \times 10^{-7}$ g to 0.5 g, or about $1 \times 10^{-7}$ g to 0.25 g, or about $1 \times 10^{-7}$ g to 0.1 g, or about $1 \times 10^{-7}$ g to $5 \times 10^{-2}$ g, or about $1 \times 10^{-7}$ to $5 \times 10^{-2}$ g, or about $1 \times 10^{-7}$ g to $2.5 \times 10^{-2}$ g, or about $1 \times 10^{-7}$ g to $1 \times 10^{-2}$ g, or about $1 \times 10^{-7}$ g to $5 \times 10^{-3}$ g, or about $1 \times 10^{-7}$ to $2.5 \times 10^{-3}$ g, or about $1 \times 10^{-7}$ g to $1 \times 10^{-3}$ g, or about $1 \times 10^{-7}$ to $5 \times 10^{-4}$ g, or about $1 \times 10^{-6}$ g to 5.0 g, or about $1 \times 10^{-6}$ g to 2.5 g, or about $1 \times 10^{-6}$ g to 1 g, or about $1 \times 10^{-6}$ g to 0.5 g, or about $1 \times 10^{-6}$ g to 0.25 g, or about $1 \times 10^{-6}$ g to 0.1 g, or about $1 \times 10^{-6}$ g to $5 \times 10^{-2}$ g, or about $1 \times 10^{-6}$ to $5 \times 10^{-2}$ g, or about $1 \times 10^{-6}$ g to $2.5 \times 10^{-2}$ g, or about $1 \times 10^{-6}$ g to $1 \times 10^{-2}$ g, or about $1 \times 10^{-6}$ g to $5 \times 10^{-3}$ g, or about $1 \times 10^{-6}$ to $2.5 \times 10^{-3}$ g, or about $1 \times 10^{-6}$ g to $1 \times 10^{-3}$ g, or about $1 \times 10^{-6}$ g to $5 \times 10^{-4}$ g, or about $1 \times 10^{-5}$ g to 5 g, or about $1 \times 10^{-5}$ g to 2.5 g, or about $1 \times 10^{-5}$ g to 1 g, or about $1 \times 10^{-5}$ g to 0.5 g, or about $1 \times 10^{-5}$ g to 0.25 g, or about $1 \times 10^{-5}$ g to 0.1 g, or about $1 \times 10^{-5}$ g to 0.05 g, or about $1 \times 10^{-5}$ g to $2.5 \times 10^{-2}$ g, or about $1 \times 10^{-5}$ g to $1 \times 10^{-2}$ g, or about $1 \times 10^{-5}$ g to $5 \times 10^{-3}$ g, or about $1 \times 10^{-5}$ g to $2.5 \times 10^{-3}$ g, or about $1 \times 10^{-5}$ g to $1 \times 10^{-3}$ g, or about $1 \times 10^{-5}$ g to $5 \times 10^{-4}$ g.

In some embodiments, the daily dose of the amorphous form or any of crystalline Forms A, B, C, D, or E, or a combination thereof, of the compound of Formula I is about $1 \times 10^{-10}$, about $1 \times 10^{-9}$, about $1 \times 10^{-8}$, about $1 \times 10^{-7}$, about $1 \times 10^{-6}$, about $1 \times 10^{-5}$, about $1 \times 10^{-4}$, about $1 \times 10^{-3}$ g, about $1 \times 10^{-2}$ g, about $1 \times 10^{1}$ g, or about 1 g. In some embodiments, the daily dose of the amorphous form or any of crystalline Forms A, B, C, D, or E, or a combination thereof, of the compound of Formula I is about $1 \times 10^{-10}$ g. In some embodiments, the daily dose of the amorphous form or any of crystalline Forms A, B, C, D, or E, or a combination thereof, of the compound of Formula I is about $1 \times 10^{-9}$ g. In some embodiments, the daily dose of the amorphous form or any of crystalline Forms A, B, C, D, or E, or a combination thereof, of the compound of Formula I is about $1 \times 10^{-8}$ g. In some embodiments, the daily dose of the amorphous form or any of crystalline Forms A, B, C, D, or E, or a combination thereof, of the compound of Formula I is about $1 \times 10^{-7}$ g. In some embodiments, the daily dose of the amorphous form or any of crystalline Forms A, B, C, D, or E, or a combination thereof, of the compound of Formula I, is about $1 \times 10^{-5}$ g. In some embodiments, the daily dose of the amorphous form or any of crystalline Forms A, B, C, D, or E, or a combination thereof, of the compound of Formula I, is about $1 \times 10^{-3}$ g. In some embodiments, the daily dose of the amorphous form or any of crystalline Forms A, B, C, D, or E, or a combination thereof, of the compound of Formula I, is about $1 \times 10^{-2}$ g. In some embodiments the individual dose ranges from about $1 \times 10^{-10}$ g to 5.0 g, or about $1 \times 10^{-10}$ g to 2.5 g, or about $1 \times 10^{-10}$ g to 1.00 g, or about $1 \times 10^{-10}$ g to 0.5 g, or about $1 \times 10^{-10}$ g to 0.25 g, or about $1 \times 10^{-10}$ g to 0.1 g, or about $1 \times 10^{-10}$ g to 0.05 g, or about $1 \times 10^{-10}$ g to 0.025 g, or about $1 \times 10^{-10}$ g to $1 \times 10^{-2}$ g, or about $1 \times 10^{-10}$ g to $5 \times 10^{-3}$ g, or about $1 \times 10^{-10}$ g to $2.5 \times 10^{-3}$ g, or about $1 \times 10^{-10}$ g to $1 \times 10^{-3}$ g, or about $1 \times 10^{-10}$ g to $5 \times 10^{-4}$ g, or $1 \times 10^{-10}$ g to $2.5 \times 10^{-4}$ g, or about $1 \times 10^{-10}$ g to $1 \times 10^{-4}$ g, or about $1 \times 10^{-10}$ g to $5 \times 10^{-5}$ g, or $1 \times 10^{-10}$ g to $2.5 \times 10^{-5}$ g, or about $1 \times 10^{-10}$ g to $1 \times 10^{-5}$ g, or about $1 \times 10^{-10}$ g to $5 \times 10^{-6}$ g, or about $1 \times 10^{-9}$ g to 1.00 g, or about $1 \times 10^{-9}$ g to 0.5 g, or about $1 \times 10^{-9}$ g to 0.25 g, or about $1 \times 10^{-9}$ g to 0.1 g, or about $1 \times 10^{-9}$ g to 0.05 g, or about $1 \times 10^{-9}$ g to 0.025 g, or about $1 \times 10^{-9}$ g to $1 \times 10^{-2}$ g, or about $1 \times 10^{-9}$ g to $5 \times 10^{-3}$ g, or about $1 \times 10^{-9}$ g to $2.5 \times 10^{-3}$ g, or about $1 \times 10^{-9}$ g to $1 \times 10^{-3}$ g, or about $1 \times 10^{-9}$ g to $5 \times 10^{-4}$ g, or about $1 \times 10^{-8}$ g to 5.0 g, or about $1 \times 10^{-8}$ g to 2.5 g, or about $1 \times 10^{-8}$ g to 1 g, or about $1 \times 10^{-8}$ g to 0.5 g, or about $1 \times 10^{-8}$ g to 0.25 g, or about $1 \times 10^{-8}$ g to 0.1 g, or about $1 \times 10^{-8}$ g to $5 \times 10^{-2}$ g, or about $1 \times 10^{-8}$ to $5 \times 10^{-2}$ g, or about $1 \times 10^{-8}$ g to $2.5 \times 10^{-2}$ g, or about $1 \times 10^{-8}$ g to $1 \times 10^{-2}$ g, or about $1 \times 10^{-8}$ g to $5 \times 10^{-3}$ g, or about $1 \times 10^{-8}$ to $2.5 \times 10^{-3}$ g, or about $1 \times 10^{-8}$ g to $1 \times 10^{-3}$ g, or about $1 \times 10^{-8}$ g to $5 \times 10^{-4}$ g, or about $1 \times 10^{-7}$ g to 5.0 g, or about $1 \times 10^{-7}$ g to 2.5 g, or about $1 \times 10^{-7}$ g to 1 g, or about $1 \times 10^{-7}$ g to 0.5 g, or about $1 \times 10^{-7}$ g to 0.25 g, or about $1 \times 10^{-7}$ g to 0.1 g, or about $1 \times 10^{-7}$ g to $5 \times 10^{-2}$ g, or about $1 \times 10^{-7}$ to $5 \times 10^{-2}$ g, or about $1 \times 10^{-7}$ g to $2.5 \times 10^{-2}$ g, or about $1 \times 10^{-7}$ g to $1 \times 10^{-2}$ g, or about $1 \times 10^{-7}$ g to $5 \times 10^{-3}$ g, or about $1 \times 10^{-7}$ to $2.5 \times 10^{-3}$ g, or about $1 \times 10^{-7}$ g to $1 \times 10^{-3}$ g, or about $1 \times 10^{-7}$ to $5 \times 10^{-4}$ g, or about $1 \times 10^{-6}$ g to 5.0 g, or about $1 \times 10^{-6}$ g to 2.5 g, or about $1 \times 10^{-6}$ g to 1 g, or about $1 \times 10^{-6}$ g to 0.5 g, or about $1 \times 10^{-6}$ g to 0.25 g, or about $1 \times 10^{-6}$ g to 0.1 g, or about $1 \times 10^{-6}$ g to $5 \times 10^{-2}$ g, or about $1 \times 10^{-6}$ to $5 \times 10^{-2}$ g, or about $1 \times 10^{-6}$ g to $2.5 \times 10^{-2}$ g, or about $1 \times 10^{-6}$ g to $1 \times 10^{-2}$ g, or about $1 \times 10^{-6}$ g to $5 \times 10^{-3}$ g, or about $1 \times 10^{-6}$ to $2.5 \times 10^{-3}$ g, or about $1 \times 10^{-6}$ g to $1 \times 10^{-3}$ g, or about $1 \times 10^{-6}$ g to $5 \times 10^{-4}$ g, or about $1 \times 10^{-5}$ g to 5 g, or about $1 \times 10^{-5}$ g to 2.5 g, or about $1 \times 10^{-5}$ g to 1 g, or about $1 \times 10^{-5}$ g to 0.5 g, or about $1 \times 10^{-5}$ g to 0.25 g, or about $1 \times 10^{-5}$ g to 0.1 g, or about $1 \times 10^{-5}$ g to 0.05 g, or about $1 \times 10^{-5}$ g to $2.5 \times 10^{-2}$ g, or about $1 \times 10^{-5}$ g to $1 \times 10^{-2}$ g, or about $1 \times 10^{-5}$ g to $5 \times 10^{-3}$ g, or about $1 \times 10^{-5}$ g to $2.5 \times 10^{-3}$ g, or about $1 \times 10^{-5}$ g to $1 \times 10^{-3}$ g, or about $1 \times 10^{-5}$ g to $5 \times 10^{-4}$ g.

In some embodiments, the individual doses as described above, is repeated 1, 2, 3, 4, 5, 6, 7, 8, 9, or 10 times per day.

For other forms of administration, the daily dosages may range about the range described for systemic administration or may range about the range described for topical administration.

For slow or sustained release devices and formulations, in some embodiments, a typical dose range is about 0.1 mg to about 100 mg of the amorphous form or any of crystalline Forms A, B, C, D, or E, or a combination thereof, of the compound of Formula I, released over the dosing period. In other embodiments, about 1 mg to about 50 mg, about 1 to about 25 mg, about 5 mg to about 100 mg, about 5 to about 50 mg, about 5 to about 25 mg, about 10 mg to about 100 mg, about 10 mg to about 50 mg, about 10 mg to about 25 mg, or about 15 mg to about 50 mg is released over the dosing period. The dosing period for slow release devices and formulations, typically range from about 10 days to about 1 year, about 30 days to about 1 year, about 60 days to about 1 year, about 3 months to about 1 year, about 4 months to about 1 year, about 5 months to about 1 year, or about 6 months to about 1 year. In some embodiments, the slow release devices and formulations release the amorphous form or any of crystalline Forms A, B, C, D, or E, or a combination thereof, of the compound of Formula I, over the period of about 1 month to about 9 months, about 1 month to about 8 months, about 1 month to about 7 months, about 1 month, to about 6 months, about 1 month to about 5 months, about 1 month to about 4 months, or about 1 month to about 3 months. In other embodiments the slow release formulations and devices release the amorphous form or any of crystalline Forms A, B, C, D, or E, or a combination thereof, of the compound of Formula I, for up to 1 month, 2 months, 3 months, 4 months, 5 months, 6 months, 7 months, 8 months, 9 months, 10 months, 12 months, 18 months, 2 years, 30 months, or 3 years. In some embodiments the slow or sustained release device is a periocular insert, intraocular insert, periocular implant, intraocular implant. In some embodiments, the slow or sustained release device is a pump. In some slow or sustained release formulations, it is a gel. In some slow or sustained release formulations, it is a biocompatible solid. In some slow or sustained release formulations, it is a biodegradable solid.

In some embodiments of the invention, the sustained release formulation and/or implantations release sufficient therapeutic agent to sustain a locally effective level of therapeutic agent from the amorphous form or any of crystalline Forms A, B, C, D, or E, or a combination thereof, of the compound of Formula I, of at least about 10 nM, about 50 nM, about 100 nM, about 150 nM, about 200 nM, about 250 nM, about 300 nM, about 350 nM, about 500 nM, about 600 nM, about 700 nM, about 800 nM, about 900 nM, about 1 µM, about 2 µM, about 3 µM, about 5 µM, about 6 µM, about 7 µM, about 8 µM, about 9 µM, about 10 µM, about 15 µM, about 20 µM, about 25 µM, about 30 µM, about 35 µM, about 40 µM, about 45 µM, about 50 µM, about 55 µM, about 60 µM, about 65 µM, about 70 µM, about 75 µM, about 80 µM, about 85 µM, about 90 µM, about 95 µM, or about 100 µM across 1 year. In some embodiments of the invention, the sustained release formulation and/or implantations release sufficient therapeutic agent intraocularly or periocularly to sustain a local level of the amorphous form or any of crystalline Forms A, B, C, D, or E, or a combination thereof, of the compound of Formula I, of at least about 10 nM, about 50 nM, about 100 nM, about 150 nM, about 200 nM, about 250 nM, about 300 nM, about 350 nM, about 500 nM, about 600 nM, about 700 nM, about 800 nM, about 900 nM, about 1 µM, about 2 µM, about 3 µM, about 5 µM, about 6 µM, about 7 µM, about 8 µM, about 9 µM, about 10 µM, about 15 µM, about 20 µM, about 25 µM, about 30 µM, about 35 µM, about 40 µM, about 45 µM, about 50 µM, about 55 µM, about 60 µM, about 65 µM, about 70 µM, about 75 µM, about 80 µM, about 85 µM, about 90 µM, about 95 µM, or about 100 µM across 6 months.

Formulations

The pharmaceutical compositions of the invention may be formulated as a gel, cream, lotion, solution, suspension, emulsion, ointment, powder, crystalline forms, spray, aerosol, foam, salve, paste, plaster, paint, microparticle, nanoparticle, or bioadhesive, and may be prepared so as to contain liposomes, micelles and/or microspheres.

Formulations for topical use of the pharmaceutical compositions of the present invention can be provided as a topical composition wherein the pharmacologically active ingredients are mixed with excipients to form a semisolid consistency. Examples of such topical pharmaceutical compositions include, but are not limited to, a gel, cream, lotion, suspension, emulsion, ointment, foam, paste and the like. Alternatively, the topical pharmaceutical compositions of the present invention can be formulated in a semi-liquid formulation. Examples of such topical pharmaceutical compositions include, but are not limited to, a topical solution, spray, mist, drops and the like. Alternatively, the topical pharmaceutical compositions of the present invention can be formulated in a dry powder form. The pharmaceutical compositions can also be administered by a transdermal patch.

Ointments, as is well known in the art of pharmaceutical formulation, are semi-solid preparations that are typically based on petrolatum or other petroleum derivatives. As an ointment, the composition has a consistency suitable for uniform dermal application. Additionally, the ointment may be substantially viscous to remain in contact with the skin regardless of perspiration, excess moisture or environmental conditions. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable-bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Some water-soluble ointment bases are prepared from polyethylene glycols of varying molecular weight; again, see Remington: The Science and Practice of Pharmacy for further information.

Creams, as also well known in the art, are viscous liquids or semi-solid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic, or amphoteric surfactant.

Gels are semi-solid, suspension-type systems and are well known in the art. Gel forming agent for use herein can be any gelling agent typically used in the pharmaceutical art for topical semi solid dosage forms. Single-phase gels contain organic macromolecules distributed substantially uniformly throughout the carrier liquid, which is typically aqueous, but also can contain an alcohol and optionally an oil. In order to prepare a uniform gel, dispersing agents such as alcohol or glycerin can be added, or the gelling agent can be dispersed by tritration, mechanical mixing or stirring, or combinations thereof. The amount of gelling agents varies widely and will ordinarily range from about 0.1% to about 2.0% by weight, based on the total weight of the composition. The gel forming agent also works by the principle of copolymerization. Under alkaline pH, carbomer in presence of water undergoes cross linking and forms a gel like structure. The degree of polymerization is dependent upon the pH. At a threshold pH, the viscosities achieved by the polymer grade is the maximum.

Lotions, are preparations to be applied to the skin surface without friction, and are typically semi-liquid preparations in which solid particles, including the active agent, are present in a water or alcohol base. Lotions are usually suspensions of solids, and comprise a liquid oily emulsion of the oil-in-water type. Lotions may be useful formulations herein for treating large body areas, because of the ease of applying a more fluid composition. It desirable that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like.

Pastes are semi-solid dosage forms in which the active agent is suspended in a suitable base. Depending on the nature of the base, pastes are divided between fatty pastes or those made from a single-phase aqueous gels. The base in a fatty paste is generally petrolatum or hydrophilic petrolatum or the like. The pastes made from single-phase aqueous gels generally incorporate carboxymethylcellulose or the like as a base.

Plasters are comprised of a pasty mixture that is spread on the body, either directly or after being saturated into a base material such as cloth. Medications, including the pharmacologically active bases of the invention, may be dissolved or dispersed within the plaster to make a medicated plaster.

Bioadhesives are preparations that adhere to surfaces of body tissues. Polymeric bioadhesive formulations are well known in the art; see, for example, Heller et al., "Biodegradable polymers as drug delivery systems", in Chasin, M. and Langer, R., eds.: Dekker, N.Y., pp. 121-161 (1990); and U.S. Pat. No. 6,201,065. Suitable non-polymeric bioadhesives are also known in the art, including certain fatty acid esters (U.S. Pat. No. 6,228,383).

The amorphous form or any of the crystalline forms of the compound of Formula I, or a combination thereof, may be formulated as a sterile solution or suspension, in suitable vehicles, well known in the art. Suitable formulations and additional carriers and excipients are described in Remington "The Science and Practice of Pharmacy" ($20^{th}$ Ed., Lippincott Williams & Wilkins, Baltimore Md.), the teachings of which are incorporated by reference in their entirety herein.

For injectable formulations, the vehicle may be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation may also comprise polymer compositions which are biocompatible, biodegradable, such as poly(lactic-co-glycolic)acid. These materials may be made into micro or nanospheres, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

The concentration of drug may be adjusted, the pH of the solution buffered and the isotonicity adjusted to be compatible with intravenous injection, as is well known in the art.

Oral formulations can be tablets, capsules, troches, pills, wafers, chewing gums, lozenges, aqueous solutions or suspensions, oily suspensions, syrups, elixirs, or dispersible powders or granules, and the like and may be made in any way known in the art. Oral formulations may also contain sweetening, flavoring, coloring and preservative agents.

Intranasal administration may utilize an aerosol suspension of respirable particles comprised of the amorphous form or any of the crystalline forms of the compound of Formula I, or a combination thereof, along with an aerosol propellant which the individual inhales. The compound of the invention are absorbed into the lining of the lung. Alternatively, aerosol delivery to the eye may deliver the compound of Formula I to the lacrimal tissues via nasolacrimal ducts, and subsequently be delivered to the retinal tissues in a pharmaceutically effective amount.

The pharmaceutical compositions may include one or more inert excipients, which include water, buffered aqueous solutions, surfactants, volatile liquids, starches, polyols, granulating agents, microcrystalline cellulose, diluents, lubricants, acids, bases, salts, emulsions, such as oil/water emulsions, oils such as mineral oil and vegetable oil, wetting agents, chelating agents, antioxidants, sterile solutions, complexing agents, disintegrating agents and the like. The CTFA Cosmetic Ingredient Handbook, Seventh Edition, 1997 and the Eighth Edition, 2000, which is incorporated by reference herein in its entirety, describes a wide variety of cosmetic and pharmaceutical ingredients commonly used in skin care compositions, which are suitable for use in the compositions of the present invention. Examples of these functional classes disclosed in this reference include: absorbents, abrasives, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, preservatives, reducing agents, skin bleaching agents, skin-conditioning agents (emollient, humectants, miscellaneous, and occlusive), skin protectants, solvents, foam boosters, hydrotropes, solubilizing agents, steroidal anti-inflammatory agents, surfactants/emulsifying agents, suspending agents (nonsurfactant), sunscreen agents, topical analgesics, ultraviolet light absorbers, SPF boosters, thickening agents, waterproofing agents, and viscosity increasing agents (aqueous and nonaqueous).

Pharmaceutically acceptable excipients for tablet forms may comprise nontoxic ingredients such as inert diluents, such as calcium carbonate, sodium carbonate, lactose, calcium phosphate, or sodium phosphate, and the like. In the case of tablets for oral use, carriers which are commonly used include lactose and corn starch, and lubricating agents such as magnesium stearate are commonly added. For oral administration in capsule form, useful carriers include lactose and corn starch. Further nonlimiting examples of carriers and excipients include milk, sugar, certain types of clay, gelatin, stearic acid or salts thereof, calcium stearate, talc, vegetable fats or oils, gums and glycols.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

In some embodiments of the invention, the surfactant may be the sodium salt form of the compound, which may include the monosodium salt form. Suitable sodium salt surfactants may be selected based on desirable properties, including high speed of polymerization, small resultant particle sizes suitable for delivery, good polymerization yields, stability including freeze-thaw and shelf-life stability, improved surface tension properties, and lubrication properties.

The surfactant may be any suitable, non-toxic compound that is non-reactive with the medicament and that substantially reduces the surface tension between the medicament, the excipient and the site of administration. Some useful surfactants are: oleic acid available under the tradenames Mednique 6322 and Emersol 6321 (from Cognis Corp., Cincinnati, Ohio); cetylpyridinium chloride (from Arrow Chemical, Inc. Westwood, N.J.); soya lecithin available under the tradename Epikuron 200 (from Lucas Meyer Decatur, Ill.); polyoxyethylene (20) sorbitan monolaurate available under the tradename Tween 20 (from ICI Specialty Chemicals, Wilmington, Del.); polyoxyethylene (20) sorbitan monostearate available under the tradename Tween 60 (from ICI); polyoxyethylene (20) sorbitan monooleate available under the tradename Tween 80 (from ICI); polyoxyethylene (10) stearyl ether available under the tradename Brij 76 (from ICI); polyoxyethylene (2) oleyl ether available under the tradename Brij 92 (frown ICI); Polyoxyethylene-polyoxypropylene-ethylenediamine block copolymer available under the tradename Tetronic 150 R1 (from BASF); polyoxypropylene-polyoxyethylene block copolymers available under the tradenames Pluronic L-92, Pluronic L-121 end Pluronic F 68 (from BASF); castor oil ethoxylate available under the tradename Alkasurf CO-40 (from Rhone-Poulenc Mississauga Ontario, Canada); and mixtures thereof.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, some ionic surfactants include, by way of example: lecithins, lysolecithin, phospholipids, lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, some lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

Surfactants may be used in any formulation of the invention where its use is not otherwise contradicted. In some embodiments of the invention, the use of no surfactants or limited classes of surfactants may be preferred. The topical formulations according to the invention may contain no, or substantially no surfactant, i.e. contain less than approximately 0.0001% by weight of surface-active agents. If desired, however, the formulations can contain surface-active agents conventionally employed in topical formulations, such as oleic acid, lecithin, sorbitan trioleate, cetylpyridinium chloride, benzalkonium chloride, polyoxyethylene (20) sorbitan monolaurate, polyoxyethylene (20) sorbitan monostearate, polyoxyethylene (20) sorbitan mono-oleate, polyoxypropylene/polyoxyethylene block copolymers, polyoxypropylene/polyoxyethylene/ethylenediamine block copolymers, ethoxylated castor oil and the like, where the proportion of surface-active agents, if present, can be about 0.0001 to 1% by weight, or about 0.001 to 0.1% by weight, based on the total formulation. Other suitable surfactant/emulsifying agents would be known to one of skill in the art and are listed in the CTFA International Cosmetic Ingredient Dictionary and Handbook, Vol. 2, 7 th Edition (1997).

Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Chelating agents which can be used to form pharmaceutical compositions and dosage forms of the invention include, but are not limited to, ethylene diaminetetraacetic acid (EDTA), EDTA disodium, calcium disodium edetate, EDTA trisodium, albumin, transferrin, desferoxamine, desferal, desferoxamine mesylate, EDTA tetrasodium and EDTA dipotassium, sodium metasilicate or combinations of any of these.

Preservatives which can be used to form pharmaceutical compositions and dosage forms of the invention include, but are not limited to, purite, peroxides, perborates, imidazolidinyl urea, diazolidinyl urea, phenoxyethanol, alkonium chlorides including benzalkonium chlorides, methylparaben, ethylparaben and propylparaben. In other embodiments, suitable preservatives for the compositions of the invention include: benzalkonium chloride, purite, peroxides, perborates, thimerosal, chlorobutanol, methyl paraben, propyl paraben, phenylethyl alcohol, edetate disodium, sorbic acid, Onamer M, or other agents known to those skilled in the art. In some embodiments of the invention, such preservatives may be employed at a level of from 0.004% to 0.02% W/V. In some compositions of the present application the preservative, for example, benzalkonium chloride, methyl paraben, and/or propyl paraben, may be employed at a level of from about 0.001% to less than about 0.01%, e.g. from about 0.001% to about 0.008%, or about 0.005% W/V. It has been found that a concentration of benzalkonium chloride of about 0.005% may be sufficient to preserve the compositions of the present invention from microbial attack. One of skill in the art could determine the proper concentration of ingredients as well as combinations of various ingredients for generating a suitable topical formulation. For example, ophthalmic drops or formulations for application to skin may use a mixture of methyl and propyl parabens at about 0.02% W/V and about 0.04% W/V respectively. In some embodiments, these formulations use methyl paraben and/or propyl paraben in amounts up to about 0.02% W/V and up to about 0.04% W/V respectively, which encompasses the embodiments where no methyl paraben or no propyl paraben is used.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

Thickening agents which can be used to form pharmaceutical compositions and dosage forms of the invention include, but are not limited to, isopropyl myristate, isopropyl palmitate, isodecyl neopentanoate, squalene, mineral oil, $C_{12}$-$C_{15}$ benzoate and hydrogenated polyisobutene. Agents which would not disrupt other compounds of the final product may be desirable, such as non-ionic thickening agents. The selection of additional thickening agents is well within the skill of one in the art.

Skin conditioning agents can be emollients, humectants and moisturizers. A humectant is a moistening agent that promotes retention of water due to its hygroscopic properties. Suitable skin conditioning agents include urea; guanidine; aloe vera; glycolic acid and glycolate salts such as ammonium and quaternary alkyl ammonium; lactic acid and lactate salts such as sodium lactate, ammonium lactate and quaternary alkyl ammonium lactate; polyhydroxy alcohols such as sorbitol, glycerol, mannitol, xylitol, hexanetriol, propylene glycol, butylene glycol, hexylene glycol, polymeric glycols such as polyethylene glycol and polypropylene glycol; carbohydrates such as alkoxylated glucose; starches; starch derivatives; glycerin; pyrrolidone carboxylic acid (PCA); lactamide monoethanolamine; acetamide monoethanolamine; volatile silicone oils; nonvolatile silicone oils; and mixtures thereof. Suitable silicone oils can be polydialkylsiloxanes, polydiarylsiloxanes, polyalkarylsiloxanes and cyclomethicones having 3 to 9 silicon atoms.

An emollient is an oleaginous or oily substance which helps to smooth and soften the skin, and may also reduce its roughness, cracking or irritation. Typical suitable emollients include mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural sonora jojoba oils, safflower oil, corn oil, liquid lanolin, cottonseed oil and peanut oil. In some embodiments, the emollient is a cocoglyceride, which is a mixture of mono, di and triglycerides of cocoa oil, sold under the trade name of Myritol 331 from Henkel KGaA, or Dicaprylyl Ether available under the trade name Cetiol OE from Henkel KGaA or a $C_{12}$-$C_{15}$ Alkyl Benzoate sold under the trade name Finsolv TN from Finetex. Another suitable emollient is DC 200 Fluid 350, a silicone fluid, available Dow Corning Corp.

Other suitable emollients include squalane, castor oil, polybutene, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe vera extract.

Other suitable emollients which are solids or semi-solids at ambient temperatures may be used. Such solid or semi-solid cosmetic emollients include glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the formulation.

Anti-oxidants which can be used to form pharmaceutical compositions and dosage forms of the invention include, but are not limited to, propyl, octyl and dodecyl esters of gallic acid, butylated hydroxyanisole (BHA, usually purchased as a mixture of ortho and meta isomers), green tea extract, uric acid, cysteine, pyruvate, nordihydroguaiaretic acid, ascorbic acid, salts of ascorbic acid such as ascorbyl palmitate and sodium ascorbate, ascorbyl glucosamine, vitamin E (i.e., tocopherols such as α-tocopherol), derivatives of vitamin E (e.g., tocopheryl acetate), retinoids such as retinoic acid, retinol, trans-retinol, cis-retinol, mixtures of trans-retinol and cis-retinol, 3-dehydroretinol and derivatives of vitamin A (e.g., retinyl acetate, retinal and retinyl palmitate, also known as tetinyl palmitate), sodium citrate, sodium sulfite, lycopene, anthocyanids, bioflavinoids (e.g., hesperitin, naringen, rutin and quercetin), superoxide dismutase, glutathione peroxidase, butylated hydroxytoluene (BHT), indole-3-carbinol, pycnogenol, melatonin, sulforaphane, pregnenolone, lipoic acid and 4-hydroxy-5-methyl-3[2H]-furanone.

Skin protecting agents are agents that protect the skin against chemical irritants and/or physical irritants, e.g., UV light, including sunscreens, anti-acne additives, anti-wrinkle and anti-skin atrophy agents. Suitable sunscreens as skin protecting agents include 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomethyl salicylate, octyl salicylate, 4,4'-methoxy-t-butyldibenzoylmethane, 4-isopropy dibenzoylmethane, 3-benzylidene camphor, 3-(4-methylbenzylidene) camphor, anthanilates, ultrafine titanium dioxide, zinc oxide, iron oxide, silica, 4-N,N-(2-ethylhexyl)methylaminobenzoic acid ester of 2,4-dihydroxybenzophenone, 4-N,N-(2-ethylhexyl)-methylaminobenzoic acid ester with 4-hydroxydibenzoylmethane, 4-N,N-(2-ethylhexyl)-methylaminobenzoic acid ester of 2-hydroxy-4-(2-hydroxyethoxy) benzophenone and 4-N,N(2-ethylhexyl)-methylaminobenzoic acid ester of 4-(2-hydroxyethoxy)dibenzoylmethane. Suitable anti-acne agents include salicylic acid; 5-octanoyl salicylic acid; resorcinol; retinoids such as retinoic acid and its derivatives; sulfur-containing D and L amino acids other than cysteine; lipoic acid; antibiotics and antimicrobials such as benzoyl peroxide, octopirox, tetracycline, 2,4,4'-trichloro-2'-hydroxydiphenyl ether, 3,4,4'-trichlorobanilide, azelaic acid, phenoxyethanol, phenoxypropanol, phenoxisopropanol, ethyl acetate, clindamycin and melclocycline; flavonoids; and bile salts such as scymnol sulfate, deoxycholate and cholate. Examples of anti-wrinkle and anti-skin atrophy agents are retinoic acid and its derivatives, retinol, retinyl esters, salicylic acid and its derivatives, sulfur-containing D and L amino acids except cysteine, alpha-hydroxy acids (e.g., glycolic acid and lactic acid), phytic acid, lipoic acid and lysophosphatidic acid.

The formulations may also contain irritation-mitigating additives to minimize or eliminate the possibility of skin irritation or skin damage resulting from the permeation-enhancing base or other components of the composition. Suitable irritation-mitigating additives include, for example: -tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the present formulations at a concentration effective to mitigate irritation or skin damage, typically representing not more than about 20 wt. %, more typically not more than about 5 wt. %, of the composition.

A dry-feel modifier is an agent which when added to an emulsion, imparts a "dry feel" to the skin when the emulsion dries. Dry feel modifiers can include talc, kaolin, chalk, zinc oxide, silicone fluids, inorganic salts such as barium sulfate, surface treated silica, precipitated silica, fumed silica such as an Aerosil available from Degussa Inc. of New York, N.Y. U.S.A. Another dry feel modifier is an epichlorohydrin cross-linked glyceryl starch of the type that is disclosed in U.S. Pat. No. 6,488,916.

Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, purite, peroxides, perborates and combinations thereof.

The formulation may also contain an aesthetic agent. Examples of aesthetic agents include fragrances, pigments, colorants, essential oils, skin sensates and astringents. Suitable aesthetic agents include clove oil, menthol, camphor, eucalyptus oil, eugenol, methyl lactate, bisabolol, witch hazel distillate and green tea extract.

Fragrances are aromatic substances which can impart an aesthetically pleasing aroma to the composition. Typical fragrances include aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. One or more fragrances can optionally be included in the composition in an amount ranging from about 0.001 to about 5 weight percent, or about 0.01 to about 0.5 percent by weight. Additional preservatives may also be used if desired and include well known preservative compositions such as benzyl alcohol, phenyl ethyl alcohol and benzoic acid, diazolydinyl, urea, chlorphenesin, iodopropynyl and butyl carbamate, among others.

In order to increase the degree and rate at which a drug penetrates the skin when delivering the compound of Formula I via topical administration, various approaches have been followed, each of which involves the use of either a chemical penetration enhancer or a physical penetration enhancer. Physical enhancements of skin permeation include, for example, electrophoretic techniques such as iontophoresis. The use of ultrasound (or "phonophoresis") as a physical penetration enhancer has also been researched. Chemical penetration enhancers are more commonly used. These are compounds that are topically administered along with a drug (or, in some cases, prior to drug administration) in order to increase the permeability of the stratum corneum, and thereby provide for enhanced penetration of the drug through the skin. Ideally, such chemical penetration enhancers (or "permeation enhancers," as the compounds are referred to herein) are compounds that are innocuous and serve merely to facilitate diffusion of the drug through the stratum corneum.

Various compounds for enhancing the permeability of skin are known in the art. Compounds that have been used to enhance skin permeability include: sulfoxides such as dimethylsulfoxide (DMSO) and decylmethylsulfoxide ($C_{10}MSO$); ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80), and lecithin (U.S. Pat. No. 4,783,450); the 1-substituted azacycloheptan-2-ones, particularly 1-n-dodecylcyclazacycloheptan-2-one (available under the trademark Azone.®. from Nelson Research & Development Co., Irvine, Calif.; see U.S. Pat. Nos. 3,989,816, 4,316,893, 4,405,616, and 4,557,934); alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly salicylic acid and salicylates, citric acid, and succinic acid. (See Percutaneous Penetration Enhancers, Smith et al., editors, CRC Press, 1995, for a number of chemical and physical enhancers.)

It has long been thought that strong bases, such as NaOH, were not suitable as permeation enhancers because they would damage skin. It has been now been discovered that the skin permeability of various drugs could be enhanced without skin damage by exposing the skin to a base or basic solution, in a skin contacting formulation or patch. The desired pH of the solution on the skin can be obtained using a variety of bases or base concentrations. Accordingly, the pH is selected so as to be low enough so as to not cause skin damage, but high enough to enhance skin permeation to various active agents. As such, it is important that the amount of base in any patch or formulation is optimized so as to increase the flux of the drug through the body surface while minimizing any possibility of skin damage. In general, this means that the pH at the body surface in contact with a formulation or drug delivery system of the invention may be in the range of approximately 8.0-13.0, about 8.0-11.5, about 8.5 to 11.5, or about 8.5-10.5. In some embodiments, the pH will be in the range of about 9.5 to 11.5, or about 10.0 to 11.5.

In one embodiment, the pH at the skin surface is the primary design consideration, i.e., the composition or system is designed so as to provide the desired pH at the skin surface. Anhydrous formulations and transdermal systems may not have a measurable pH, and the formulation or system can be designed so as to provide a target pH at the skin surface. Moisture from the body surface can migrate into the formulation or system, dissolve the base and thus release the base into solution, which will then provide the desired target pH at body surface. In those instances, a hydrophilic composition may be preferred. In addition, when using aqueous formulations, the pH of the formulation may change over time after it is applied on the skin. For example, gels, solutions, ointments, etc., may experience a net loss of moisture after being applied to the body surface, i.e., the amount of water lost is greater than the amount of water received from the body surface. In that case, the pH of the formulation may be different than its pH when manufactured. This problem can be easily remedied by designing the aqueous formulations to provide a target pH at the body surface.

In other embodiments of the invention, the pH of the formulation or the drug composition contained within a delivery system will be in the range of approximately pH 8.0 to about pH 13.0, about pH 8.0 to about pH 11.5, about pH 8.5 to about pH 11.5, or about pH 8.5 to about pH 10.5. In some embodiments, the pH will be in the range of about pH 9.5 to about pH 11.5, or about pH 10.0 to about pH 11.5. In one embodiment of the invention the pH of the formulation is higher than the pH at the body surface. For example, if an aqueous formulation is used, moisture from the body surface can dilute the formulation, and thus provide for a different pH at the body surface, which will typically be lower than that of the formulation itself.

In one embodiment, the body surface is exposed to a base or basic solution for a sufficient period of time so as to provide a high pH at the skin surface, thus creating channels in the skin or mucosa for the drug to go through. It is expected that drug flux is proportional to the strength of the solution and the duration of exposure. However, it is desirable to balance the maximization of drug flux with the minimization of skin damage. This can be done in numerous ways. For example, the skin damage may be minimized by selecting a lower pH within the 8.0 to 13.0 range, by exposing the skin to the formulation or system for a shorter period of time, or by including at least one irritation-mitigating additive. Alternatively, the patient can be advised to change the location of application with each subsequent administration.

While certain amounts are set forth below, it is understood that, for all of the inorganic and organic bases described herein, the optimum amount of any such base will depend on the strength or weakness of the base and its molecular weight, and other factors such as the number of ionizable sites in the active agent being administered and whether there are any acidic species present in the formulation or patch. One skilled in the art may readily determine the optimum amount for any particular base such that the degree of enhancement is optimized while the possibility of damage to the body surface is eliminated or at least substantially minimized.

Exemplary inorganic bases are inorganic hydroxides, inorganic oxides, inorganic salts of weak acids, and combinations thereof. Some useful inorganic bases include those whose aqueous solutions have a high pH, and are acceptable as food or pharmaceutical additives. Examples of such inorganic bases include ammonium hydroxide, sodium hydroxide, potassium hydroxide, calcium hydroxide, magnesium hydroxide, magnesium oxide, calcium oxide, $Ca(OH)_2$, sodium acetate, sodium borate, sodium metaborate, sodium carbonate, sodium bicarbonate, sodium phosphate, potassium carbonate, potassium bicarbonate, potassium citrate, potassium acetate, potassium phosphate and ammonium phosphate and combinations thereof.

Inorganic hydroxides include, for example, ammonium hydroxide, alkali metal hydroxide and alkaline earth metal hydroxides, and mixtures thereof. Some useful inorganic hydroxides include ammonium hydroxide; monovalent alkali metal hydroxides such as sodium hydroxide and potassium hydroxide; divalent alkali earth metal hydroxides such as calcium hydroxide and magnesium hydroxide; and combinations thereof.

The amount of inorganic hydroxide included in the compositions and systems of the invention, will typically represent about 0.3-7.0 W/V %, about 0.5-4.0 W/V %, about 0.5-3.0 W/V %, or about 0.75-2.0 W/V %, of a topically applied formulation or of a drug reservoir of a drug delivery system, or patch.

Inorganic oxides include, for example, magnesium oxide, calcium oxide, and the like.

The amount of inorganic oxide included in the compositions and systems of the invention may be substantially higher than the numbers set forth above for the inorganic hydroxide, and may be as high as 20 wt %, in some cases as high as 25 wt % or higher, but will generally be in the range of about 2-20 wt %. These amounts may be adjusted to take into consideration the presence of any base-neutralizable species.

Inorganic salts of weak acids include, ammonium phosphate (dibasic); alkali metal salts of weak acids such as sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic); alkaline earth metal salts of weak acids such as magnesium phosphate and calcium phosphate; and the like, and combinations thereof.

Organic bases suitable for use in the invention are compounds having an amino group, amido group, an oxime, a cyano group, an aromatic or non-aromatic nitrogen-containing heterocycle, a urea group, and combinations thereof. More specifically, examples of suitable organic bases are nitrogenous bases, which include, but are not limited to, primary amines, secondary amines, tertiary amines, amidines, guanidines, hydroxylamines, cyano guanidines, cyanoamidines, oximes, cyano (—CN) containing groups, aromatic and non-aromatic nitrogen-containing heterocycles, urea, and mixtures thereof. In some embodiments, the organic bases are primary amines, secondary amines, tertiary amines, aromatic and non-aromatic nitrogen-containing heterocycles, and mixtures thereof.

For all permeation-enhancing bases herein, the optimum amount of any particular agent will depend on the strength or weakness of the base, the molecular weight of the base, and other factors such as the number of ionizable sites in the drug administered and any other acidic species in the formulation or patch. One skilled in the art may readily determine the optimum amount for any particular agent by ensuring that a formulation is effective to provide a pH at the skin surface, upon application of the formulation, in the range of about pH 7.5 to about pH 13.0, about pH 8.0 to about pH 11.5, or about pH 8.5 to about pH 10.5. In some embodiments, the pH will be in the range of about pH 9.5 to about pH 11.5, or about pH 10.0 to about pH 11.5. This in turn ensures that the degree of treatment is maximized while the possibility of damage to the body surface is eliminated or at least substantially minimized.

In the case of intranasal administration, such solutions or suspensions may be isotonic relative to nasal secretions and of about the same pH, ranging e.g., from about pH 4.0 to about pH 7.4 or, from about pH 6.0 to about pH 7.0. Buffers should be physiologically compatible and include, simply by way of example, phosphate buffers. For example, a representative nasal decongestant is described as being buffered to a pH of about 6.2 (Remington's Pharmaceutical Sciences 16th edition, Ed. Arthur Osol, page 1445 (1980)). One skilled in the art can readily determine a suitable saline content and pH for an innocuous aqueous solution for nasal and/or upper respiratory administration. An example of a suitable formulation for intranasal administration, is an aqueous solution buffered to a pH of about 6.0 to about 8.0 with Sodium Phosphate, Monobasic, comprising about 1% W/V of the LFA-1 antagonist, up to about 0.1% W/V EDTA, and, optionally, up to about 0.4% w/w Methylparaben and up to about 0.02% w/w Propylparaben.

Additional permeation enhancers will be known to those of ordinary skill in the art of topical drug delivery, and/or are described in the pertinent texts and literature. See, e.g., Percutaneous Penetration Enhancers, Smith et al., eds. (CRC Press, 1995).

The compositions of the invention may comprise pharmaceutically acceptable salts of the amorphous form or any of the crystalline forms of the compound of Formula I, or a combination thereof, and which refers to those salts which are suitable for pharmaceutical use, preferably for use in the tissues of humans and lower animals without undue irritation, allergic response and the like. Pharmaceutically acceptable salts of amines, carboxylic acids, and other types of compounds, are well known in the art. For example, S. M. Berge, et al., describe pharmaceutically acceptable salts in detail in J Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzoate, bisulfate, borate, butyrate, camphorate, camphorsulfonate, citrate, cyclopentanepropionate, digluconate, dodecylsulfate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, nicotinate, nitrate, oleate, oxalate, palmitate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed by direct reacton with the drug carboxylic acid or by using counterions such as halide, hydroxide, carboxylate, sulfate, phosphate, nitrate, sulfonate and aryl sulfonate.

It is envisioned additionally, that the amorphous form or any of the crystalline forms of the compound of Formula I, or a combination thereof, may be attached releasably to biocompatible polymers for use in sustained release formulations on, in or attached to inserts for topical, intraocular, periocular, or systemic administration. The controlled release from a biocompatible polymer may be utilized with a water soluble polymer to form an instillable formulation, as well. The controlled release from a biocompatible polymer, such as for example, PLGA microspheres or nanospheres, may be utilized in a formulation suitable for intra ocular implantation or injection for sustained release administration, as well. Any suitable biodegradable and biocompatible polymer may be used.

Additionally, the amorphous form or any of the crystalline Forms A, B, C, D, and E, or combinations thereof, of the compound of Formula I may be suitable for use in sustained release formulations where the drug entity may remain as a solid. Further, the calcium salt of the free acid of any of these forms is envisioned to be useful in slow release formulations, as a solid formulation, gel formulation or liquid formulation.

The amorphous form or any of the crystalline Forms A, B, C, D, and E, or combinations thereof, of the compound of Formula I may be milled to provide more suitable properties for formulation. Milling may provide smaller particle size with greater surface area exposure, which can provide faster solubilization in-vivo or during formulation. Alternatively, milling to a smaller particle size may provide the amorphous form or any of the crystalline Forms A, B, C, D, or E, or a combination thereof, with the capacity to pass through biological barriers, such as the skin or gut wall, directly, without initial solubilization, permitting the use of the amorphous form or any of the crystalline Forms A, B, C, D, and E, or combinations thereof, as a solid in the formulation, which may provide additional benefits of temperature stability, shelf life, ease of transport, and ease of use by the subject. Milled solid particles of the amorphous form or any of the crystalline Forms A, B, C, D, and E, or combinations thereof, may also provide greater bioavailability, and more desirable or controllable pharmacokinetics in the formulations. The size of the milled particle can affect the rate of distribution of the compound of Formula I upon administration or rate of release of the compound of Formula I from a sustained or slow release formulation. Further, milling of the particles of the amorphous form or any of the crystalline Forms A, B, C, D, and E, or combinations thereof, may be performed to create either a narrower or more symmetrical particle size distribution within a particular formulation or lot of material which may be subjected to formulation. The size of the particles of the amorphous form or any of the crystalline Forms A, B, C, D, and E, or combinations thereof, may be selected as is well known in the art, to obtain the desired physical characteristics for ease of formulation or the ability to be distributed from the formulation in a controlled fashion over a preselected period under conditions of use. The size of the particles can be represented as the D50, which represents the median or $50^{th}$ percentile of the diameter of a particle within the lot of material under discussion. Another measure of the size of the particles in a lot of material is the D90, which is the $90^{th}$ percentile of the particle size diameter in the particle size distribution.

In the formulations of the invention, the diameter of the particles of the amorphous form or any of the crystalline Forms A, B, C, D, and E, or combinations thereof of the compound of Formula I are in the range from about 5 nm to about 100 µm, from about 50 nm to about 100 µm, from about 100 nm to about 100 µm, from about 250 nm to about 100 µm, from about 500 nm to about 100 µm, from about 750 nm to about 100 µm, from about 1 µm to about 100 µm, or from about 10 µm to about 100 µm; from about 5 nm to about 50 µm, from about 50 nm to about 50 µm, from about 100 nm to about 50 µm, from about 250 nm to about 50 µm, from about 500 nm to about 50 µm, from about 750 nm to about 50 µm, from about 1 µm to about 50 µm, or from about 10 µm to about 50 µm; from about 5 nm to about 10 µm, from about 50 nm to about 10 µm, from about 100 nm to about 10 µm, from about 250 nm to about 10 µm, from about 500 nm to about 10 µm, from about 750 nm to about 10 µm, or from about 1 µm to about 10 µm; from about 5 nm to about 1 µm, from about 50 nm to about 1 µm, from about 100 nm to about 1 µm, from about 250 nm to about 1 µm, from about 500 nm to about 1 µm, or from about 750 nm to about 1 µm; from about 5 nm to about 1 µm, from about 50 nm to about 1 µm, from about 100 nm to about 1 µm, from about 250 nm to about 1 µm, from about 500 nm to about 1 µm, or from about 750 nm to about 1 µm; from about 5 nm to about 1 µm, from about 50 nm to about 1 µm, from about 100 nm to about 1 µm, from about 250 nm to about 1 µm, from about 500 nm to about 1 µm, or from about 750 nm to about 1 µm; from about 5 nm to about 900 nm, from about 50 nm to about 900 nm, from about 100 nm to about 900 nm, from about 250 nm to about 900 nm, from about 500 nm to about 900 nm, or from about 750 nm to about 900 nm; from about 5 nm to about 900 nm, from about 50 nm to about 900 nm, from about 100 nm to about 900 nm, from about 250 nm to about 900 nm, from about 500 nm to about 900 nm, or from about 750 nm to about 900 nm; from about 5 nm to about 900 nm, from about 50 nm to about 900 nm, from about 100 nm to about 900 nm, from about 250 nm to about 900 nm, from about 500 nm to about 900 nm, or from about 750 nm to about 900 nm; from about 5 nm to about 750 nm, from about 50 nm to about 750 nm, from about 100 nm to about 750 nm, from about 250 nm to about 750 nm, from about 500 nm to about 750 nm, from about 750 nm to about 750 nm, or from about 1 µm to about 750 nm; from about 5 nm to about 750 nm, from about 50 nm to about 750 nm, from about 100 nm to about 750 nm, from about 250 nm to about 750 nm, or from about 500 nm to about 750 nm; from about 5 nm to about 750 nm, from about 50 nm to about 750 nm, from about 100 nm to about 750 nm, from about 250 nm to about 750 nm, or from about 500 nm to about 750 nm; from about 5 nm to about 500 nm, from about 50 nm to about 500 nm, from about 100 nm to about 500 nm, or from about 250 nm to about 500 nm; from about 5 nm to about 250 m, from about 50 nm to about 250 nm, or from about 100 nm to about 250 nm; from about 5 nm to about 500 nm, from about 10 nm to about 500 nm, from about 20 nm to about 500 nm, from about 30 nm to about 500 nm, from about 40 nm to about 500 nm, from about 50 nm to about 500 nm, from about 60 nm to about 500 nm, from about 70 nm to about 500 nm, from about 80 nm to about 500 nm, from about 90 nm to about 500 nm, from about 100 nm to about 500 nm, from about 200 nm to about 500 nm, or from about 300 nm to about 500 nm.

In the formulations of the invention, the D50 of the diameter of the particles of the amorphous form or any of the crystalline Forms A, B, C, D, and E, or combinations thereof of the compound of Formula I are about 100 µm, about 90 µm, about 80 µm, about 70 µm, about 60 µm, about 50 µm, about 45 µm, about 40 µm, about 35 µm, about 30 µm, about 25 µm, about 20 µm, about 19 µm, about 18 µm, about 17 µm, about 16 µm, about 15 µm, about 14 µm, about 13 µm, about 12 µm, about 11 µm, about 10 µm, about 9 µm, about 8 µm, about 7 µm, about 6 µm, about 5 µm, about 4 µm, about 3 µm, about 2 µm, about 1 µm, about 950 nm, about 900 nm, about 850 nm, about 800 nm, about 750 nm, about 700 nm, about 650 nm, about 600 nm, about 550 nm, about 500 nm, about 450 nm, about 350 nm, about 300 nm, about 250 nm, about 200 nm, about 150 nm, about 100 nm, about 95 nm, about 90 nm, about 85 nm, about 80 nm, about 75 nm, about 70 nm, about 65 nm, about 60 nm, about 55 nm, about 50 nm, about 45 nm, about 40 nm, about 35 nm, about 30 nm, about 25 nm, about 20 nm, about 19 nm, about 18 nm, about 17 nm, about 16 nm, about 15 nm, about 14 nm, about 13 nm, about 12 nm, about 11 nm, about 10 nm, about 9 nm, about 8 nm, about 7 nm, about 6 nm, or about 5 nm.

In the formulations of the invention, the D50 of the diameter of the particles of the amorphous form or any of the crystalline Forms A, B, C, D, and E, or combinations thereof of the compound of Formula I are less than about 100 µm, about 90 µm, about 80 µm, about 70 µm, about 60 µm, about 50 µm, about 45 µm, about 40 µm, about 35 µm, about 30 µm, about 25 µm, about 20 µm, about 19 µm, about 18 µm, about 17 µm, about 16 µm, about 15 µm, about 14 µm, about 13 µm, about 12 µm, about 11 µm, about 10 µm, about 9 µm, about 8 µm, about 7 µm, about 6 µm, about 5 µm, about 4 µm, about 3 µm, about 2 µm, about 1 µm, about 950 nm, about 900 nm, about 850 nm, about 800 nm, about 750 nm, about 700 nm, about 650 nm, about 600 nm, about 550 nm, about 500 nm, about 450 nm, about 350 nm, about 300 nm, about 250 nm, about 200 nm, about 150 nm, about 100 nm, about 95 nm, about 90 nm, about 85 nm, about 80 nm, about 75 nm, about 70 nm, about 65 nm, about 60 nm, about 55 nm, about 50 nm, about 45 nm, about 40 nm, about 35 nm, about 30 nm, about 25 nm, about 20 nm, about 19 nm, about 18 nm, about 17 nm, about 16 nm, about 15 nm, about 14 nm, about 13 nm, about 12 nm, about 11 nm, about 10 nm, about 9 nm, about 8 nm, about 7 nm, about 6 nm, or about 5 nm.

In the formulations of the invention, the D50 of the diameter of the particles of the amorphous form or any of the crystalline Forms A, B, C, D, and E, or combinations thereof of the compound of Formula I are no more than about 100 µm, about 90 µm, about 80 µm, about 70 µm, about 60 µm, about 50 µm, about 45 µm, about 40 µm, about 35 µm, about 30 µm, about 25 µm, about 19 µm, about 18 µm, about 17 µm, about 16 µm, about 20 µm, about 15 µm, about 14 µm, about 13 µm, about 12 µm, about 11 µm, about 10 µm, about 9 µm, about 8 µm, about 7 µm, about 6 µm, about 5 µm, about 4 µm, about 3 µm, about 2 µm, about 1 µm, about 950 nm, about 900 nm, about 850 nm, about 800 nm, about 750 nm, about 700 nm, about 650 nm, about 600 nm, about 550 nm, about 500 nm, about 450 nm, about 350 nm, about 300 nm, about 250 nm, about 200 nm, about 150 nm, about 100 nm, about 95 nm, about 90 nm, about 85 nm, about 80 nm, about 75 nm, about 70 nm, about 65 nm, about 60 nm, about 55 nm, about 50 nm, about 45 nm, about 40 nm, about 35 nm, about 30 nm, about 25 nm, about 20 nm, about 19 nm, about 18 nm, about 17 nm, about 16 nm, about 15 nm, about 14 nm, about 13 nm, about 12 nm, about 11 nm, about 10 nm, about 9 nm, about 8 nm, about 7 nm, about 6 nm, or about 5 nm.

In the formulations of the invention, the D90 of the diameter of the particles of the amorphous form or any of the crystalline Forms A, B, C, D, and E, or combinations thereof of the compound of Formula I are about 100 µm, about 90 µm, about 80 µm, about 70 µm, about 60 µm, about 50 µm, about 45 µm, about 40 µm, about 35 µm, about 30 µm, about 25 µm, about 20 µm, about 19 µm, about 18 µm, about 17 µm, about 16 µm, about 15 µm, about 14 µm, about 13 µm, about 12 µm, about 11 µm, about 10 µm, about 9 µm, about 8 µm, about 7 µm, about 6 µm, about 5 µm, about 4 µm, about 3 µm, about 2 µm, about 1 µm, about 950 nm, about 900 nm, about 850 nm, about 800 nm, about 750 nm, about 700 nm, about 650 nm, about 600 nm, about 550 nm, about 500 nm, about 450 nm, about 350 nm, about 300 nm, about 250 nm, about 200 nm, about 150 nm, about 100 nm, about 95 nm, about 90 nm, about 85 nm, about 80 nm, about 75 nm, about 70 nm, about 65 nm, about 60 nm, about 55 nm, about 50 nm, about 45 nm, about 40 nm, about 35 nm, about 30 nm, about 25 nm, about 20 nm, about 19 nm, about 18 nm, about 17 nm, about 16 nm, about 15 nm, about 14 nm, about 13 nm, about 12 nm, about 11 nm, about 10 nm, about 9 nm, about 8 nm, about 7 nm, about 6 nm, or about 5 nm.

In the formulations of the invention, the D90 of the diameter of the particles of the amorphous form or any of the crystalline Forms A, B, C, D, and E, or combinations thereof of the compound of Formula I are less than about 100 µm, about 90 µm, about 80 µm, about 70 µm, about 60 µm, about 50 µm, about 45 µm, about 40 µm, about 35 µm, about 30 µm, about 25 µm, about 20 µm, about 19 µm, about 18 µm, about 17 µm, about 16 µm, about 15 µm, about 14 µm, about 13 µm, about 12 µm, about 11 µm, about 10 µm, about 9 µm, about 8 µm, about 7 µm, about 6 µm, about 5 µm, about 4 µm, about 3 µm, about 2 µm, about 1 µm, about 950 nm, about 900 nm, about 850 nm, about 800 nm, about 750 nm, about 700 nm, about 650 nm, about 600 nm, about 550 nm, about 500 nm, about 450 nm, about 350 nm, about 300 nm, about 250 nm, about 200 nm, about 150 nm, about 100 nm, about 95 nm, about 90 nm, about 85 nm, about 80 nm, about 75 nm, about 70 nm, about 65 nm, about 60 nm, about 55 nm, about 50 nm, about 45 nm, about 40 nm, about 35 nm, about 30 nm, about 25 nm, about 20 nm, about 19 nm, about 18 nm, about 17 nm, about 16 nm, about 15 nm, about 14 nm, about 13 nm, about 12 nm, about 11 nm, about 10 nm, about 9 nm, about 8 nm, about 7 nm, about 6 nm, or about 5 nm.

In the formulations of the invention, the D90 of the diameter of the particles of the amorphous form or any of the crystalline Forms A, B, C, D, and E, or combinations thereof of the compound of Formula I are no more than about 100 µm, about 90 µm, about 80 µm, about 70 µm, about 60 µm, about 50 µm, about 45 µm, about 40 µm, about 35 µm, about 30 µm, about 25 µm, about 20 µm, about 19 µm, about 18 µm, about 17 µm, about 16 µm, about 15 µm, about 14 µm, about 13 µm, about 12 µm, about 11 µm, about 10 µm, about 9 µm, about 8 µm, about 7 µm, about 6 µm, about 5 µm, about 4 µm, about 3 µm, about 2 µm, about 1 µm, about 950 nm, about 900 nm, about 850 nm, about 800 nm, about 750 nm, about 700 nm, about 650 nm, about 600 nm, about 550 nm, about 500 nm, about 450 nm, about 350 nm, about 300 nm, about 250 nm, about 200 nm, about 150 nm, about 100 nm, about 95 nm, about 90 nm, about 85 nm, about 80 nm, about 75 nm, about 70 nm, about 65 nm, about 60 nm, about 55 nm, about 50 nm, about 45 nm, about 40 nm, about 35 nm, about 30 nm, about 25 nm, about 20 nm, about 19 nm, about 18 nm, about 17 nm, about 16 nm, about 15 nm, about 14 nm, about 13 nm, about 12 nm, about 11 nm, about 10 nm, about 9 nm, about 8 nm, about 7 nm, about 6 nm, or about 5 nm.

In the formulations of the invention, the ratio of D50 to D90 of the diameter of the particles of the amorphous form or any of the crystalline Forms A, B, C, D, and E, or combinations thereof of the compound of Formula I is about 1:1.10; about 1:1.20; about 1:1.30; about 1:1.40; about 1:1.50; about 1:1.60; about 1:1.70; about 1:1.80; about 1:1.90; about 1:2.00; about 1:2.10; about 1:2.20; about 1:2.30; about 1:2.40; about 1:2.50; about 1:2.60; about 1:2.70; about 1:2.80; about 1:2.90; about 1:3.00; about 1:3.10; about 1:3.20; about 1:3.30; about 1:3.40; about 1:3.50; about 1:3.60; about 1:3.70; about 1:3.80; about 1:3.90; about 1:4.00; about 1:4.10; about 1:4.20; about 1:4.30; about 1:4.40; about 1:4.50; about 1:4.60; about 1:4.70; about 1:4.80; about 1:4.90; about 1:5.0; about 1:5.5; about 1:6.0; about 1:6.5; about 1:7.0; about 1:7.5; about 1:8.0; about 1:9.0; or about 1:10.0.

For transdermal administration, any suitable formulation known in the art may be utilized, either as a solution, suspension, gel, powder, cream, oil, solids, dimethylsulfoxide (DMSO)-based solutions or liposomal formulation for use in a patch or other delivery system known in the art. The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For topical administration, all the formulations for topical ocular administration used in the field of ophthalmology (e.g., eye drops, inserts, eye packs, impregnated contact lenses, pump delivery systems, dimethylsulfoxide (DMSO)-based solutions suspensions, liposomes, and eye ointment) and all the formulations for external use in the fields of dermatology and otolaryngology (e.g., ointment, cream, gel, powder, salve, lotion, crystalline forms, foam, and spray) may be utilized as is known in the art. Additionally all suitable formulations for topical administration to skin and mucus membranes of the nasal passages may be utilized to deliver the compounds of the invention. The pharmaceutical compositions of the present invention may be a liposomal formulation for topical or oral administration, any of which are known in the art to be suitable for the purpose of this invention. For topical ocular administration, the concentration of the drug may be adjusted, the pH of the solution buffered, and/or the isotonicity adjusted to be compatible with tear, nonirritating and well tolerated by the subject as is well known in the art.

Compositions may administered via oral delivery. Oral formulations can comprise liquid formulations which are encapsulated or not. A liquid formulation may be an aqueous solution of the LFA-1 antagonist, and may contain buffering agents and may or may not have preservatives included. Orally administered formulations such as tablets may optionally be coated or scored and may be formulated so as to provide sustained, delayed or controlled release of the active ingredient therein. Examples of solid formulations may be as described in U.S. Pat. No. 5,424,289. Oral formulations can also have increased bioavailability, such as described in U.S. Pat. No. 7,097,851, location and time dependent in delivery, such as described in U.S. Pat. No. 5,840,332, or delivered to specific regions of the gastrointestinal system, for example, as described in U.S. Pat. No. 5,849,327, where coating of an enteric material that remains intact until the dosage form reaches the lower gastrointestinal tract.

Formulations may use enteric coatings which are available for tablets and capsules. Enteric coatings can remain intact in the stomach but rapidly dissolve when they arrive at the small intestine, thereafter releasing the drug at sites downstream in the intestine (e.g., the ileum and colon), thus delivering a LFA-1 antagonist to the mucosa thereof. Enteric coatings are well known in the art and are discussed at, for example, Remington's Pharmaceutical Sciences, Mack Publishing Co., Easton, Pa.; and Polymers for Controlled Drug Delivery, Chapter 3, CRC Press, 1991. Some non-limiting examples of enteric coatings include cellulose acetate phthalate, polyvinyl acetate phthalate, methacrylic acid-methacrylic acid ester copolymers, carboxymethyl ethylcellulose, and hydroxypropyl methylcellulose acetate succinates. Alternatively, a controlled release oral delivery vessel designed to release the formulations comprising a LFA-1 antagonist after a predetermined period of time, and thus after the vessel has passed into the ileum or colon, can also be used to deliver the formulation of the present invention. Such vessels include, but are not limited to, the CHRONSET™ delivery device (ALZA Corporation, Palo Alto, Calif.) and the Pulsincap™ delivery device (R.P. Scherer Co.). Other coating agents may include, but not be limited to: sodium carboxymethyl cellulose, cellulose acetate phthalate, ethylcellulose, gelatin, pharmaceutical glaze, hydroxypropyl cellulose, hydroxypropyl methylcellulose, hydroxypropyl methyl cellulose phthalate, methylcellulose, polyethylene glycol, polyvinyl acetate phthalate, shellac, sucrose, titanium dioxide, carnauba wax, microcrystalline wax, or mixtures thereof.

Controlled release oral formulations of the LFA-1 antagonist can also be formed wherein the LFA-1 antagonist is incorporated within a biocompatible and/or biodegradable matrix. The matrix can be hydrophilic or hydrophobic. Three main mechanisms exist by which an active ingredient can be released from a hydrophilic matrix: dissolution, erosion and diffusion. An active ingredient will be released by the dissolution mechanism when it is homogeneously dispersed in a matrix network of a soluble polymer. The network will gradually dissolve in the gastrointestinal tract, thereby gradually releasing its load. The matrix polymer can also gradually be eroded from the matrix surface, likewise releasing the active ingredient in time. When an active ingredient is processed in a matrix made up of an insoluble polymer, it will be released by diffusion: the gastro-intestinal fluids penetrate the insoluble, sponge-like matrix and diffuse back out loaded with drug.

The formulations of the present invention can contain the LFA-1 antagonist as either a carboxylic acid or as a salt. The formulations can include a polymer such as polylactic-glycoloic acid (PLGA), poly-(l)-lactic-glycolic-tartaric acid (P(I)LGT) (WO 01/12233), polyglycolic acid (U.S. Pat. No. 3,773,919), polylactic acid (U.S. Pat. No. 4,767,628), poly (M-caprolactone) and poly(alkylene oxide) (U.S. 2003/

0068384) to create a sustained release formulation, which may be liquid, gel, or a solid. Such formulations can be used to manufacture implants that release a LFA-1 antagonist over a period of a few days, a few weeks or several months depending on the polymer, the particle size of the polymer, and the size of the implant (see, e.g., U.S. Pat. No. 6,620,422). Other sustained release formulations and polymers for use in are described in EP 0 467 389 A2, WO 93/24150, U.S. Pat. No. 5,612,052, WO 97/40085, WO 03/075887, WO 01/01964 A2, U.S. Pat. No. 5,922,356, WO 94/155587, WO 02/074247 A2, WO 98/25642, U.S. Pat. Nos. 5,968,895, 6,180,608, U.S. 20030171296, U.S. 20020176841, U.S. Pat. Nos. 5,672,659, 5,893,985, 5,134,122, 5,192,741, 5,192,741, 4,668,506, 4,713,244, 5,445,832 4,931,279, 5,980,945, WO 02/058672, WO 9726015, WO 97/04744, and US20020019446. In sustained release formulations forming implants, microparticles of LFA-1 antagonist are combined with microparticles of polymer. One or more sustained release implants can be placed in the large intestine, the small intestine or both. U.S. Pat. No. 6,011,011 and WO 94/06452 describe a sustained release formulation providing either polyethylene glycols (i.e. PEG 300 and PEG 400) or triacetin.

Another formulation which may both enhance bioavailability and provide controlled release of the LFA-1 antagonist within the GI tract, is a variant of that described in WO 03/053401. Such a controlled release formulation includes a permeation enhancer, the LFA-1 antagonist, and a carrier that exhibits in-site gelling properties, such as a nonionic surfactant. The formulation is delivered within the GI tract as a liquid having at least some affinity for the surface of the GI mucosal membrane. Once released, the liquid formulation can spread across one or more areas on the surface of the GI mucosal membrane, where the carrier of the formulation then transitions into a bioadhesive gel in-situ. As a bioadhesive gel, the formulation of the present invention not only adheres to the mucosal membrane of the GI tract, but also reduces or minimizes dilution of both the permeation enhancer and the LFA-1 antagonist included in the formulation by lumenal fluids and secretions. Bioavailability of the LFA-1 antagonist may be increased by presenting the LFA-1 antagonist, together with a suitable permeation enhancer, at the surface of the mucosal membrane of the GI tract at concentrations sufficient to increase absorption of the LFA-1 antagonist through the GI mucosal membrane over a period of time.

Permeation enhancers suitable for use in a controlled formulation of this type include, but are not limited to, ethylenediamine tetra-acetic acid (EDTA), bile salt permeation enhancers, such as sodium deoxycholate, sodium taurocholate, sodium deoxycholate, sodium taurodiliydrofusidate, sodium dodecylsulfate, sodium glycocholate, taurocholate, glycocholate, taurocheno-deoxycholate, taurodeoxycholate, deoxycholate, glycodeoxycholate, and ursodeoxycholate, fatty acid permeation enhancers, such as sodium caprate, sodium laurate, sodium caprylate, capric acid, lauric acid, and caprylic acid, acyl carnitines, such as palmitoyl carnitine, stearoyl carnitine, myristoyl carnitine, and lauroyl carnitine, and salicylates, such as sodium salicylate, 5-methoxy salicylate, and methyl salicylate. Permeation enhancers may act to open the tight junctions formed between epithelial cells of the GI mucosal membrane, and thereby allow diffusion of the LFA-1 antagonist into the intestinal mucosa (i.e., pericellular absorption). Though the amount of permeation enhancer included in the formulation of the present invention may range from about 10 wt % to about 40 wt %, the nature and precise amount of permeation enhancer included in the formulation of the present invention will vary depending on, for example, the LFA-1 antagonist to be delivered, the nature of the permeation enhancer itself, and the dose of formulation to be administered. The amount of permeation enhancer included in the formulation should be sufficient to maintain an effective concentration of permeation enhancer (i.e., a concentration above the critical concentration for the permeation enhancer used) at or near the surface of the GI mucosal membrane over a period of time sufficient to increase the bioavailability of the LFA-1 antagonist. Where possible, the permeation enhancer can be chosen such that the permeation enhancer not only facilitates absorption of the LFA-1 antagonist, but also resists dilution by lumenal fluids or secretions. Permeation enhancers may also be used in formulations of the invention which are not controlled release formulations.

The carrier of a controlled release formulation containing a permeation enhancer, the LFA-1 antagonist, and the carrier exhibiting in-site gelling properties will permit a transition from a relatively non-adhesive, low viscosity liquid to a relatively viscous, bioadhesive gel after the formulation has been delivered within the GI tract of a subject. The carrier is chosen such that the transition from a relatively non-adhesive, low viscosity liquid to a relatively viscous, bioadhesive gel occurs after the formulation has been released within the GI tract and had some opportunity to arrive at the surface of the GI mucosal membrane. Hence, the carrier of the formulation of the present invention enables the in-situ transition of the formulation from a liquid to a bioadhesive gel. Due to its high viscosity and bioadhesive properties, the gel formed by the formulation of the present invention holds the permeation enhancer and the LFA-1 antagonist together at the surface of the GI mucosal membrane and protects both such components from dilution and enzymatic degradation over a period of time. Suitable carriers include non-ionic surfactants that transition from a relatively non-adhesive, low viscosity liquid to a relatively viscous, bioadhesive liquid crystal state as they absorb water. Specific examples of non-ionic surfactants that may be used as the carrier in the formulation of the present invention include, but are not limited to, Cremophor (e.g., Cremophor EL and Cremophor RH), Incordas 30, polyoxyethylene 5 castor oil, polyethylene 9 castor oil, polyethylene 15 castor oil, d-a-tocopheryl polyethylene glycol succinate (TPGS), monoglycerides, such as myverol, aliphatic alcohol based nonionic surfactants, such as oleth-3, oleth-5, polyoxyl 10 oleyl ether, oleth-20, steareth-2, steareth-10, steareth-20, ceteareth-20, polyoxyl 20 cetostearyl ether, PPG-5 ceteth-20, and PEG-6 capryl/capric triglyceride, Pluronic@ and tetronic block copolymer non-ionic surfactants, such as Pluronic@ L10, L31, L35, L42, L43, L44, L62, L61, L63, L72, L81, L101, L121, and L122, polyoxylene sorbitan fatty acid esters, such as Tween 20, Tween 40, Tween 60, Tween 65, Tween 80, Tween 81, and Tween 85, and ethoxylated glycerides, such as PEG 20 almond glycerides, PEG-60 almond glycerides, PEG-20 corn glycerides, and PEG-60 corn ARC 2921 PCT 11 glycerides. The carrier may be present in about 35 wt % to about 88 wt % of the formulation.

As water is added to the controlled release formulation having a non-ionic surfactant as the carrier, the initial viscosity of the formulation will increase. However, as water content increases, the increase in viscosity of nonionic surfactants tends to be non-linear. Often, as the water content of a nonionic surfactant exceeds a certain threshold, the viscosity of the nonionic surfactant increases rapidly as the nonionic surfactant transitions to its gelling state. If a relatively quick conversion is desired, a formulation including a nonionic surfactant may be provided more water, thereby placing the formulation closer to the water content threshold at which the formulation will rapidly convert to a bioadhesive gel. In contrast, if a relatively slow conversion is desired, the formulation may include less water or no water, thereby placing the formulation farther from the gelling threshold.

Additionally, the controlled release formulation containing a permeation enhancer, the LFA-1 antagonist, and the carrier exhibiting in-site gelling properties may also include a viscosity reducing agent that reduces the initial viscosity of the formulation. Reducing the initial viscosity of the formulation may further facilitate spreading of the formulation of the present invention across one or more areas of the GI mucosal membrane after the formulation is delivered within the GI tract but before the formulation transitions into a bioadhesive gel.

Exemplary viscosity reducing agents that may be used include, but are not limited to, polyoxyethylene 5 castor oil, polyoxyethylene 9 castor oil, labratil, labrasol, capmul GMO (glyceryl mono oleate), capmul MCM (medium chain mono- and diglyceride), capmul MCM C8 (glyceryl mono caprylate), capmul MCM C10 (glyceryl mono caprate), capmul GMS-50 (glyceryl mono stearate), caplex 100 (propylene glycol didecanoate), caplex 200 (propylene glycol dicaprylate/dicaprate), caplex 800 (propylene glycol di 2-ethyl hexanoate), captex 300 (glyceryl tricapryl/caprate), captex 1000 (glyceryl tricaprate), captex 822 (glyceryl triandecanoate), captex 350 (glyceryl tricaprylate/caprate/laurate), caplex 810 (glyceryl tricaprylate/caprate/linoleate), capmul PG8 (propylene mono caprylate), propylene glycol, and propylene glycol laurate (PGL). Where a viscosity reducing agent is included, the viscosity reducing agent may be present in amounts up to about 10 wt % of the formulation.

Further, the dosage form of the controlled release formulation containing a permeation enhancer, the LFA-1 antagonist, and the carrier exhibiting in-site gelling properties may include a hard or soft gelatin capsule. In some embodiments, the dosage form is designed, such as by use of enteric coatings, to delay release of the formulation until the dosage form has passed through the stomach and at least entered the small intestine.

Additional controlled release formulations are described in WO 02/38129, EP 326 151, U.S. Pat. No. 5,236,704, WO 02/30398, WO 98/13029; U.S. 20030064105, U.S. 20030138488 A1, U.S. 20030216307 A1, U.S. Pat. No. 6,667,060, WO 01/49249, WO 01/49311, WO 01/49249, WO 01/49311, and U.S. Pat. No. 5,877,224. An example of a solid controlled release formulation may include hydrophilic polymers such as starch, cellulosic polymers, polyacrylic acids, or polymethacrylic acids to entrap the LFA-1 antagonist; cyclodextrins such as alpha, beta, or gamma cyclodextrins and further including substituted cyclodextrins such as sulfobutyl cyclodextrins or hydroxypropyl beta cyclodextrin, which complex with the LFA-1 antagonist and act to provide a more regulated release of the LFA-1 antagonist from the solid controlled release formulation.

The oral administration formulations may utilize gastroretentive formulations to enhance absorption from the gastrointestinal (GI) tract. A formulation which is retained in the stomach for several hours may release compounds of the invention to provide a sustained release in the upper gastrointestinal region that may be desirable in some embodiments of the invention. Disclosure of such gastro-retentive formulations are found in Klausner, E. A.; Lavy, E.; Barta, M.; Cserepes, E.; Friedman, M.; Hoffman, A. 2003 "Novel gastroretentive dosage forms: evaluation of gastroretentivity and its effect on levodopa in humans." Pharm. Res. 20, 1466-73, Hoffman, A.; Stepensky, D.; Lavy, E.; Eyal, S. Klausner, E.; Friedman, M. 2004 "Pharmacokinetic and pharmacodynamic aspects of gastroretentive dosage forms" Int. J. Pharm. 11, 141-53, Streubel, A.; Siepmann, J.; Bodmeier, R.; 2006 "Gastroretentive drug delivery systems" Expert Opin. Drug Deliver. 3, 217-3, and Chavanpatil, M. D.; Jain, P.; Chaudhari, S.; Shear, R.; Vavia, P. R. "Novel sustained release, swellable and bioadhesive gastroretentive drug delivery system for olfoxacin" Int. J. Pharm. 2006 epub Mar. 24. Expandable, floating and bioadhesive techniques may be utilized to maximize the extent and/or duration of absorption of the compounds of the invention. Materials such as cross povidone, pysllium husk, chitosan, cellulosic polymers, amongst other materials, can be selected and combined to vary the buoyancy lag time, duration of buoyancy, dimensional stability, drug content and drug release profile. Variation of the physical characteristics of the formulation can also used to vary these parameters of drug delivery. For example, a biodegradable membrane may be included as part of a gastroretentive formulation, which membrane is buoyant in the stomach and is exposed to the gastric environment only over a predetermined time period. This membrane may be formed of materials that only release LFA-1 antagonist after this initial exposure period, thus, in combination with an immediately releasing portion of the gastroretentive formulation, providing LFA-1 antagonist over a much extended period of time relative to a formulation comprising only immediate release compositions.

An aerosol suspension of respirable particles may be solid or liquid, with suitably sized particles, as is known in the art to be effective for absorption. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in pharmaceutically acceptable solvents may be nebulized by use of inert gases. Nebulized solutions may be inhaled directly from the nebulizing device or the nebulizing device may be attached to a face mask tent, or intermittent positive pressure breathing machine. Alternatively a pressurized metered dose device may be used to deliver the drug, or dry powder inhaler devices. Solution, suspension, or powder compositions may be administered, topically, orally or nasally, from devices that deliver the formulation in an appropriate manner.

Eye drops may be prepared by dissolving the amorphous form or any of the crystalline forms of the compound of Formula I, or a combination thereof, in a sterile aqueous solution such as physiological saline, buffering solution, etc., or by combining powder compositions to be dissolved before use. Other vehicles may be chosen, as is known in the art, including but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.;

e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

In some embodiments of the invention, addition of sodium bicarbonate is made to the amorphous form or any of crystalline forms A, B, C, D, or E, or a mixture thereof of the compound of Formula I to convert it to a sodium salt. In some embodiments of the invention, the amorphous form or any of the crystalline forms A, B, C, D, or E are formulated as their sodium, potassium, lithium, magnesium, zinc, or calcium salts.

The solubility of the components of the present compositions may be enhanced by a surfactant or other appropriate co-solvent in the composition. Such cosolvents include polysorbate 20, 60, and 80, Pluronic F68, F-84 and P-103, cyclodextrin, or other agents known to those skilled in the art. Such co-solvents may be employed at a level of from about 0.01% to 2% by weight.

The composition of the invention can be formulated as a sterile unit dose type containing no preservatives.

The compositions of the invention may be formulated as a sterile unit dose type containing preservatives. Suitable preservatives include benzalkonium chloride, thimerosal, chlorobutanol, methyl paraben, ethyl paraben, propyl paraben, phenylethyl alcohol, imidazolidinyl urea, diazolidinyl urea, phenoxyethanol, edetate disodium, sorbic acid, Onamer M, purite, peroxides, perborates, and other agents known to one of skill in the art. The preservatives may be employed at a level from about 0.004% to about 0.02% W/W.

The compositions of the invention may be packaged in multidose form. Preservatives may be preferred to prevent microbial contamination during use. Suitable preservatives include: benzalkonium chloride, thimerosal, chlorobutanol, methyl paraben, ethyl paraben, propyl paraben, phenylethyl alcohol, imidazolidinyl urea, diazolidinyl urea, phenoxyethanol, edetate disodium, sorbic acid, Onamer M, or other agents known to those skilled in the art. In the prior art ophthalmic products, such preservatives may be employed at a level of from 0.004% to 0.02%.

In some of the compositions of the present application, methyl paraben and propyl paraben are used in combination.

In the compositions of the present application the preservative benzalkonium chloride, may be employed at a level of from about 0.001% to less than about 0.01%, e.g. from about 0.001% to about 0.008%, or about 0.005% by weight. It has been found that a concentration of benzalkonium chloride of about 0.005% may be sufficient to preserve the compositions of the present invention from microbial attack.

The amount of administration and the number of administrations of the active ingredient used in the present invention vary according to sex, age and body weight of patient, symptoms to be treated, desirable therapeutic effects, administration routes and period of treatment. For eye drops for an adult, the formulations containing the amorphous form or the crystalline forms of the compound of Formula I may range in concentration from about 0.0001% to 10.0 W/V %, about 0.005% to 10.0 W/V %, about 0.01% to 10.0 W/V %, about 0.05% to 10.0 W/V %, about 0.1% to 10.0 W/V %, about 0.5% to 10.0 W/V %, about 1.0% to 10.0 W/V %, about 2.0% to 10.0 W/V %, about 3.0% to 10.0 W/V %, about 4.0% to 10.0 W/V %, or about 5.0% to 10.0 W/V %; about 1% to about 20.0 W/V %, about 5% to about 20.0 W/V %, about 7% to about 20.0 W/V %, about 10% to about 20.0 W/V %, about 12% to about 20.0 W/V %, about 15% to about 20.0 W/V %, or about 17% to about 20.0 W/V %; about 5% to about 25.0 W/V %, about 7% to about 25.0 W/V %, about 10% to about 25.0 W/V %, about 12% to about 25.0 W/V %, about 15% to about 25.0 W/V %, about 17% to about 25.0 W/V %, about 20% to about 25.0 W/V %, or about 22% to about 25.0 W/V %; about 5% to about 35.0 W/V %, about 7% to about 35.0 W/V %, about 10% to about 35.0 W/V %, about 12% to about 35.0 W/V %, about 15% to about 35.0 W/V %, about 17% to about 35.0 W/V %, about 20% to about 35.0 W/V %, 22% to about 35.0 W/V %, 25% to about 35.0 W/V %, 27% to about 35.0 W/V %, 30% to about 35.0 W/V %, or about 32% to about 35.0 W/V %; about 5% to about 40.0 W/V %, about 7% to about 40.0 W/V %, about 10% to about 40.0 W/V %, about 12% to about 40.0 W/V %, about 15% to about 40.0 W/V %, about 17% to about 40.0 W/V %, about 20% to about 40.0 W/V %, 22% to about 40.0 W/V %, 25% to about 40.0 W/V %, 27% to about 40.0 W/V %, 30% to about 40.0 W/V %, 33% to about 40.0 W/V %, 35% to about 40.0 W/V %, or about 37% to about 40.0 W/V %; about 5% to about 50.0 W/V %, about 10% to about 50.0 W/V %, about 12% to about 50.0 W/V %, about 15% to about 50.0 W/V %, about 20% to about 50.0 W/V %, about 22% to about 50.0 W/V %, about 25% to about 50.0 W/V %, about 27% to about 50.0 W/V %, about 30% to about 50.0 W/V %, about 32% to about 50.0 W/V %, about 35% to about 50.0 W/V %, about 37% to about 50.0 W/V %, about 40% to about 50.0 W/V %, about 42% to about 50.0 W/V %, about 45% to about 50.0 W/V %, or about 47% to about 50.0 W/V %. One embodiment of the invention has a formulation of about 1.0% to 10.0 W/V % of the compounds of the invention. One embodiment of the invention has a formulation of about 0.01% to 10.0 W/V % of the compounds of the invention. One embodiment of the invention has a formulation of about 5.0% to 10.0 W/V % of the compounds of the invention. One embodiment of the invention has a formulation of about 10% to about 50.0 W/V % of the compounds of the invention. One embodiment of the invention has a formulation of about 10% to about 20.0 W/V % of the compounds of the invention. One embodiment of the invention has a formulation of about 10% to about 35.0 W/V % of the compounds of the invention. The administration may be administered several times a day per eye, one to ten times, one to four times, or once a day. The size of the drop administered may be in the range of about 10-100 µl about 10-90 µl about 10-80 µl, about 10-70 µl about 10-60 µl about 10-50 µl, about 10-40 µl, about 10-30 µl, about 20-100 µl about 20-90 µl about 20-80 µl, about 20-70 µl, about 20-60 µl, about 20-50 µl, about 20-40 µl, or about 20-30 µl. One embodiment of the invention administers a drop in the range of 10-30 µl. One embodiment of the invention administers a drop in the range of 10-100 µl. One embodiment of the invention administers a drop in the range of 20-50 µl. One embodiment of the invention administers a drop in the range of 10-60 µl.

The formulations of the invention may be administered several drops per time, one to four drops one to three drops, one to two drops, or one drop per day.

In formulations for ointment, cream, lotion or spray, the concentration of the amorphous form or any of the crystalline Forms of the compound of Formula I or a combination thereof in the formulations may range about 0.0001% to 10.0 W/V %, about 0.005% to 10.0 W/V %, about 0.01% to 10.0 W/V %, about 0.05% to 10.0 W/V %, about 0.1% to 10.0 W/V %, about 0.5% to 10.0 W/V %, about 1.0% to 10.0 W/V %, about 2.0% to 10.0 W/V %, about 3.0% to 10.0 W/V %, about 4.0% to 10.0 W/V %, or about 5.0% to 10.0 W/V %; about 1% to about 20.0 W/V %, about 5% to about 20.0 W/V %, about 7% to about 20.0 W/V %, about 10% to about 20.0 W/V %, about 12% to about 20.0 W/V %, about 15% to about 20.0 W/V %, or about 17% to about 20.0 W/V %; about 5% to about 25.0

W/V %, about 7% to about 25.0 W/V %, about 10% to about 25.0 W/V %, about 12% to about 25.0 W/V %, about 15% to about 25.0 W/V %, about 17% to about 25.0 W/V %, about 20% to about 25.0 W/V %, or about 22% to about 25.0 W/V %; about 5% to about 35.0 W/V %, about 7% to about 35.0 W/V %, about 10% to about 35.0 W/V %, about 12% to about 35.0 W/V %, about 15% to about 35.0 W/V %, about 17% to about 35.0 W/V %, about 20% to about 35.0 W/V %, 22% to about 35.0 W/V %, 25% to about 35.0 W/V %, 27% to about 35.0 W/V %, 30% to about 35.0 W/V %, or about 32% to about 35.0 W/V %; about 5% to about 40.0 W/V %, about 7% to about 40.0 W/V %, about 10% to about 40.0 W/V %, about 12% to about 40.0 W/V %, about 15% to about 40.0 W/V %, about 17% to about 40.0 W/V %, about 20% to about 40.0 W/V %, 22% to about 40.0 W/V %, 25% to about 40.0 W/V %, 27% to about 40.0 W/V %, 30% to about 40.0 W/V %, 33% to about 40.0 W/V %, 35% to about 40.0 W/V %, or about 37% to about 40.0 W/V %; about 5% to about 50.0 W/V %, about 10% to about 50.0 W/V %, about 12% to about 50.0 W/V %, about 15% to about 50.0 W/V %, about 20% to about 50.0 W/V %, about 22% to about 50.0 W/V %, about 25% to about 50.0 W/V %, about 27% to about 50.0 W/V %, about 30% to about 50.0 W/V %, about 32% to about 50.0 W/V %, about 35% to about 50.0 W/V %, about 37% to about 50.0 W/V %, about 40% to about 50.0 W/V %, about 42% to about 50.0 W/V %, about 45% to about 50.0 W/V %, or about 47% to about 50.0 W/V %. One embodiment of the invention has a formulation of about 1.0% to 10.0 W/V % of the compounds of the invention. One embodiment of the invention has a formulation of about 0.01% to 10.0 W/V % of the compounds of the invention. One embodiment of the invention has a formulation of about 5.0% to 10.0 W/V % of the compounds of the invention. One embodiment of the invention has a formulation of about 10% to about 50.0 W/V % of the compounds of the invention. One embodiment of the invention has a formulation of about 10% to about 20.0 W/V % of the compounds of the invention. One embodiment of the invention has a formulation of about 10% to about 35.0 W/V % of the compounds of the invention. These formulations may be applied or sprayed several times a day, one to six times, one to four times, or once a day. The compounding ratio of each ingredient may be suitably increased or decreased based on the degree of inflammations or infections.

The formulations of the invention can further include other pharmacological active ingredients as far as they do not contradict the purpose of the present invention. In a combination of plural active ingredients, their respective contents may be suitably increased or decreased in consideration of their effects and safety.

V. Kits

The invention also provides kits. The kits include a compound of the invention in suitable packaging, and written material that can include instructions for use, discussion of clinical studies, listing of side effects, and the like. The kit may further contain another therapeutic agent that is co-administered with the amorphous form or any of the crystalline Forms of the compound of Formula I or a combination thereof. In some embodiments, the therapeutic agent and the amorphous form or any of the crystalline Forms of the compound of Formula I or a combination thereof are provided as separate compositions in separate containers within the kit. In some embodiments, the therapeutic agent and the amorphous form or any of the crystalline forms of the compound of Formula I or a combination thereof are provided as a single composition within a container in the kit. Suitable packaging and additional articles for use (e.g., measuring cup for liquid preparations, foil wrapping to minimize exposure to air, dispensers, and the like) are known in the art and may be included in the kit.

EXAMPLES

Example 1

Human T-Cell Adhesion Assay

The T-cell adhesion assay was performed using the human T-lymphoid cell line HuT 78 (ATCC TIB-161). Goat anti-HuIgG(Fc) was diluted to 2 µg/ml in PBS and 96-well plates were coated with 50 µl/well at 37° C. for 1 h. Plates were washed with PBS and blocked for 1 h at room temperature with 1% BSA in PBS. 5 domain ICAM-Ig was diluted to 100 ng/ml in PBS and 50 µl/well was added to the plates 0/N at 4° C. HuT 78 cells were centrifuged at 100 g and the cell pellet was treated with 5 mM EDTA for ~5' at 37° C. in a 5% $CO_2$ incubator. Cells were washed in 0.14 M NaCl, 0.02 M Hepes, 0.2% glucose and 0.1 mM $MnCl_2$ (assay buffer) and centrifuged. The cells were resuspended in assay buffer to $3.0 \times 10^6$ c/ml Inhibitors were diluted in assay buffer to a 2× final concentration and pre-incubated with HuT78 cells for 30' at room temperature. 100 µl/well of cells and inhibitors were added to the plates and incubated at room temperature for 1 h. 100 µl/well PBS was added and the plates were sealed and centrifuged inverted at 100 g for 5'. Unattached cells were flicked out of the plate and excess PBS was blotted on a paper towel. 60 µl/well p-nitrophenyl n-acetyl-β-D-glucosaminide (0.257 g to 100 ml citrate buffer) was added to the plate and incubated for 1.5 h at 37° C. The enzyme reaction was stopped with 90 µl/well 50 mM glycine/5 mM EDTA and read on a platereader at 405 nM. HUT 78 cell adhesion to 5dICAM-Ig was measured using the p-nitrophenyl n-acetyl-β-D-glucosaminide method of Landegren, U. (1984). J. Immunol. Methods 57, 379-388. The compound of Formula was shown to be a potent inhibitor of T-cell adhesion with an EC 50 of less than 50 nM/

Example 2

LFA-1:ICAM-1 Receptor Binding Assay Using Forward Format Assay

Competitive inhibition of the LFA-1:ICAM-1 interaction is quantitated by adding known amounts of inhibitors.

Purified full length recombinant human LFA-1 protein is diluted to 2.5 µg/ml in 0.02 M Hepes, 0.15M NaCl, and 1 mM $MnCl_2$ and 96-well plates (50 µl/well) are coated overnight at 4° C. The plates are washed with wash buffer (0.05% Tween in PBS) and blocked for 1 h at room temperature with 1% BSA in 0.02M Hepes, 0.15 M NaCl, and 1 mM $MnCl_2$. Plates are washed. 50 µl/well inhibitors, appropriately diluted in assay buffer (0.5% BSA in 0.02M Hepes, 0.15M NaCl, and 1 mM $MnCl_2$), are added to a 2× final concentration and incubated for 1 h at room temperature. 50 µl/well of purified recombinant human 5 domain ICAM-Ig, diluted to 50 ng/ml in assay buffer, is added and incubated 2 h at room temperature. Plates are washed and bound ICAM-Ig is detected with Goat anti-HuIgG(Fc)-HRP for 1 h at room temperature. Plates are washed and developed with 100 µl/well TMB substrate for 10-30' at room temperature. Colorimetric development is stopped with 100 µl/well 1M $H_2PO_4$ and read at 450 nM on a platereader. The compound of Formula I is expected to demonstrate potent competitive inhibition of the interaction between LFA-1 and ICAM-1.

Example 3

In-Vitro Inhibition of Antigen Stimulated Release of Cytokines From Human Peripheral Blood Monocytes (PBMC)

One form of the LFA-1 antagonist, the compound of Formula I, was evaluated for its ability to inhibit release of inflammatory cytokines, in human mononuclear cells (PBMC) stimulated with staphylococcal enterotoxin B (SEB). Stock solutions of the compound of Formula I, Rebamipide (a mucosal protective agent), and Cyclosporin A (CsA) were prepared in culture media and dilutions were prepared by addition of culture media to achieve the desired concentration. Negative controls were prepared without SEB stimulation. SEB stimulation with vehicle (0.25% DMSO/media) was used as the positive control. The compound of Formula I was shown to have EC50 of 150 nM or less.

Human PBMC, frozen in cryopreservation media were thawed, washed with RPMI culture media containing 10% FBS in growth media and seeded onto a 96 well plate at 20,000 cells/well containing 180 µl culture media. Cells were incubated in the presence of the compound of Formula I, Rebamipide or CsA at 37° C. for 1 hour prior to stimulation with SEB. SEB was added at 1 ng/ml and cell supernatants were harvested at 6, 16, and 48 hours. Cytokine levels in the assay supernatants were determined using a Luminex multiplex assay.

The compound of Formula I demonstrated potent inhibition of the release of inflammatory cytokines, particularly the T-cell regulating cytokines, IL-2 and IL-4, with increasing dose. The results are shown in Tables 7, 8, and 9. The pattern of cytokine release inhibited by more than 50% with the compound of Formula I is similar to that seen in comparison with CsA. The exceptions to this similarity include IL-3, 11-6, and IL-12p40.

TABLE 7

EC50 Concentrations for Inhibition of IL-2, IFNγ, MIP-1α, and TNF-α.

| | EC50 µM Cytokine Release | | | |
|---|---|---|---|---|
| | IL-2 | IFNγ | MIP-1α | TNF-α |
| Compound of Formula I | 0.0018 | 0.0016 | 0.020 | 0.076 |
| Rebamipide | >1000 | >1000 | >1000 | >1000 |
| Cyclosporine A | 0.00094 | 0.00050 | 0.0011 | 0.00049 |

TABLE 8

EC50 Concentrations for Inhibition of IL-4, IL-10, IP-10, GM-CSF and MCP-1.

| | EC50 µM Cytokine Release | | | | |
|---|---|---|---|---|---|
| | IL-4 | IL-10 | IP-10 | GM-CSF | MCP-1 |
| Compound of Formula I | 0.143 | 0.147 | 1.158 | 0.545 | 0.0050 |
| Rebamipide | >1000 | >1000 | >1000 | >1000 | >1000 |
| Cyclosporine A | 0.0063 | 0.0292 | 0.167 | 0.0202 | 0.0926 |

TABLE 9

EC50 Concentrations for Inhibition of IL-1α, IL-1β, IL-3, IL-5, IL-6, IL-12p40, and IL-13.

| | EC50 µM Cytokine Release | | | | | | |
|---|---|---|---|---|---|---|---|
| | IL-1α | IL-1β | IL-3 | IL-5 | IL-6 | IL-12p40 | IL-13 |
| Compound of Formula I | 0.24 | 0.36 | 52.23 | 0.11 | 43.51 | >1000 | 0.36 |
| Rebamipide | >1000 | >1000 | >1000 | >1000 | >1000 | >1000 | >1000 |
| Cyclosporine A | 0.002 | 0.003 | 0.002 | 0.073 | 0.001 | 0.002 | 0.074 |

Example 4

Formulations of LFA-1 Antagonist

The compound of Formula I was formulated in several compositions for administration as gels, lotions, ointments, and solutions, for administration by varying routes, including but not limited to topical, via instillation, aerosol, transdermal patch, via insert, or oral administration.

TABLE 10

Gel Formulations 1 and 2 of the Compound of Formula I.

| Formulation 1 (% w/w) | Formulation 2 (% w/w) |
|---|---|
| 1% Form A of the compound of Formula I | 1% Form A of the compound of Formula I |
| 15% Dimethyl Isosorbide | 15% Dimethyl Isosorbide |
| 25% Transcutol | 25% Transcutol |

TABLE 10-continued

Gel Formulations 1 and 2 of the Compound of Formula I.

| Formulation 1 (% w/w) | Formulation 2 (% w/w) |
|---|---|
| 12% Hexylene glycol | 12% Hexylene glycol |
| 5% Propylene Glycol | 5% Propylene Glycol |
| 0.15% Methylparaben | 0.15% Methylparaben |
| 0.05% Propylparaben | 0.05% Propylparaben |
| 0.01% EDTA | 0.01% EDTA |
| 0.5% Penmulen TR-1 | 1% Hydroxyethyl Cellulose |
| q.s. pH 6.0 25% Trolamine | q.s. pH 4.5 25% Trolamine |
| q.s. 100 Water | q.s. 100 Water |

TABLE 11

Lotion Formulations 3 and 4 of the Compound of Formula I.

| Formulation 3 (% w/w) | Formulation 4 (% w/w) |
|---|---|
| 1% Form A | 1% Form A |
| 13% Dimethyl Isosorbide | 13% Dimethyl Isosorbide |
| 20% Transcutol | 20% Transcutol |
| 10% Hexylene glycol | 10% Hexylene glycol |

TABLE 11-continued

Lotion Formulations 3 and 4 of the Compound of Formula I.

| Formulation 3 (% w/w) | Formulation 4 (% w/w) |
|---|---|
| 4% Propylene Glycol | 4% Propylene Glycol |
| 0.15% Methylparaben | 0.15% Methylparaben |
| 0.05% Propylparaben | 0.05% Propylparaben |
| 0.01% EDTA | 0.01% EDTA |
| 0.5% Carbopol Ultrez 10 | 0.3% Carbopol Ultrez 10 |
| 0.2% Penmulen TR-1 | 0.2% Penmulen TR-1 |
| 3% Isopropyl Myristate | 2% Cetyl Alcohol |
| 5% Olelyl Alcohol | 5.5% Light Mineral Oil |
| 5% White Petrolatum | 5% Oleic Acid |
| 0.02% Butylated Hydroxytoluene | 0.02% Butylated Hydroxytoluene |
| q.s. pH 6.0 25% Trolamine | q.s. pH 6.0 25% Trolamine |
| q.s. 100 Water | q.s. 100 Water |

TABLE 12

Ointment Formulations 5 and 6 of the Compound of Formula I.

| Formulation 5 (% w/w) | Formulation 6 (% w/w) |
|---|---|
| 1% Form A | 1% Form A |
| 15% PEG 400 | 10% Dimethyl Isosorbide |
| 0.02% Butylated Hydroxytoluene | 0.02% Butylated Hydroxytoluene |
| 2% Span 80 | 2% Span 80 |

TABLE 12-continued

Ointment Formulations 5 and 6 of the Compound of Formula I.

| Formulation 5 (% w/w) | Formulation 6 (% w/w) |
|---|---|
| 10% White Wax | 10% White Wax |
| 71.98% White Petrolatum | 76.98% White Petrolatum |

TABLE 13

Solution Formulations 7, 8, and 9 of the Compound of Formula I.

| Formulation 7 (% w/w) | Formulation 8 (% w/w) | Formulation 9 (% w/w) |
|---|---|---|
| 1% Form A | 1% Form A | 1% Form A |
| 15% Dimethyl Isosorbide | 15% Dimethyl Isosorbide | 99% Dimethyl Sulfoxide |
| 25% Transcutol | 25% Transcutol | |
| 12% Hexylene glycol | 12% Hexylene glycol | |
| 5% Propylene Glycol | 5% Propylene Glycol | |
| q.s. pH 4.5 | q.s. pH 6.0 | |
| 25% Trolamine | 25% Trolamine | |
| q.s. 100 Water | q.s. 100 Water | |

TABLE 14

Solution Formulations 10, 11, 12, 13 and 14 of the Compound of Formula I.

| W/W % | Formulation 10 | Formulation 11 | Formulation 12 | Formulation 13 | Formulation 14 |
|---|---|---|---|---|---|
| Form A | 0.1% | 0.3% | 1% | 3% | 5% |
| Sodium Bicarbonate | 0.015% | 0.046% | 0.15% | 0.46% | 0.77% |
| 0.1% EDTA | | | | | |
| 0.12% Sodium Phosphate, Monobasic | | | | | |
| 0.4% Methylparaben | | | | | |
| 0.02% Propylparaben | | | | | |
| q.s. Osmolality 270, Sodium Chloride | | | | | |
| q.s. pH 7.0 1% Sodium Hydroxide | | | | | |
| q.s. pH 7.0 1% HCl | | | | | |
| q.s. Water | | | | | |

TABLE 15

Solution Formulation 15 of the Compound of Formula I.

| Formulation 15 |
|---|
| 1 ml of a solution of the compound of Formula I |
| 10% W/W in water, plus |
| 0.158 mmol sodium bicarbonate |
| 9 ml PBS |

The compound of Formula I can be supplied as a sterile, clear, colorless liquid solution containing 0.1%, 1.0%, and 5.0% (w/w) Active Pharmaceutical Ingredient (API) concentrations (pH 7.0). Each mL of a 1% solution contains 10 mg of the active ingredient. In addition to the compound of Formula I, other components of a drug product solution, their functions, and their compendial grade can include propylparaben (preservative; National Formulary (NF)), methylparaben (preservative, NF), EDTA (antioxidant, United States Pharmacopeia (USP)), sodium bicarbonate (buffering agent, USP), monobasic sodium phosphate (buffering agent, USP), dibasic sodium phosphate (buffering agent, USP), and sterile water (diluent, USP). All excipients can be of compendial grade and of non-human or non-animal origin.

Formulated drug product solution can be packaged under aseptic conditions into sterile 7.0 mL High Density Polyethylene (HDPE) bottles equipped with a dropper tip that delivers an approximate per drop volume of 0.35 μL and a protective cap. The dropper bottle can have a 40 μL tip. Unpreserved study drug (no methyl or propylparabens in the formulation) can be provided in 0.5 mL unit dose Low Density Polyethylene (LDPE) containers manufactured using a blow fill seal process and stored in aluminum foil pouches.

Drug solutions can be stored refrigerated (2-8° C.). The stability of the drug at 5° C. and 25° C. can be out to 9 months or longer.

Example 5

In-Vitro Percutaneous Absorption of the Compound of Formula I Following Topical Application Bioavailability following topical application in-vivo was assessed using in-vito percutaneous absorption test methods, using procedures adapted from Skelly et al., Pharmaceutical Research 1987 4(3): 265-276, "FDA and AAPS Report of the Workshop on Principles and Practices of In-Vitro Percutaneous Penetration Studies: Relevance to Bioavailability and Bioequivalence".

Formulations 1-9 were applied to dermatomed human skin tissue excised from a single donor in a single clinically relevant dose of 5 mg/cm$^2$, which is equivalent to a 30-35 m dose. The thickness of the tissue ranges form 0.023 to 0.039 inches (0.584 to 0.991 mm) with a mean+/−standard deviation in thickness of 0.030+/−0.004 inches (0.773+/−0.111 mm) and a coefficient of variation of 14.4%. The tissue samples were mounted in Bronaugh flow-through diffusion cells. The cells were maintained at a constant temperature of 32° C. using recirculating water baths. The cells have a nominal diffusion area of 0.64 cm$^2$. PBS, at pH 7.4, with 0.1% sodium azide and 4% Bovine Serum Albumin was used as the receptor phase below the mounted tissue. Fresh receptor phase was continuously pumped under the tissue at a flow rate of nominally 1.0 ml/hr and collected in 6 hour intervals. The receptor phases were collected for analysis.

The tissue samples were exposed to Formulations 1-9 for 24 hours. The excess formulation residing on the strateum corneum at that timepoint was removed by tape-stripping with CuDerm D-Squame stripping discs. The tape strips were discarded. The epidermis and dermis were separated by blunt dissection. Epidermis, dermis and receptor phase were analyzed for content of the compound of Formula I. The results are represented in Table 16.

Tissue permeation levels (the receptor phase) of the compound of Formula I for all formulations except for Formulation 9, which contained 99% DMSO, were below the limits of quantitation, which was 0.54 ng/ml (which is equivalent to 0.013% of the applied dose). Formulation 9, in contrast, provided 1.4% of the applied dose, permeating through all the layers of the skin tissue over the exposure period of 24 hours.

Epidermal deposition of the compound of Formula I over the 24 hour exposure period was very high and consistent with a large percentage of the applied dose being retained in the upper layers of the epidermis. The levels reported in Table 10 were obtained from small volume samples, which could not be re-assayed, and thus are considered underestimates of the amount of drug present in the epidermis.

Analytical data for the dermis fell within the linearity range established for the compound of Formula I, and are quantitative. Dermal deposition of the compound of Formula I following a 24 hour exposure ranged from 0.66% (Formulation 6, 0.258 μg/cm$^2$) to 4.4% (Formulation 7, 34.3 μg/cm$^2$) of the applied dose. The concentration of the compound of Formula I (633.5 g/mole) in the dermis is thereby calculated as 6.7 μM (Formulation 6) or greater (i.e., Formulation 7 provides a concentration in the dermis of 54.1 μM) for Formulations 1 to 9 in the dermis. These concentrations are well above the in-vitro EC50 concentration for half maximal effect in inhibiting release of inflammatory cytokines by the compound of Formula I, as shown in Example 3. These results are therefore predictive for the ability of a variety of formulations, which incorporate 1% W/W of the compound of Formula I, to provide therapeutically effective levels of in-vivo inhibition of cytokine release.

TABLE 16

Cumulative Receptor Phase and Tissue Levels of the Compound of Formula I After 24 Hours of Topical Exposure.

| Formulation # | | Receptor Phase Content at 24 hours | | Epidermis | | Dermis | | |
|---|---|---|---|---|---|---|---|---|
| | | μg/cm$^2$ | % Dose Applied | μg/cm$^2$ | % Dose Applied | μg/cm$^2$ | μg/ml | % Dose Applied |
| 1 | Mean | <Limit of Quantitation | | 3.93 | 7.48 | 1.14 | 18.8 | 2.15 |
| | SD[1] | | | 2.92 | 5.50 | 0.91 | 14.9 | 1.73 |
| | % CV[2] | | | 74 | 74 | 80 | 80 | 80 |
| 2 | Mean | <Limit of Quantitation | | 6.03 | 11.9 | 0.750 | 12.3 | 1.49 |
| | SD | | | 2.56 | 5.1 | 0.304 | 5.0 | 0.63 |
| | % CV | | | 43 | 42 | 40 | 40 | 42 |
| 3 | Mean | <Limit of Quantitation | | 6.03 | 12.1 | 1.40 | 23.0 | 2.74 |
| | SD | | | 2.97 | 6.4 | 0.27 | 4.4 | 0.47 |
| | % CV | | | 49 | 53 | 19 | 19 | 17 |
| 4 | Mean | <Limit of Quantitation | | 7.92 | 17.0 | 0.975 | 16.0 | 2.10 |
| | SD | | | 3.41 | 7.2 | 0.350 | 5.8 | 0.75 |
| | % CV | | | 43 | 42 | 36 | 36 | 36 |
| 5 | Mean | <Limit of Quantitation | | 5.71 | 14.6 | 0.670 | 11.0 | 1.71 |
| | SD | | | 1.73 | 4.2 | 0.351 | 5.8 | 0.87 |
| | % CV | | | 30 | 29 | 52 | 52 | 51 |
| 6 | Mean | <Limit of Quantitation | | 6.47 | 16.8 | 0.258 | 4.25 | 0.657 |
| | SD | | | 1.07 | 2.7 | 0.158 | 2.6 | 0.394 |
| | % CV | | | 17 | 16 | 61 | 61 | 60 |

TABLE 16-continued

Cumulative Receptor Phase and Tissue Levels of the Compound of Formula I After 24 Hours of Topical Exposure.

| Formulation # | | Receptor Phase Content at 24 hours | | Epidermis | | Dermis | | |
|---|---|---|---|---|---|---|---|---|
| | | µg/cm$^2$ | % Dose Applied | µg/cm$^2$ | % Dose Applied | µg/cm$^2$ | µg/ml | % Dose Applied |
| 7 | Mean | <Limit of Quantitation | | 7.22 | 15.0 | 2.08 | 34.3 | 4.35 |
|   | SD   |                        | | 2.15 | 4.5  | 0.84 | 13.7 | 1.83 |
|   | % CV |                        | | 30   | 30   | 40   | 40   | 42   |
| 8 | Mean | <Limit of Quantitation | | 8.58 | 18.0 | 1.48 | 24.3 | 3.09 |
|   | SD   |                        | | 3.53 | 7.7  | 0.99 | 16.2 | 2.07 |
|   | % CV |                        | | 41   | 43   | 67   | 67   | 67   |
| 9 | Mean | 0.660 | 1.43 | 5.78 | 13.2 | 1.19 | 19.6 | 2.63 |
|   | SD   | 0.253 | 0.49 | 3.18 | 8.3  | 0.49 | 8.1  | 1.15 |
|   | % CV | 38    | 34   | 55   | 63   | 41   | 41   | 44   |

[1]Standard Deviation.
[2]Percent Coefficient of Variation.

Example 6

Pharmacological Activity of the Compound of Formula I for Treatment of Keratoconjunctivitis Sicca (KCS)

Dogs were enrolled in this study if the following criteria were met: more than one year of age, a Schimer tear test (STT) of less than 10 mm wetting per minute, bilateral involvement, and at least one of the following clinical signs: blepharospasm, conjunctivial hyperemia, exposure keratopathy (irregular surface), corneal pigmentation, corneal neovascularization or ropey mucopurulent discharge, no congenital KCS, no traumatic KCS, toxic KCS, and no facial nerve paralysis. If dogs had been treated with topical CsA or tacrolimus in the previous six months, they were not enrolled.

The dogs were administered one 35 µl drop of the compound of Formula I, 1% solution (Formulation 15, 0.35 mg/eye), in each affected eye three times daily, with approximately 4 hours (±1 hour) between the daily doses for 12 weeks. CsA will be administered for a further four weeks by administering commercially available 0.2% ointment three times a day, after the compound of Formula I is discontinued at twelve weeks.

Animals were subjected to an ocular examination once during the initial visit and during five visits over sixteen weeks of the study (Weeks, 2, 4, 8, 12 and 16). The last OE was approximately four weeks after the last dose of the compound of Formula I and after one month of CsA treatment. The adnexa and anterior portions of both eyes were examined using an indirect opthalmoscope. The eyes were dilated with a mydriatic when applicable, to allow evaluation of the lens and fundus, including the retina. An evaluation using a modified McDonald-Shaddock scoring system was performed in conjunction with the slitlamp ocular examinations at each interval.

Tears were measured using STT strips during the initial visit and each of the five follow-up visits on Weeks 2, 4, 8, 12 and 16. One strip of STT paper was used for each eye for each interval. At each collection interval, the STT paper was folded and placed in the inferior cul de sac for sixty seconds. The length, in mm, of wetting below the notch of the paper was recorded.

Fluorescein and rose bengal staining was performed at the each of the initial and follow up examinations. Intraocular pressure measurements (IOPs) were performed using a Tono-Pet Vet® in conjunction with each of the OEs. Digital ocular images were taken before and after staining (with fluorescein and rose bengal) during each of the OEs.

Conjunctival biopsies were taken at the initial (pretreatment) visit and the Week 12 visit. The second biopsy was taken more lateral (approx. 1 mm) to the initial biopsy. Following appropriate preparation a small conjunctival biopsy was taken from the ventral formix of each eye.

Figure 27:
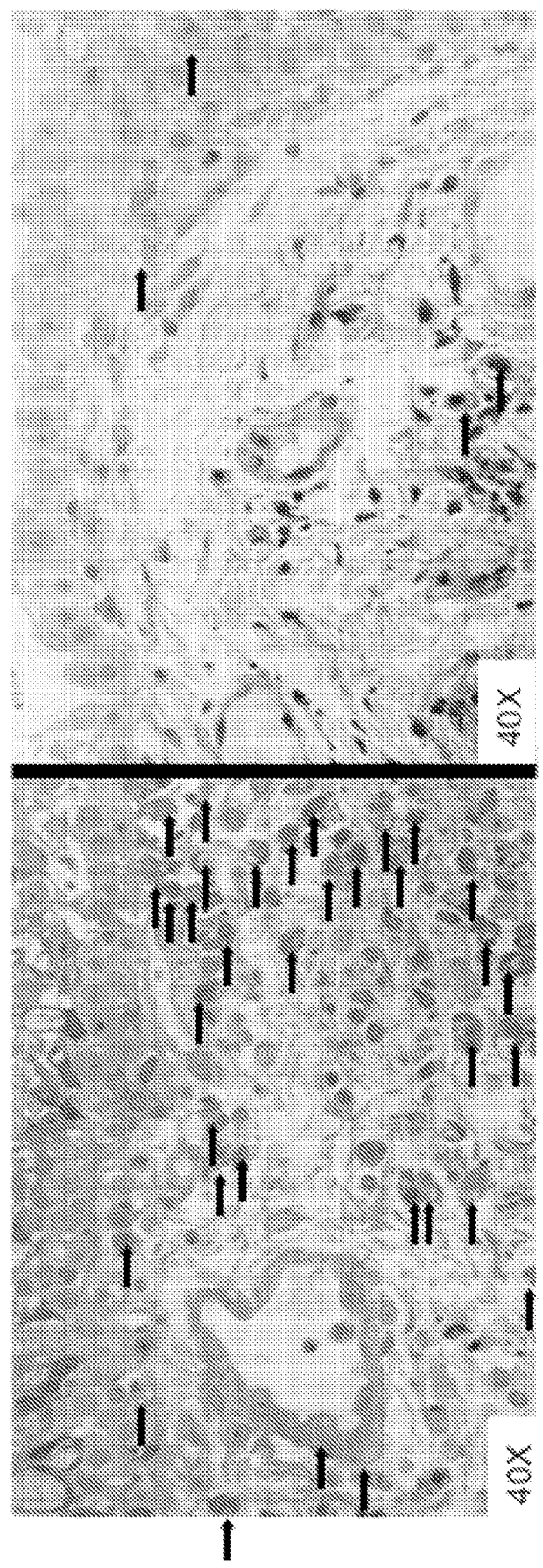
FIG. 27 is a graphical representation of histopathological evaluation of biopsies taken before and after treatment of a dog eye with the compound of Formula I.

Seven dogs completed the study; for two dogs, only one eye was studied. The results are shown in Tables 17 and 18. Overall, a 3.3 mm average improvement in OD (right eye) STT and 4.5 mm in OS (left eye) STT was observed during the treatment period with the compound of Formula I. Results for all 12 eyes show an average of 4 mm improvement. A Maximum-Minimum analysis was performed using the maximal change in STT values for each eye in each dog over weeks 1-12, as shown in Table 19. This calculation yields a total maximal change in STT for total of eyes of 72 mm, which upon division by 12 (number of KCS eyes in the analysis), yields a 6.0 mm average improvement. Other clinical signs improved in some dogs, such as a decrease in mucopurulent discharge or conjunctival erythema. Histopathological evaluation of biopsies taken before and after the compound of Formula I revealed an attenuation of lymphocyte accumulation. FIG. 27 illustrates this phenomenon in samples taken from dog #1. No significant additional benefit was seen from four subsequent weeks of CsA administration.

TABLE 17

Schirmer Tear Test Results (OD).

| Dog ID | Week 1 | Week 2 | Week 4 | Week 8 | Week 12 | Week 16 |
|---|---|---|---|---|---|---|
| 1 | 15 | 18 | 12 | 16 | 13 | 12 |
| 2 | 0  | 2  | 0  | 8  | 8  | 8  |
| 3 | 6  | 11 | 5  | 7  | 7  | 8  |
| 4 | 5  | 11 | 10 | 7  | 13 | 8  |
| 5 | 8  | 11 | 10 | 11 | 9  | 22 ** |
| 6 | 8  | 10 | 15 | 17 | 16 | 18 |
| 7 | 6  | 2  | 2  | 1  | 0  | 12 |
| Mean * | 5.5 | 7.8 | 7.0 | 8.5 | 8.8 | 11.7 |

* Dog #1 not included in mean or Maximum-Minimum analysis for OD as there is no KCS in that eye for that animal.
** Data for Dog #5 is anomalous for this day, and is not included in the mean or Maximum-Minimum analysis.

TABLE 18

Schirmer Tear Test Results (OS).

| Dog ID | Week 1 | Week 2 | Week 4 | Week 8 | Week 12 | Week 16 |
|---|---|---|---|---|---|---|
| 1 | 0 | 0 | 0 | 0 | 3 | 3 |
| 2 | 0 | 0 | 0 | 2 | 7 | 5 |
| 3 | 9 | 14 | 7 | 17 | 15 | 16 |
| 4 | 0 | 3 | 5 | 6 | 4 | 7 |
| 5 | 7 | 8 | 14 | 8 | 8 | 19 |
| 6 | 9 | 4 | 14 | 8 | 8 | 17 |
| 7 | 18 | NA | NA | 19 | 18 | 18 |
| Mean * | 4.2 | 4.8 | 6.7 | 6.5 | 8.7 | 11.0 |

* Dog #7 not included in mean or Maximum-Minimum analysis for OS as there is no KCS in that eye for that animal.

TABLE 19

Maximum-Minimum Analysis for Weeks 1-12 of the compound of Formula I Administration.

| OD | OS |
|---|---|
| NA | 3 |
| 8 | 7 |
| 5 | 10 |
| 8 | 6 |
| 3 | 7 |
| 8 | 11 |
| −4 | NA |
| Total = 28 | Total = 44 |

Figure 28:
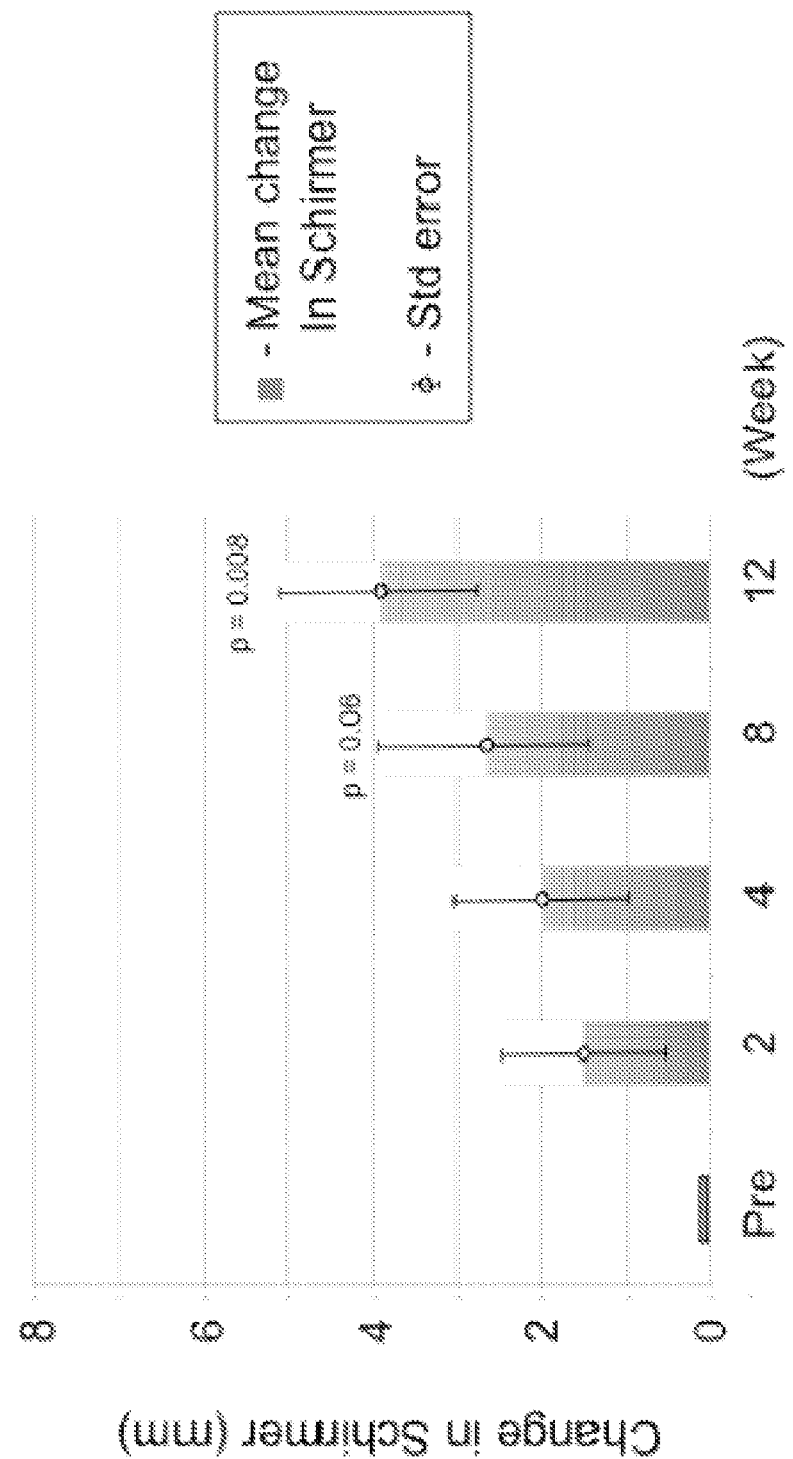
FIG. 28 illustrates the mean change in Schirmer test score at weeks, 2, 4, 8, and 12 for eyes in dogs treated with the compound of Formula I.

Total OD plus Total OS: 72
Grand Total/Number of Eligible Eyes: 6.0 mm Average Improvement FIG. 28 illustrates the mean change in Schirmer test score at weeks 2, 4, 8, and 12. Significant improvement in Schirmer test scores over pretreatment was observed in week 12.

Figure 29:
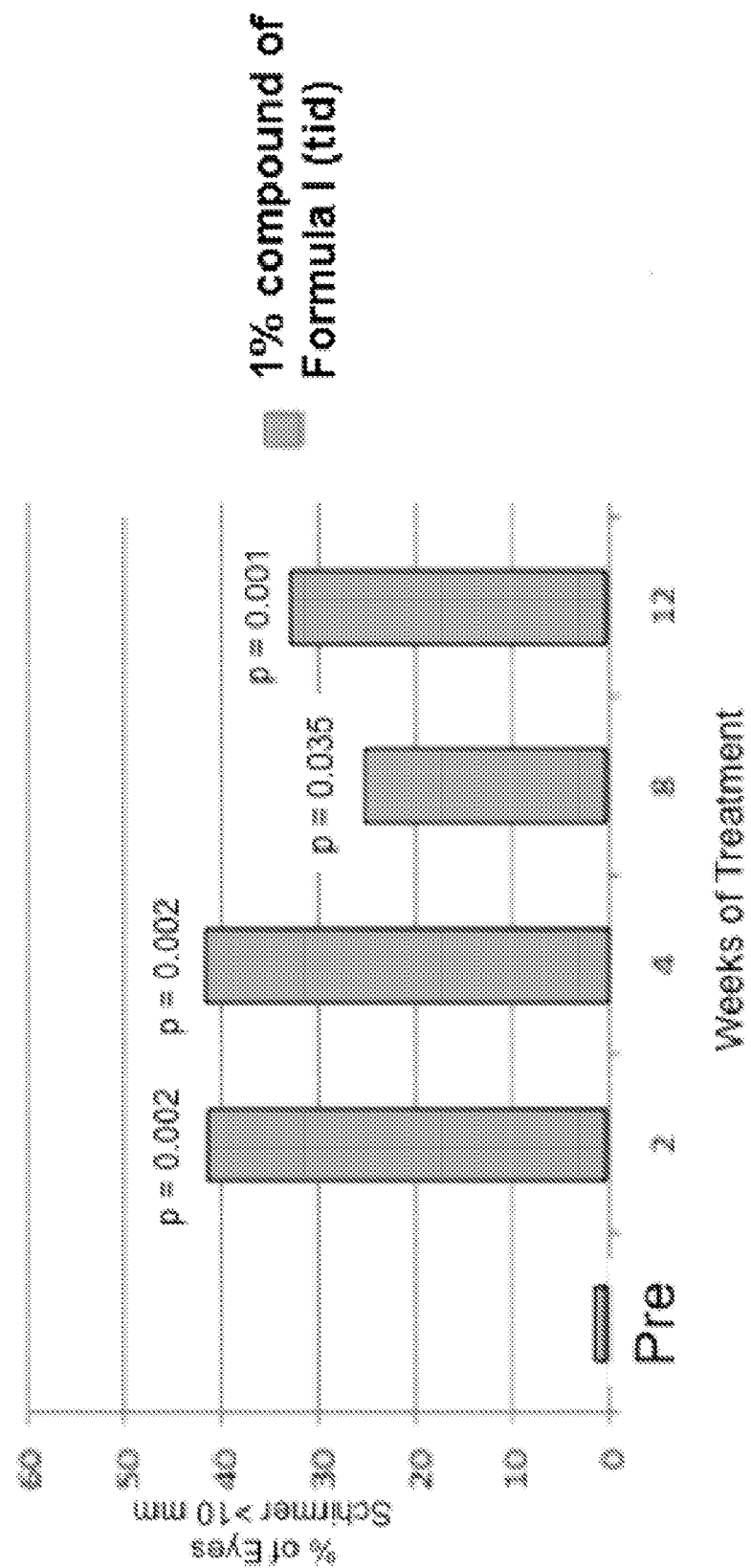
FIG. 29 illustrates percentage of dog eyes with a Schirmer test score of greater than 10 mm at 2, 4, 8, and 12-weeks with a formulation of 1% compound of Formula I (TID; three times daily).

FIG. 29 illustrates the percentage of eyes with a Schirmer test score of greater than 10 mm at 2, 4, 8, and 12-weeks with 1% the compound of Formula I (TID). The compound of Formula I canine KCS study results exceeded human CsA data. The basis of restasis approval was an improvement of Schirmer test score to greater than 10 m. Restasis treatment resulted in 15% of eyes with Schirmer test score greater than 10 mm.

Figure 30:
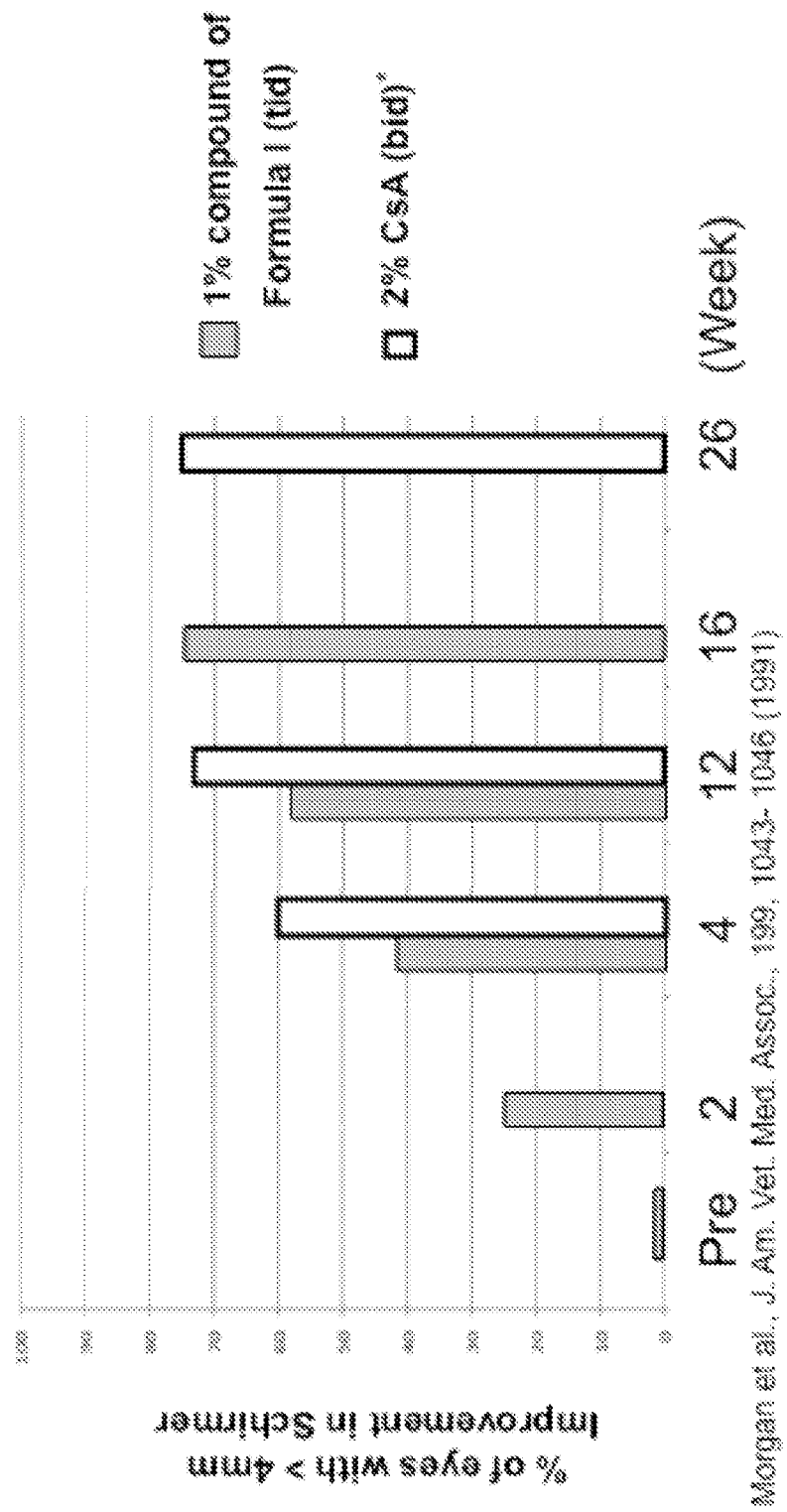
FIG. 30 illustrates percentage of eyes with a greater than 4 mm improvement in Schirmer test score at 2, 4, 12, 16, and 26 weeks for subjects treated with a formulation of 1% compound of Formula I (TID) compared to literature results for 2% CsA (BID; two times daily).

FIG. 30 illustrates the percentage of eyes with a greater than 4 mm improvement in Schirmer test score at 2, 4, 12, 16, and 26 weeks for subjects treated with 1% the compound of Formula I (tid) or 2% CsA (bid) (using historic CsA data; Morgan et al., J. Am. Vet. Med. Assoc., 199, 1043-1046 (1991)). The compound of Formula I timecourse was similar to historic CsA data.

In summary, the Canine KCS study demonstrated that administering the compound of Formula I resulted in rapid improvement in Schirmer test score in 2-8 weeks, improvement in histology, and rapid anti-inflammatory effect.

Example 7

T-Cell Proliferation Assay

This assay is an in vitro model of lymphocyte proliferation resulting from activation, induced by engagement of the T-cell receptor and LFA-1, upon interaction with antigen presenting cells (Springer, Nature 346: 425 (1990)).

Microtiter plates (Nunc 96 well ELISA certified) are pre-coated overnight at 4° C. with 50 µl of 2 µg/ml of goat anti-human Fc(Caltag H10700) and 50 µl of 0.07 µg/ml monoclonal antibody to CD3 (Immunotech 0178) in sterile PBS. The next day coat solutions are aspirated. Plates are then washed twice with PBS and 100 µl of 17 ng/ml 5d-ICAM-1-IgG is added for 4 hours at 37° C. Plates are washed twice with PBS prior to addition of CD4+ T cells. Lymphocytes from peripheral blood are separated from heparinized whole blood drawn from healthy donors. An alternative method is to obtain whole blood from healthy donors through leukophoresis. Blood is diluted 1:1 with saline, layered and centrifuged at 2500×g for 30 minutes on LSM (6.2 g Ficoll and 9.4 g sodium diztrizoate per 100 ml) (Organon Technica, N.J.). Monocytes are depleted using a myeloid cell depletion reagent method (Myeloclear, Cedarlane Labs, Hornby, Ontario, Canada). PBLs are resuspended in 90% heat-inactivated Fetal Bovine serum and 10% DMSO, aliquoted, and stored in liquid nitrogen. After thawing, cells are resuspended in RPMI 1640 medium (Gibco, Grand Island, N.Y.) supplemented with 10% heat-inactivated Fetal Bovine serum (Intergen, Purchase, N.Y.), 1 mM sodium pyruvate, 3 mM L-glutamine, 1 mM nonessential amino acids, 500 µg/ml penicillin, 50 µg/ml streptomycin, 50 µg/ml gentamycin (Gibco).

Purification of CD4+ T cells are obtained by negative selection method (Human CD4 Cell Recovery Column Kit #CL110-5 Accurate). 100,000 purified CD4+ T cells (90% purity) per microtiter plate well are cultured for 72 hours at 37° C. in 5% $CO_2$ in 100 ml of culture medium (RPMI 1640 (Gibco) supplemented with 10% heat inactivated FBS (Intergen), 0.1 mM non-essential amino acids, 1 nM Sodium Pyruvate, 100 units/ml Penicillin, 100 µg/ml Streptomycin, 50 µg/ml Gentamicin, 10 mM Hepes and 2 mM Glutamine) Inhibitors are added to the plate at the initiation of culture. Proliferative responses in these cultures are measured by addition of 1 µCi/well titrated thymidine during the last 6 hours before harvesting of cells. Incorporation of radioactive label is measured by liquid scintillation counting (Packard 96 well harvester and counter). Results are expressed in counts per minute (cpm).

Example 8

In Vitro Mixed Lymphocyte Culture Model

The mixed lymphocyte culture model, which is an in vitro model of transplantation (A. J. Cunningham, "Understanding Immunology, Transplantation Immunology" pages 157-159 (1978) examines the effects of various LFA-1 antagonists in both the proliferative and effector arms of the human mixed lymphocyte response.

Isolation of Cells: Mononuclear cells from peripheral blood (PBMC) are separated from heparanized whole blood drawn from healthy donors. Blood is diluted 1:1 with saline, layered, and centrifuged at 2500×g for 30 minutes on LSM (6.2 g Ficoll and 9.4 g sodium diztrizoate per 100 ml) (Organon Technica, N.J.). An alternative method is to obtain whole blood from healthy donors through leukophoresis. PBMCs are separated as above, resuspended in 90% heat inactivated Fetal Bovine serum and 10% DMSO, aliquoted and stored in liquid nitrogen. After thawing, cells are resuspended in RPMI 1640 medium (Gibco, Grand Island, N.Y.) supplemented with 10% heat-inactivated Fetal Bovine serum (Intergen, Purchase, N.Y.), 1 mM sodium pyruvate, 3 mM L-glutamine, 1 mM nonessential amino acids, 500 µg/ml penicillin, 50 µg/ml streptomycin, 50 µg/ml gentamycin (Gibco).

Mixed Lymphocyte Response (MLR): One way human mixed lymphocyte cultures are established are in 96-well flat-bottomed microtiter plates. $1.5 \times 10^5$ responder PBMCs are co-cultured with an equal number of allogeneic irradiated (3000 rads for 3 minutes, 52 seconds stimulator PBMSc in 200 µl of complete medium. LFA-1 antagonists are added at the initiation of cultures. Cultures are incubated at 37° C. in 5% $CO_2$ for 6 days, then pulsed with 1 µCi/well of 3H-thymidine (6.7 Ci/mmol, NEN, Boston, Mass.) for 6 hours. Cultures are harvested on a Packard cell harvester (Packard, Canberra, Canada). [$^3$H] TdR incorporation is measured by liquid scintillation counting. Results are expressed as counts per minute (cpm).

Example 9

T-Cell Adhesion Assay Using Jurkat Cells

The purpose of this study was to evaluate the anti-adhesive properties of the compound of Formula I on the attachment of Jurkat cells to ICAM-1 following in vitro exposure.

Stock solutions of the compound of Formula I and positive control were prepared in DMSO/water (1:1) and diluted into assay media and subsequent dilutions were prepared by addition of assay media to achieve the desired concentration. A reported LFA-1 antagonist was used as the positive control.

Jurkat cells were labeled with an 8 µM solution of BCECF-AM (2',7'-bis-(2-carboxyethyl)-5-(and-6)-carboxyfluorescein) in growth media at room temperature for 15 minutes. Labeled cells were incubated in 70 µL of assay media in each well of a 96 well plate at 500,000 cells per well with 70 µL of the compound of Formula I or positive control in assay media at 37° C. for 30 minutes. A 100 µL aliquot of this fluorescently labeled Jurkat cell suspension was allowed to settle in the presence of the compound of Formula I or the positive control in wells of a 96 well plate coated with recombinant human ICAM-1 expressed as an Fc chimera at 37° C. for 1 hour. Non-adherent cells were removed by washing and centrifugation at 100 g for 1 minute. Adherent cells were determined as adherent fluorescent units on a fluorescent plate reader. The test article, the compound of Formula I, demonstrated inhibition of Jurkat cell attachment with increasing dose. The dose response curve and $IC_{50}$ of the compound of Formula I in this assay was comparable to that of the known direct competitive LFA-1 antagonist. This demonstrates the compound of Formula I is an antagonist of LFA-1/ICAM-1 binding.

Example 10

Murine Pseudomonis Corneal Keratitis

The cornea is normally clear and leukocyte free. Bacterial infection induces complement mediated leukocyte recruitment and inflammation into the cornea. A murine model of neutrophil keratitis has been developed which inserts a defined number of tobramycin killed Pseudomonas into a surgical cut in the cornea. Neutrophil influx and corneal haze are scored at 24 hours. The system provides a pharmacodynamic model of neutrophil adhesion in vasculature and migration into tissue. The system has been described in Sun Y. and Pearlman E. (2009) *Invest Ophthalmol Vis Sci.* 50:1247-54.

Example 11

Preclinical and Clinical Safety and Tolerability: pk and Systemic and Local Distribution Results A. Effects in Humans 1. Phase 1 Clinical Trial Using the Compound of Formula I A Phase 1 single center randomized, prospective, double masked, placebo controlled study of escalating doses of topical compound of Formula I Ophthalmic Solution was conducted in 4 cohorts (0.1%, 0.3%, 1% and 5% compound of Formula I dose strengths) in 28 healthy adults (7 subjects per cohort: 5 received compound of Formula I Ophthalmic Solution and 2 received placebo solution). The objectives of the trial were to measure safety and tolerability, and pharmacokinetics in tear and plasma. The dosing schedule (OU; Oculus Uterque (each eye or both eyes)) was divided into 3 periods, each separated by a 72-hour wash out interval: once/day×1 day (drug one eye; placebo fellow eye), twice/day×10 days, and thrice/day×10 days, 14-day observation. Slit lamp examination of the eye, BCVA (Best Corrected Visual Acuity), STTs (Schirmer Tear Test), TBUT (Tear Break-Up Time), IOP (Intraocular pressure) were assessed at screening and the beginning and end of each period. For each cohort, masked safety data was reviewed by a Safety Committee prior to allowing dose escalation of the next cohort. A total of 2856 doses (102 drops/subject) were administered over 1148 total subject study days (41 study days/subject) in 56 eyes. All subjects in all cohorts completed the study, and no study drug doses were missed.

No deaths, discontinuations, serious or severe ocular or non-ocular AEs (adverse effects) considered related to the compound of Formula I Ophthalmic Solution administration occurred at any dose strength or in any dose regimen.

Blood pressure, heart rate, respiratory rate, temperature, body weight, and EKG results were within normal ranges throughout the trial.

All hematologic results and all but one serum chemistry result were within normal ranges with no observable study drug-related trends measured across study duration, dose-strength, or schedule. Total lymphocyte count, CD3, CD4, and CD8 cell counts were within normal ranges with no evidence of lymphocyte or neutrophil suppression. Urinalysis results were unremarkable throughout the trial.

Serum chemistry results were within normal range with no observable study drug-related trends measured across study duration, dose-strength, or schedule.

No serious or severe ocular or non-ocular AEs occurred during the study; there were 38 ocular (N=11 subjects) and 21 non ocular (N=11 subjects) AEs, respectively. There were no trends in the frequency of ocular AEs when analyzed by dose group or by study period. No significant safety trends were noted on BCVA, slit-lamp biomicroscopy, STT, TBUT, or IOP assessments, nor was there evidence of ocular infection, or localized immunosuppression. There was no evidence of localized ocular irritation or infection.

There were no trends in the frequency of non-ocular AEs when analyzed by dose group or by study period. No significant safety trends were noted on vital signs, EKG, laboratory studies (chemistry, liver functions, blood panels); there was no evidence of CD3, CD4, or CD8 T-cell suppression, bone marrow suppression, or clinical evidence of increased infections.

2. Pharmacokinetics in Tear and Plasma

Plasma and tear samples were obtained at baseline and during scheduled intervals in each dosing period to characterize the pharmacokinetics (PK) of the compound of Formula I Ophthalmic Solution following ocular administration.

a. Plasma PK Analysis

Samples for plasma compound of Formula I analysis were obtained pre-dose, at 5 and 30 minutes post-dose, and at 1, 4, 8, 24 hours post-dose on Days 1, 5, 14, 18 and 27. Samples were also obtained at 48 hours post dose on Days 1, 14 and 27 and a single blood sample was collected at the follow-up visit at the end of the study. Plasma compound of Formula I concentrations were determined using a validated LC/MS/MS (liquid chromatography tandem mass spectrometry) method with a LLOQ (Lower Limit of quantitation) of 0.500 ng/mL.

b. Plasma PK Results

Figure 31:
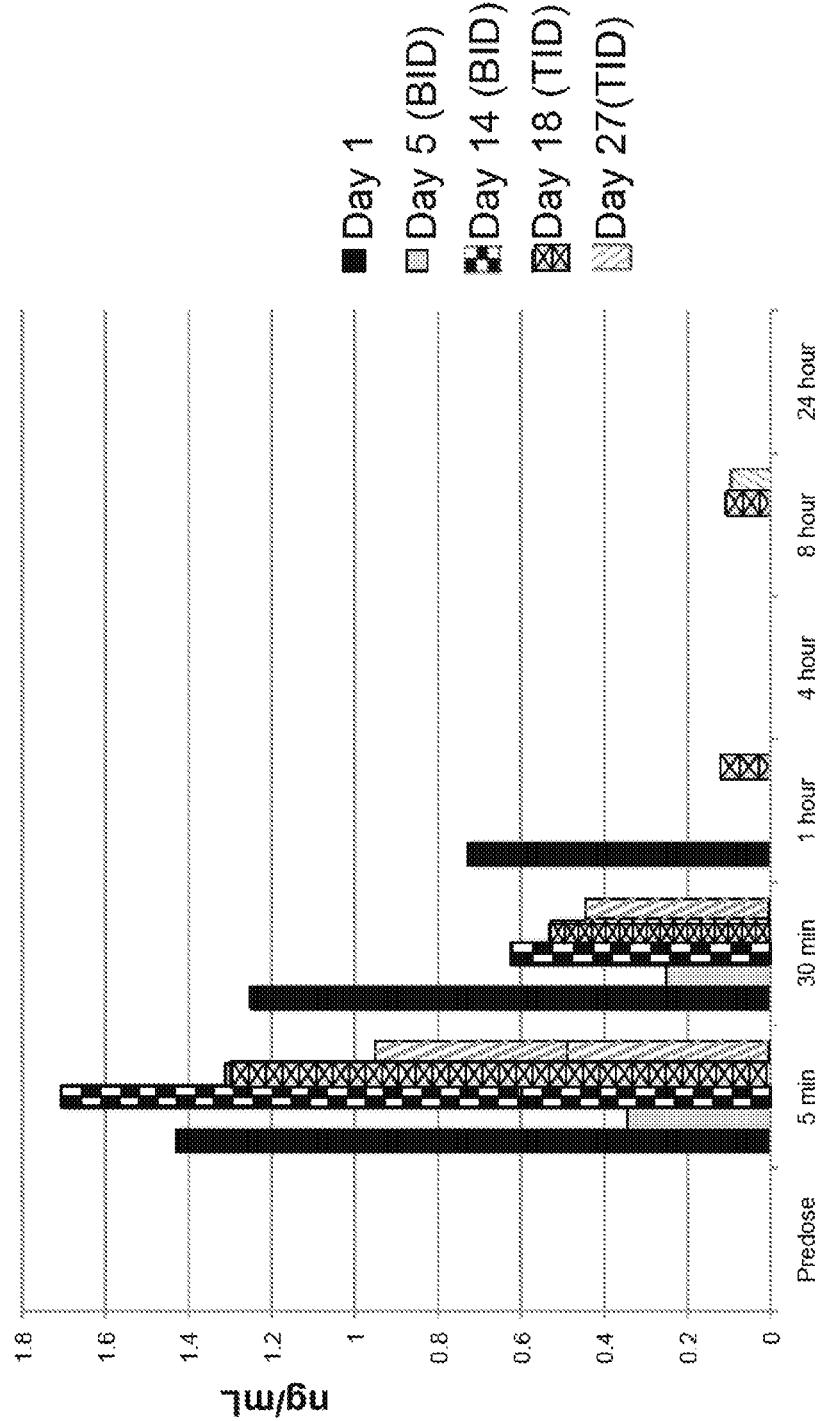
FIG. 31 illustrates a timecourse of mean plasma levels of the compound of Formula I treatment (human) with 5% compound of Formula I.

The compound of Formula I plasma concentrations were BLOQ (Below the limits of quantitation, <0.500 ng/mL) at all timepoints following single- and multiple-doses of 0.1% and 0.3% the compound of Formula I dose strengths and in 3 of 5 subjects that received the 1% compound of Formula I dose strength. Measureable levels of the compound of Formula I were seen in the plasma of one subject dosed with 1% compound of Formula I at the earliest timepoint (5 minutes post-dose) on Days 14 and 27 but were BLOQ for subsequent timepoints. Measurable levels were observed more frequently following administration of the 5% dose strength throughout the trial, although levels were quite low (<3 ng/mL) and generally were not detectable after the first hour following administration (FIG. 31). LFA-1 levels in in vitro cell assays (cell attachment and SEB IL-2 release) where IC50 values of 2 nM have been observed are approximately 0.1 nM. LFA-1 levels in blood are approximately 10 nM. The IC50 for compound of Formula I inhibition of SEB stimulated IL-2 release in whole human blood is 69 nM. Compound of Formula I levels greater than LFA-1 levels are needed to inhibit leukocyte function. Therefore, no significant inhibition of systemic leukocytes is expected from compound of Formula I ophthalmic drops.

Plasma compound of Formula I half-life or exposure parameters could not be accurately assessed following administration of the compound of Formula I Ophthalmic Solution at any dose strength in any study period because the plasma compound of Formula I concentrations were not detectable or rapidly declined BLOQ within 1 to 4 hours of dosing.

c. Tear PK Analysis

Tear samples of the compound of Formula I were collected in both eyes pre-dose, at 30 minutes post-dose and at 1, 4, 8, and 24 hours post-dose on Days 1, 5, 14, 18, and 27 of the Phase 1 study using paper Schirmer tear strips. A 48-hour post-dose sample was obtained following Day 1, 14, and 27. Tear compound of Formula I concentrations were determined using a validated LC/MS/MS method with a LLOQ of 0.500 ng/mL.

d. Tear PK Results

Dose related increases in tear AUC (area under the concentration-time curve) and C (maximum observed plasma concentration) values were seen on dosing day 1 and were generally maintained at the timepoints evaluated throughout the trial. BID (two times daily) and TID (three times daily) dosing produced higher C and AUC values relative to a single dose, but there were no significant differences in exposure between BID and TID dose schedules. There was clear evidence of compound of Formula I exposure in the anticipated therapeutic dose range and no obvious evidence of accumulation with multiple ocular dose administration.

Figure 32:
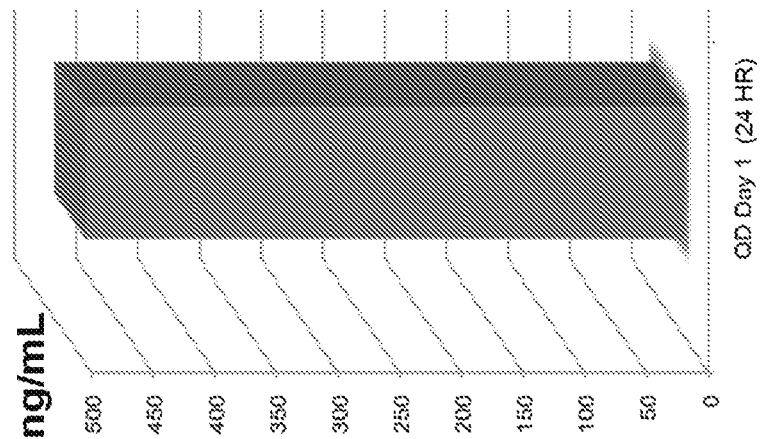
FIG. 32 illustrates tear $C_{min}$ levels for human subjects treated with 1% compound of Formula I QD (once a day).
Figure 33:
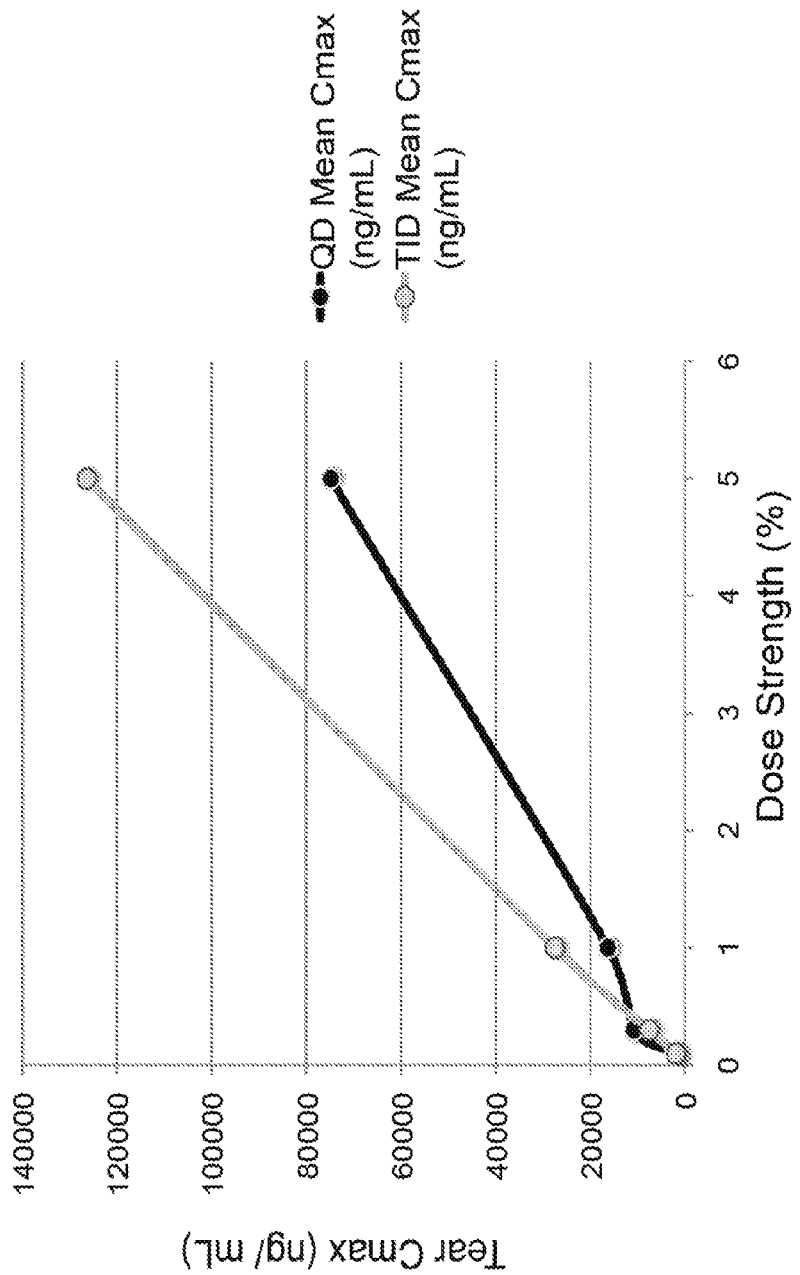
FIG. 33 illustrates the dose/drug $C_{max}$ tear level relationship for administration of the compound of Formula I in humans (QD and TID).
Figure 34:
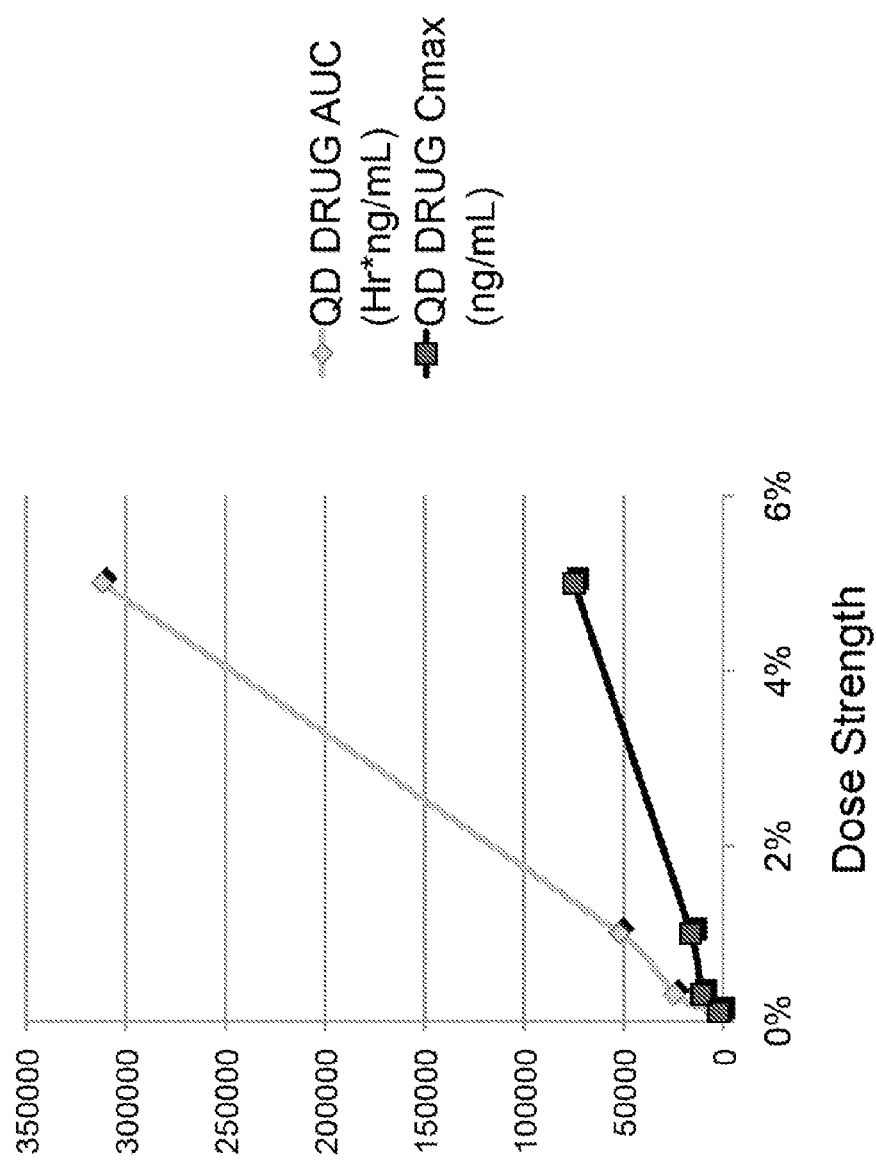
FIG. 34 illustrates the dose/AUC and dose/mean $C_{max}$ tear level relationship for human subjects treated QD with the compound of Formula I.

FIG. 32 illustrates 1% compound of Formula I tear $C_{min}$ levels. FIG. 33 illustrates that dose was proportional to the compound of Formula I $C_{max}$ tear levels. FIG. 34 illustrates that dose was proportional to the compound of Formula I QD AUC and $C_{max}$ in tears.

Overall, compound of Formula I Ophthalmic Solution administered by topical ocular instillation to healthy adult subjects at dose strengths up to 5% TID appears safe and well-tolerated and appropriate for further investigation in subjects with ocular inflammation secondary to allergic conjunctivitis or dry eye.

B. Nonclinical Studies the Compound of Formula I IND-Enabling Nonclinical Program (Safety Pharmacology and Toxicology Studies)

1. Preclinical Toxicology Formulation

TABLE 20

Phosphate buffered saline
pH 7
290 mOsM/l
compound of Formula I
sodium salt
4 dose levels (0.1% to 3%)
EDTA
Parabens preservative
0.02% methyl parabens
0.04% propyl parabens
Multidose dropper bottle 2. Safety Pharmacology An in vitro study to evaluate the effects of the compound of Formula I on hERG channel current (a surrogate for $I_{Kr}$, the rapidly activating, delayed rectifier cardiac potassium current) was conducted in stably transfected kidney HEK293 cells. Single doses of the compound of Formula I were 20 µM, 100 µM, 200 µM, and 600 µM. Compound of Formula I effects on the current were weak ($IC_{50}$ of 478 µM) indicating minimal risk of $I_{Kr}$ channel inhibition given the low systemic exposure observed following topical ocular administration.

The cardiovascular effects of the compound of Formula I in conscious telemetry-instrumented dogs (beagles) when administered via IV bolus injection were assessed. No effects on electrocardiography or hemodynamic parameters were observed.

The effects of the compound of Formula I on the CNS when administered as a single dose via bolus IV injection were assessed in rats. Transient miosis was observed in animals given 10.0 mg/kg from 1 minute to 6 hours postdose in 2/6 animals at each time point. No effect on any other parameters was observed.

Respiratory function (tidal volume, respiration rate, and minute volume) in rats following a single IV bolus dose of the compound of Formula I using head-out plethysomograph chambers was assessed. No adverse changes in respiratory function or adverse effects were observed at any dose.

3. Genotoxicity studies:

the compound of Formula I displayed no effect in in vitro Ames chromosomal aberration assays or an in vivo rat micronucleus study.

a. In Vitro Ames Bacterial Reverse Mutation Assay

In an Ames assay, the compound of Formula I did not cause an increase in the mean number of revertants per plate with any of the tester strains either in the presence or absence of microsomal (S9) enzymes. Therefore, the compound of Formula I was judged to be not mutagenic.

b. In Vitro Chromosomal Abberation Assay in CHO cells

The ability of the compound of Formula I to induce chromosomal aberrations was assessed in cultured Chinese hamster ovary (CHO) cells with and without an exogenous metabolic activation following 20 hours of co-incubation. The compound of Formula I is considered negative for inducing structural chromosomal aberrations in CHO cells with and without metabolic activation, except at a single toxic dose without metabolic activation (3-hour treatment; 3500 µg/mL). The biological relevance of this response is equivocal due to cytotoxicity.

c. In Vivo Mouse Bone Marrow Micronucleus Assay

The ability of repeated IV administrations of the compound of Formula I to induce in vivo clastogenic activity and/or disruption of the mitotic apparatus, by detecting micronuclei in polychromatic erythrocytes (PCE), was assessed in CD-1® (ICR) BR mice by evaluating their bone marrow. Based on the results of this study, the compound of Formula I is considered negative in the mouse bone marrow micronucleus assay.

4. Acute Toxicity Studies:

For single dose IV in rats, the no observable adverse effect level (NOAEL) was 10 mg/kg IV. For escalating single dose IV and 7-day repeated dose with TK (toxicokinetics) in dogs, the NOAEL was 10 mg/kg IV. For single dose ocular tolerance in rabbits, the NOAEL was 3.5 mg/eye/3× per day (10%).

5. Repeated Dose Toxicity Studies:

In a 4-week IV toxicity study in dogs with 2-week recovery, the NOAEL was 10 mg/kg. In a 13-week IV toxicity study in rats with 4-week recovery, the NOAEL was 30 mg/kg. In a 13-week ocular toxicity study in rabbits with a 4-week recovery, the NOAEL was 1.05 mg/eye/3× per day (3%). In a 13-week ocular toxicity study in dogs with a 4-week recovery, the NOAEL was 1.05 mg/eye/3× per day (3%).

6. ADME Studies

The absorption, distribution, metabolism and excretion (ADME) of the compound of Formula I was characterized in studies conducted in rats, rabbits and dogs utilizing two routes of administration; intravenous and topical ocular administration, the clinical route of administration. An in vitro hepatocyte study was also performed.

The compound of Formula I levels were assessed in plasma, tear and vitreous humor samples by tandem mass spectrometry. Some in vivo studies used [$^{14}$C]-compound of Formula I to determine PK and the extent of absorption, distribution, and excretion of [$^{14}$C]-compound of Formula I derived radioactivity. Additionally, the metabolic profile and identification of metabolites of [$^{14}$C]-compound of Formula I were determined in plasma, urine and feces.

Single dose ocular and IV dose administration ADME studies were conducted in pigmented (Long-Evans strain) and albino (Sprague Dawley strain) rats using [$^{14}$C]-compound of Formula I. Quantitative whole body radiography assessments were performed.

Male and female rats received a single dose of 1 mg/eye or 10 mg/kg IV [$^{14}$C]-compound of Formula I. The main route of excretion following either ocular or IV administration was the feces, accounting for approximately 60% (ocular administration) and 95% (IV administration) of the administered radioactivity over 0 to 168 hours postdose. Urinary excretion accounted for up to 2% of the administered radioactivity. The highest tissue levels of [$^{14}$C]-compound of Formula I were measured in the tissues of the gastrointestinal tract with either ocular or IV dosing. With ocular administration, [$^{14}$C]-compound of Formula I was also measured in ocular tissues and those of excretion, indicating that the administered dose passed from the eye through the nasal turbinates, into the esophagus and was ultimately excreted through the gastrointestinal tract. These data indicate that ocular, nasal, or oral administration of the compound of Formula I will result in ultimate excretion through the gastrointestinal tract. A significant proportion of drug dose administered as ocular drops, distributed locally to the periocular region, and more interestingly via nasal turbinates into the gastrointestinal tract. Drug is seen to accumulate first in the epithelium of the GI tract and pass into the liver via the portal vein, where it is eliminated from the liver and re-delivered back to the lower GI tract. Little or no drug is observed in systemic distribution. Therefore, for administration of the compound of Formula I via either aerosol or drops to the nose, or via oral administration may provide similar specific direct localized delivery to the epithelium of the upper GI and localized delivery to the lower GI via clearance through the liver. In both cases, little or no systemic delivery of drug may be delivered.

Figure 35:
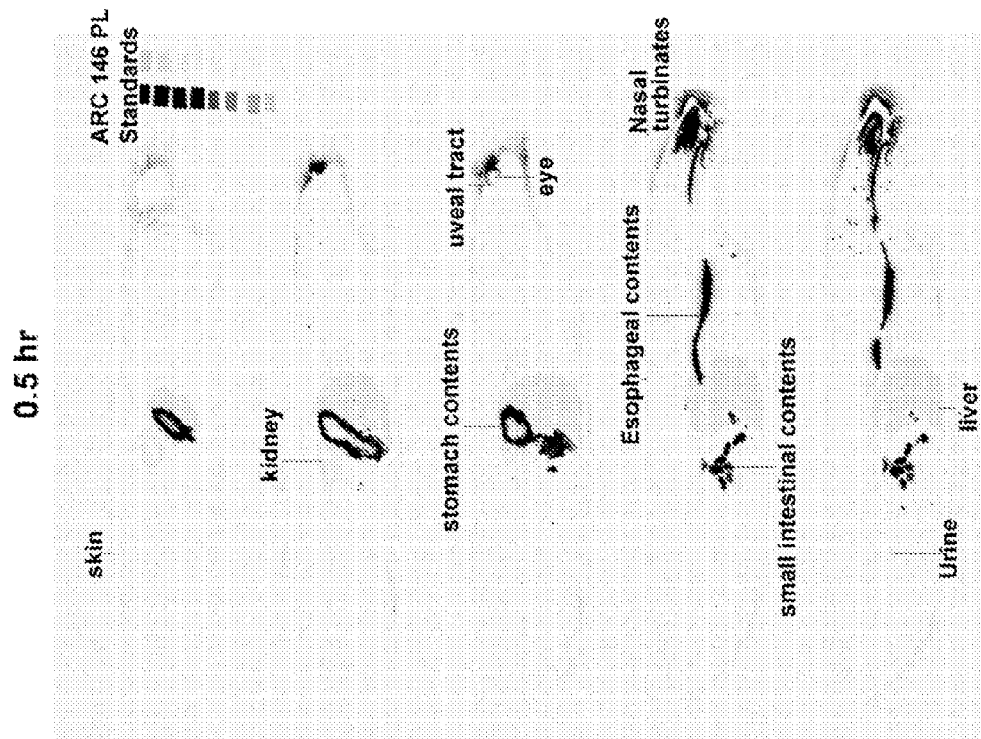
FIG. 35 is a graphical representation of a whole body autoradiograph for a male Sprague Dawley Animal 0.5 hour after a single topical ocular administration of [$^{14}$C]-compound of Formula I (1 mg/eye).

Following a topical ocular dose of [$^{14}$C]-compound of Formula I to male Sprague Dawley (albino) rats, the distribution of radioactivity into tissues was limited at the first time point (0.5 hour postdose) and was generally associated with the gastrointestinal tract, the tissues associated with metabolism, and the eye. FIG. 35 illustrates a whole body autoradiograph for a male Sprague Dawley Animal 0.5 hour after a single topical ocular administration of [$^{14}$C]-compound of Formula I (1 mg/eye). The highest concentrations of radioactivity were determined at this time point in esophageal contents, nasal turbinates, and small intestinal contents, with concentrations of 399000, 352000, and 349000 ng equivalents [$^{14}$C]-compound of Formula I/g, respectively. However, it should be noted that the measurements in these tissues were above the upper limit of quantification and therefore should be interpreted with some caution. High levels of radioactivity were also determined in the esophagus and stomach contents. Radioactivity was detected in the eye at this time point, with a concentration of 18100 ng equivalents [$^{14}$C]-compound of Formula I/g. Low levels of radioactivity were also associated with the liver (272 ng equivalents [$^{14}$C]-compound of Formula I/g), kidney (151 ng equivalents [$^{14}$C]-compound of Formula I/g) and uveal tract (9330 ng equivalents [$^{14}$C]-compound of Formula I/g).

Figure 36:
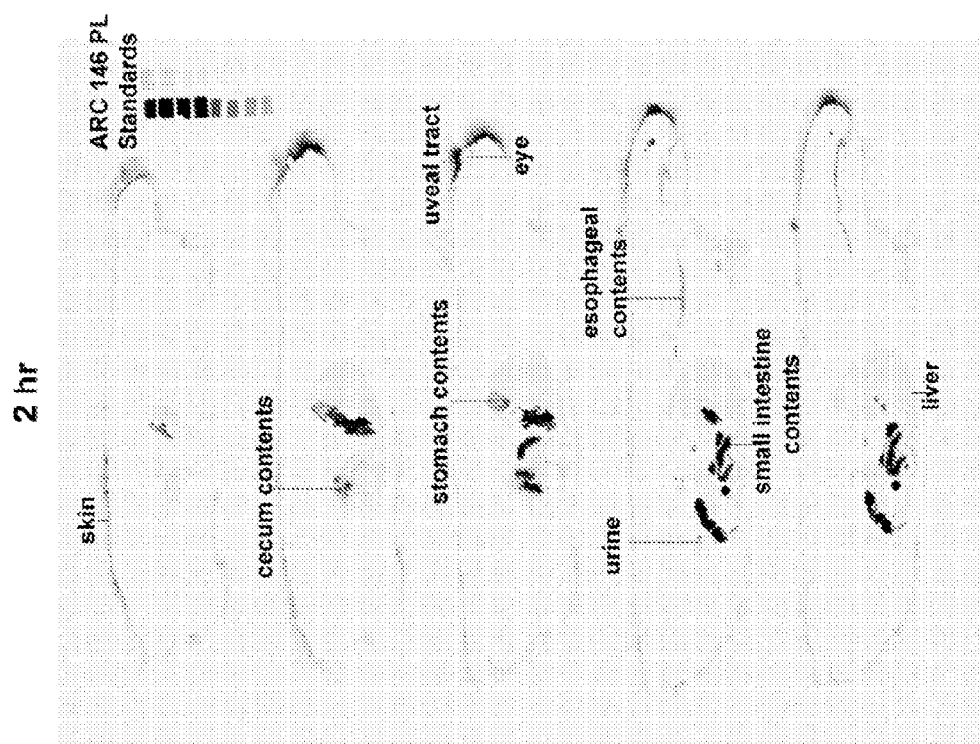
FIG. 36 is a graphical representation of a whole-body autoradiograph for a male Sprague Dawley Animal 2 hours after a single topical ocular administration of [$^{14}$C]-compound of Formula I (1 mg/eye).
Figure 37:
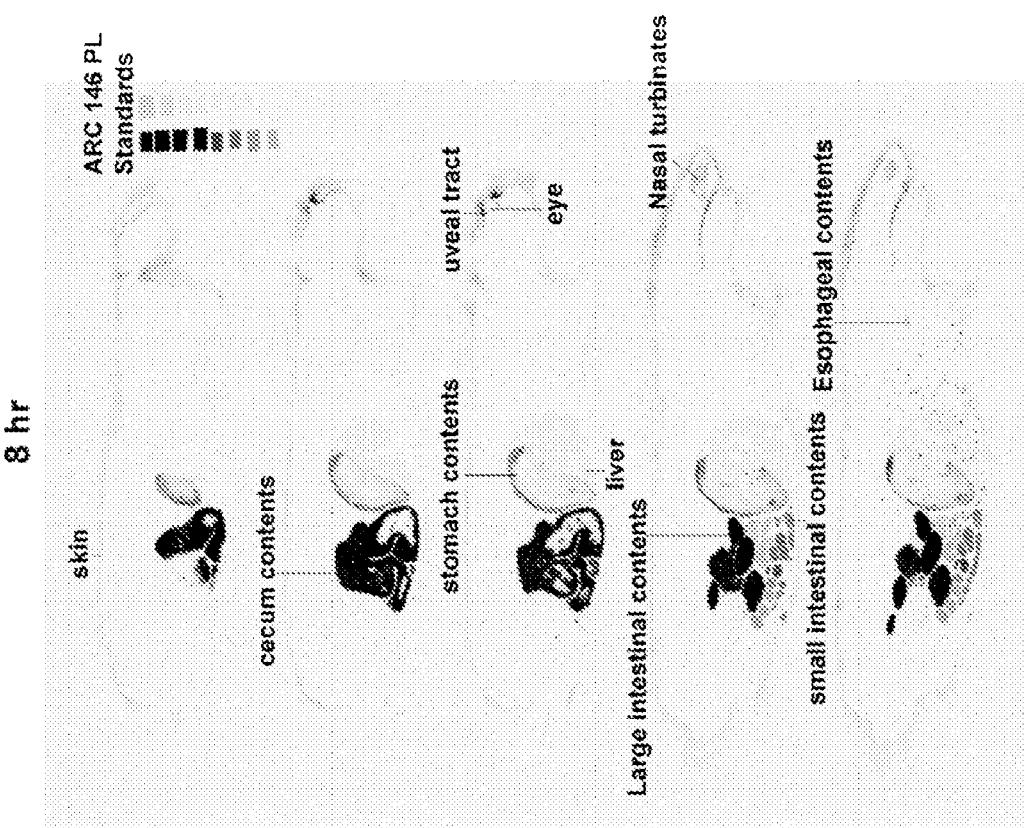
FIG. 37 is a graphical representation of a whole-body autoradiograph for a male Sprague Dawley Animal 8 hours after a single topical ocular administration of [$^{14}$C]-compound of Formula I (1 mg/eye).

Concentrations of radioactivity in the eye and eye lens had declined considerably by 2 hours postdose; with the level in the eye lens BLQ. Radioactivity concentrations had also declined in the esophagus and esophageal contents by approximately 50- and 100-fold at 2 hours postdose. FIG. 36 illustrates a whole-body autoradiograph for a male Sprague Dawley Animal 2 hours after a single topical ocular administration of [$^{14}$C]-compound of Formula I (1 mg/eye). At 8 hours postdose level of radioactivity had fallen in all tissues; however, high concentrations were associated with the large intestinal contents (133000 ng equivalents [$^{14}$C]-compound of Formula I/g) and cecum contents (57600 ng equivalents [$^{14}$C]-compound of Formula I/g), indicating the passage of radioactivity through the gastrointestinal tract. FIG. 37 illustrates a whole-body autoradiograph for a male Sprague Dawley Animal 8 hours after a single topical ocular administration of [$^{14}$C]-compound of Formula I (1 mg/eye).

Figure 38:
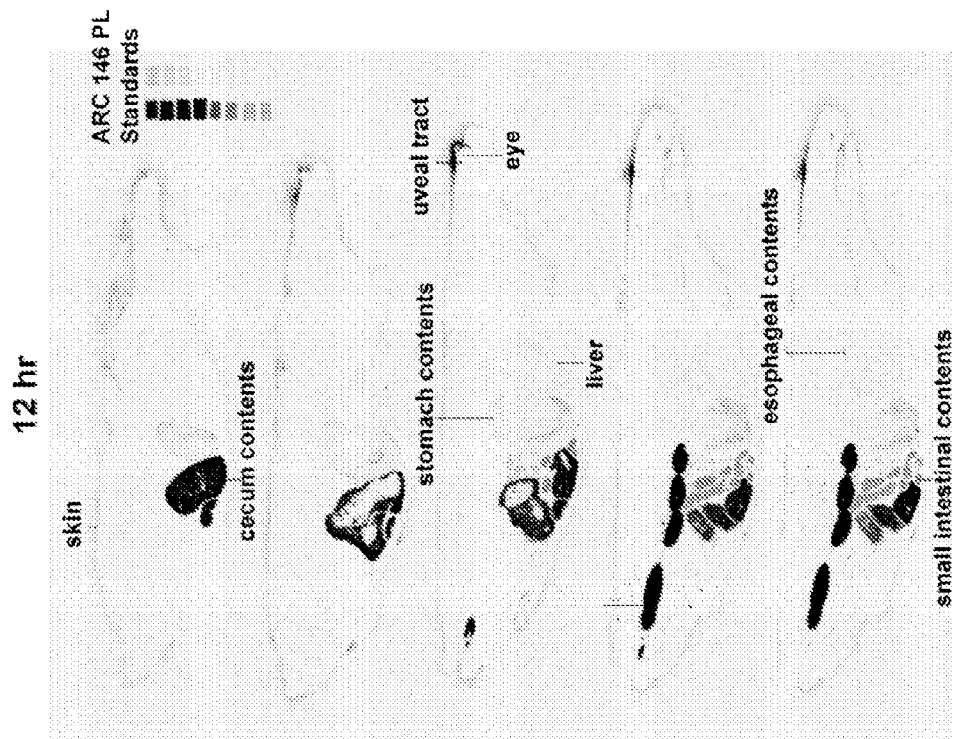
FIG. 38 is a graphical representation of a whole-body autoradiograph for a male Sprague Dawley Animal 12 hours after a single topical ocular administration of [$^{14}$C]-compound of Formula I (1 mg/eye).

By 12 hours postdose radioactivity concentrations had decreased further, the maximal concentrations being associated with the cecum and large intestinal contents. The concentration determined in the uveal tract increased at this time point to 610 ng equivalents [$^{14}$C]-compound of Formula I/g. FIG. 38 illustrates a whole-body autoradiograph for a male Sprague Dawley Animal 12 hours after a single topical ocular administration of [$^{14}$C]-compound of Formula I (1 mg/eye).

Figure 39:
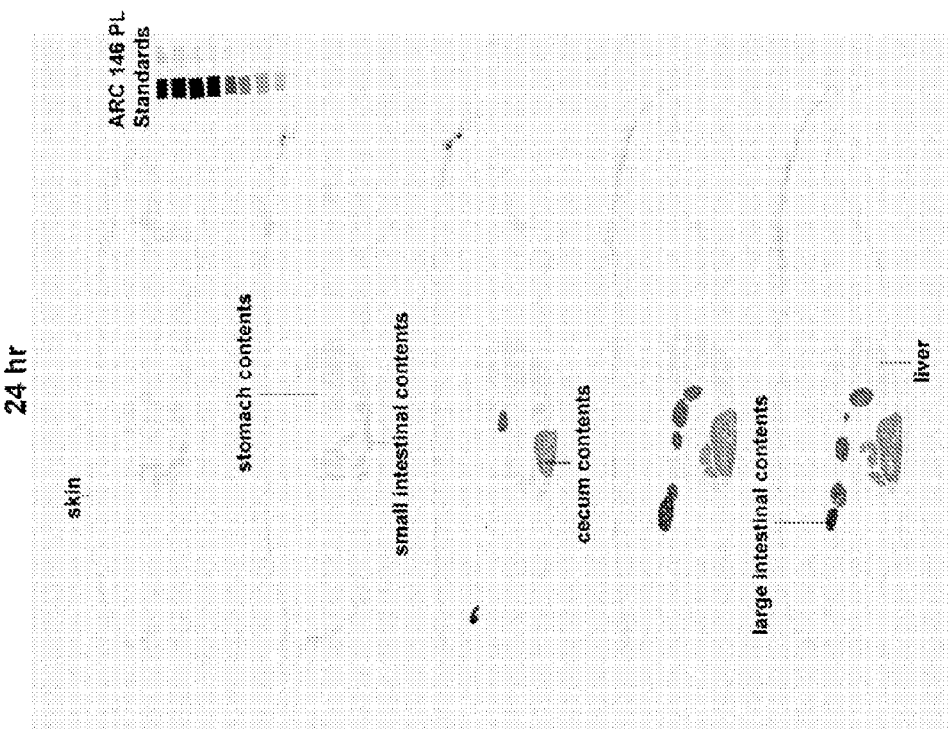
FIG. 39 is a graphical representation of a whole-body autoradiograph for a male Sprague Dawley Animal 24 hours after a single topical ocular administration of [$^{14}$C]-compound of Formula I (1 mg/eye).

Radioactivity concentrations at 24 hours postdose were maximal in the cecum contents (5870 ng equivalents [$^{14}$C]-compound of Formula I/g) and the large intestinal contents (18000 ng equivalents [$^{14}$C]-compound of Formula I/g); low levels were also present in the small intestinal and stomach contents. FIG. 39 illustrates a whole-body autoradiograph for a male Sprague Dawley Animal 24 hours after a single topical ocular administration of [$^{14}$C]-compound of Formula I (1 mg/eye). For all other tissues, with the exception of the non-pigmented skin and the liver radioactivity was not detectable.

Figure 40:
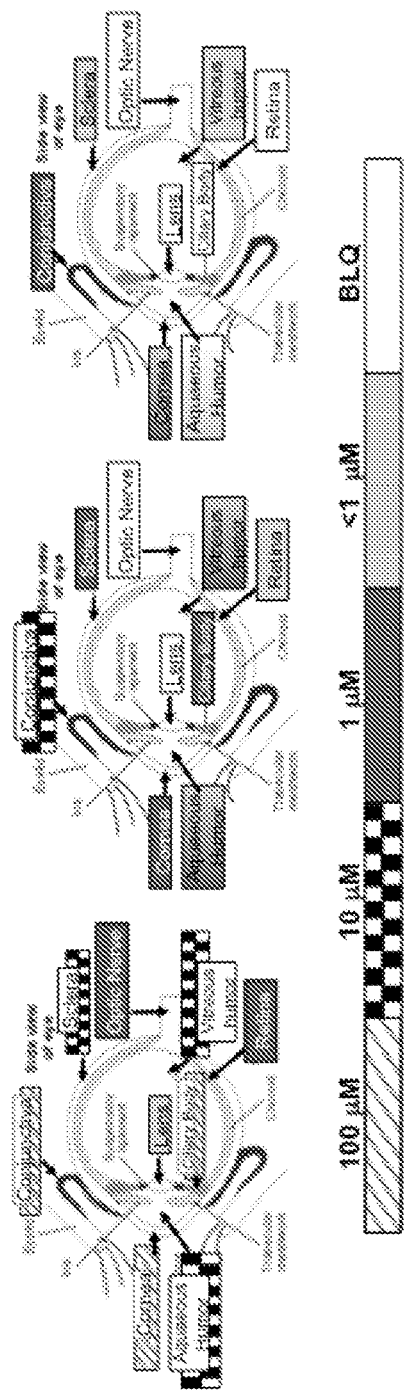
FIG. 40 illustrates rat ocular pharmacokinetics of [$^{14}$C]-compound of Formula I.

Low levels of [$^{14}$C]-compound of Formula I were measured in the vitreous humor at all timepoints following ocular dosing and up to 2 hrs following an IV dose (see schematic in FIG. 40 and Table 21 for ocular dosing in rats).

TABLE 21

Compound of Formula I Concentration, ng Equivalents [$^{14}$C]-compound of Formula I/g tissue.

| Physical region | 0.5 hour after administration | 4.0 hours after administration |
|---|---|---|
| Aqueous humor | 1770 | 116 |
| Conjunctiva (bulbar) | 31500 | 4480 |
| Conjunctiva (palpebral) | 26300 | 21830 |
| Cornea | 17150 | 1346 |
| Iris-ciliary body | 17550 | 500 |
| Lens | 38.8 | 9.69 |
| Optic Nerve | 796 | 0 |
| Retina and Choroid (with RPE) | 510 | 46.7 |
| Sclera | 2750 | 387 |
| Vitreous Humor | 1330 | 183 |

Tissue distribution of [$^{14}$C]-compound of Formula I in pigmented and albino rats was comparable and indicated that compound of Formula I did not preferentially bind to melanin. There were no obvious differences seen in results from male and female rats. Furthermore, no preferential distribution of [$^{14}$C]-compound of Formula I-derived radioactivity was seen in red blood cells and no metabolites were isolated from samples of pooled plasma, urine and fecal homogenates collected up to 168 hrs following either a topical ocular or IV dose administration of [$^{14}$C]-compound of Formula I.

Figure 41:
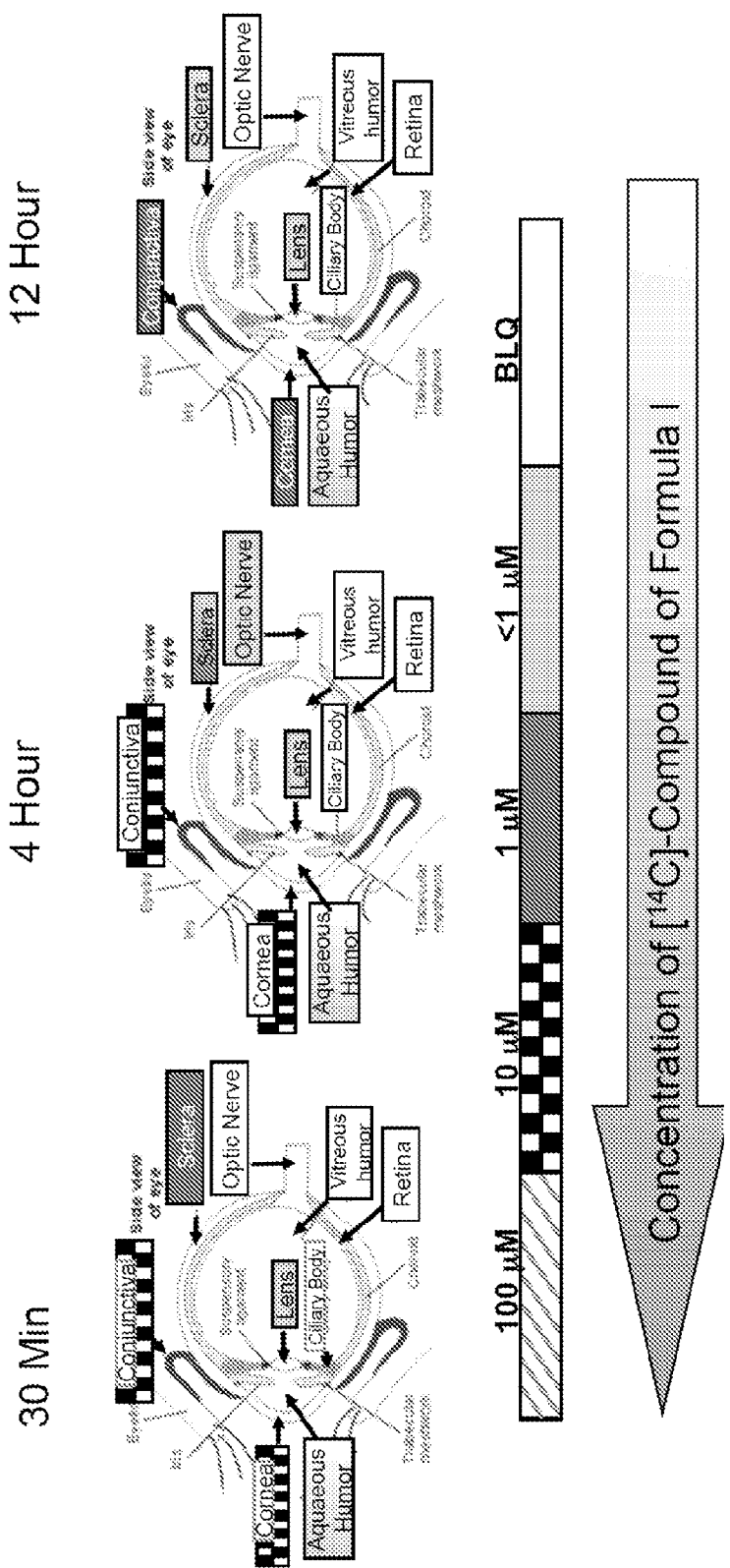
FIG. 41 illustrates dog ocular pharmacokinetics of [$^{14}$C]-compound of Formula I.

Similar single dose studies using [$^{14}$C]-compound of Formula I utilizing the same routes of administration were conducted in male and female dogs (3 mg/eye or 3 mg/dog) and showed comparable patterns of excretion, distribution and metabolism as rats. Following an ocular dose, the highest average [$^{14}$C]-compound of Formula I levels were detected in anterior ocular tissues (see FIG. 41). Lower levels were detected in posterior ocular tissues, indicating that absorption into the eye had occurred. The metabolic profile in pooled plasma, urine and fecal homogenate samples was comparable to that seen in rats, with no metabolites detected up to 168 hrs post-dose. No differences in results from male and female dogs were observed.

The compound of Formula I levels in conjunctiva/cornea are greater than 1 micromolar/100 nanomolar for 16 hrs (dog/rat).

Figure 42:
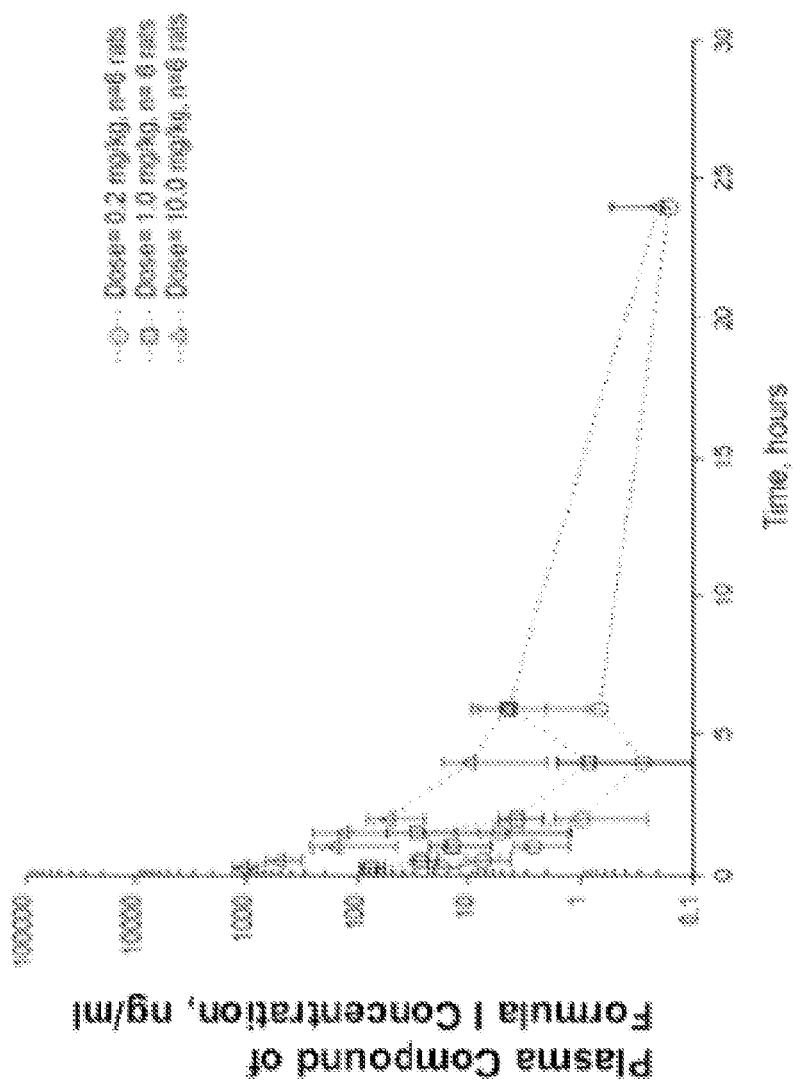
FIG. 42 is a graphical representation of the timecourse of drug plasma levels for the compound of Formula I following single IV doses in rats.
Figure 43:
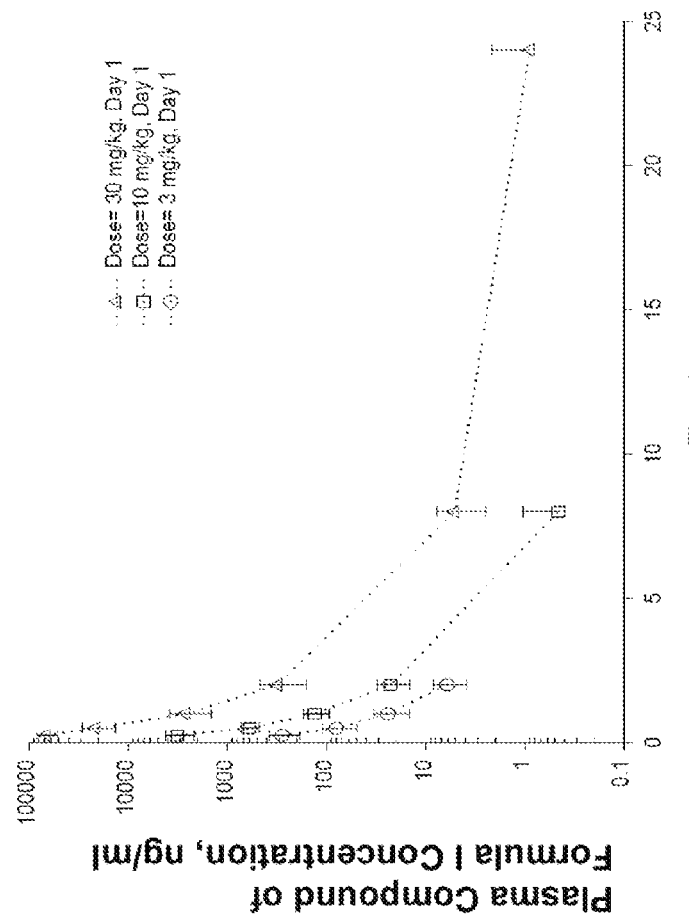
FIG. 43 is a graphical representation of the timecourse of drug plasma levels for the compound of Formula I following single IV doses in dogs.

FIGS. 42 and 43, respectively. Plasma concentrations of the compound of Formula I declined in an expected, exponential manner following a single IV bolus dose in both species.

The plasma PK parameters determined using standard non-compartmental methods after a single IV administration of the compound of Formula I to rats at doses ranging from 0.2 to 30.0 mg/kg or to dogs after single doses up to 30 mg/kg and 7 daily doses of 3 or 10 mg/kg are shown in Table 22 (rats). PK results from both species show very high clearance of the compound of Formula I (liver blood flow is ~3.3 L/hr/kg and 1.9 L/hr/kg in rats and dogs, respectively; (Davies, 1993, Pharm Res). Rat PK data indicated a high distribution volume, and moderate half-life following a single IV dose while low distribution volume and a shorter half-life drug was seen following IV administration to dogs. There was no obvious accumulation of the compound of Formula I in plasma after daily administration of the compound of Formula I for 7 days as plasma compound of Formula I $C_{max}$ and $AUC_{0-n}$ values measured on Study Day 1 approximated those obtained on Study Day 7.

TABLE 22

Summary of Plasma PK Parameters Rats Following a Single IV Bolus Dose of the Compound of Formula I[3]

| Dose | CL L/hr/kg | Vss L/kg | $T_{1/2}$ hr | MRT hr | $C_{max}$ ng/mL[1] | $AUC_{0-n}$ hr × ng/mL[2] |
|---|---|---|---|---|---|---|
| 10.0 mg/kg | 10.4 | 9.56 | 3.76 | 0.920 | 1056 | 728 |
| 30.0 mg/kg[4] | — | — | — | — | 5117.3 | 2345.5 |

[1]Maximum observed plasma compound of Formula I concentration estimated from the mean concentration versus time profile.
[2]Plasma compound of Formula I $AUC_{0-n}$ during the dose interval estimated from the mean concentration versus time profile.
[3]Estimated from mean plasma compound of Formula I concentration versus time profiles.
[4]From rat safety pharmacology study In longer term repeated-dose studies, dogs and rats received daily IV bolus doses of 3, 10 or 30 mg/kg/day for 4 and 13 weeks, respectively. As was seen in the 7-day dog study, plasma compound of Formula I concentrations declined in an expected, exponential manner and there was no evidence of compound of Formula I accumulation in the plasma. The plasma clearance, distribution volume, and half-life of compound of Formula I in dogs were dose-dependent over the dose range of 3 mg/kg to 30 mg/kg. In rats, the plasma compound of Formula I exposure data suggested non-linear disposition of compound of Formula I following daily IV doses ranging from 10 to 30 mg/kg and unexpected accumulation at Week 13 (Table 23).

TABLE 23

Plasma compound of Formula I Exposure Parameters in Rats Following Daily IV Bolus Doses for 13 Weeks[3]

| | Dose = 3 mg/kg | | Dose = 10 mg/kg | | Dose = 30 mg/kg | |
|---|---|---|---|---|---|---|
| | $C_{max}$ ng/mL[1] | $AUC_{0-n}$ hr × ng/mL[2] | $C_{max}$ ng/mL[1] | $AUC_{0-n}$ hr × ng/mL[2] | $C_{max}$ ng/mL[1] | $AUC_{0-n}$ hr × ng/mL[2] |
| Day 1 | 305.2 | 148.3 | 1045.3 | 535.6 | 5117.3 | 2345.5 |
| Week 13 | 377.5 | 241.4 | 1691.5 | 907.1 | 16932.8 | 7471.5 |

Figure 44:
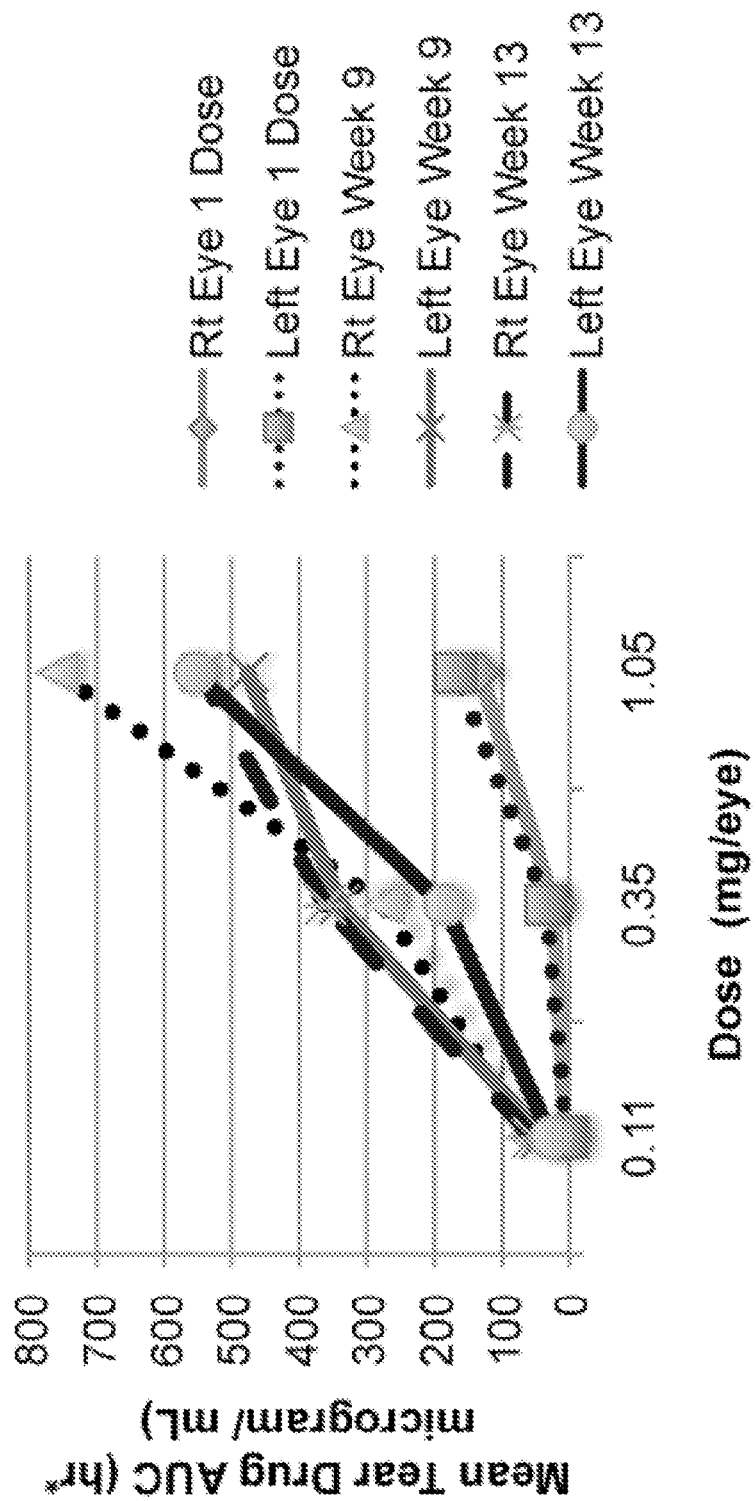
FIG. 44 illustrates the dose/drug AUC (in tears) relationship for the compound of Formula I administered to dogs.

[1]Maximum observed plasma compound of Formula I concentration during the dose interval.
[2]Plasma compound of Formula I $AUC_{0-n}$ during the dose interval.
[3]Estimated from mean plasma compound of Formula I concentration versus time profile, n = 6 rats (3 males and 3 females) per timepoint.

a. Compound of Formula I Pharmacokinetics after Single and Repeated IV Administration Plasma compound of Formula I concentrations over time following a single IV doses in rats and dogs are shown in b. Compound of Formula I Pharmacokinetics after Single and Repeated Ocular Administration After a single topical ocular instillation of a 0.1, 1.0 or 3.0% dose strength of compound of Formula I Ophthalmic Solution (0.105, 0.35 and 1.05 mg/eye, respectively), mean tear compound of Formula I concentrations rose in a dose-related manner achieving maximal values within 30 minutes of administration and returning to baseline by 4 hours. The tear $C_{max}$ and $AUC_{0-n}$ of compound of Formula I generally increased with increasing dose. FIG. 44 illustrates that the dose of compound of Formula I is proportional to PK in tears (AUC) for dogs. For example, mean tear $C_{max}$ values were 34,014 ng/mL, 21460 ng/mL and 313,906 ng/mL in the right eyes of rabbits dosed with 0.105, 0.35 and 1.05 mg/eye, respectively. Mean tear AUCs were 18864 hr×ng/mL, 18931 hr×ng/mL and 182978 hr×ng/mL in the right eyes from the same dose groups, respectively.

Plasma compound of Formula I concentrations rose after topical ocular instillation as the drug moved from the ocular application site into the plasma circulation. Dose-related amounts of compound of Formula I were detected in the plasma of dogs and rabbits 30 minutes following topical ocular administration. Plasma compound of Formula I concentrations rapidly declined from maximum values measured at about 0.25 hrs post-dose to baseline levels by about 4 hours, probably owing to the high compound of Formula I plasma clearance as seen in the IV administration studies. Plasma $C_{max}$ (mean±SD) values were 11.7±8.80 ng/mL, 13.1±2.12 ng/mL, and 38.9±19.7 ng/mL and $AUC_{0-n}$ (mean±SD) values were 5.19±5.39 hr×ng/mL, 7.35±1.52 hr×ng/mL, and 22.9±10.1 hr×ng/mL in the 0.105, 0.35, and 1.05 mg/eye/dose groups, respectively.

Figure 45:
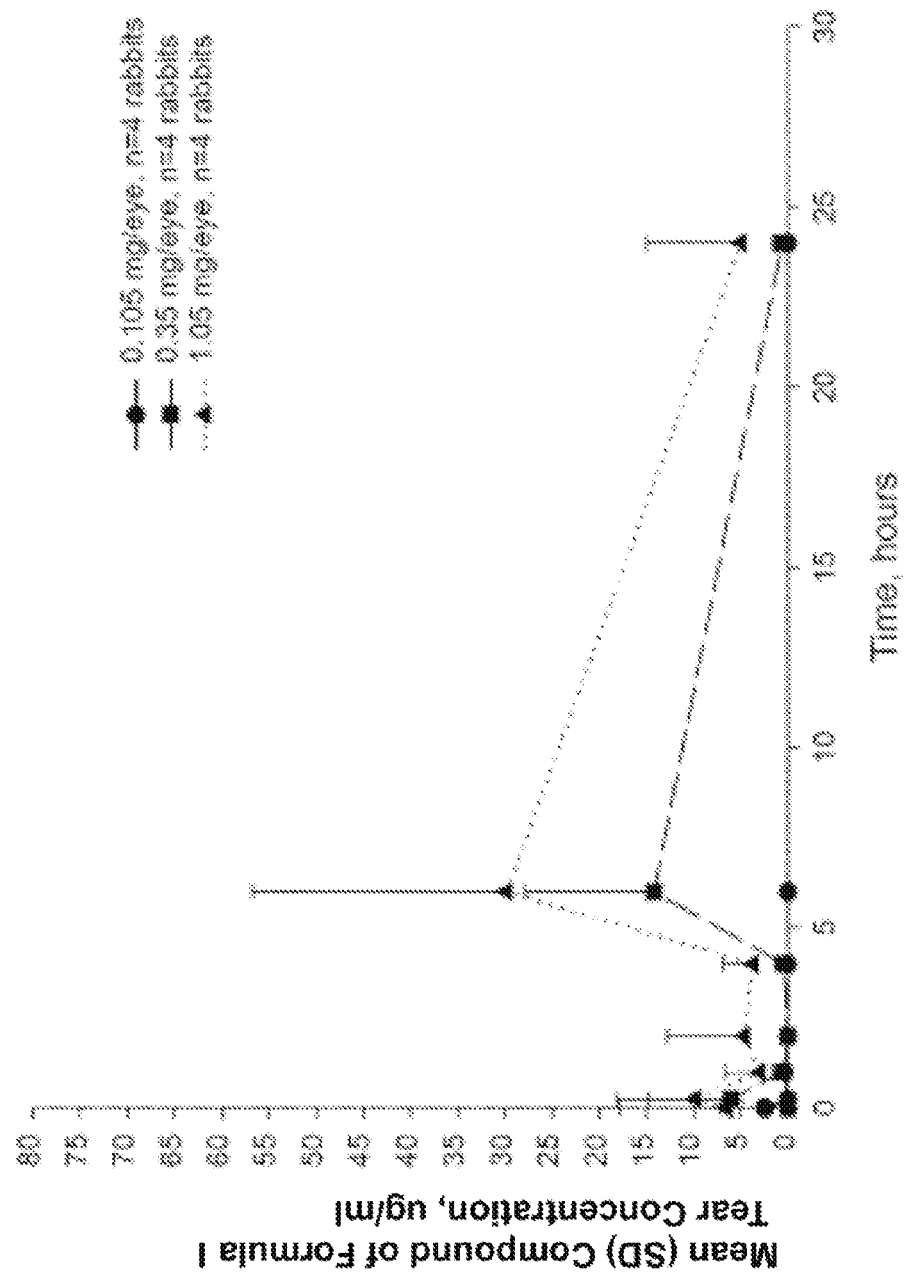
FIG. 45 illustrates the drug tear concentration profiles measured after 13 weeks of TID ocular dosing in rabbits.
Figure 46:
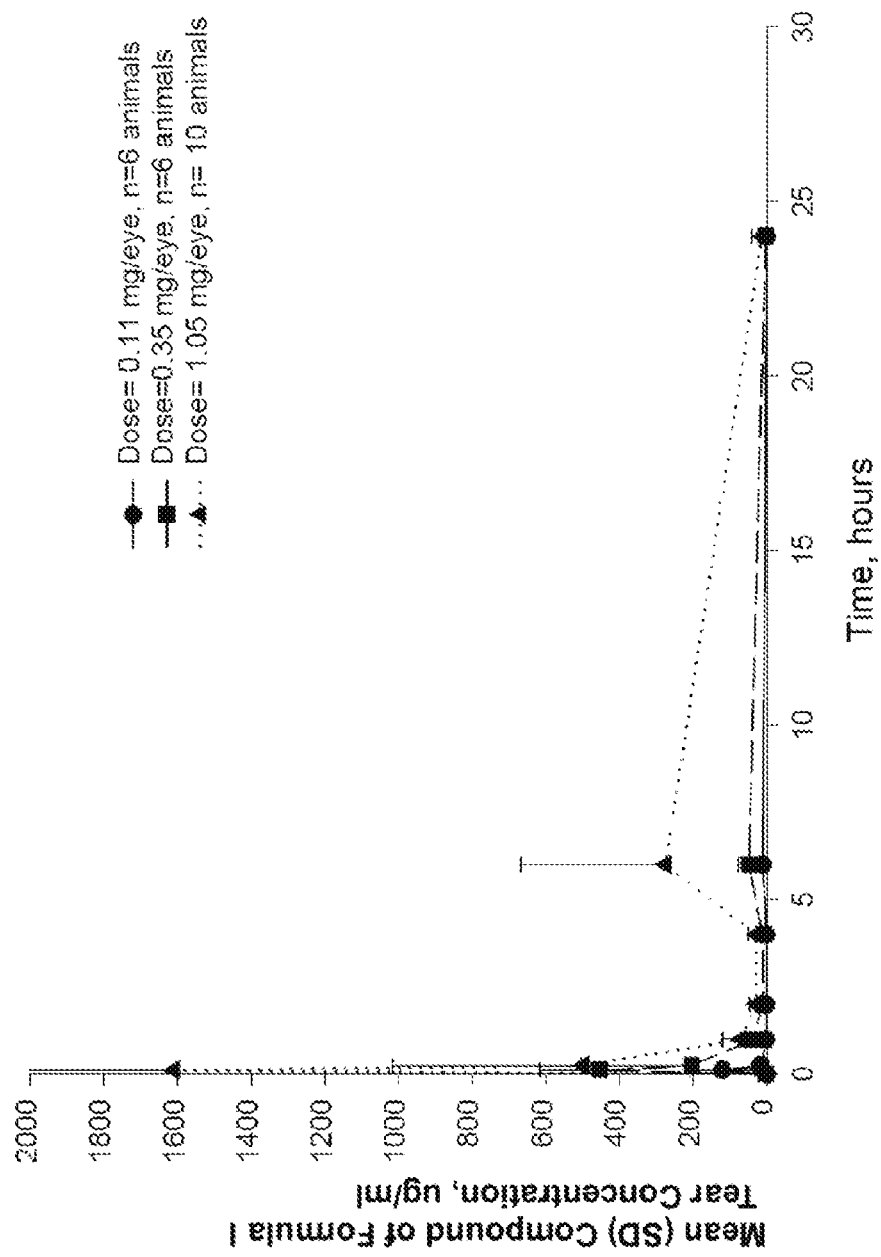
FIG. 46 illustrates the drug tear concentration profiles measured after 13 weeks of TID ocular dosing in dogs.
Figure 47:
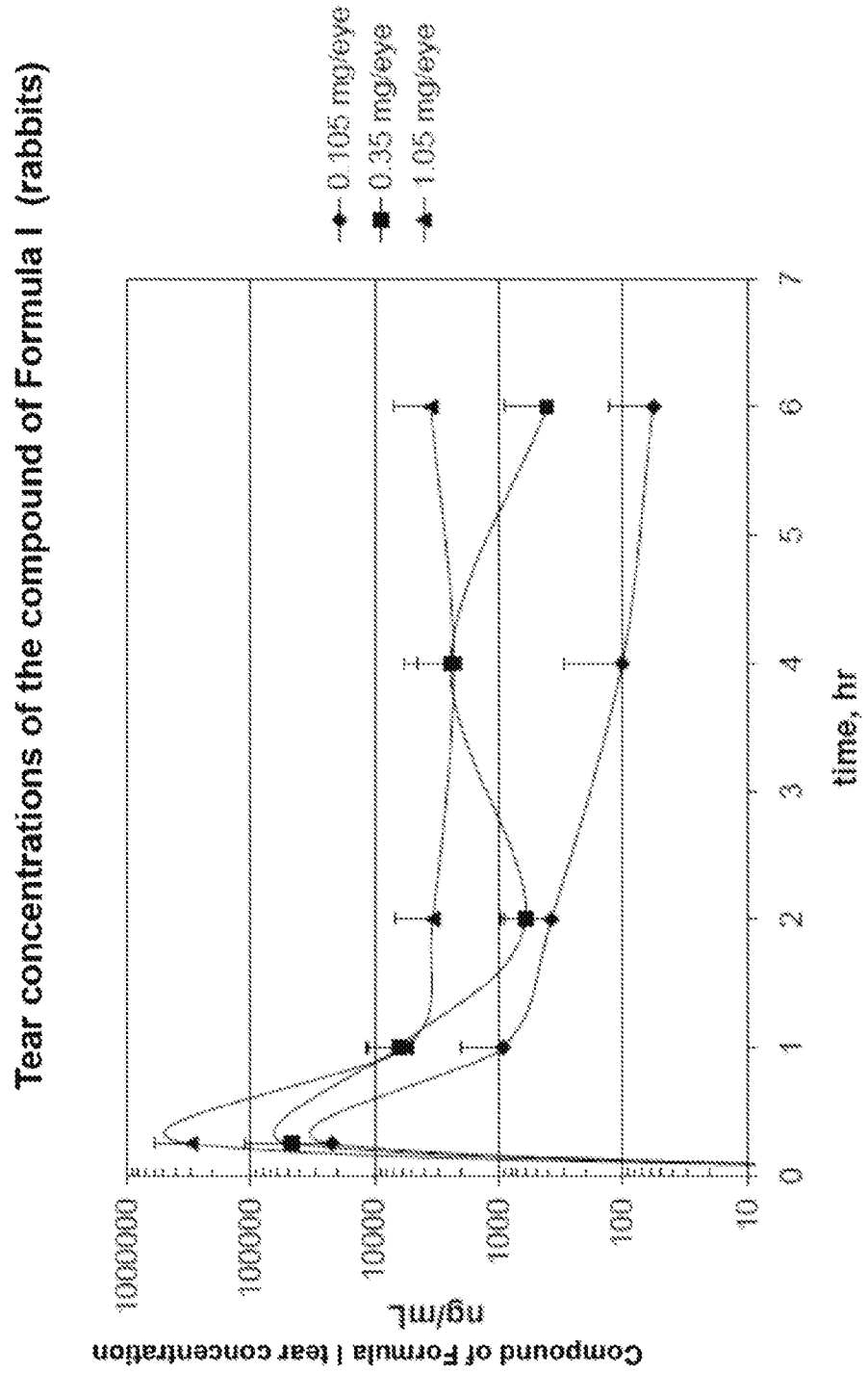
FIG. 47 illustrates mean drug tear concentrations in right and left eyes of rabbits following topical instillation of a single dose of the compound of Formula I.

In repeated dose studies conducted in rabbits and dogs, compound of Formula I Ophthalmic Solution was administered TID by bilateral ocular instillation at the same doses as for single dose studies for 13 weeks. A pilot study in dogs administered 3.5 mg/eye (10% dose strength) for 3 days. The $C_{max}$ and $AUC_{0-n}$ of compound of Formula I in tear samples increased expectedly with increasing dose in rabbits and dogs. The $C_{max}$ and $AUC_{0-n}$ data indicate that compound of Formula I accumulated in dog tears by Week 9 during TID instillation, but thereafter continued accumulation was not noted. A similar pattern was observed in the rabbit study. Representative tear concentration over time profiles measured after 13 weeks of TID ocular dosing in rabbits and dogs are shown in FIGS. 45 and 46, respectively (left eye, TID, ~4 hours apart). TK (toxicokinetics) analyses indicate adequate ocular compound of Formula I exposure with tear levels above 1 µM (600 ng/mL) throughout the day. FIG. 47 illustrates mean compound of Formula I tear concentrations in right and left eyes of rabbits following topical instillation of a single dose.

Compound of Formula I was not detected in the vitreous fluid in both 13-week rabbit and dog studies in samples obtained at sacrifice (terminal and recovery phase sacrifices). Variable levels of compound of Formula I were seen in the vitreous fluid of dogs dosed TID for three days with 3.5 mg/eye (10%) and ranged from BLOQ to 18 ng/mL.

Nonclinical studies showed that about 6.9 to 32% of the compound of Formula I ocular dose was absorbed from the ocular topical instillation site into the systemic circulation but this systemic availability estimate has been based on limited available data which includes an ocular dose that is $\frac{1}{100}^{th}$ the intravenous dose. Low systemic plasma exposure to the drug was observed in animals after ocular instillation. Importantly, the compound of Formula I plasma clearance is high in these species indicating that the absorbed compound of Formula I is efficiently removed from the systemic circulation, thereby assisting to minimize systemic exposure.

The PK profiles from all nonclinical species support a clinical dose topical ocular instillation regimen of up to three times per day for at least 13 weeks.

c. Pilot Ocular Tolerance of Topically Administered compound of Formula I in Dogs-PK A pilot ocular tolerance of topically administered compound of Formula I in dogs-PK was performed. Animals were dosed with 35 µL of compound of Formula I TID (0, 4, 8 hrs). 1% solution was administered on days 1-14; 3% solution was administered on Days 17-21, and 10% solution was administered on Days 24-27. Compound of Formula I trough levels in tear/periocular tissue are greater than 1000 times the $IC_{50}$ for T-cell attachment/IL-2 release. The compound of Formula I is safe and well tolerated at up to 10% strength at 3 doses/day. Dose dependent increases in compound of Formula I concentration were detected in tear (30 min-16 hours) and plasma (30 min) following ocular instillation. Vitreous concentrations of compound of Formula I were greater than 1000 fold lower.

C. Dermal

1. Compound of Formula I Preclinical Dermal Studies

The compound of Formula I displays 2% (w/w) solubility in water/glycol/transcutol solution and 10% (w/w) solubility in ethanol/glycol/transcutol solution. Solubility studies suggest an emulsion formulation. Prototypes have been developed and tested on microtomed human skin from elective surgery at 1% (w/w). The forms include gels, ointment, or lotion. Stability and compatibility has been demonstrated in all formulations. Skin transport studies performed with LC/MS/MS analysis indicate high compound of Formula I levels in epidermis and dermis and low levels in the receiver. There can be greater than 10 micromolar compound of Formula I in dermis, with 2-4% dose penetration, as determined using [$^{14}$C]-compound of Formula I. Pilot rat and mini-pig studies demonstrate low systemic exposure which indicates drug penetration into vascularized levels of skin (i.e. dermis).

2. Nonclinical Dermal Program

Dermal Sensitization Study in Guinea-Pigs: Buehler test A Buehler test using healthy, young adult (4 to 6 weeks), randomly bred albino guinea pigs (strain Crl:(Ha)BR) is used to determine the potential of compound of Formula I to induce hypersensitivity. The diet consists of certified guinea pig diet (#5026, PMI Nutrition International LLC) ad libitum. Water is administered ad libitum. Room temperature is 18 to 26° C., relative humidity is 30 to 70%, and a 12-hour light/12-hour dark cycle is used. Animals are acclimated for at least 5 days.

Experimental design: 34 acclimated animals are placed in an irritation screening group of 4 guinea pigs, a test group of 10 guinea pigs (Group 1), a naive control group of 5 guinea pigs (Group 2), 10 positive control guinea pigs (Group 3), and 5 positive naive control guinea pigs (Group 4).

Irritation screen: Hair from the back of 4 animals is removed by clipping and four application sites per animal are selected. Each site is treated with 0.4 mL of 0.1%, 1%, or 10% w/v compound of Formula I and 0.4-g dose of compound of Formula I. Appropriate concentrations of compound of Formula I are selected for induction exposure (highest to cause mild-to-moderate skin irritation) and challenge exposure (highest non-irritant dose).

Definitive phase: Prior to the test, hair is removed using electric clippers from animals in Group 1. Occlusive patch systems (Hill Top Chamber®, 25-mm diameter) are saturated with 0.4 mL solution of vehicle with a concentration of compound of Formula I as determined in the irritation screen. The occlusive patches are applied to the flanks of Group 1 guinea pigs for 6 hours. Restraints are used to maintain even pressure over the patches. The procedure is repeated on days 6-8 and 13-15 after the initial exposure. The positive control material, HCA (alpha-hexylcinnamaldehyde), 2.5% w/v in ethanol, is applied in a similar manner to the Group 3 guinea pigs. The naive control animals (Groups 2 and 4) are not treated during the induction phase.

Two weeks after the last induction patch, animals are challenged with patches saturated with a nonirritating concentration of compound of Formula I applied to the dorsal anterior right quandrant, and along the dorsal anterior left quadrant with a challenge application of water. Group 2 animals (naive control) are shaved with electric clippers and treated on the dorsal anterior right quadrant with compound of formula I and along the dorsal anterior left quandrant with vehicle. HCA is administered at 5.0% and 7.0% w/v in acetone on two respective challenge sites along the right side of each animal in Group 3 in the same manner as the induction phase (0.4 mL dose volume). Group 4 animals are treated with two challenge applications of the positive control material in the same manner as Group 3.

After 6 hr, the patches are removed and the area depilated (by applying Nair®). Test sites are evaluated visually 24 and 48 hr after patch removal. Animals developing erythematous responses are considered sensitized (if irritant control animals do not respond). The number of positive reactions and the average intensity of the responses are calculated. Reactions to the challenge doses determine the sensitization. Grades of 1 or greater in the test animals to a respective material indicates evidence of sensitization, provided that grades of less than one are seen in the naive control animals to this same material. If grades of one or greater are noted in the naive control animals, then the reactions of test animals exceeding the most severe naive control reactions are considered sensitization reactions.

3. Compound of Formula I Pilot Rat Dermal Study

Figure 48:
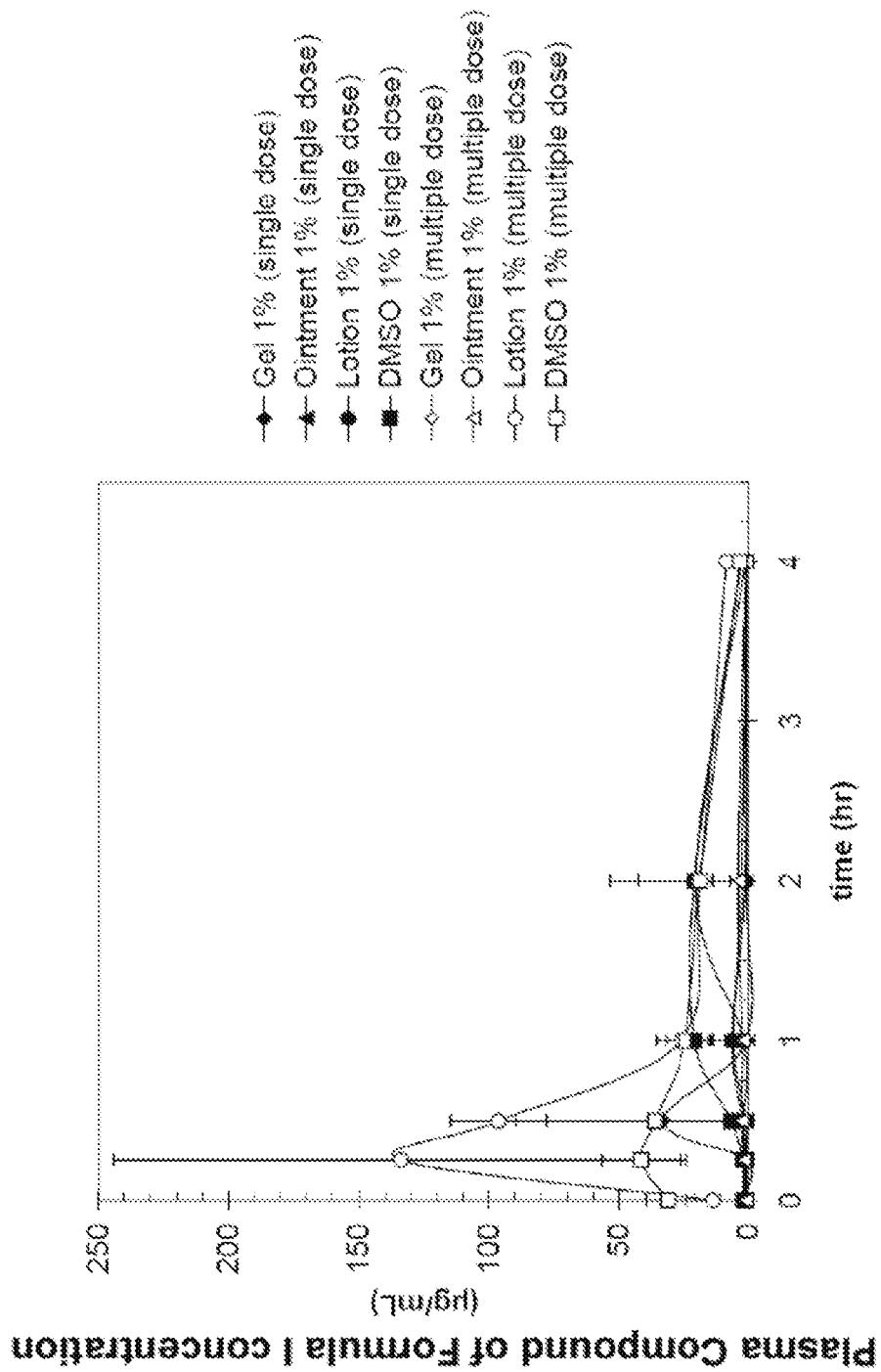
FIG. 48 illustrates the drug plasma level in rats for various topical applications of the compound of Formula I.

The safety and tolerability of prototypical dermal formulations (1% lotion, ointment, and gel) were assessed on rats given TID for seven consecutive days—approximately 6 cm$^2$ with 10 mg/cm$^2$. 1% DMSO was given as a high bioavailability control. FIG. 48 illustrates that the compound of Formula I is detectable in serum.

4. Compound of Formula I Pilot Mini-Pig Dermal Study

The tolerability and systemic exposure of various formulations of the compound of Formula I (DMSO, gel, ointment, lotion at 1%) was assessed by giving these formulations to mini-pigs as multiple dermal does TID for 7 days, approximately 50 cm$^2$ with 10 mg/cm$^2$. One pig/dose formulation was used. In-life PK analysis was completed. No toxicity was reported with any formulation. Plasma PK revealed low levels of the compound of Formula I in all groups but below the LLOQ of 0.5 ng/ml.

The rat and mini-pig pilot studies indicate that PK were comparable with gel and ointment and the compound of Formula I is safe for evaluation in humans as a gel or ointment formulation.

Prototypical 1% topical derm formulations have been developed (lotion, gel, and ointment). There is good delivery of the compound of Formula I to epidermis and dermis in human skin Franz cell. Pilot toxicology studies of lotion, gel, and ointment reveal the PK demonstrates good bioavailability.

Example 12

Phase 2 Trial Allergic Conjunctivitis

Subjects with positive history of ocular allergies and a positive skin test reaction to cat hair, cat dander, dog dander, grasses, ragweed, trees, dust mites, and/or cockroaches within the past 24 months (as demonstrated by positive skin tests) will be challenged with allergen administered to the conjunctiva to induce ocular itching and conjunctival redness. Subjects will be treated with both preserved and unpreserved formulations of the compound of Formula I ophthalmic drops. Unpreserved drug will be supplied as a sterile unit dose in a single use blow-fill-seal container containing the compound of Formula I formulated in PBS. Preserved drug will be supplied as a sterile multi-use container containing the compound of Formula I formulated in PBS containing preservative. Each group of test subjects will be treated QD, BID or TID with different dose strengths of the compound of Formula I or placebo in preserved or unpreserved formulations. Drug will be self administered by each subject as a single drop to each eye once, twice or three times a day as directed. Administered dose strengths will include placebo (PBS vehicle) 0.1%, 0.3%, 1% and 5% solutions of compound of Formula I.

At enrollment, subjects will be evaluated for sensitivity to allergen using a conjunctival provocation test (also referred to as a "conjunctival allergen challenge test"). Patients responding with itchiness and redness of at least 2.0 [0-4 point scale with 0.5 point increments] will be supplied with drug and required to record the administration of each drug dose in patient diaries. Patient response to allergen (itchiness and redness) will be assessed in follow-up visits with subsequent challenges 6, 7 days and/or 13, 14 days after their enrollment. Challenges in these visits will occur at variable times (approximately 15 minutes, 8 hours, or 24 hours) after their last compound of Formula I dose. Conversely, patients will be challenged with allergen and then treated with compound of Formula I at variable times (5 minutes, 10 minutes, 20 minutes, 40 minutes or 1 hour) after the challenge. Patient exams will include assessments of safety, visual acuity, slit-lamp exam, dilated fundoscopy. A mean difference of at least 1.0 point [0-4 point scale with 0.5 point increments] in ocular itching and hyperemia comparing compound of Formula I and vehicle is considered clinically meaningful when evaluated in the first 10 minutes following allergen challenge.

Objective measures of efficacy (physician reported) will include: 1) conjunctival hyperemia, 2) episcleral hyperemia, 3) ciliary hyperemia, and 4) chemosis.

Subjective measures of efficacy (patient reported) will include: 1) ocular itching, 2) blepharitis, 3) rhinorrhea, 4) nasal congestion, and 5) nasal pruritus.

For seasonal allergies, subjects will be treated daily at QD, BID or TID doses for up to 8 consecutive weeks during peak allergy season for common grass and tree pollens (also referred to as "environmental studies"). Similar measures of objective and subjective efficacy measures will be evaluated.

For either environmental or conjunctival provocation studies, a safety trial of at least 6 months will be conducted in normal adult and pediatric patients.

Results of this trial will support regulatory claims to the treatment or prevention of signs and symptoms from allergic conjunctivitis (both seasonal and perennial); steroid sparing treatment of allergic conjunctivitis—no steroid safety events (glaucoma, cataracts); compound of Formula I can be used in conjunction with mast cell stabilizers and antihistamines to enhance or prolong efficacy; treatment of both ocular and nasal signs and symptoms of allergy.

Example 13

Phase 2 Trial for Dry Eye

Subjects with moderate to severe dry eye will be treated for 12 weeks (efficacy trials) and up to 1 year (safety trials) with both preserved and unpreserved formulations of compound of Formula I ophthalmic drops. Unpreserved drug will be supplied as a sterile unit dose in a single use blow-fill-seal container containing compound of Formula I formulated in PBS. Preserved drug will be supplied as a sterile multi-use container containing compound of Formula I formulated in PBS containing preservative. Each group of test subjects will be treated QD or BID with different dose strengths of compound of Formula I or placebo in preserved or unpreserved formulations. Drug will be self administered by each subject as a single drop to each eye once or twice a day. Administered dose strengths will include placebo (PBS vehicle) 0.1%, 0.3%, 1% and 5% solutions of compound of Formula I.

At enrollment, subjects will be evaluated for signs and symptoms of Dry Eye. Patients will be supplied with drug and required to record the administration of each drug dose in patient diaries. Patient signs and symptoms of Dry Eye will be assessed in follow-up visits at the end of week 2, week 4, week 6, week 8 and/or week 12. Patient exams will include assessments of safety, visual acuity, slit-lamp exam, dilated fundoscopy. Endpoints will be measured at the clinic in normal office conditions (referred to as "environmental" conditions) and measured during and/or immediately following prolonged exposure to a controlled environment (i.e., controlled humidity, temperature, air-flow, and visual tasking; also referred to as a "controlled ambient environment").

Objective clinical measures of efficacy will include: 1) corneal staining with fluorescein, 2) conjunctival staining with lissamine green, 3) tear film break up time with fluorescein, 4) Schirmer tear tests with and without anesthesia, 5) conjunctival impression cytology (ICAM-1), 6) tear osmolarity, 7) blink rate, 8) ocular hyperemia, 9) Cochet Bonnet corneal sensitivity, 10) tear fluorophotometry, and 11) ocular protection index.

Subjective clinical measures of efficacy will include: 1) Ocular Surface Disease Index, 2) Patient global self-assessment (self-scored ocular discomfort) 3) Visual analog scale, and 4) drop comfort (tolerability assessment).

Results of this trial will support regulatory claims to the treatment or prevention of signs and symptoms from keratoconjunctivitis sicca (dry eye) with or without concomitant use of lubricating eye drops.

Example 14

Diabetic Retinopathy (DR) and Diabetic Macular Edema (DME)

DR and DME are leukocyte mediated diseases. Adhesion of leukocyte to capillary epithelial cells seems critical in ischemia reperfusion mechanism.

Human Study

Subjects with type I or type II diabetes will be treated with compound of Formula I for up to 3 years with both preserved and unpreserved formulations of compound of Formula I ophthalmic drops. Unpreserved drug will be supplied as a sterile unit dose in a single use blow-fill-seal container containing compound of Formula I formulated in PBS. Preserved drug will be supplied as a sterile multi-use container containing compound of Formula I formulated in PBS containing preservative. Each group of test subjects will be treated QD, BID or TID with different dose strengths of compound of Formula I ophthalmic drops or placebo in preserved or unpreserved formulations. Drug will be self administered by each subject as a single drop to each eye once, twice or three times a day. Administered dose strengths will include placebo (PBS vehicle) 0.1%, 0.3%, 1% and 5% solutions of compound of Formula I. To enhance patient compliance, compound of Formula I can be administered as a slow release formulation which delivers drug to the retina over the course of the study.

At enrollment, patients must have a diagnosis of type I or type II diabetes and non-proliferative diabetic retinopathy. Patients may also have concomitant diabetic macular edema. Patients will be supplied with drug and required to record the administration of each drug dose in patient diaries. Patients will be assessed every 2 months for the duration of the study. Each patient exam will include assessments of safety, visual acuity, slit-lamp exam, dilated fundoscopy.

Objective measures of efficacy will include: 1) Best corrected visual acuity using Early Treatment of Diabetic Retinopathy (ETDRS) method at 4 meters, 2) Reduction in retinal thickness measured by optical coherence tomography (OCT), and 3) Progression of diabetic retinopathy.

Subjective clinical measures of efficacy will include: 1) improvement NEI-VFQ 25 and other validated patient-reported outcome instruments.

Results of this trial will support regulatory claims to the prevention of the progression of diabetic retinopathy at 4, 8 weeks, 1, 2, and 3 years; maintenance or improvement in visual acuity; prevention, treatment, and/or reduction in macular edema; can be used in combination with focal and grid laser, intravitreal steroids, photodynamic therapy, and/or anti-VEGF therapies.

Rat STZ model of Diabetic Macular Edema (DME) Pilot study Anti-ICAM antibodies have shown efficacy in a rat STZ model of DME. Compound of Formula I radiolabel distribution studies in rat demonstrate delivery to retina. STZ (strptozocin) is used to generate an animal model for Type 1 diabetes. A definitive STZ rat study with compound of Formula I will include 5 groups with 18 animals. Group no. 1 is normal SD rats that will receive no treatment. Group no. 2 is STZ rats that receive vehicle drops BID/2 months. Group no. 3 is STZ rats that receive 1% compound of Formula I drops BID/2 months. Group no. 4 is STZ rats that will receive 5% compound of Formula I drops BID/2 months. Group no. 5 is STZ rats that will receive celecoxib positive control. Endpoints for the study will include: retinal FITC-dextran leakage, vitreous-plasma protein ratio, myeloperoxidase assay, and retinal leukostasis.

Leukostasis is studied as described in U.S. Patent Application No. 20080019977 using Acridine Orange Leukocyte Fluorography (AOLF) and Fluorescein Angiography. Leukocyte dynamics in the retina are studied with AOLF (Miyamoto, K., et al., Invest. Opthalmol. Vis. Sci., 39:2190-2194 (1998); Nishiwaki, H., et al., Invest. Opthalmol. Vis. Sci., 37:1341-1347 (1996); Miyamoto, K., et al., Invest. Opthalmol. Vis. Sci., 37:2708-2715 (1996)). Intravenous injection of acridine orange causes leukocytes and endothelial cells to fluoresce through the non-covalent binding of the molecule to double stranded nucleic acid. When a scanning laser opthalmoscope is utilized, retinal leukocytes within blood vessels can be visualized in vivo. Twenty minutes after acridine orange injection, static leukocytes in the capillary bed can be observed. Immediately after observing and recording the static leukocytes, fluorescein angiography is performed to study the relationship between static leukocytes and retinal vasculature.

Twenty-four hours before AOLF and fluorescein angiography is performed, all rats had a heparin-lock catheter surgically implanted in the right jugular vein for the administration of acridine orange or sodium fluorescein dye. The catheter is subcutaneously externalized to the back of the neck. The rats are anesthetized for this procedure with xylazine hydrochloride (4 mg/kg) and ketamine hydrochloride (25 mg/kg). Immediately before AOLF, each rat is again anesthetized, and the pupil of the left eye is dilated with 1% tropicamide to observe leukocyte dynamics. A focused image of the peripapillary fundus of the left eye is obtained with a scanning laser opthalmoscope (SLO). Acridine orange is dissolved in sterile saline (1.0 mg/ml) and 3 mg/kg is injected through the jugular vein catheter at a rate of 1 ml/min. The fundus is observed with the SLO using the argon blue laser as the illumination source and the standard fluorescein angiography filter in the 40° field setting for 1 minute. Twenty minutes later, the fundus is again observed to evaluate leukostasis in the retina. Immediately after evaluating retinal leukostasis, 20 μl of 1% sodium fluorescein dye is injected into the jugular vein catheter. The images are recorded on a videotape at the rate of 30 frames/sec. The video recordings are analyzed on a computer equipped with a video digitizer that digitizes the video image in real time (30 frames/sec) to 640×480 pixels with an intensity resolution of 256 steps. For evaluating retinal leukostasis, an observation area around the optic disc measuring ten disc diameters in diameter is determined by drawing a polygon surrounded by the adjacent major retinal vessels. The area is measured in pixels and the density of trapped leukocytes is calculated by dividing the number of trapped leukocytes, which are recognized as fluorescent dots, by the area of the observation region. The leukocyte densities are calculated generally in eight peripapillary observation areas and an average density is obtained by averaging the eight density values.

Compound of Formula I is expected to reduce leukostasis and blood-retinal barrier leakage in STZ treated rats.

Example 15

Age Related Macular Degeneration (AMD)

Subjects with wet or dry AMD will be treated with compound of Formula I for up to 3 years with both preserved and unpreserved formulations of compound of Formula I ophthalmic drops. Unpreserved drug will be supplied as a sterile unit dose in a single use blow-fill-seal container containing compound of Formula I formulated in PBS. Preserved drug will be supplied as a sterile multi-use container containing compound of Formula I formulated in PBS containing preservative. Each group of test subjects will be treated QD, BID or TID with different dose strengths of compound of Formula I ophthalmic drops or placebo in preserved or unpreserved formulations. Drug will be self administered by each subject as a single drop to each eye once, twice, or three times a day. Administered dose strengths will include placebo (PBS vehicle) 0.1%, 0.3%, 1% and 5% solutions of compound of Formula I. To enhance patient compliance, compound of Formula I can be administered as a slow release formulation which delivers drug to the retina over the course of the study.

At enrollment, patients must have a diagnosis of wet or dry AMD. Patients may also have concomitant diabetic macular edema. Patients will be supplied with drug and required to record the administration of each drug dose in patient diaries. Patients will be assessed every 2 months for the duration of the study. Each patient exam will include assessments of safety, visual acuity, slit-lamp exam, dilated fundoscopy.

Objective measures will include: best corrected visual acuity; prevention of progression of geographic atrophy; and prevention of conversion to neovascular (wet AMD).

Results of this trial will support regulatory claims to the prevention of geographic atrophy related to dry AMD; can be used in conjunction with genetic biomarker or other type of diagnostic study that predicts subjects at high risk; and can be used in conjunction with anti-oxidant and/or anti-neovascular or anti-VEGF agents.

Example 16

Phase 2 Atopic Dermatitis

Subjects with atopic dermatitis will be treated with compound of Formula I for up to 12 months. Drug will be supplied as a suitable dermatologic formulation for local application (cream, lotion, gel or ointment) containing compound of Formula I. Each group of test subjects will be treated QD, BID or TID with different dose strengths of compound of Formula I ophthalmic drops or placebo in formulation. Drug will be self administered by each subject by gentle rubbing onto the effected area. Administered dose strengths will include placebo (vehicle) 0.1%, 0.3%, 1%, and 2% preparations of compound of Formula I. To enhance effect, treated areas may covered with an occlusive dressing. To improve patient compliance, drug may be administered as a slow release drug-impregnated patch.

At enrollment, patients must have a diagnosis of atopic dermatitis. Patients will be supplied with drug and required to record the administration of each drug dose in patient diaries. Patients will be assessed every 2 weeks for the duration of the study. Each patient exam will include assessments of safety and tolerability. Measures of efficacy will include a physician's global assessment, a reduction in affected body surface area or a reduction in pruritis score.

Results of this trial will support regulatory claims to treatment of atopic dermatitis.

Example 17

Crohn's Disease, Ulcerative Colitis or IBD

Subjects with Crohn's disease, ulcerative colitis or IBD will be treated with compound of Formula I for up to 12 months. Drug will be supplied as a formulation suitable for oral administration (solution, pill, or capsule) containing compound of Formula I. A typical oral solution dosage form would include compound of Formula I dissolved in PBS adjusted to pH 7. Each group of test subjects will be treated QD, BID or TID with different dose strengths of compound of Formula I or placebo in formulation. Drug will be self administered by each subject by mouth. Administered dose strengths will include placebo (vehicle) 1 mg per dose, 5 mg per dose, 10 mg per dose and up to 100 mg per dose of compound of Formula I in formulation.

At enrollment, patients must have a diagnosis of Crohn's disease, ulcerative colitis or IBD. Patients will be supplied with drug and required to record the administration of each drug dose in patient diaries. Treatment with compound of Formula I can be used in conjunction with current anti-inflammatories (eg, salicylates) and immunosuppressants (methotrexates, steroids, antibodies).

Patients will be assessed every 2 weeks for the duration of the study. Each patient exam will include assessments of safety and tolerability. Measures of efficacy will include the Crohn's Disease Activity Index (CDAI); disease activity index or similar scale for ulcerative colitis.

Results of this trial will support regulatory claims to the treatment and maintenance of remission of Crohn's disease, ulcerative colitis and/or IBD.

While selected embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising a compound of Formula I:

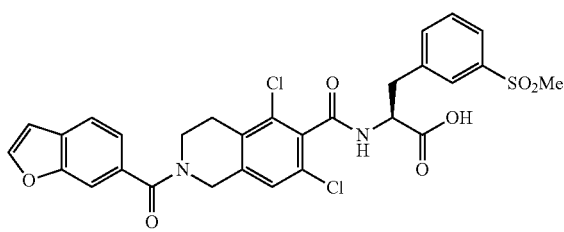

Formula I comprising a purity of greater than about 90%, and/or a pharmaceutically acceptable salt thereof.

2. The composition of claim 1, wherein the purity is greater than about 98%.

3. The composition of claim 1, wherein the compound comprises at least about 95% of an S-enantiomer.

4. The composition of claim 1, wherein the compound is not the calcium salt of the free acid.

5. The composition of claim 1, wherein the compound is a crystalline form (Form A) comprising an X-ray powder diffraction pattern having characteristic peaks at a reflection angle 2θ of about 18.2, 21.4, and 22.7 degrees.

6. The composition of claim 5, wherein the form undergoes a predominant endotherm at about 145° C.

7. The composition of claim 5, wherein the form is produced by isolating the form from a suspension of the compound in an organic solvent which is acetonitrile, methyl ethyl ketone, or water.

8. The composition of claim 1, wherein the compound is a crystalline form (Form B) comprising an X-ray powder diffraction pattern having characteristic peaks at a reflection angle 2θ of about 12.1, 17.1, and 18.5 degrees.

9. The composition of claim 1, wherein the compound is a crystalline form (Form C) comprising an X-ray powder diffraction pattern having characteristic peaks at a reflection angle 2θ of about 4.8, 17.8, and 21.5 degrees.

10. The composition of claim 1, wherein the compound is a crystalline form (Form D) comprising an X-ray powder diffraction pattern having characteristic peaks at a reflection angle 2θ of about 17.6, 21.7, and 24.8 degrees.

11. The composition of claim 1, wherein the compound is a crystalline form (Form E) comprising an X-ray powder diffraction pattern having characteristic peaks at a reflection angle 2θ of about 5.12, 8.26, and 17.8 degrees.

12. The composition of claim 1, wherein the compound is an amorphous form.

13. The composition of claim 1, wherein the compound comprises less than 0.5% of any one byproduct of chemical synthesis of the compound.

14. The composition of claim 1, wherein the compound comprises less than a total of 1.5% of all byproducts of the chemical synthesis.

15. A method of producing the form of the compound of claim 5:

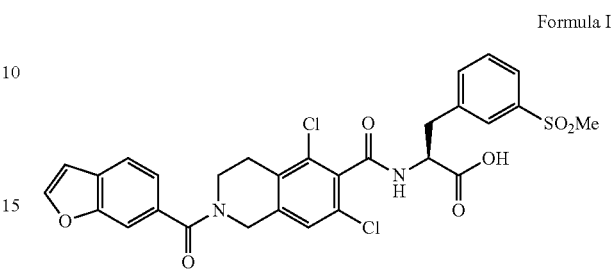

Formula I comprising the steps of:
a) suspending the compound of Formula I in a solvent;
b) filtering the suspension to isolate a crystalline product; and
c) washing the crystalline product with water thereby obtaining the form of the compound of claim 5.

16. The method of claim 15 wherein the solvent is acetonitrile or methyl ethyl ketone.

17. A pharmaceutical composition comprising a pharmaceutically acceptable carrier and the compound of claim 1.

18. The pharmaceutical composition of claim 17, wherein said compound has been converted to a salt.

19. The pharmaceutical composition of claim 17, wherein said compound comprises the amorphous form or any of crystalline Forms A, B, C, D, or E, or a combination thereof, of said compound.

20. The pharmaceutical composition of claim 17, wherein said carrier further comprises one or more pharmaceutically acceptable excipients.

21. The pharmaceutical composition of claim 17, further comprising at least one additional therapeutic agent.

22. The pharmaceutical composition of claim 21, wherein the additional therapeutic agent is an antioxidant, antiinflammatory agent, antimicrobial agent, antiangiogenic agent, anti-apoptotic agent, vascular endothelial growth factor inhibitor, antiviral agent, calcineurin inhibitor, corticosteroid, antihistamine, mast cell stabilizing agent, or immunomodulator.

23. The pharmaceutical composition of claim 17, wherein the pharmaceutical composition is a gel comprising about 1% W/V of said compound; and further wherein said pharmaceutically acceptable carrier comprises up to about 15% W/V Dimethyl Isosorbide; up to about 25% W/V Transcutol; up to about 12% W/V Hexylene glycol, up to about 0.15% W/V Methylparaben; up to about 0.05% W/V Propylparaben; up to about 1% W/V Hydroxyethyl Cellulose; and water.

24. The pharmaceutical composition of claim 17, wherein the pharmaceutical composition is an ointment comprising about 1% W/V of said compound; and further wherein said pharmaceutically acceptable carrier comprises up to about 10% W/V Dimethyl Isosorbide; up to about 0.02% W/V Butylated Hydroxytoluene; up to about 2% W/V Span 80; up to about 10% W/V White Wax; and White Petrolatum.

25. The pharmaceutical composition of claim 17, wherein the pharmaceutical composition is a water based lotion comprising about 1% W/V of said compound; and further wherein said pharmaceutically acceptable carrier comprises up to about 15% W/V Dimethyl Isosorbide; up to about 25% W/V Transcutol; up to about 12% W/V Hexylene glycol; up to about 5% W/V Propylene Glycol; and pH 6.0 25% Trolamine, wherein the lotion is buffered to a pH of about pH 4.0 to about pH 7.5.

26. The pharmaceutical composition of claim 17, wherein the pharmaceutical composition is an aqueous solution buffered to a pH of about 6.0 to about 8.0 with Sodium Phosphate, Monobasic, and further wherein said pharmaceutically acceptable carrier comprises about 1% W/V of the compound of claim 1, up to about 0.1% W/V EDTA, and, optionally, up to about 0.4% w/w Methylparaben, and optionally, up to about 0.02% w/w Propylparaben.

27. The pharmaceutical composition of claim 17, wherein the pharmaceutical composition is a biocompatible solid or gel.

28. The pharmaceutical composition of claim 27 wherein the biocompatible solid is biodegradable.

29. The pharmaceutical composition of claim 17, wherein the composition is suitable for administration via instillation, via aerosol, via inhalation, orally, topically, transdermally, via insert, or via injection.

30. The pharmaceutical composition of claim 17, wherein the pharmaceutical composition is formulated to deliver a therapeutically effective amount of the compound of Formula I locally.

31. The pharmaceutical composition of claim 17, wherein the pharmaceutical composition is formulated to deliver less than a therapeutically effective amount of the compound of Formula I systemically.

32. A method of treating disease in a subject, comprising the steps of administering an effective amount of the pharmaceutical composition of claim 17 to the subject in need thereof, wherein said disease is an inflammation-mediated disease.

33. The method of claim 32, wherein the disease is an inflammatory eye disorder which is intraocular, periocular and ocular surface inflammation, Keratoconjunctivitis, keratoconjunctivitis sicca (KCS, aka Dry Eye), KCS in patients with Sjogren's syndrome, allergic conjunctivitis, uveitis, inflammation of the eye, the cornea and periocular tissue from contact lens wear, inflammation of the eye following surgery including LASIK, intraocular inflammation including inflammation of the retina and the anterior and posterior segments of the eye, uveitis, retinitis, edema and retinopathies including diabetic macular edema and diabetic retinopathy, corneal inflammation including rejection of corneal transplants Graves' disease (Basedow disease), or Graves ophthalmopathy.

34. The method of claim 32, wherein the disease is an allergic disease which is allergic conjunctivitis, allergic rhinitis, allergic asthma, or allergic contact dermatitis.

35. The method of claim 32, wherein the disease is psoriasis, irritant contact dermatitis, eczematous dermatitises, seborrhoeic dermatitis, cutaneous manifestations of immunologically-mediated disorders, alopecia, alopecia areata, or scar formation.

36. The pharmaceutical composition of claim 27, comprising a compound of Formula I:

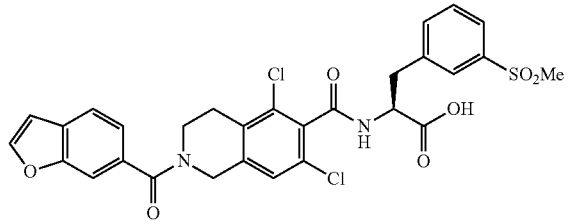

Formula I which comprises a purity greater than about 90% and a pharmaceutically acceptable biocompatible matrix wherein the compound comprises a solid form within the biocompatible matrix.

37. The pharmaceutical composition of claim 36, wherein the solid form is the amorphous form or any of crystalline Forms A, B, C, D, or E, or a combination thereof, of said compound.

38. The pharmaceutical composition of claim 36, wherein the biocompatible matrix is a polyacrylate, methacyrlate, polyolefin, polyamide, fluoropolymer, cellulose derivative, polyvinyl alcohol, polyvinylpyrrolidone, coated zeolite, or PLGA microsphere or nanosphere.

39. The pharmaceutical composition of claim 36, wherein the biocompatible matrix is biodegradable.

40. The pharmaceutical composition of claim 36, wherein a release of the compound from the biocompatible matrix comprises a slow release profile or a sustained release profile.

41. A compound of the formula:

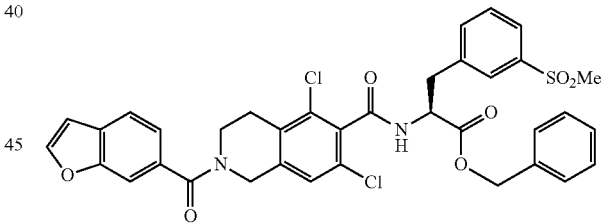

or its pharmaceutically acceptable salts.

* * * * *